US012807601B2

(12) United States Patent
Kilaru et al.

(10) Patent No.: US 12,807,601 B2
(45) Date of Patent: Nov. 24, 2026

(54) 2-[3-[1 [(QUINAZOLIN-4-YL)AMINO]ETHYL]-PYRAZIN-2-YL]THIAZOLE-5-CARBONITRILE DERIVATIVES AND SIMILAR COMPOUNDS AS PESTICIDES

(71) Applicant: SYNGENTA CROP PROTECTION AG, Basel (CH)

(72) Inventors: Jagadeesh Prathap Kilaru, Corlim (IN); Mangala Phadte, Corlim (IN); Simone Berardozzi, Stein (CH); Roger Graham Hall, Stein (CH); Matthias Weiss, Stein (CH); Thomas Pitterna, Stein (CH); André Jeanguenat, Stein (CH)

(73) Assignee: SYNGENTA CROP PROTECTION AG, Basel (CH)

( * ) Notice: Subject to any disclaimer, the term of this patent is extended or adjusted under 35 U.S.C. 154(b) by 247 days.

(21) Appl. No.: 18/570,477

(22) PCT Filed: Jun. 16, 2022

(86) PCT No.: PCT/EP2022/066501
§ 371 (c)(1),
(2) Date: Dec. 14, 2023

(87) PCT Pub. No.: WO2022/268648
PCT Pub. Date: Dec. 29, 2022

(65) Prior Publication Data

US 2024/0294517 A1 Sep. 5, 2024

(30) Foreign Application Priority Data

Jun. 24, 2021 (IN) ............................. 202111028439
Dec. 15, 2021 (IN) ............................. 202111058395

(51) Int. Cl.
*C07D 417/14* (2006.01)
*A01N 43/78* (2006.01)
*A01N 43/82* (2006.01)
*A01P 7/04* (2006.01)

(52) U.S. Cl.
CPC ........... *C07D 417/14* (2013.01); *A01N 43/78* (2013.01); *A01N 43/82* (2013.01); *A01P 7/04* (2021.08)

(58) Field of Classification Search
None
See application file for complete search history.

(56) References Cited

FOREIGN PATENT DOCUMENTS

| | | | | |
|---|---|---|---|---|
| WO | 2021083936 A1 | | 5/2021 | |
| WO | 2021105091 A1 | | 6/2021 | |
| WO | WO 2021/177160 A1 | * | 9/2021 | ........... C07D 401/14 |

OTHER PUBLICATIONS

International Search Report and Written Opinion of the International Searching Authority issued in International Patent Application No. PCT/EP2022/066501 dated Sep. 15, 2022.

* cited by examiner

*Primary Examiner* — Brian J Davis
(74) *Attorney, Agent, or Firm* — BakerHostetler; Toni-Junell Herbert

(57) ABSTRACT

The present invention relates to compounds of formula I wherein Q is as pesticides for combating and controlling insects, acarines, nematodes or molluscs. An exemplary compound is e.g. 2-[3-[1[[6-chloro-8-(trifluoromethyl) quinazolin-4-yl]amino]ethyl]pyrazin-2-yl]thiazole-5-carbonitrile (compound P5). Comparative biological data is provided:

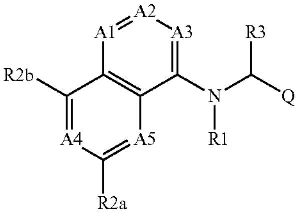

I

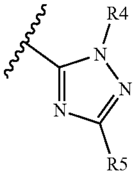

$Q^a$ or

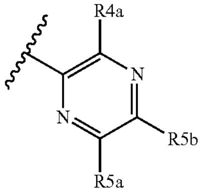

$Q^b$

19 Claims, No Drawings

2-[3-[1 [(QUINAZOLIN-4-YL)AMINO]ETHYL]-PYRAZIN-2-YL]THIAZOLE-5-CARBONITRILE DERIVATIVES AND SIMILAR COMPOUNDS AS PESTICIDES

CROSS-REFERENCE TO RELATED APPLICATIONS

This application is a U.S. National Stage Application, filed under 35 U.S.C. § 371, of International Application No. PCT/EP2022/066501, filed Jun. 16, 2022, which claims priority to IN 202111058395, filed Dec. 15, 2021, and IN 202111028439, filed Jun. 24, 2021, the entire contents of which are incorporated by reference herein.

The present invention relates to pesticidally active, in particular insecticidally active quinazoline compounds, to processes for their preparation, to compositions comprising those compounds, and to their use for controlling animal pests, including arthropods and in particular insects or representatives of the order Acarina.

WO 2021/083936, WO 2021/148639 and WO 2021/177160 describe certain quinazoline, quinazolinone and quinoline compounds.

There have now been found further novel pesticidally active quinazoline and quinoline compounds.

The present invention accordingly relates, in a first aspect, to a compound of the formula I

I

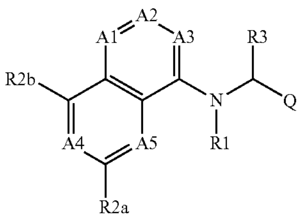

wherein:

$A_1$, $A_2$ and $A_3$ are, independently from each other, N or $CR_Y$; or $A_1$=$A_2$-$A_3$, taken together, are NR—C(═X)—N;

$A_4$ and $A_5$ are, independently from each other, N or $CR_{YY}$;

Q is $Q^a$

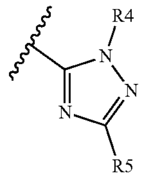

or $Q^b$

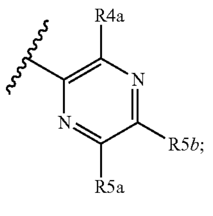

R is hydrogen, $C_1$-$C_3$alkyl, $C_1$-$C_3$haloalkyl, $C_1$-$C_3$alkoxy, or $C_1$-$C_3$haloalkoxy;

$R_1$ is hydrogen, $C_1$-$C_6$alkyl, $C_1$-$C_6$cyanoalkyl, aminocarbonyl$C_1$-$C_6$alkyl, hydroxycarbonyl$C_1$-$C_6$alkyl, $C_1$-$C_6$nitroalkyl, trimethylsilane$C_1$-$C_6$alkyl, $C_1$-$C_3$alkoxy-$C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_3$-$C_4$cycloalkyl$C_1$-$C_2$alkyl-, $C_3$-$C_4$cycloalkyl$C_1$-$C_2$alkyl- wherein the $C_3$-$C_4$cycloalkyl group is substituted with 1 or 2 halogen atoms, oxetan-3-yl-$CH_2$—, $C_1$-$C_6$alkylcarbonyl, $C_1$-$C_6$alkoxycarbonyl, phenyloxycarbonyl, benzyloxycarbonyl, benzyl or benzyl substituted with 1 to 3 substituents independently selected from halogen, $C_1$-$C_6$alkoxy and $C_1$-$C_6$haloalkyl;

$R_{2a}$ and $R_{2b}$ are each independently selected from hydrogen, $C_1$-$C_3$alkyl, $C_1$-$C_3$haloalkyl, $C_1$-$C_3$haloalkylsuflanyl, $C_1$-$C_3$alkoxy, $C_1$-$C_3$haloalkoxy, halogen, $NO_2$, $SF_5$, CN, C(O)$NH_2$, C(O)OH, C(S)$NH_2$, $C_3$-$C_6$cycloalkyl, $C_3$-$C_6$cycloalkyl substituted with one to three substituents independently selected from $R_x$, $C_3$-$C_6$cycloalkylcarbonyl, phenyl, phenyl substituted with one to three substituents independently selected from $R_x$, heteroaryl, heteroaryl substituted with one to three substituents independently selected from $R_x$, $OR_6$, piperidin-2-one-1-yl, piperidin-2-one-1-yl substituted with one to two substituents independently selected from $R_x$, pyridin-2-one-1-yl, pyridin-2-one-1-yl substituted with one to two substituents independently selected from $R_x$, azetidin-1-yl, azetidin-1-yl substituted with one to two substituents independently selected from $R_x$ pyrrolidin-1-yl, pyrrolidin-1-yl substituted with one to two substituents independently selected from $R_x$, $C_3$-$C_6$cycloalkyl$C_1$-$C_4$alkyl, $C_3$-$C_6$cycloalkyl$C_1$-$C_4$alkyl substituted with one to two substituents independently selected from $R_z$; $C_3$-$C_6$cycloalkyl$C_1$-$C_3$alkoxy, $C_3$-$C_6$cycloalkyl$C_1$-$C_3$alkoxy substituted with one to two substituents independently selected from $R_x$, $C_1$-$C_5$cyanoalkyl, $C_1$-$C_5$cyanoalkoxy, $C_1$-$C_4$alkylsulfanyl, $C_1$-$C_4$alkylsulfanyl substituted with one to three substituents independently selected from $R_x$, $C_1$-$C_4$alkylsulfonyl, $C_1$-$C_4$alkylsulfonyl substituted with one to three substituents independently selected from $R_x$, $C_1$-$C_4$alkylsulfinyl, and $C_1$-$C_4$alkylsulfinyl substituted with one to three substituents independently selected from $R_x$;

$R_3$ is $C_1$-$C_3$alkyl or $C_1$-$C_3$haloalkyl;

$R_4$ is thiazol-2-yl, thiazol-4-yl, thiazol-5-yl, isothiazol-3-yl, isothiazol-4-yl, isothiazol-5-yl, 1,2,4-thiadiazol-3-yl, 1,3,4-thiadiazol-2-yl or 1,2,4-thiadiazol-5-yl; or $R_4$ is thiazol-2-yl, thiazol-4-yl, thiazol-5-yl, isothiazol-3-yl, isothiazol-4-yl, isothiazol-5-yl, 1,2,4-thiadiazol-3-yl, 1,3,4-thiadiazol-2-yl or 1,2,4-thiadiazol-5-yl each of which, independently of each other, is substituted with one to two substituents independently selected from $C_1$-$C_3$alkyl, $C_1$-$C_3$haloalkyl, $C_1$-$C_3$alkoxy, $C_3$-$C_4$cycloalkyl, halo, hydroxyl, CN, $C_1$-$C_6$haloalkoxy, $C_2$-$C_6$haloalkenyloxy, $C_2$-$C_6$haloalkynyloxy, $C_3$-$C_4$halocycloalkoxy, $NH_2$C(O)—, $NH_2$C(S)—, (OH)N═C($NH_2$)— and a 5-membered heteroaryl ring optionally substituted by 1 to 3 substituents independently selected from halogen, $C_1$-$C_3$alkyl, $C_1$-$C_3$haloalkyl, $C_1$-$C_3$alkoxy and $C_1$-$C_3$haloalkoxy;

$R_{4a}$ is thiazol-2-yl, thiazol-4-yl, thiazol-5-yl, isothiazol-3-yl, isothiazol-4-yl, isothiazol-5-yl, 1,2,4-thiadiazol-3-yl, 1,3,4-thiadiazol-2-yl or 1,2,4-thiadiazol-5-yl; or $R_{4a}$ is thiazol-2-yl, thiazol-4-yl, thiazol-5-yl, isothiazol-3-yl, isothiazol-4-yl, isothiazol-5-yl, 1,2,4-thiadiazol-3-yl, 1,3,4-thiadiazol-2-yl or 1,2,4-thiadiazol-5-yl each of which, independently of each other, is substituted with one to two substituents independently selected from $C_1$-$C_3$alkyl, $C_1$-$C_3$haloalkyl, $C_1$-$C_3$alkoxy, $C_3$-$C_4$cycloalkyl, halogen, hydroxyl, cyano, and $C_1$-$C_3$haloalkoxy;

$R_5$ is hydrogen, $C_1$-$C_3$alkyl, $C_1$-$C_3$haloalkyl, $C_3$-$C_4$cycloalkyl, $C_1$-$C_3$alkoxy, $C_3$-$C_4$alkoxyC(O)—, ($C_1$-$C_3$alkoxy)$_2$CH—, halogen, CN, $NH_2C(O)$, amino (i.e. $NH_2$), ($C_1$-$C_3$alkyl)amino, di($C_1$-$C_3$alkyl)amino, hydroxy, $C_3$-$C_4$halocycloalkyl, $C_3$-$C_4$cyanocycloalkyl, $C_2$-$C_6$alkenyl, $C_2$-$C_6$haloalkenyl, $C_2$-$C_6$alkynyl, $C_2$-$C_6$haloalkynyl, $C_1$-$C_4$haloalkylsulfanyl, $C_1$-$C_4$haloalkylsulfinyl, $C_1$-$C_4$haloalkylsulfonyl, $C_1$-$C_4$alkylsulfanyl, $C_1$-$C_4$alkylsulfinyl, $C_1$-$C_4$alkylsulfonyl, $C_1$-$C_3$alkoxy-$C_1$-$C_3$alkyl, $C_1$-$C_3$alkoxy-$C_1$-$C_3$alkoxy-$C_1$-$C_3$alkyl, ($C_1$-$C_3$alkyl) sulfonylamino, ($C_1$-$C_3$alkyl)sulfonyl($C_1$-$C_3$alkyl) amino, ($C_1$-$C_3$alkyl)NHC(O), ($C_1$-$C_3$alkyl)$_2$NC(O), ($C_1$-$C_3$cycloalkyl)NHC(O), ($C_1$-$C_3$cycloalkyl)($C_1$-$C_3$alkyl)NC(O), ($C_1$-$C_3$alkyl)C(O)($C_1$-$C_3$alkyl)N, ($C_1$-$C_3$alkyl)C(O)NH, ($C_1$-$C_3$alkyl)C(O), ($C_1$-$C_3$alkoxy)C (O), HC(O), diphenylmethanimine, $C_1$-$C_3$haloalkoxy, phenyl, or a 5-membered heteroaromatic ring; or $R_5$ is phenyl substituted with one to three substituents selected from $C_1$-$C_3$alkyl, $C_1$-$C_3$haloalkyl, $C_1$-$C_3$alkoxy, $C_3$-$C_4$cycloalkyl, halogen, CN and hydroxyl; or $R_5$ is a 5-membered heteroaromatic ring substituted with one to three substituents selected from $C_1$-$C_3$alkyl, $C_1$-$C_3$haloalkyl, $C_1$-$C_3$alkoxy, $C_3$-$C_4$cycloalkyl, halogen, CN and hydroxyl;

$R_{5a}$ and $R_{5b}$ are, independently of each other, selected from hydrogen, halogen, CN, $C_1$-$C_3$alkyl, $C_1$-$C_3$haloalkyl, $C_3$-$C_4$cycloalkyl, $C_1$-$C_3$alkoxy, and $C_1$-$C_3$haloalkoxy;

$R_6$ is phenyl, benzyl, heteroaryl, or $C_3$-$C_6$ cycloalkyl; or $R_6$ is phenyl, benzyl, heteroaryl, or $C_3$-$C_6$ cycloalkyl, each of which, independent of each other, is substituted with one to three substituents independently selected from $R_x$;

$R_x$ is independently selected from halogen, $C_1$-$C_3$alkyl, $C_1$-$C_3$haloalkyl, $C_1$-$C_3$alkoxy, $C_1$-$C_3$haloalkoxy, $NO_2$, $SF_5$, CN, $C(O)NH_2$, $C(S)NH_2$, $C_1$-$C_4$haloalkylsulfanyl, $C_1$-$C_4$haloalkylsulfinyl, $C_1$-$C_4$haloalkylsulfonyl, $C_1$-$C_4$alkylsulfanyl, $C_1$-$C_4$alkylsulfinyl and $C_1$-$C_4$alkylsulfonyl;

$R_Y$ is selected from hydrogen, $C_1$-$C_3$ alkyl, $C_1$-$C_3$ haloalkyl, hydroxy, $C_1$-$C_3$ alkoxy, $C_1$-$C_3$ haloalkoxy, halogen, CN and cyclopropyl;

$R_{YY}$ is selected from hydrogen, $C_1$-$C_3$ alkyl, $C_1$-$C_3$ haloalkyl, hydroxy, $C_1$-$C_3$ alkoxy, $C_1$-$C_3$ haloalkoxy, halogen, CN and cyclopropyl;

$R_Z$ is selected from oxo, halogen, $C_1$-$C_3$ alkyl, $C_1$-$C_3$haloalkyl, $C_1$-$C_3$alkoxy, $C_1$-$C_3$haloalkoxy and CN; and X is O or S;

or an agrochemically acceptable salt, stereoisomer, enantiomer, tautomer and N-oxide of the compound of formula I.

Compounds of formula I which have at least one basic centre can form, for example, acid addition salts, for example with strong inorganic acids such as mineral acids, for example perchloric acid, sulfuric acid, nitric acid, nitrous acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. Compounds of formula I which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine.

In each case, the compounds of formula I according to the invention are in free form, in oxidized form as a N-oxide or in salt form, e.g. an agronomically usable salt form.

N-oxides are oxidized forms of tertiary amines or oxidized forms of nitrogen containing heteroaromatic compounds. They are described for instance in the book "Heterocyclic N-oxides" by A. Albini and S. Pietra, CRC Press, Boca Raton 1991.

The compounds of formula I according to the invention also include hydrates which may be formed during the salt formation.

The term "$C_1$-$C_n$alkyl" as used herein refers to a saturated straight-chain or branched hydrocarbon radical attached via any of the carbon atoms having 1 to n carbon atoms, for example, any one of the radicals methyl, ethyl, n-propyl, 1-methylbutyl, 2-methylbutyl, 3-methylbutyl, 2, 2-dimethylpropyl, 1-ethylpropyl, n-hexyl, n-pentyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, or 1-ethyl-2-methylpropyl.

The term "$C_1$-$C_n$haloalkyl" as used herein refers to a straight-chain or branched saturated alkyl radical attached via any of the carbon atoms having 1 to n carbon atoms (as mentioned above), where some or all of the hydrogen atoms in these radicals may be replaced by fluorine, chlorine, bromine and/or iodine, i.e., for example, any one of chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl. Accordingly a term "$C_1$-$C_2$fluoroalkyl" would refer to a $C_1$-$C_2$alkyl radical which carries 1, 2, 3, 4, or 5 fluorine atoms, for example, any one of difluoromethyl, trifluoromethyl, 1-fluoroethyl, 2-fluoroethyl, 2,2-difluoroethyl, 2,2,2-trifluoroethyl, 1,1,2,2-tetrafluoroethyl or pentafluoroethyl.

The term "$C_1$-$C_n$alkoxy" as used herein refers to a straight-chain or branched saturated alkyl radical having 1 to n carbon atoms (as mentioned above) which is attached via an oxygen atom, i.e., for example, any one of the radicals methoxy, ethoxy, n-propoxy, 1-methylethoxy, n-butoxy, 1-methylpropoxy, 2-methylpropoxy or 1,1-dimethylethoxy. The term "halo$C_1$-$C_n$alkoxy" as used herein refers to a $C_1$-$C_n$alkoxy radical where one or more hydrogen atoms on the alkyl radical is replaced by the same or different halo atom(s)—examples include trifluoromethoxy, 2-fluoroethoxy, 3-fluoropropoxy, 3,3,3-trifluoropropoxy, 4-chlorobutoxy.

The term "$C_1$-$C_n$cyanoalkyl" as used herein refers to a straight chain or branched saturated $C_1$-$C_n$alkyl radical having 1 to n carbon atoms (as mentioned above), where one of the hydrogen atoms in these radicals is be replaced by a cyano group: for example, cyanomethyl, 2-cyanoethyl, 2-cyanopropyl, 3-cyanopropyl, 1-(cyanomethyl)-2-ethyl, 1-(methyl)-2-cyanoethyl, 4-cyanobutyl, and the like.

The term "$C_3$-$C_n$cycloalkyl" as used herein refers to 3-n membered cycloalkyl groups such as cyclopropane, cyclobutane, cyclopentane and cyclohexane.

The term "$C_3$-$C_n$cycloalkylcarbonyl" as used herein refers to a 3-n membered cycloalkyl group attached to a carbonyl (C═O) group, which carbonyl group is connected to the rest of the molecule. Similarly the terms "$C_1$-$C_n$alkylcarbony", "$C_1$-$C_n$alkoxycarbonyl", "phenyloxycarbonyl" and "benzyloxycarbonyl" as used herein refers to an alkyl, alkoxy, phenyloxy and benzyloxy group attached to a carbonyl (C═O) group, which carbonyl group is connected to the rest of the molecule.

The term "$C_3$-$C_4$cycloalkyl-$C_1$-$C_2$alkyl" as used herein refers to 3 or 4 membered cycloalkyl group with either a methylene or ethylene group, which methylene or ethylene group is connected to the rest of the molecule.

In the instance, the $C_3$-$C_4$cycloalkyl-$C_1$-$C_2$alkyl- group is substituted, the substituent(s) can be on the cycloalkyl group and/or on the alkyl group.

The term "$C_3$-$C_6$cycloalkyl$C_1$-$C_4$haloalkoxy" as used herein refers to a 3 to 6 membered cycloalkyl group connected to a 1 to 4 membered haloalkoxy, which haloalkoxy group is connected to the rest of the molecule.

The term "aminocarbonyl$C_1$-$C_n$alkyl" as used herein refers to an alkyl radical where one of the hydrogen atoms in the radical is replaced by CONH2 group.

The term "hydroxycarbonyl$C_1$-$C_n$alkyl" as used herein refers to an alkyl radical where one of the hydrogen atoms in the radical is replaced by COOH group.

The term "$C_1$-$C_n$alkylsulfanyl" as used herein refers to a $C_1$-$C_n$alkyl moiety linked through a sulfur atom. Similarly, the term "$C_1$-$C_n$haloalkylthio" or "$C_1$-$C_n$haloalkylsulfanyl" as used herein refers to a $C_1$-$C_n$haloalkyl moiety linked through a sulfur atom. Similarly, the term "$C_3$-$C_n$cycloalkylsulfanyl" refers to 3-n membered cycloalkyl moiety linked through a sulfur atom.

The term "$C_1$-$C_n$alkylsulfinyl" as used herein refers to a $C_1$-$C_n$alkyl moiety linked through the sulfur atom of the S(═O) group. Similarly, the term "$C_1$-$C_n$haloalkylsulfinyl" or "$C_1$-$C_n$haloalkylsulfinyl" as used herein refers to a $C_1$-$C_n$-haloalkyl moiety linked through the sulfur atom of the S(═O) group. Similarly, the term "$C_3$-$C_n$cycloalkylsulfinyl" refers to 3-n membered cycloalkyl moiety linked through the sulfur atom of the S(═O) group.

The term "$C_1$-$C_n$alkylsulfonyl" as used herein refers to a $C_1$-$C_n$alkyl moiety linked through the sulfur atom of the $S(=O)_2$ group. Similarly, the term "$C_1$-$C_n$haloalkylsulfonyl" or "$C_1$-$C_n$haloalkylsulfonyl" as used herein refers to a $C_1$-$C_n$haloalkyl moiety linked through the sulfur atom of the $S(=O)_2$ group. Similarly, the term "$C_3$-$C_n$cycloalkylsulfonyl" refers to 3-n membered cycloalkyl moiety linked through the sulfur atom of the $S(=O)_2$ group The term "trimethylsilane$C_1$-$C_n$alkyl" as used herein refers to an alkyl radical where one of the hydrogen atoms in the radical is replaced by a —$Si(CH_3)_3$group.

The term "$C_2$-$C_n$alkenyl" as used herein refers to a straight or branched alkenyl chain having from two to n carbon atoms and one or two double bonds, for example, ethenyl, prop-1-enyl, but-2-enyl.

The term "$C_2$-$C_n$haloalkenyl" as used herein refers to a $C_2$-$C_n$alkenyl moiety substituted with one or more halo atoms which may be the same or different.

The term "$C_2$-$C_n$alkynyl" as used herein refers to a straight or branched alkynyl chain having from two to n carbon atoms and one triple bond, for example, ethynyl, prop-2-ynyl, but-3-ynyl.

The term "$C_2$-$C_n$haloalkynyl" as used herein refers to a $C_2$-$C_n$alkynyl moiety substituted with one or more halo atoms which may be the same or different.

Halogen or "halo" is generally fluorine, chlorine, bromine or iodine. This also applies, correspondingly, to halogen in combination with other meanings, such as haloalkyl The term "heteroaryl" as used herein refers to a 5- or 6-membered aromatic monocyclic ring having 1 to 3 heteroatoms independently selected from N, O and S. Examples are heteroaryls J-1 to J-41 shown in Scheme A below. Preferred heteroaryl is pyridyl, pyrimidyl, and pyrazolyl.

Scheme A: Heteroaryl J-1 to J-41

J-1

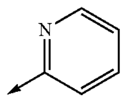

J-2

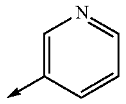

J-3

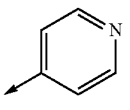

J-4

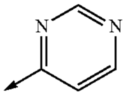

J-5

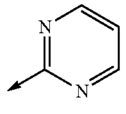

J-6

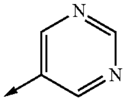

J-7

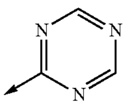

-continued
J-8
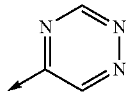
J-9
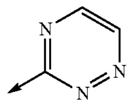
J-10
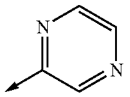
J-11
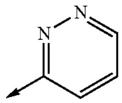
J-12
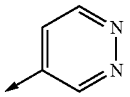
J-13
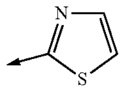
J-14
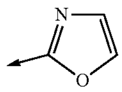
J-15
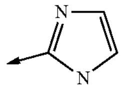
J-16
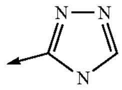
J-17
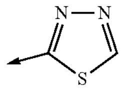
J-18
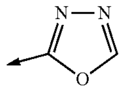
J-19
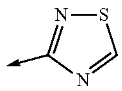
J-20
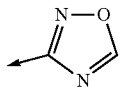
J-21
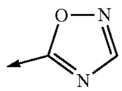
J-22
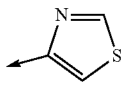
-continued
J-23
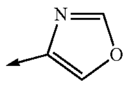
J-24
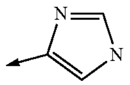
J-25
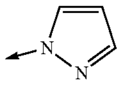
J-26
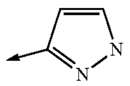
J-27
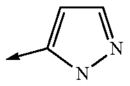
J-28
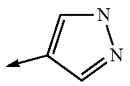
J-29
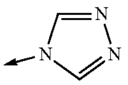
J-30
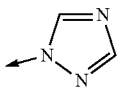
J-31
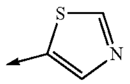
J-32
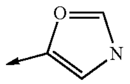
J-33
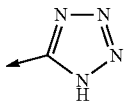
J-34
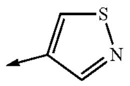
J-35
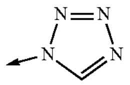
J-36
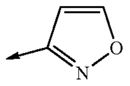
J-37
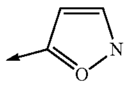
J-38
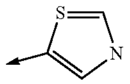

-continued

J-39

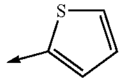

J-40

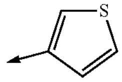

J-41

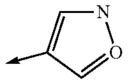

The pyridine, pyrimidine, pyrazine and pyridazine groups (unsubstituted or substituted) for $R_4$ and $R_{4a}$ are each connected via a carbon atom on the respective ring to the rest of the compound.

As used herein, the term "controlling" refers to reducing the number of pests, eliminating pests and/or preventing further pest damage such that damage to a plant or to a plant derived product is reduced.

The staggered line as used herein, for example, in $Q^a$-1 and $Q^b$-1, represent the point of connection/attachment to the rest of the compound.

As used herein, the term "pest" refers to insects, and molluscs that are found in agriculture, horticulture, forestry, the storage of products of vegetable origin (such as fruit, grain and timber); and those pests associated with the damage of man-made structures. The term pest encompasses all stages in the life cycle of the pest.

As used herein, the term "effective amount" refers to the amount of the compound, or a salt thereof, which, upon single or multiple applications provides the desired effect.

An effective amount is readily determined by the skilled person in the art, by the use of known techniques and by observing results obtained under analogous circumstances. In determining the effective amount a number of factors are considered including, but not limited to: the type of plant or derived product to be applied; the pest to be controlled & its lifecycle; the particular compound applied; the type of application; and other relevant circumstances.

As one of ordinary skill in the art will appreciate, compounds of formula I contain a stereogenic centre which is indicated with an asterisk in the structure below:

I*

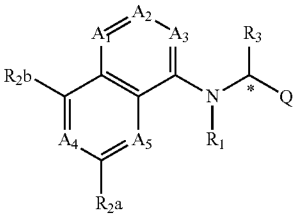

where $R_1$, $R_{2a}$, $R_{2b}$, $R_3$, Q, $A_1$, $A_2$, $A_3$, $A_4$, and $A_5$ are as defined in the first aspect.

The present invention contemplates both racemates and individual enantiomers. Compounds having preferred stereochemistry are set out below.

I'a

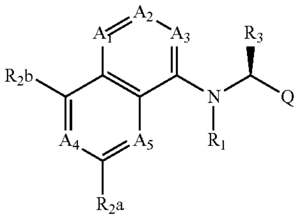

Particularly preferred compounds of the present invention are compounds of formula I'a:

where $R_1$, $R_{2a}$, $R_{2b}$, $R_3$, Q, $A_1$, $A_2$, $A_3$, $A_4$, and $A_5$ are as defined in the first aspect, and stereoisomers, enantiomers, tautomers and N-oxides of the compounds of formula (I'a), and agrochemically acceptable salts thereof.

The term "optionally substituted" as used herein means that the group referenced is either unsubstituted or is substituted by a designated substituent, for example, "$C_3$-$C_4$cycloalkyl is optionally substituted with 1 or 2 halo atoms" means $C_3$-$C_4$cycloalkyl, $C_3$-$C_4$cycloalkyl substituted with 1 halo atom and $C_3$-$C_4$cycloalkyl substituted with 2 halo atoms.

Embodiments according to the invention are provided as set out below.

In an embodiment of each aspect of the invention,

A. X is oxygen; or

B. X is sulfur.

In an embodiment of each aspect of the invention, in the instance X is oxygen, R is not hydrogen.

In an embodiment of each aspect of the invention,

A. $A_1$, $A_2$ and $A_3$ are, independently from each other, N or $CR_Y$, with the proviso that no more than two out of the three are N; or B. $A_1$ and $A_3$ are N and $A_2$ is $CR_Y$; or C. $A_1$, $A_2$ and $A_3$ are, independently from each other, N or CH; or D. $A_1$, $A_2$ and $A_3$ are, independently from each other, N or CH, with the proviso that no more than two out of the three are N; or E. $A_1$ is N, and $A_2$ and $A_3$ are CH; or F. $A_1$ and $A_2$ CH, and $A_3$ is N; or G. $A_1$ and $A_3$ are N, and $A_2$ is CH; or H. $A_1$=$A_2$-$A_3$, taken together, are NR—C(=X)—N; or I. $A_1$=$A_2$-$A_3$, taken together, are NH—C(=X)—N; or J. $A_1$=$A_2$-$A_3$, taken together, are NR—C(=O)—N; or K. $A_1$=$A_2$-$A_3$, taken together, are NH—C(=O)—N; or L. $A_1$=$A_2$-$A_3$, taken together, are NR—C(=S)—N; or M. $A_1$=$A_2$-$A_3$, taken together, are NH—C(=S)—N.

In an embodiment of each aspect of the invention,

A. $A_4$ is $CR_{YY}$, and $A_5$ is N; or

B. $A_4$ is $CR_Y$, and $A_5$ is CH; or

C. $A_4$ is CH, and $A_5$ is N; or

D. $A_4$ is N, and $A_5$ is CH; or

E. $A_4$ and $A_5$ are both CH.

In an embodiment of each aspect of the invention,

A. $A_1$ is N, $A_2$ and $A_3$ are CH, and $A_4$ and A5 are both CH; or

B. $A_1$ and $A_2$ are CH, $A_3$ is N, and $A_4$ and $A_5$ are both CH.

C. $A_1$ and $A_3$ are N, $A_2$ is CH, and $A_4$ is $CR_Y$ and $A_5$ is CH; or

D. $A_1$ and $A_3$ are N, $A_2$ is CH, and $A_4$ is CH and $A_5$ is N; or

E. $A_1$ and $A_3$ are N, $A_2$ is CH, and $A_4$ is N and $A_5$ is CH; or

F. $A_1$ and $A_3$ are N, $A_2$ is CH, and $A_4$ is N or CH and $A_5$ is CH; or

G. $A_1$ and $A_3$ are N, $A_2$ is CH, and $A_4$ is CH and $A_5$ is N or CH; or

H. $A_1$ and $A_3$ are N, $A_2$ is CH, and $A_4$ and $A_5$ are both N; or

I. $A_1$ and $A_3$ are N, $A_2$ is CH, and $A_4$ and $A_5$ are both CH; or

J. $A_1$=$A_2$-$A_3$, taken together, are NH—C(═O)—N and $A_4$ and $A_5$ are both CH.

In an embodiment of each aspect of the invention, R is

A. hydrogen, methyl, ethyl, difluoroethyl or trifluoroethyl; or

B. hydrogen; methyl, ethyl, 2,2-difluoroethyl or 2,2,2,-trifluoroethyl or

C. hydrogen; or

D. methyl, or 2,2,2,-trifluoroethyl; or

E. methyl; or

F. hydrogen, or methyl.

In an embodiment of each aspect of the invention, $R_1$ is

A. hydrogen, $C_1$-$C_6$alkyl, $C_1$-$C_6$cyanoalkyl, aminocarbonyl$C_1$-$C_6$alkyl, hydroxycarbonyl$C_1$-$C_6$alkyl, $C_1$-$C_6$nitroalkyl, trimethylsilane$C_1$-$C_6$alkyl, $C_1$-$C_3$alkoxy-$C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_3$-$C_4$cycloalkyl$C_1$-$C_2$alkyl-, $C_3$-$C_4$cycloalkyl$C_1$-$C_2$alkyl- wherein the $C_3$-$C_4$cycloalkyl group is substituted with 1 or 2 halogen atoms, oxetan-3-yl-$CH_2$—, $C_1$-$C_3$alkylcarbonyl, $C_1$-$C_3$alkoxycarbonyl, phenyloxycarbonyl, benzyloxycarbonyl, or benzyl; or B. hydrogen, $C_1$-$C_6$alkyl, $C_1$-$C_6$cyanoalkyl, aminocarbonyl$C_1$-$C_6$alkyl, hydroxycarbonyl$C_1$-$C_6$alkyl, $C_1$-$C_6$nitroalkyl, trimethylsilane$C_1$-$C_6$alkyl, $C_1$-$C_3$alkoxy-$C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_3$-$C_4$cycloalkyl$C_1$-$C_2$alkyl-, benzyloxycarbonyl, or benzyl; or C. hydrogen, $C_1$-$C_6$alkyl, $C_1$-$C_6$cyanoalkyl, aminocarbonyl$C_1$-$C_6$alkyl, hydroxycarbonyl$C_1$-$C_6$alkyl, $C_1$-$C_3$alkoxy-$C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_3$-$C_4$cycloalkyl$C_1$-$C_2$alkyl-, benzyloxycarbonyl, or benzyl; or D. hydrogen, $C_1$-$C_6$alkyl, $C_1$-$C_6$cyanoalkyl, $C_1$-$C_3$alkoxy-$C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_3$-$C_4$cycloalkyl$C_1$-$C_2$alkyl-, benzyloxycarbonyl, or benzyl; or E. hydrogen, $C_1$-$C_3$alkyl, $C_1$-$C_3$cyanoalkyl, $C_1$-$C_3$alkoxy-$C_1$-$C_3$alkyl, $C_1$-$C_3$haloalkyl, $C_2$-$C_4$alkenyl, $C_2$-$C_4$haloalkenyl, $C_2$-$C_4$alkynyl, $C_2$-$C_4$haloalkynyl, $C_3$-$C_4$cycloalkyl$C_1$-$C_2$alkyl-, benzyloxycarbonyl, or benzyl; or F. hydrogen, $C_1$-$C_3$alkyl, $C_1$-$C_3$cyanoalkyl, $C_1$-$C_3$alkoxy-$C_1$-$C_3$alkyl, $C_1$-$C_3$haloalkyl, $C_2$-$C_4$alkenyl, $C_2$-$C_4$haloalkenyl, $C_2$-$C_4$alkynyl, $C_2$-$C_4$haloalkynyl, $C_3$-$C_4$cycloalkyl$C_1$-$C_2$alkyl-, benzyloxycarbonyl, or benzyl; or G. hydrogen, methyl, ethyl, cyanomethyl, methoxymethyl, cyclopropyl-methyl, allyl, propargyl, benzyloxycarbonyl, or benzyl; or H. hydrogen, methyl, ethyl, allyl, propargyl or cyclopropyl-methyl; or I. hydrogen, methyl, propargyl or cyclopropyl-methyl;

In an embodiment of each aspect of the invention, $R_{2a}$ is

A. hydrogen, halogen, $C_1$-$C_3$alkyl, $C_1$-$C_3$haloalkyl, $C_1$-$C_3$alkoxy, $C_1$-$C_3$haloalkoxy, CN, $C_3$-$C_4$cycloalkyl, $C_3$-$C_6$cycloalkylcarbonyl, phenyl, heteroaryl selected from J-1 and J-41, each of $C_3$-$C_4$cycloalkyl, phenyl or heteroaryl, independent of each other, is substituted with one to three substituents $R_x$, $OR_6$, piperidin-2-one-1-yl, pyridin-2-one-1-yl, azetidin-1-yl optionally substituted with $R_x$, pyrrolidin-1-yl, $C_3$-$C_6$cycloalkyl$C_1$-$C_4$alkyl substituted with one or two substituents $R_Z$, $C_3$-$C_6$cycloalkyl$C_1$-$C_3$alkoxy optionally substituted with $R_x$, $C_1$-$C_5$cyanoalkyl, $C_1$-$C_5$cyanoalkoxy, $C_1$-$C_4$alkylsulfanyl optionally substituted by one to three substituents $R_x$, $C_1$-$C_4$alkylsulfonyl optionally substituted by one to three substituents $R_x$, or $C_1$-$C_4$alkylsulfinyl optionally substituted by one to three substituents $R_x$; or B. hydrogen, halogen, $C_1$-$C_3$alkyl, $C_1$-$C_3$haloalkyl, $C_1$-$C_3$alkoxy, $C_1$-$C_3$haloalkoxy, CN, $C_3$-$C_4$cycloalkyl, $C_3$-$C_6$cycloalkylcarbonyl, phenyl, pyrazolyl, each of $C_3$-$C_4$cycloalkyl, phenyl, pyrazolyl, independent of each other, is substituted with one to three substituents $R_x$, $OR_6$, piperidin-2-one-1-yl, pyridin-2-one-1-yl, azetidin-1-yl optionally substituted with $R_x$, pyrrolidin-1-yl, $C_3$-$C_6$cycloalkyl$C_1$-$C_4$alkyl optionally substituted with one or two substituents $R_Z$, $C_3$-$C_6$cycloalkyl$C_1$-$C_3$alkoxy optionally substituted with $R_x$, $C_1$-$C_5$cyanoalkyl, $C_1$-$C_5$cyanoalkoxy, $C_1$-$C_4$alkylsulfanyl optionally substituted by one to three substituents $R_x$, $C_1$-$C_4$alkylsulfonyl optionally substituted by one to three substituents $R_x$, or $C_1$-$C_4$alkylsulfinyl optionally substituted by one to three substituents $R_x$; or C. hydrogen, halogen, $C_1$-$C_3$alkyl, $C_1$-$C_3$haloalkyl, $C_1$-$C_3$alkoxy, $C_1$-$C_3$haloalkoxy, CN, $C_3$-$C_4$cycloalkyl, $C_3$-$C_6$cycloalkylcarbonyl, phenyl or pyrazolyl, each of $C_3$-$C_4$cycloalkyl, phenyl, pyrazolyl, independent of each other, is substituted with one to two substituents $R_x$, $OR_6$, azetidin-1-yl optionally substituted with $R_x$, $C_3$-$C_6$cycloalkyl$C_1$-$C_4$alkyl optionally substituted with one or two substituents $R_Z$, $C_3$-$C_6$cycloalkyl$C_1$-$C_3$alkoxy optionally substituted with $R_x$, $C_1$-$C_4$alkylsulfanyl optionally substituted by one to three substituents $R_x$, $C_1$-$C_4$alkylsulfonyl optionally substituted by one to three substituents $R_x$, or $C_1$-$C_4$alkylsulfinyl optionally substituted by one to three substituents $R_x$; or D. hydrogen, halogen, $C_1$-$C_3$alkyl, $C_1$-$C_3$haloalkyl, $C_1$-$C_3$alkoxy, $C_1$-$C_3$haloalkoxy, CN, $C_3$-$C_4$cycloalkyl, $C_3$-$C_4$cycloalkyl substituted with one to two substituents $R_x$, $C_3$-$C_6$cycloalkylcarbonyl, $OR_6$, $C_3$-$C_6$cycloalkyl$C_1$-$C_4$alkyl, $C_3$-$C_6$cycloalkyl$C_1$-$C_4$alkyl substituted with one or two substituents $R_Z$, $C_1$-$C_4$alkylsulfanyl, $C_1$-$C_4$alkylsulfanyl substituted by one to three substituents $R_x$, $C_1$-$C_4$alkylsulfonyl, $C_1$-$C_4$alkylsulfonyl substituted by one to three substituents $R_x$, $C_1$-$C_4$alkylsulfinyl, or $C_1$-$C_4$alkylsulfinyl substituted by one to three substituents $R_x$; or E. hydrogen, halogen, $C_1$-$C_3$alkyl, $C_1$-$C_3$haloalkyl, $C_1$-$C_3$alkoxy, $C_1$-$C_3$haloalkoxy, CN, $C_3$-$C_4$cycloalkyl, $C_3$-$C_4$cycloalkyl substituted with one to two substituents independently selected from halogen, $C_1$-$C_3$alkyl and $C_1$-$C_3$haloalkyl, $C_3$-$C_4$cycloalkylcarbonyl, $C_3$-$C_4$cycloalkylmethyl, $C_3$-$C_4$cycloalkylmethyl substituted with one to two substituents independently selected from oxo, halogen, $C_1$-$C_3$alkyl, and $C_1$-$C_3$haloalkyl, $C_1$-$C_2$alkylsulfanyl substituted with one to three halogens or $C_1$-$C_2$alkylsulfonyl substituted with one to three halogens; or F. hydrogen, halogen, $C_1$-$C_3$alkyl, $C_1$-$C_3$haloalkyl, $C_1$-$C_3$alkoxy, $C_1$-$C_3$haloalkoxy, cyclopropyl, cyclopropyl substituted with one to two substituents independently selected from halogen, methyl, and trifluoromethyl, cyclopropylcarbonyl, cyclopropylmethyl substituted with one to two substituents independently selected from oxo, halogen, and trifluoromethyl, or $C_1$-$C_2$alkylsulfanyl substituted with one to three halogens or $C_1$-$C_2$alkylsulfonyl substituted with one to three halogens; or G. hydrogen, halogen, $C_1$-$C_3$alkyl, $C_1$-$C_3$haloalkyl, $C_1$-$C_3$haloalkylsulfanyl, $C_1$-$C_3$alkoxy, $C_1$-$C_3$haloalkoxy, CN, $C_3$-$C_6$cycloalkyl, $C_3$-$C_6$cycloalkyl substituted with one to three substituents independently selected from $C_1$-$C_3$alkyl, $C_1$-$C_3$haloalkyl, cyano, and halogen, cyclopropylcarbonyl, $C_3$-$C_6$cycloalkyl$C_1$-$C_4$alkyl, $C_3$-$C_6$cycloalkyl$C_1$-$C_4$alkyl substituted with one to five substituents independently selected from oxo, $C_1$-$C_3$alkyl, $C_1$-$C_3$haloalkyl, cyano, and halogen, $C_1$-$C_5$cyanoalkyl, $C_1$-$C_4$alkylsulfonyl, $C_1$-$C_4$haloalkylsulfonyl, $C_1$-$C_4$alkylsulfinyl, $C_1$-$C_4$haloalkylsulfinyl, $C_3$-$C_6$cycloalkylsulfanyl, $C_3$-$C_6$cycloalkylsulfinyl, or $C_3$-$C_6$cycloalkylsulfonyl; or H. hydrogen, halogen, $C_1$-$C_3$alkyl, $C_1$-$C_3$haloalkyl, $C_1$-$C_3$haloalkylsulfanyl, $C_1$-$C_3$alkoxy, $C_1$-$C_3$haloalkoxy, CN, $C_3$-$C_6$cycloalkyl, $C_3$-$C_6$cycloalkyl substituted with one or two substituents independently selected from $C_1$-$C_3$haloalkyl, cyano, and halogen, $C_3$-$C_4$cycloalkylcarbonyl, $C_3$-$C_6$cycloalkyl$C_1$-$C_4$alkyl, $C_3$-$C_6$cycloalkyl$C_1$-$C_4$alkyl substituted with one to three substituents independently selected from oxo, $C_1$-$C_3$haloalkyl, cyano, and halogen, $C_1$-$C_5$cyanoalkyl, $C_1$-$C_4$alkylsulfonyl, $C_1$-$C_4$haloalkylsulfonyl, $C_1$-$C_4$alkylsulfinyl, $C_1$-$C_4$haloalkylsulfinyl, $C_3$-$C_6$cycloalkylsulfanyl, $C_3$-$C_6$cycloalkylsulfinyl, or $C_3$-$C_6$cycloalkylsulfonyl; or I. hydrogen, halogen, $C_1$-$C_3$haloalkyl, $C_1$-$C_3$haloalkylsulfanyl, $C_1$-$C_3$haloalkoxy, $C_3$-$C_6$cycloalkyl, $C_3$-$C_6$cycloalkyl substituted with one or two substituents independently selected from $C_1$-$C_3$haloalkyl, cyano, and halogen, $C_3$-$C_4$cycloalkylcarbonyl, $C_3$-$C_6$cycloalkyl$C_1$-$C_4$alkyl, $C_3$-$C_6$cycloalkyl$C_1$-$C_4$alkyl substituted with one to three substituents independently selected from oxo, $C_1$-$C_3$haloalkyl, cyano, and halogen, $C_1$-$C_5$cyanoalkyl, $C_1$-$C_4$alkylsulfonyl, $C_1$-$C_4$haloalkylsulfonyl, $C_1$-$C_4$alkylsulfinyl, $C_1$-$C_4$haloalkylsulfinyl, $C_3$-$C_6$cycloalkylsulfanyl, $C_3$-$C_6$cycloalkylsulfinyl, or $C_3$-$C_6$cycloalkylsulfonyl; or J. hydrogen, halogen, $C_3$-$C_4$cycloalkyl, $C_3$-$C_4$cycloalkylcarbonyl, $C_3$-$C_4$cycloalkyl-$C_1$-$C_2$alkyl optionally substituted with one to two substituents selected from oxo, halogen, $C_1$-$C_3$alkyl and $C_1$-$C_3$haloalkyl, $C_1$-$C_3$haloalkyl, $C_1$-$C_3$haloalkylsulfanyl, $C_1$-$C_3$haloalkysulfonyl, $C_1$-$C_3$alkoxy, $C_1$-$C_3$haloalkoxy, or CN; or K. halogen, $C_1$-$C_3$haloalkyl, $C_1$-$C_3$haloalkylsulfanyl, $C_1$-$C_3$haloalkysulfonyl, or $C_1$-$C_3$haloalkoxy; or L. halogen, $C_1$-$C_2$haloalkyl, $C_1$-$C_2$haloalkylsulfanyl, $C_1$-$C_2$haloalkysulfonyl, or $C_1$-$C_2$haloalkoxy; or M. chlorine, fluorine, bromine, iodine, difluoromethyl, trifluoromethyl, trifluoromethylsulfanyl or trifluoromethylsulfonyl; or N. fluorine, chlorine, bromine, iodine, trifluoromethylsulfanyl, trifluoromethylsulfonyl or trifluoromethyl; or O. trifluoromethyl, fluorine, bromine, trifluoromethylsulfonyl or chlorine; or P. trifluoromethyl, bromine, or chlorine.

In an embodiment of each aspect of the invention, $R_{2b}$ is

A. hydrogen, halogen, $C_1$-$C_3$alkyl, $C_1$-$C_3$haloalkyl, $C_3$-$C_4$cycloalkyl, cyclopropylcarbonyl, $C_3$-$C_6$cycloalkyl$C_1$-$C_4$alkyl optionally substituted with one or two substituents $R_Z$, $C_1$-$C_3$alkoxy, $C_1$-$C_3$haloalkoxy, or CN, $C_1$-$C_4$alkylsulfanyl optionally substituted by one to three substituents $R_x$, $C_1$-$C_4$alkylsulfonyl optionally substituted by one to three substituents $R_x$, or $C_1$-$C_4$alkylsulfinyl optionally substituted by one to three substituents $R_x$; or B. hydrogen, halogen, $C_3$-$C_4$cycloalkyl, cyclopropylcarbonyl, $C_3$-$C_4$cycloalkyl-$C_1$-$C_2$alkyl optionally substituted with one to two substituents selected from oxo, halogen, $C_1$-$C_3$alkyl and $C_1$-$C_3$haloalkyl, $C_1$-$C_3$haloalkyl, $C_1$-$C_3$haloalkysulfanyl, $C_1$-$C_3$haloalkysulfonyl, $C_1$-$C_3$alkoxy, $C_1$-$C_3$haloalkoxy, or CN; or C. halogen, $C_1$-$C_3$haloalkyl, $C_1$-$C_3$haloalkylsulfanyl, $C_1$-$C_3$haloalkysulfonyl, or $C_1$-$C_3$haloalkoxy; or D. halogen, $C_1$-$C_2$haloalkyl, $C_1$-$C_2$haloalkylsulfanyl, $C_1$-$C_2$haloalkysulfonyl, or $C_1$-$C_2$haloalkoxy; or E. chlorine, fluorine, bromine, iodine, difluoromethyl, trifluoromethyl, trifluoromethylsulfanyl, trifluoromethylsulfonyl; or F. fluorine, chlorine, bromine, iodine, trifluoromethylsulfanyl, trifluoromethylsulfonyl or trifluoromethyl; or G. trifluoromethyl, fluorine, bromine or chlorine; or H. trifluoromethyl or chlorine.

In an embodiment of each aspect of the invention, $R_3$ is

A. $C_1$-$C_3$alkyl or $C_1$-$C_3$haloalkyl; or

B. methyl or trifluoromethyl; or

C. methyl.

In an embodiment of each aspect of the invention, Q is

A. $Q^a$; or

B. $Q^b$.

In an embodiment of each aspect of the invention, $Q^a$ is

A. selected from $Q^a$-1 to $Q^a$-11 and $Q^a$-13 to $Q^a$-16; or

B. selected from $Q^a$1, $Q^a$-6, $Q^a$-7, $Q^a$-10, and $Q^a$-15; or

C. $Q^a$-1 or $Q^a$-15.

$Q^a$-1

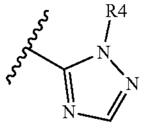

$Q^a$-2

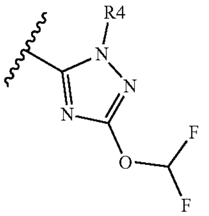

-continued
$Q^a$-3
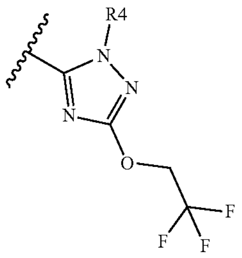
$Q^a$-4
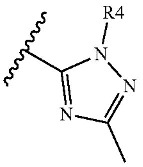
$Q^a$-5
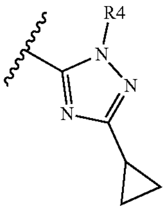
$Q^a$-6
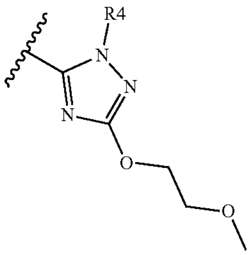
$Q^a$-7
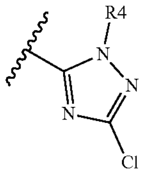
$Q^a$-8
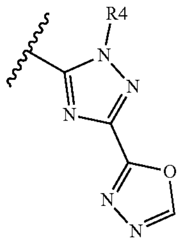
$Q^a$-9
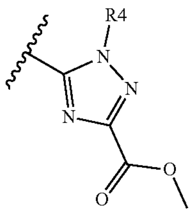
-continued
$Q^a$-10
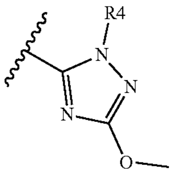
$Q^a$-11
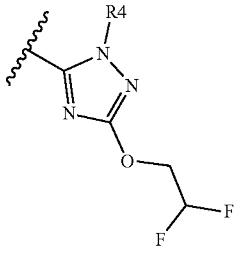
$Q^a$-13
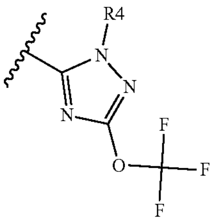
$Q^a$-14
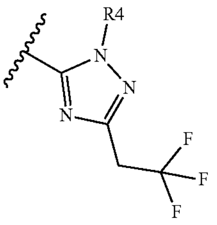
$Q^a$-15
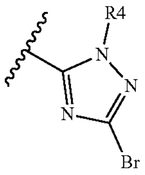
$Q^a$-16
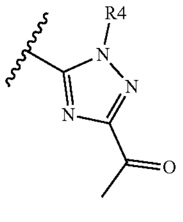
In an embodiment of each aspect of the invention, $Q^b$ is
A. selected from $Q^b$-1 to $Q^b$-13; or
B. $Q^b$-1.
$Q^b$-1
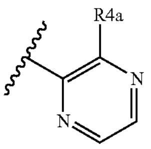

-continued $Q^b$-2

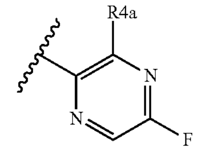

$Q^b$-3

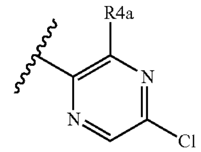

$Q^b$-4

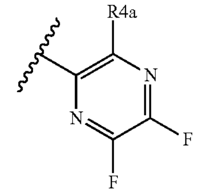

$Q^b$-5

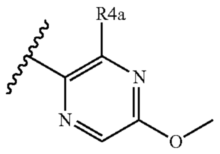

$Q^b$-6

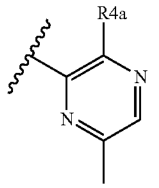

$Q^b$-7

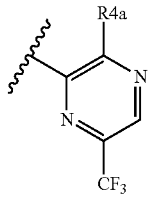

$Q^b$-8

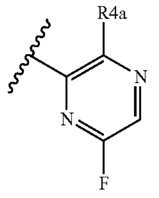

$Q^b$-9

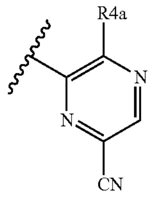

-continued $Q^b$-10

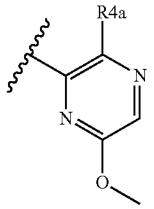

$Q^b$-11

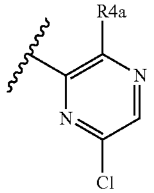

$Q^b$-12

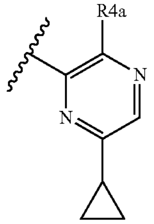

$Q^b$-13

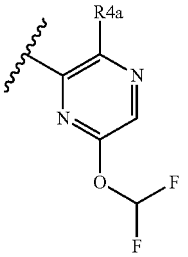

In an embodiment of each aspect of the invention, $R_4$ is

A. thiazol-2-yl, thiazol-4-yl, thiazol-5-yl, 1,2,4-thiadiazol-3-yl, 1,3,4-thiadiazol-2-yl or 1,2,4-thiadiazol-5-yl, each of which, independently of each other, is unsubstituted or substituted with one to two substituents independently selected from $C_1$-$C_3$alkyl, $C_1$-$C_3$haloalkyl, $C_1$-$C_3$alkoxy, $C_3$-$C_4$cycloalkyl, halo, hydroxyl, CN, $C_1$-$C_6$haloalkoxy, $C_2$-$C_6$haloalkenyloxy, $C_2$-$C_6$haloalkynyloxy, $C_3$-$C_4$halocycloalkoxy, $NH_2C(O)$—, $NH_2C(S)$—, $(OH)N{=}C(NH_2)$— and a 5-membered heteroaryl ring optionally substituted by 1 to 3 substituents independently selected from halogen, $C_1$-$C_3$alkyl, $C_1$-$C_3$haloalkyl, $C_1$-$C_3$alkoxy and $C_1$-$C_3$haloalkoxy; or B. 1,2,4-thiadiazol-3-yl, 1,3,4-thiadiazol-2-yl or 1,2,4-thiadiazol-5-yl, each of which, independently of each other, is unsubstituted or substituted with one to two substituents independently selected from $C_1$-$C_3$alkyl, $C_1$-$C_3$haloalkyl, $C_1$-$C_3$alkoxy, $C_3$-$C_4$cycloalkyl, halo, hydroxyl, CN, $C_1$-$C_6$haloalkoxy, $C_2$-$C_6$haloalkenyloxy, $C_2$-$C_6$haloalkynyloxy, $C_3$-$C_4$halocycloalkoxy, $NH_2C(O)$—, $NH_2C(S)$—, $(OH)N{=}C(NH_2)$— and a 5-membered heteroaryl ring optionally substituted by 1 to 3 substituents independently selected from halogen, $C_1$-$C_3$alkyl, $C_1$-$C_3$haloalkyl, $C_1$-$C_3$alkoxy and $C_1$-$C_3$haloalkoxy; or C. thiazol-2-yl, thiazol-4-yl or thiazol-5-yl, each of which, independently of each other, is unsubstituted or substituted with one to two substituents independently selected from $C_1$-$C_3$alkyl, $C_1$-$C_3$haloalkyl, $C_1$-$C_3$alkoxy, $C_3$-$C_4$cycloalkyl, halo, hydroxyl, CN, $C_1$-$C_6$haloalkoxy, $C_2$-$C_6$haloalkenyloxy, $C_2$-$C_6$haloalkynyloxy, $C_3$-$C_4$halocycloalkoxy, $NH_2C(O)$—, $NH_2C(S)$—, $(OH)N{=}C(NH_2)$— and a 5-membered heteroaryl ring optionally substituted by 1 to 3 substituents independently selected from halogen, $C_1$-$C_3$alkyl, $C_1$-$C_3$haloalkyl, $C_1$-$C_3$alkoxy and $C_1$-$C_3$haloalkoxy; or D. thiazol-2-yl or thiazol-4-yl, each of which, independently of each other, is unsubstituted or substituted with one to two substituents independently selected from $C_1$-$C_3$alkyl, $C_1$-$C_3$haloalkyl, $C_1$-$C_3$alkoxy, $C_3$-$C_4$cycloalkyl, halo, hydroxyl, CN, $C_1$-$C_6$haloalkoxy, $C_2$-$C_6$haloalkenyloxy, $C_2$-$C_6$haloalkynyloxy, $C_3$-$C_4$halocycloalkoxy, $NH_2C(O)$—, $NH_2C(S)$—, $(OH)N{=}C(NH_2)$— and a 5-membered heteroaryl ring optionally substituted by 1 to 3 substituents independently selected from halogen, $C_1$-$C_3$alkyl, $C_1$-$C_3$haloalkyl, $C_1$-$C_3$alkoxy and $C_1$-$C_3$haloalkoxy; or E. thiazol-2-yl; which is unsubstituted or substituted with one to two substituents independently selected from $C_1$-$C_3$alkyl, $C_1$-$C_3$haloalkyl, $C_1$-$C_3$alkoxy, $C_3$-$C_4$cycloalkyl, halo, hydroxyl, CN, $C_1$-$C_6$haloalkoxy, $C_2$-$C_6$haloalkenyloxy, $C_2$-$C_6$haloalkynyloxy, $C_3$-$C_4$halocycloalkoxy, $NH_2C(O)$—, $NH_2C(S)$—, $(OH)N{=}C(NH_2)$— and a 5-membered heteroaryl ring optionally substituted by 1 to 3 substituents independently selected from halogen, $C_1$-$C_3$alkyl, $C_1$-$C_3$haloalkyl, $C_1$-$C_3$alkoxy and $C_1$-$C_3$haloalkoxy; or F. thiazol-2-yl, thiazol-4-yl, thiazol-5-yl, isothiazol-3-yl, isothiazol-4-yl, isothiazol-5-yl, 1,2,4-thiadiazol-3-yl, 1,3,4-thiadiazol-2-yl or 1,2,4-thiadiazol-5-yl, each of which, independently of each other, is unsubstituted or substituted with one to two substituents independently selected from $C_1$-$C_3$alkyl, $C_1$-$C_3$haloalkyl, $C_1$-$C_3$alkoxy, $C_3$-$C_4$cycloalkyl, halo, hydroxyl, CN, $C_1$-$C_6$haloalkoxy, $C_2$-$C_6$haloalkenyloxy, $C_2$-$C_6$haloalkynyloxy and $C_3$-$C_4$halocycloalkoxy; or G. thiazol-2-yl, thiazol-4-yl, thiazol-5-yl, isothiazol-3-yl, isothiazol-4-yl, isothiazol-5-yl, 1,2,4-thiadiazol-3-yl, 1,3,4-thiadiazol-2-yl or 1,2,4-thiadiazol-5-yl each of which, independently of each other, is unsubstituted or substituted with one to two substituents independently selected from $C_1$-$C_3$haloalkyl, halo, CN and $C_1$-$C_6$haloalkoxy; or H. thiazol-2-yl, thiazol-4-yl, thiazol-5-yl, 1,2,4-thiadiazol-3-yl, 1,3,4-thiadiazol-2-yl or 1,2,4-thiadiazol-5-yl, each of which, independently of each other, is unsubstituted or substituted with one to two substituents independently selected from $C_1$-$C_3$haloalkyl, halo, CN and $C_1$-$C_6$haloalkoxy; or I. 1,2,4-thiadiazol-3-yl, 1,3,4-thiadiazol-2-yl or 1,2,4-thiadiazol-5-yl each of which, independently of each other, is unsubstituted or substituted with one to two substituents independently selected from $C_1$-$C_3$haloalkyl, halo, CN and $C_1$-$C_6$haloalkoxy; or J. thiazol-2-yl, thiazol-4-yl or thiazol-5-yl, each of which, independently of each other, is unsubstituted or substituted with one to two substituents independently selected from $C_1$-$C_3$haloalkyl, halo, CN and $C_1$-$C_6$haloalkoxy; or K. thiazol-2-yl or thiazol-4-yl, each of which, independently of each other, is unsubstituted or substituted with one to two substituents independently selected from $C_1$-$C_3$haloalkyl, halo, CN and $C_1$-$C_6$haloalkoxy; or L. thiazol-2-yl, which is unsubstituted or substituted with one to two substituents independently selected from $C_1$-$C_3$haloalkyl, halo, CN and $C_1$-$C_6$haloalkoxy; or M. thiazol-2-yl, which is unsubstituted or substituted with one substituent selected from $C_1$-$C_3$haloalkyl, chloro, bromo, CN and $C_1$-$C_6$haloalkoxy; or N. thiazol-2-yl, which is substituted with one substituent selected from chloro, bromo, and CN.

In an embodiment of each aspect of the invention, $R_{4a}$ is

A. thiazol-2-yl, thiazol-4-yl, thiazol-5-yl, 1,2,4-thiadiazol-3-yl, 1,3,4-thiadiazol-2-yl or 1,2,4-thiadiazol-5-yl, each of which, independently of each other, is unsubstituted or substituted with one to two substituents independently selected from $C_1$-$C_3$alkyl, $C_1$-$C_3$haloalkyl, $C_1$-$C_3$alkoxy, $C_3$-$C_4$cycloalkyl, halogen, hydroxyl, cyano, and $C_1$-$C_3$haloalkoxy; or B. 1,2,4-thiadiazol-3-yl, 1,3,4-thiadiazol-2-yl or 1,2,4-thiadiazol-5-yl, each of which, independently of each other, is unsubstituted or substituted with one to two substituents independently selected from $C_1$-$C_3$alkyl, $C_1$-$C_3$haloalkyl, $C_1$-$C_3$alkoxy, $C_3$-$C_4$cycloalkyl, halogen, hydroxyl, cyano, and $C_1$-$C_3$haloalkoxy; or C. thiazol-2-yl, thiazol-4-yl or thiazol-5-yl, each of which, independently of each other, is unsubstituted or substituted with one to two substituents independently selected from $C_1$-$C_3$alkyl, $C_1$-$C_3$haloalkyl, $C_1$-$C_3$alkoxy, $C_3$-$C_4$cycloalkyl, halogen, hydroxyl, cyano, and $C_1$-$C_3$haloalkoxy; or D. thiazol-2-yl or thiazol-4-yl, each of which, independently of each other, is unsubstituted or substituted with one to two substituents independently selected from $C_1$-$C_3$alkyl, $C_1$-$C_3$haloalkyl, $C_1$-$C_3$alkoxy, $C_3$-$C_4$cycloalkyl, halogen, hydroxyl, cyano, and $C_1$-$C_3$haloalkoxy; or E. thiazol-2-yl, which is unsubstituted or substituted with one to two substituents independently selected from $C_1$-$C_3$alkyl, $C_1$-$C_3$haloalkyl, $C_1$-$C_3$alkoxy, $C_3$-$C_4$cycloalkyl, halogen, hydroxyl, cyano, and $C_1$-$C_3$haloalkoxy; or F. thiazol-2-yl, thiazol-4-yl, thiazol-5-yl, isothiazol-3-yl, isothiazol-4-yl, isothiazol-5-yl, 1,2,4-thiadiazol-3-yl, 1,3,4-thiadiazol-2-yl or 1,2,4-thiadiazol-5-yl, each of which, independently of each other, is unsubstituted or substituted with one to two substituents independently selected from $C_1$-$C_3$haloalkyl, chloro, bromo, CN and $C_1$-$C_3$haloalkoxy; or G. thiazol-2-yl, thiazol-4-yl, thiazol-5-yl, 1,2,4-thiadiazol-3-yl, 1,3,4-thiadiazol-2-yl or 1,2,4-thiadiazol-5-yl, each of which, independently of each other, is unsubstituted or substituted with one to two substituents independently selected from $C_1$-$C_3$haloalkyl, chloro, bromo, CN and $C_1$-$C_3$haloalkoxy; or H. 1,2,4-thiadiazol-3-yl, 1,3,4-thiadiazol-2-yl or 1,2,4-thiadiazol-5-yl, each of which, independently of each other, is unsubstituted or substituted with one to two substituents independently selected from $C_1$-$C_3$haloalkyl, chloro, bromo, CN and $C_1$-$C_3$haloalkoxy; or I. thiazol-2-yl, thiazol-4-yl or thiazol-5-yl, each of which, independently of each other, is unsubstituted or substituted with one to two substituents independently selected from $C_1$-$C_3$haloalkyl, chloro, bromo, CN and $C_1$-$C_3$haloalkoxy; or J. thiazol-2-yl or thiazol-4-yl, each of which, independently of each other, is unsubstituted or substituted with one to two substituents independently selected from $C_1$-$C_3$haloalkyl, chloro, bromo, CN and $C_1$-$C_3$haloalkoxy; or K. thiazol-2-yl, which is unsubstituted or substituted with one to two substituents independently selected from $C_1$-$C_3$haloalkyl, chloro, bromo, CN and $C_1$-$C_3$haloalkoxy; or L. thiazol-2-yl, which is substituted with one substituent selected from $C_1$-$C_3$haloalkyl, chloro, bromo, CN and $C_1$-$C_6$haloalkoxy; or M. thiazol-2-yl, which is substituted with one substituent selected from chloro, bromo, and CN.

In an embodiment of each aspect of the invention, $R_5$ is

A. hydrogen, $C_1$-$C_3$alkyl, $C_1$-$C_3$haloalkyl, $C_3$-$C_4$cycloalkyl, $C_1$-$C_3$alkoxy, halogen, $C_1$-$C_3$alkoxy-$C_1$-$C_3$alkyl, $C_1$-$C_3$alkoxy-$C_1$-$C_3$alkoxy-$C_1$-$C_3$alkyl, ($C_1$-$C_3$alkyl)C(O), ($C_1$-$C_3$alkoxy)C(O), HC(O), $C_1$-$C_3$haloalkoxy or a 5-membered heteroaromatic ring wherein the 5-membered heteroaromatic ring can be optionally substituted with one to three substituents selected from $C_1$-$C_3$alkyl, $C_1$-$C_3$haloalkyl, $C_1$-$C_3$alkoxy, $C_3$-$C_4$cycloalkyl, halogen, CN or hydroxy; or B. hydrogen, $C_1$-$C_3$alkyl, $C_1$-$C_3$haloalkyl, $C_3$-$C_4$cycloalkyl, $C_1$-$C_3$alkoxy, halogen, $C_1$-$C_3$alkoxy-$C_1$-$C_3$alkyl, $C_1$-$C_3$alkoxy-$C_1$-$C_3$alkoxy-$C_1$-$C_3$alkyl, ($C_1$-$C_3$alkyl)C(O), ($C_1$-$C_3$alkoxy)C(O), HC(O) or $C_1$-$C_3$haloalkoxy; or C. hydrogen, $C_1$-$C_3$alkyl, $C_1$-$C_3$haloalkyl, $C_3$-$C_4$cycloalkyl, $C_1$-$C_3$alkoxy, halogen, $C_1$, Br, $C_1$-$C_3$alkoxy-$C_1$-$C_3$alkyl, $C_1$-$C_3$alkoxy-$C_1$-$C_3$alkoxy-$C_1$-$C_3$alkyl, ($C_1$-$C_3$alkyl)C(O), ($C_1$-$C_3$alkoxy)C(O), or $C_1$-$C_2$haloalkoxy; or D. hydrogen, $C_1$-$C_3$alkyl, $C_1$-$C_3$alkoxy, $C_3$-$C_4$cycloalkyl, $C_1$-$C_3$haloalkoxy, halogen, $C_1$-$C_3$alkoxy-$C_1$-$C_3$alkyl, $C_1$-$C_3$alkoxy-$C_1$-$C_3$alkoxy-$C_1$-$C_3$alkyl, ($C_1$-$C_3$alkyl)C(O), HC(O), or ($C_1$-$C_3$alkoxy)C(O); or E. hydrogen, $C_1$-$C_2$alkyl, $C_1$-$C_2$alkoxy, $C_3$-$C_4$cycloalkyl, $C_1$-$C_2$haloalkoxy, halogen, $C_1$-$C_2$alkoxy-$C_1$-$C_2$alkyl, $C_1$-$C_2$alkoxy-$C_1$-$C_2$alkoxy-$C_1$-$C_2$alkyl, ($C_1$-$C_2$alkyl)C(O), HC(O), or ($C_1$-$C_2$alkoxy)C(O); or F. hydrogen, methyl, trifluoromethoxy, methoxy, cyclopropyl, 2,2-difluroroethoxy, 2,2,2-trifluroroethoxy, difluoromethoxy, 2,2,2-trifluroroethyl, chloro, bromo, methoxyethoxy, methylcarbonyl, or methoxycarbonyl; or G. hydrogen.

In an embodiment of each aspect of the invention, $R_{5a}$ is

A. hydrogen, halogen, CN, $C_1$-$C_3$alkyl, $C_1$-$C_3$haloalkyl, $C_3$-$C_4$cycloalkyl, $C_1$-$C_3$alkoxy or $C_1$-$C_3$haloalkoxy; or B. hydrogen, halogen, CN, $C_1$-$C_3$alkyl, $C_1$-$C_3$haloalkyl, $C_3$-$C_4$cycloalkyl or $C_1$-$C_3$alkoxy; or C. hydrogen, halogen, CN, $C_1$-$C_3$alkyl, $C_1$-$C_3$haloalkyl or $C_1$-$C_3$alkoxy; or D. hydrogen, halogen, CN, $C_1$-$C_3$alkyl or $C_1$-$C_3$alkoxy; or E. hydrogen or halogen; or F. hydrogen.

In an embodiment of each aspect of the invention, $R_{5b}$ is

A. hydrogen, halogen, CN, $C_1$-$C_3$haloalkyl, $C_3$-$C_4$cycloalkyl, $C_1$-$C_3$alkoxy, or $C_1$-$C_3$haloalkoxy; or B. hydrogen, halogen or $C_1$-$C_3$alkoxy; or C. hydrogen.

In an embodiment of each aspect of the invention, $R_6$ is

A. phenyl, benzyl, heteroaryl, or $C_3$-$C_6$ cycloalkyl, each of which, independent of each other, is optionally substituted with one substituent selected from $R_x$; or B. phenyl, benzyl, cyclopropyl or cyclopropyl substituted with one substituent selected from $R_x$.

In an embodiment of each aspect of the invention, $R_x$ is independently selected from A. halogen, $C_1$-$C_3$haloalkyl, $C_1$-$C_3$alkoxy, $C_1$-$C_3$haloalkoxy or CN; or B. F, Cl, Br, $OCF_2H$, $OCH_3$ or CN.

In an embodiment of each aspect of the invention, $R_Z$ is independently selected from A. oxo, halogen, $C_1$-$C_3$haloalkyl, $C_1$-$C_3$alkoxy, $C_1$-$C_3$haloalkoxy or CN; or B. oxo, F, Cl, Br, $OCF_2H$, $OCH_3$ or CN.

In an embodiment of each aspect of the invention, $R_Y$ is independently selected from A. hydrogen, $C_1$-$C_3$ alkyl, $C_1$-$C_3$ haloalkyl, $C_1$-$C_3$ alkoxy, $C_1$-$C_3$ haloalkoxy, halogen, CN and cyclopropyl; or B. hydrogen, $C_1$-$C_3$ alkyl, $C_1$-$C_3$ haloalkyl, $C_1$-$C_3$ alkoxy, $C_1$-$C_3$ haloalkoxy, halogen, and cyclopropyl; or C. hydrogen, $C_1$-$C_3$ alkyl, $C_1$-$C_3$ haloalkyl, and $C_1$-$C_3$ alkoxy; or D. hydrogen, methyl, trifluoromethyl, and methoxy; or E. hydrogen.

In an embodiment of each aspect of the invention, $R_{YY}$ is independently selected from A. hydrogen, $C_1$-$C_3$ alkyl, $C_1$-$C_3$ haloalkyl, $C_1$-$C_3$ alkoxy, $C_1$-$C_3$ haloalkoxy, halogen, CN and cyclopropyl; or B. hydrogen, $C_1$-$C_3$ alkyl, $C_1$-$C_3$ haloalkyl, $C_1$-$C_3$ alkoxy, $C_1$-$C_3$ haloalkoxy, halogen, and cyclopropyl; or C. hydrogen, $C_1$-$C_3$ alkyl, $C_1$-$C_3$ haloalkyl, and $C_1$-$C_3$ alkoxy; or D. hydrogen, methyl, trifluoromethyl, and methoxy; or E. hydrogen.

The present invention, accordingly, makes available a compound of formula I having the substituents X, R, $R_1$, $R_{2a}$, $R_{2b}$, $R_3$, Q, $A_1$, $A_2$, $A_3$, $A_4$, and $A_5$ as defined above in all combinations/each permutation. Accordingly, made available, for example, is a compound of formula I with $A_1$, $A_2$, and $A_3$ being of the first aspect (i.e. $A_1$, $A_2$ and $A_3$ are, independently from each other, N or $CR_Y$; and where $R_Y$ is of embodiment D (i.e. $R_Y$ is independently selected from hydrogen, methyl, trifluoromethyl, and methoxy); $A_4$, and $A_5$ being of the embodiment B (i.e. $A_4$ is $CR_{YY}$, and $A_5$ is CH where $R_{YY}$ is of embodiment B (i.e. $R_Y$ hydrogen, $C_1$-$C_3$ alkyl, $C_1$-$C_3$ haloalkyl, $C_1$-$C_3$ alkoxy, $C_1$-$C_3$ haloalkoxy, halogen, or cyclopropyl); $R_1$ being embodiment B (i.e. hydrogen, $C_1$-$C_6$alkyl, $C_1$-$C_6$cyanoalkyl, aminocarbonyl$C_1$-$C_6$alkyl, hydroxycarbonyl$C_1$-$C_6$alkyl, $C_1$-$C_6$nitroalkyl, trimethylsilane$C_1$-$C_6$alkyl, $C_1$-$C_3$alkoxy-$C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_3$-$C_4$cycloalkyl$C_1$-$C_2$alkyl-, benzyloxycarbonyl, or benzyl); $R_{2a}$ being an embodiment L (i.e. halogen, $C_1$-$C_2$haloalkyl, $C_1$-$C_2$haloalkylsulfanyl, $C_1$-$C_2$haloalkysulfonyl, or $C_1$-$C_2$haloalkoxy); $R_{2b}$ being embodiment B (i.e. halogen, $C_1$-$C_3$haloalkyl, or $C_1$-$C_3$haloalkoxy); $R_3$ being embodiment B (i.e. hydrogen, halogen, $C_3$-$C_4$cycloalkyl, cyclopropylcarbonyl, $C_3$-$C_4$cycloalkyl-$C_1$-$C_2$alkyl optionally substituted with one to two substituents selected from oxo, halogen, $C_1$-$C_3$alkyl and $C_1$-$C_3$haloalkyl, $C_1$-$C_3$haloalkyl, $C_1$-$C_3$haloalkysulfanyl, $C_1$-$C_3$haloalkysulfonyl, $C_1$-$C_3$alkoxy, $C_1$-$C_3$haloalkoxy, or CN); Q being embodiment A (i.e. Q is $Q^a$, wherein $Q^a$ can be embodiment B (i.e. $Q^a$ is selected from $Q^a$-1, $Q^a$-6, $Q^a$-7, $Q^a$-10, and $Q^a$-15; and $R_4$ is embodiment G (i.e. thiazol-2-yl, thiazol-4-yl, thiazol-5-yl, isothiazol-3-yl, isothiazol-4-yl, isothiazol-5-yl, 1,2,4-thiadiazol-3-yl, 1,3,4-thiadiazol-2-yl or 1,2,4-thiadiazol-5-yl each of which, independently of each other, is unsubstituted or substituted with one to two substituents independently selected from $C_1$-$C_3$haloalkyl, halo, CN and $C_1$-$C_6$haloalkoxy).

In an embodiment, the compound of formula I is formula Iaa, Iab, Iac, Iad, Iae, Iaf or Iag (with asterisk indicating a stereogenic centre), wherein $R_1$, $R_{2a}$, $R_{2b}$, and $R_3$, are as defined in the first aspect and $Q_1$ corresponds to Q as defined in the first aspect, each with the corresponding embodiments as described above.

(Iaa)

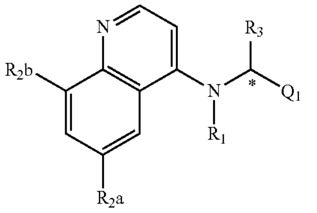

(Iab)

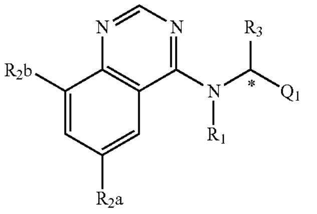

(Iac)

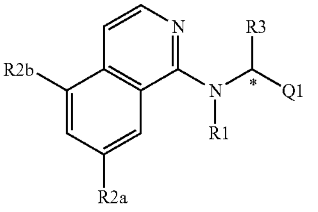

(Iad)

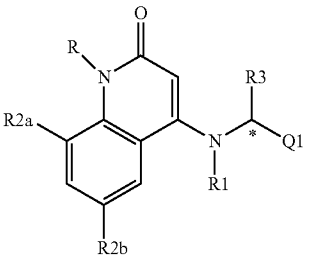

(Iae)

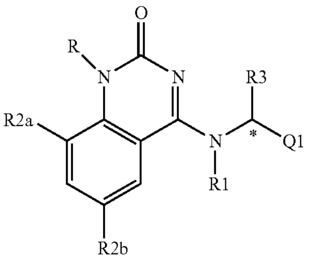

-continued (Iaf)

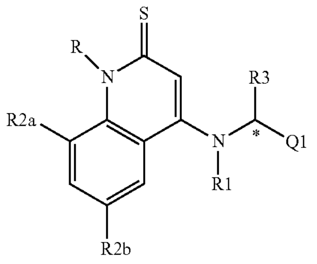

(Iag)

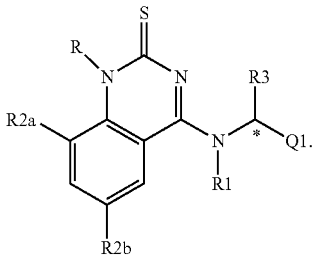

In an embodiment, compounds having preferred stereochemistry depicted in formula I'a would also be preferred for compounds of formulae Iaa, Iab and Iac. In a preferred embodiment, a compound of formulae I'ab and I'ae with the following stereochemistry is preferred:

I'ab

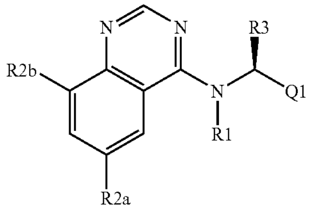

I'ae

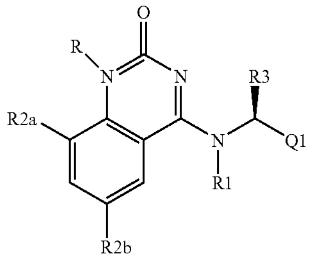

where $R_1$, $R_{2a}$, $R_{2b}$, $R_3$, $Q_1$ (corresponding to Q in formula I) are as defined in the first aspect and R is $C_1$-$C_3$alkyl, $C_1$-$C_3$haloalkyl, $C_1$-$C_3$alkoxy, or $C_1$-$C_3$haloalkoxy, and stereoisomers, enantiomers, tautomers and N-oxides of the compounds of formula (I'ab), and agrochemically acceptable salts thereof.

In an embodiment, $Q_1$ is

A. selected from $Q^{aa}$ to $Q^{al}$ and $Q^{ba}$ to $Q^{bl}$; or

B. $Q^{aa}$ or $Q^{ad}$; or

C. $Q^{ba}$ or $Q^{bd}$; or

D. selected from $Q^{aa}$, $Q^{ad}$, $Q^{ba}$ and $Q^{bd}$.

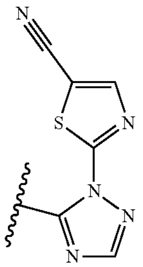
$Q^{aa}$
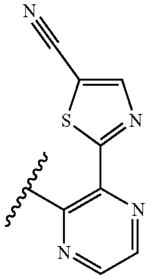
$Q^{ba}$
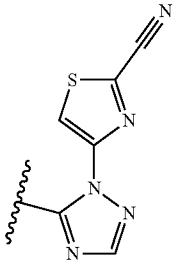
$Q^{ab}$
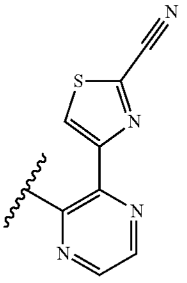
$Q^{bb}$
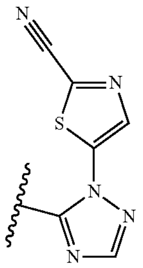
$Q^{ac}$
-continued
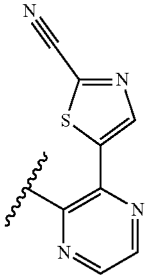
$Q^{bc}$
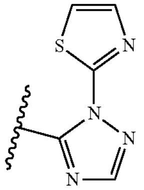
$Q^{ad}$
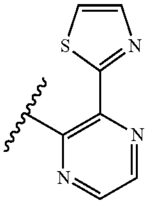
$Q^{bd}$
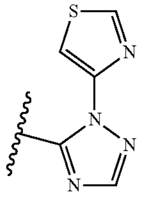
$Q^{ae}$
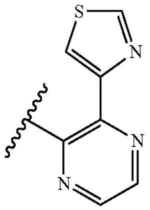
$Q^{be}$
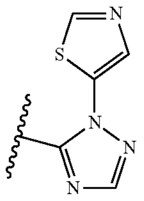
$Q^{af}$
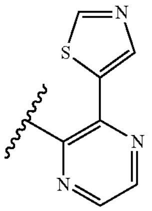
$Q^{bf}$ -continued $Q^{ag}$

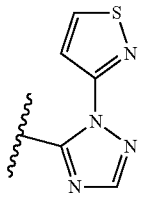

$Q^{bg}$

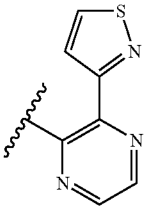

$Q^{ah}$

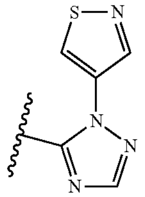

$Q^{bh}$

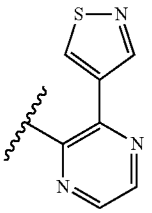

$Q^{ai}$

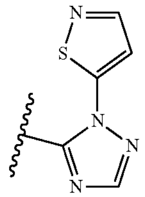

$Q^{bi}$

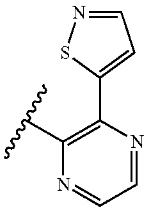

$Q^{aj}$

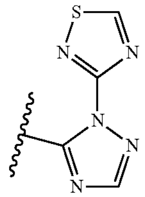

-continued $Q^{bj}$

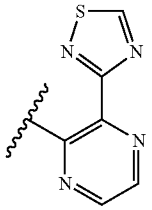

$Q^{ak}$

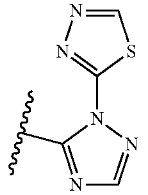

$Q^{bk}$

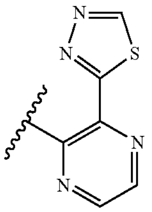

$Q^{al}$

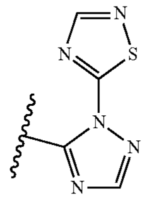

$Q^{bl}$

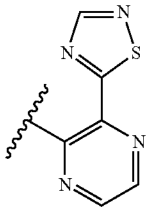

In an embodiment of each aspect of the invention, the compound of formula I has as $A_1$, $A_2$ and $A_3$, independently from each other, N or $CR_Y$ (wherein $R_Y$ is hydrogen, methyl, trifluoromethyl, and methoxy); as $A_4$ N or CH and $A_5$ as CH; as $R_1$ hydrogen, methyl, propargyl or cyclopropyl-methyl; as $R_{2a}$ hydrogen, halogen, $C_1$-$C_3$alkyl, $C_1$-$C_3$haloalkyl, $C_1$-$C_3$alkoxy, $C_1$-$C_3$haloalkoxy, cyclopropyl, cyclopropyl substituted with one to two substituents independently selected from halogen, methyl, and trifluoromethyl, cyclopropylcarbonyl, cyclopropylmethyl substituted with one to two substituents independently selected from oxo, halogen, and trifluoromethyl, or $C_1$-$C_2$alkylsulfanyl substituted with one to three halogens or $C_1$-$C_2$alkylsulfonyl substituted with one to three halogens; as $R_{2b}$ hydrogen, halogen, $C_3$-$C_4$cycloalkyl, cyclopropylcarbonyl, $C_3$-$C_4$cycloalkyl-$C_1$-$C_2$alkyl optionally substituted with one to two substituents selected from oxo, halogen, $C_1$-$C_3$alkyl and $C_1$-$C_3$haloalkyl, $C_1$-$C_3$haloalkyl, $C_1$-$C_3$haloalkysulfanyl, $C_1$-$C_3$haloalkysulfonyl, $C_1$-$C_3$alkoxy, $C_1$-$C_3$haloalkoxy, or CN; as $R_3$ methyl; and as Q selected from $Q^a$-1 to $Q^a$-11, $Q^a$-13 to $Q^a$-16 and $Q^b$-1 to $Q^b$-13; as $R_4$ (for $Q^a$-1 to $Q^a$-11 and $Q^a$-13 to $Q^a$-16) is thiazol-2-yl, thiazol- 4-yl, thiazol-5-yl, 1,2,4-thiadiazol-3-yl, 1,3,4-thiadiazol-2-yl or 1,2,4-thiadiazol-5-yl, each of which, independently of each other, is unsubstituted or substituted with one to two substituents independently selected from $C_1$-$C_3$alkyl, $C_1$-$C_3$haloalkyl, $C_1$-$C_3$alkoxy, $C_3$-$C_4$cycloalkyl, halo, hydroxyl, CN, $C_1$-$C_6$haloalkoxy, $C_2$-$C_6$haloalkenyloxy, $C_2$-$C_6$haloalkynyloxy, $C_3$-$C_4$halocycloalkoxy, $NH_2C(O)$—, $NH_2C(S)$—, (OH)N═C($NH_2$)— and a 5-membered heteroaryl ring optionally substituted by 1 to 3 substituents independently selected from halogen, $C_1$-$C_3$alkyl, $C_1$-$C_3$haloalkyl, $C_1$-$C_3$alkoxy and $C_1$-$C_3$haloalkoxy; and $R_{4a}$ (for $Q^b$-1 to $Q^b$-13) is thiazol-2-yl, thiazol-4-yl, thiazol-5-yl, isothiazol-3-yl, isothiazol-4-yl, isothiazol-5-yl, 1,2,4-thiadiazol-3-yl, 1,3,4-thiadiazol-2-yl or 1,2,4-thiadiazol-5-yl, each of which, independently of each other, is unsubstituted or substituted with one to two substituents independently selected from $C_1$-$C_3$alkyl, $C_1$-$C_3$haloalkyl, $C_1$-$C_3$alkoxy, $C_3$-$C_4$cycloalkyl, halogen, hydroxyl, cyano, and $C_1$-$C_3$haloalkoxy.

In an embodiment of each aspect of the invention, the compound of formula I has as $A_1$=$A_2$-$A_3$ taken together NR—C(═X)—N where X is sulfur or oxygen and R is hydrogen, methyl or 2,2,2-trifluoroethyl; as $A_4$ N or CH and $A_5$ as CH; as $R_1$ hydrogen, methyl, propargyl or cyclopropyl-methyl; as $R_{2a}$ hydrogen, halogen, $C_1$-$C_3$alkyl, $C_1$-$C_3$haloalkyl, $C_1$-$C_3$alkoxy, $C_1$-$C_3$haloalkoxy, cyclopropyl, cyclopropyl substituted with one to two substituents independently selected from halogen, methyl, and trifluoromethyl, cyclopropylcarbonyl, cyclopropylmethyl substituted with one to two substituents independently selected from oxo, halogen, and trifluoromethyl, or $C_1$-$C_2$alkylsulfanyl substituted with one to three halogens or $C_1$-$C_2$alkylsulfonyl substituted with one to three halogens; as $R_{2b}$ hydrogen, halogen, $C_3$-$C_4$cycloalkyl, cyclopropylcarbonyl, $C_3$-$C_4$cycloalkyl-$C_1$-$C_2$alkyl optionally substituted with one to two substituents selected from oxo, halogen, $C_1$-$C_3$alkyl and $C_1$-$C_3$haloalkyl, $C_1$-$C_3$haloalkyl, $C_1$-$C_3$haloalkysulfanyl, $C_1$-$C_3$haloalkysulfonyl, $C_1$-$C_3$alkoxy, $C_1$-$C_3$haloalkoxy, or CN; as $R_3$ methyl; and as Q selected from $Q^a$-1 to $Q^a$-11, $Q^a$-13 to $Q^a$-16 and $Q^b$-1 to $Q^b$-13; as $R_4$ (for $Q^a$-1 to $Q^a$-11, and $Q^a$-13 to $Q^a$-16) is thiazol-2-yl, thiazol-4-yl, thiazol-5-yl, 1,2,4-thiadiazol-3-yl, 1,3,4-thiadiazol-2-yl or 1,2,4-thiadiazol-5-yl, each of which, independently of each other, is unsubstituted or substituted with one to two substituents independently selected from $C_1$-$C_3$alkyl, $C_1$-$C_3$haloalkyl, $C_1$-$C_3$alkoxy, $C_3$-$C_4$cycloalkyl, halo, hydroxyl, CN, $C_1$-$C_6$haloalkoxy, $C_2$-$C_6$haloalkenyloxy, $C_2$-$C_6$haloalkynyloxy, $C_3$-$C_4$halocycloalkoxy, $NH_2C(O)$—, $NH_2C(S)$—, (OH) N═C($NH_2$)— and a 5-membered heteroaryl ring optionally substituted by 1 to 3 substituents independently selected from halogen, $C_1$-$C_3$alkyl, $C_1$-$C_3$haloalkyl, $C_1$-$C_3$alkoxy and $C_1$-$C_3$haloalkoxy; and $R_{4a}$ (for $Q^b$-1 to $Q^b$-13) is thiazol-2-yl, thiazol-4-yl, thiazol-5-yl, isothiazol-3-yl, isothiazol-4-yl, isothiazol-5-yl, 1,2,4-thiadiazol-3-yl, 1,3,4-thiadiazol-2-yl or 1,2,4-thiadiazol-5-yl, each of which, independently of each other, is unsubstituted or substituted with one to two substituents independently selected from $C_1$-$C_3$alkyl, $C_1$-$C_3$haloalkyl, $C_1$-$C_3$alkoxy, $C_3$-$C_4$cycloalkyl, halogen, hydroxyl, cyano, and $C_1$-$C_3$haloalkoxy.

In an embodiment of each aspect of the invention, the compound of formula I has as $A_1$=$A_2$-$A_3$ taken together NR—C(═O)—N where R is methyl or 2,2,2-trifluoroethyl; as $A_4$ N or CH and $A_5$ as CH; as $R_1$ hydrogen, methyl, propargyl or cyclopropyl-methyl; as $R_{2a}$ hydrogen, halogen, $C_1$-$C_3$alkyl, $C_1$-$C_3$haloalkyl, $C_1$-$C_3$alkoxy, $C_1$-$C_3$haloalkoxy, cyclopropyl, cyclopropyl substituted with one to two substituents independently selected from halogen, methyl, and trifluoromethyl, cyclopropylcarbonyl, cyclopropylmethyl substituted with one to two substituents independently selected from oxo, halogen, and trifluoromethyl, or $C_1$-$C_2$alkylsulfanyl substituted with one to three halogens or $C_1$-$C_2$alkylsulfonyl substituted with one to three halogens; as $R_{2b}$ hydrogen, halogen, $C_3$-$C_4$cycloalkyl, cyclopropylcarbonyl, $C_3$-$C_4$cycloalkyl-$C_1$-$C_2$alkyl optionally substituted with one to two substituents selected from oxo, halogen, $C_1$-$C_3$alkyl and $C_1$-$C_3$haloalkyl, $C_1$-$C_3$haloalkyl, $C_1$-$C_3$haloalkysulfanyl, $C_1$-$C_3$haloalkysulfonyl, $C_1$-$C_3$alkoxy, $C_1$-$C_3$haloalkoxy, or CN; as $R_3$ methyl; and as Q selected from $Q^a$-1 to $Q^a$-11, $Q^a$-13 to $Q^a$-16 and $Q^b$-1 to $Q^b$-13; as $R_4$ (for $Q^a$-1 to $Q^a$-11, and $Q^a$-13 to $Q^a$-16) is thiazol-2-yl, thiazol-4-yl, thiazol-5-yl, 1,2,4-thiadiazol-3-yl, 1,3,4-thiadiazol-2-yl or 1,2,4-thiadiazol-5-yl, each of which, independently of each other, is unsubstituted or substituted with one to two substituents independently selected from $C_1$-$C_3$alkyl, $C_1$-$C_3$haloalkyl, $C_1$-$C_3$alkoxy, $C_3$-$C_4$cycloalkyl, halo, hydroxyl, CN, $C_1$-$C_6$haloalkoxy, $C_2$-$C_6$haloalkenyloxy, $C_2$-$C_6$haloalkynyloxy, $C_3$-$C_4$halocycloalkoxy, $NH_2C(O)$—, $NH_2C(S)$—, (OH)N═C($NH_2$)— and a 5-membered heteroaryl ring optionally substituted by 1 to 3 substituents independently selected from halogen, $C_1$-$C_3$alkyl, $C_1$-$C_3$haloalkyl, $C_1$-$C_3$alkoxy and $C_1$-$C_3$haloalkoxy; and $R_{4a}$ (for $Q^b$-1 to $Q^b$-13) is thiazol-2-yl, thiazol-4-yl, thiazol-5-yl, isothiazol-3-yl, isothiazol-4-yl, isothiazol-5-yl, 1,2,4-thiadiazol-3-yl, 1,3,4-thiadiazol-2-yl or 1,2,4-thiadiazol-5-yl, each of which, independently of each other, is unsubstituted or substituted with one to two substituents independently selected from $C_1$-$C_3$alkyl, $C_1$-$C_3$haloalkyl, $C_1$-$C_3$alkoxy, $C_3$-$C_4$cycloalkyl, halogen, hydroxyl, cyano, and $C_1$-$C_3$haloalkoxy.

In an embodiment of each aspect of the invention, the compound of formula I has as $A_1$, $A_2$ and $A_3$, independently from each other, N or $CR_Y$ (wherein $R_Y$ is hydrogen, methyl, trifluoromethyl, and methoxy); as $A_4$ N or CH and $A_5$ as CH; as $R_1$ hydrogen, methyl, propargyl or cyclopropyl-methyl; as $R_{2a}$ hydrogen, halogen, $C_1$-$C_3$alkyl, $C_1$-$C_3$haloalkyl, $C_1$-$C_3$alkoxy, $C_1$-$C_3$haloalkoxy, cyclopropyl, cyclopropyl substituted with one to two substituents independently selected from halogen, methyl, and trifluoromethyl, cyclopropylcarbonyl, cyclopropylmethyl substituted with one to two substituents independently selected from oxo, halogen, and trifluoromethyl, or $C_1$-$C_2$alkylsulfanyl substituted with one to three halogens or $C_1$-$C_2$alkylsulfonyl substituted with one to three halogens; as $R_{2b}$ hydrogen, halogen, $C_3$-$C_4$cycloalkyl, cyclopropylcarbonyl, $C_3$-$C_4$cycloalkyl-$C_1$-$C_2$alkyl optionally substituted with one to two substituents selected from oxo, halogen, $C_1$-$C_3$alkyl and $C_1$-$C_3$haloalkyl, $C_1$-$C_3$haloalkyl, $C_1$-$C_3$haloalkysulfanyl, $C_1$-$C_3$haloalkysulfonyl, $C_1$-$C_3$alkoxy, $C_1$-$C_3$haloalkoxy, or CN; as $R_3$ methyl; and as Q selected from $Q^{aa}$ to $Q^{ag}$ and $Q^{ba}$ to $Q^{bg}$.

In an embodiment of each aspect of the invention, the compound of formula I has as $A_1$, $A_2$ and $A_3$, independently from each other, N or CH; as $A_4$ and $A_5$ each CH; as $R_1$ hydrogen, methyl, propargyl or cyclopropyl-methyl; as $R_{2a}$ hydrogen, halogen, $C_1$-$C_3$alkyl, $C_1$-$C_3$haloalkyl, $C_1$-$C_3$alkoxy, $C_1$-$C_3$haloalkoxy, cyclopropyl, cyclopropyl substituted with one to two substituents independently selected from halogen, methyl, and trifluoromethyl, cyclopropylcarbonyl, cyclopropylmethyl substituted with one to two substituents independently selected from oxo, halogen, and trifluoromethyl, or $C_1$-$C_2$alkylsulfanyl substituted with one to three halogens or $C_1$-$C_2$alkylsulfonyl substituted with one to three halogens; as $R_{2b}$ hydrogen, halogen, $C_3$-$C_4$cycloalkyl, cyclopropylcarbonyl, $C_3$-$C_4$cycloalkyl-$C_1$-$C_2$alkyl optionally substituted with one to two substituents selected from oxo, halogen, $C_1$-$C_3$alkyl and $C_1$-$C_3$haloalkyl, $C_1$-$C_3$haloalkyl, $C_1$-$C_3$haloalkysulfanyl, $C_1$-$C_3$haloalkysulfonyl, $C_1$-$C_3$alkoxy, $C_1$-$C_3$haloalkoxy, or CN; as $R_3$ methyl; and as Q selected from $Q^{aa}$ to $Q^{ag}$ and $Q^{ba}$ to $Q^{bg}$.

In an embodiment of each aspect of the invention, the compound of formula I has as $A_1$, $A_2$ and $A_3$, independently from each other, N or CH; as $A_4$ and $A_5$ each CH; as $R_1$ hydrogen, methyl, propargyl or cyclopropyl-methyl; as $R_{2a}$ halogen, $C_1$-$C_3$haloalkyl, $C_1$-$C_3$haloalkoxy, cyclopropyl, cyclopropyl substituted with one to two substituents independently selected from halogen, methyl, and trifluoromethyl, cyclopropylcarbonyl, cyclopropylmethyl substituted with one to two substituents independently selected from oxo, halogen, and trifluoromethyl, or $C_1$-$C_2$alkylsulfanyl substituted with one to three halogens or $C_1$-$C_2$alkylsulfonyl substituted with one to three halogens; as $R_{2b}$ halogen, $C_3$-$C_4$cycloalkyl, cyclopropylcarbonyl, $C_3$-$C_4$cycloalkyl-$C_1$-$C_2$alkyl optionally substituted with one to two substituents selected from oxo, halogen, $C_1$-$C_3$alkyl and $C_1$-$C_3$haloalkyl, $C_1$-$C_3$haloalkyl, $C_1$-$C_3$haloalkysulfanyl, $C_1$-$C_3$haloalkysulfonyl, $C_1$-$C_3$alkoxy, $C_1$-$C_3$haloalkoxy, or CN; as $R_3$ methyl; and as Q selected from $Q^{aa}$ to $Q^{ag}$ and $Q^{ba}$ to $Q^{bg}$.

In an embodiment of each aspect of the invention, the compound of formula I has as $A_1$=$A_2$-$A_3$ taken together NR—C(=O)—N where R is methyl or 2,2,2-trifluoroethyl; as $A_4$ N or CH and $A_5$ as CH; as $R_1$ hydrogen, methyl, propargyl or cyclopropyl-methyl; as $R_{2a}$ hydrogen, halogen, $C_1$-$C_3$alkyl, $C_1$-$C_3$haloalkyl, $C_1$-$C_3$alkoxy, $C_1$-$C_3$haloalkoxy, cyclopropyl, cyclopropyl substituted with one to two substituents independently selected from halogen, methyl, and trifluoromethyl, cyclopropylcarbonyl, cyclopropylmethyl substituted with one to two substituents independently selected from oxo, halogen, and trifluoromethyl, or $C_1$-$C_2$alkylsulfanyl substituted with one to three halogens or $C_1$-$C_2$alkylsulfonyl substituted with one to three halogens; as $R_{2b}$ hydrogen, halogen, $C_3$-$C_4$cycloalkyl, cyclopropylcarbonyl, $C_3$-$C_4$cycloalkyl-$C_1$-$C_2$alkyl optionally substituted with one to two substituents selected from oxo, halogen, $C_1$-$C_3$alkyl and $C_1$-$C_3$haloalkyl, $C_1$-$C_3$haloalkyl, $C_1$-$C_3$haloalkysulfanyl, $C_1$-$C_3$haloalkysulfonyl, $C_1$-$C_3$alkoxy, $C_1$-$C_3$haloalkoxy, or CN; as $R_3$ methyl; and as Q selected from $Q^{aa}$ to $Q^{ag}$ and $Q^{ba}$ to $Q^{bg}$.

In an embodiment of each aspect of the invention, the compound of formula I has as $A_1$, $A_2$ and $A_3$, independently from each other, N or CH; as $A_4$ and $A_5$ each CH; as $R_1$ hydrogen, methyl, propargyl or cyclopropyl-methyl; as $R_{2a}$ halogen, $C_1$-$C_3$haloalkyl, or $C_1$-$C_2$alkylsulfonyl substituted with one to three halogens; as $R_{2b}$ halogen, or $C_1$-$C_3$haloalkyl; as $R_3$ methyl; and as Q selected from $Q^{aa}$ to $Q^{ag}$ and $Q^{ba}$ to $Q^{bg}$.

In a second aspect, the present invention makes available a composition comprising a compound of formula I as defined in the first aspect, one or more auxiliaries and diluent, and optionally one or more other active ingredient.

In a third aspect, the present invention makes available a method of combating and controlling insects, acarines, nematodes or molluscs which comprises applying to a pest, to a locus of a pest, or to a plant susceptible to attack by a pest an insecticidally, acaricidally, nematicidally or molluscicidally effective amount of a compound as defined in the first aspect or a composition as defined in the second aspect.

In a fourth aspect, the present invention makes available a method for the protection of plant propagation material from the attack by insects, acarines, nematodes or molluscs, which comprises treating the propagation material or the site, where the propagation material is planted, with an effective amount of a compound of formula I as defined in the first aspect or a composition as defined in the second aspect.

In a fifth aspect, the present invention makes available a plant propagation material, such as a seed, comprising, or treated with or adhered thereto, a compound of formula I as defined in the first aspect or a composition as defined in the second aspect.

The present invention in a further aspect provides a method of controlling parasites in or on an animal in need thereof comprising administering an effective amount of a compound of the first aspect. The present invention further provides a method of controlling ectoparasites on an animal in need thereof comprising administering an effective amount of a compound of formula I as defined in the first aspect. The present invention further provides a method for preventing and/or treating diseases transmitted by ectoparasites comprising administering an effective amount of a compound of formula I as defined in the first aspect, to an animal in need thereof.

Compounds of formula I can be prepared by those skilled in the art following known methods. More specifically compounds of formulae I, and I'a, and intermediates therefor can be prepared as described below in the schemes and examples. Certain stereogenic centers have been left unspecified for the clarity and are not intended to limit the teaching of the schemes in any way.

The process according to the invention for preparing compounds of formula I is carried out by methods known to those skilled in the art.

Compounds of formula I can be made, for example, as shown in scheme 1.

Scheme 1

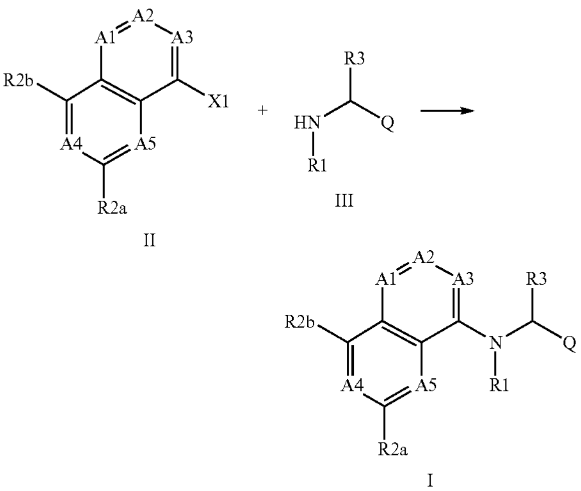

II III

I

Reaction of a compound of the formula II, wherein X1 is a leaving group, such as a halogen or sulfonate, for instance chloride, with a compound of formula III, or a salt thereof (such as a hydrohalide salt, preferably a hydrochloride or a hydrobromide salt, or a trifluoroacetic acid salt, or any other equivalent salt), gives a compound of the formula I, wherein A1, A2, A3, A4, A5, $R_1$, $R_{2a}$, $R_{2b}$, $R_3$ and Q have the same meaning as given above for compounds of the formula I. The reaction can be conducted neat or in a solvent, preferably in a solvent, such as an organic solvent, for instance acetonitrile, ethyl acetate, N,N-dimethylacetamide or N,N-dimethylformamide, in a temperature range of −100 to +300° C., preferably between ambient temperature and 200° C., with or without the presence of a catalyst, for instance a metal catalyst, such as a palladium complex, and with or without the addition of a base, such as an inorganic base, for instance sodium, potassium or cesium carbonate, or an organic base, such as, for example, triethylamine, diisopropylethylamine or pyridine.

Compounds of the formula II are either known, or can be prepared in analogy to descriptions found for example in WO 2021/083936 and WO 2021/177160, or they can be prepared by methods known to a person skilled in the art.

Scheme 2

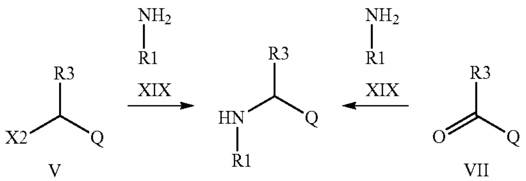

V III VII

Compounds of formula III, or a salt thereof, can be made, for example, as shown in scheme 2. Treatment of a compound of the formula V, wherein X2 is a leaving group, such as a halogen or sulfonate, for instance bromide, with an amine of the formula XIX, or a salt thereof, gives compounds of the formula III. The reaction can be conducted neat or in a solvent, preferably in a solvent, such as an organic solvent, for instance acetonitrile, in a temperature range of −100 to +300° C., preferably between ambient temperature and 200° C., with or without the addition of a base, such as an inorganic base, for instance potassium carbonate, or an organic base, such as, for example, triethylamine.

Alternatively, treatment of a compound of the formula VII with an amine of the formula XIX, or a salt thereof, gives compounds of the formula III. This reaction is done in the presence of a reducing agent, such as for example hydrogen, or a hydride, such as sodium borohydride, with or without a catalyst, such as a hydrogenation catalyst, for example palladium on carbon, with or without the presence of an acid, such as acetic acid, or a Lewis acid, such as zinc bromide, in a solvent or without a solvent, such as, for instance, methanol. The reaction can be conducted in a temperature range of −100 to +300° C., preferably between ambient temperature and 200° C.

Such methods, and the range of conditions to perform them, for the alkylation of amines and for the reductive alkylation of amines are well known to a person skilled in the art. The amines of formula XIX, or a salt thereof, are either known, or they can be prepared by methods known to a person skilled in the art.

Scheme 3

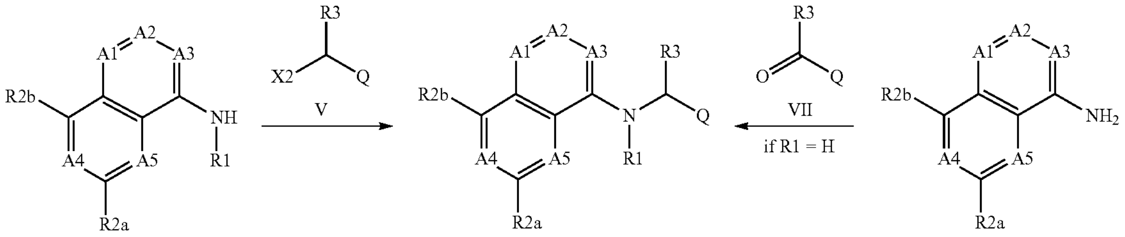

Ia I IVa

Alternatively, compounds of formula I can be made, for example, as shown in scheme 3. Reaction of an amine of the formula IV with a compound of the formula V, wherein X2 is a leaving group, such as a halogen or sulfonate, for instance bromide, gives a compound of formula I, wherein A1, A2, A3, A4, A5, R1, $R_{2a}$, $R_{2b}$, R3 and Q have the same meaning as given above for compounds of the formula I. The reaction can be conducted neat or in a solvent, preferably in a solvent, such as an organic solvent, for instance acetonitrile, in a temperature range of −100 to +300° C., preferably between ambient temperature and 200° C., with or without the addition of a base, such as an inorganic base, for instance potassium carbonate, or an organic base, such as, for example, triethylamine. Such methods for the alkylation of amines, and the range of conditions to perform them, are well known to a person skilled in the art.

Alternatively, reaction of an amine of the formula IVa with a compound of the formula VII gives a compound of the formula I wherein R1 is H and A1, A2, A3, A4, A5, $R_{2a}$, $R_{2b}$, R3 and Q have the same meaning as given above for compounds of the formula I. This reaction is done in the presence of a reducing agent, such as for example hydrogen, or a hydride, such as sodium borohydride, with or without a catalyst, such as a hydrogenation catalyst, for example palladium on carbon, with or without the presence of an acid, such as acetic acid, or a Lewis acid, such as zinc bromide, in a solvent or without a solvent, such as, for instance, methanol. The reaction can be conducted in a temperature range of −100 to +300° C., preferably between ambient temperature and 200° C.

Such methods for the reductive alkylation of amines, and the range of conditions to perform them, are well known to a person skilled in the art.

Scheme 4

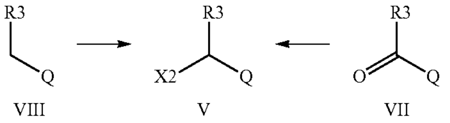

VIII V VII

Compounds of formula V can be made, for example, as shown in scheme 4. Treatment of a compound of the formula VIII with a halogenating agent, such as chlorine or bromine or N-bromosuccinimide, for example, gives compound of the formula V, wherein the leaving group Q is a halogen, for instance chloride or bromide. This reaction is done with or without a solvent, preferably in a solvent, with or without an additive, such as a radical starter, such as, for example, benzoyl peroxide or azoisobutyronirile. The reaction can be done with or without exposure to visible light, or to UV light, and it can be conducted in a temperature range of −100 to +300° C., preferably between ambient temperature and 200° C.

Alternatively, a compound of the formula VII can be treated with a reducing agent, followed by reaction with a sulfonyl chloride, for instance methanesulfonyl chloride, to give a compound of the formula V, wherein the leaving group Q is a sulfonate, for instance a mesylate. This reaction can be done in a solvent, or without a solvent, in the presence of a base, such as an inorganic base, for instance potassium carbonate, or an organic base, such as an amine base, for instance trimethylamine, or without a base, and it can be conducted in a temperature range of −100 to +300° C., preferably between ambient temperature and 200° C. A suitable reducing agent could be, for example, hydrogen, or a hydride, such as sodium borohydride, with or without a catalyst, such as a hydrogenation catalyst, for example palladium on carbon, with or without the presence of an acid, such as acetic acid, or a Lewis acid, such as zinc bromide, in a solvent or without a solvent, such as, for instance, methanol. The reaction can be conducted in a temperature range of −100 to +300° C., preferably between ambient temperature and 200° C.

Such methods for the halogenation, the reduction of carbonyl compounds and the sulfonylation of alcohols, and the range of conditions to perform them, are well known to a person skilled in the art. The amines of formula VII and the compounds of formula VIII are either known, or they can be prepared by methods known to a person skilled in the art.

Scheme 5

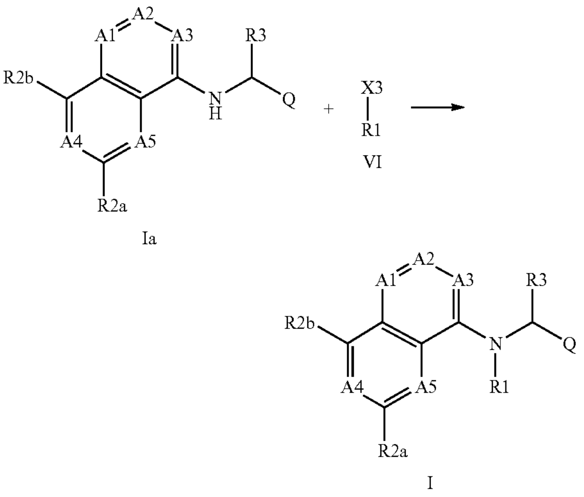

Ia

VI

I

Alternatively, compounds of formula I wherein $R_1$ is different from H can be made, for example, as shown in scheme 5. A compound of the formula Ia can be reacted with a compound of the formula VI wherein X3 is a leaving group, such as a halogen or sulfonate, for instance a chloride, bromide, iodide or mesylate, to give a compound of formula I, wherein A1, A2, A3, A4, A5, $R_1$, $R_{2a}$, $R_{2b}$, R3 and Q have the same meaning as given above for compounds of the formula I. This reaction can be conducted neat or in a solvent, preferably in a solvent, such as an organic solvent, for instance acetonitrile, N,N-dimethylformamide (DMF) or N,N-dimethylacetamide (DMA), or mixtures thereof, in a temperature range of −100 to +300° C., preferably between ambient temperature and 200° C., with or without the addition of a base, such as an inorganic base, for instance sodium, potassium or cesium carbonate, or an organic base, such as, for example, triethylamine, diisopropylethylamine or pyridine. Such methods for the alkylation of amines, and the range of conditions to perform them, are well known to a person skilled in the art, and are described for example in WO 2021/083936.

Scheme 6

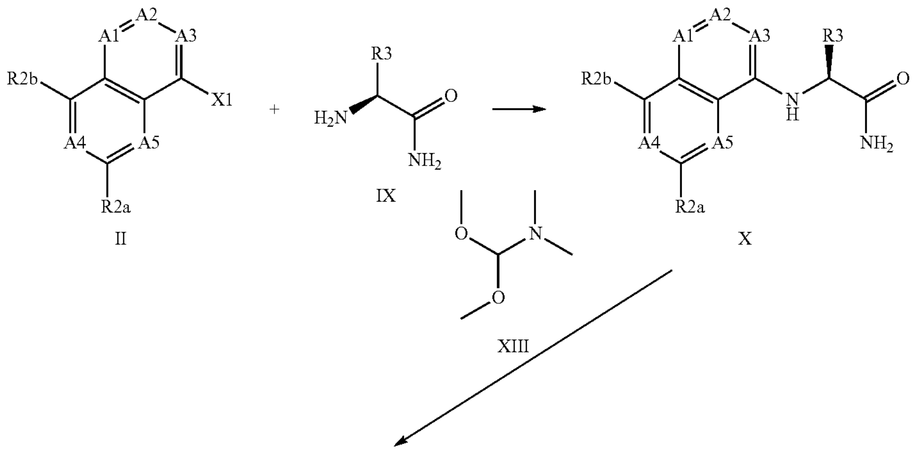

II IX X XIII

-continued

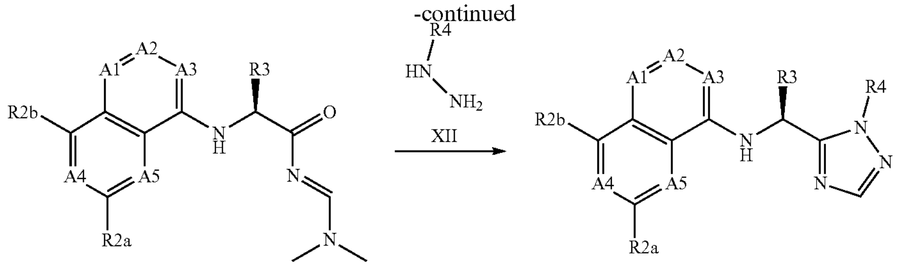

XI Ib

Compounds of formula Ib can be made, for example, as shown in scheme 6. Reaction of a compound of the formula II, wherein X1 is a leaving group, such as a halogen or sulfonate, for instance chloride, with a compound of formula IX gives a compound of the formula X. The reaction can be conducted neat or in a solvent, preferably in a solvent, such as an organic solvent, for instance acetonitrile or N,N-dimethylformamide, in a temperature range of −100 to +300° C., preferably between ambient temperature and 200° C., with or without the presence of a catalyst, for instance a metal catalyst, such as a palladium complex, and with or without the addition of a base, such as an inorganic base, for instance potassium carbonate, or an organic base, such as, for example, triethylamine.

Subsequent treatment of compound X with the known compound XIII gives a compound of the formula XI. This reaction can be conducted neat or in a solvent, preferably in a solvent, such as an organic solvent, for instance dichloromethane, in a temperature range of −100 to +300° C., preferably between ambient temperature and 100° C., or between ambient temperature and 50° C., without a base or in the presence of a base, such as an inorganic base, for instance potassium carbonate, or an organic base, such as, for example, triethylamine.

Further reaction of compound XI with hydrazine XII gives the compound of formula Ib, wherein A1, A2, A3, A4, A5, $R_{2a}$, $R_{2b}$, $R_3$ and R4 have the same meaning as given above for compounds of the formula I. This reaction can be conducted neat or in a solvent, preferably in a solvent, such as an organic solvent, for instance 1,4-dioxane, or acetic acid, or a mixture of 1,4-dioxane and acetic acid, in a temperature range of −100 to +300° C., preferably between ambient temperature and 200° C., or between ambient temperature and 80° C.

Within this sequence of transformations, the intermediate compounds of formula X and of formula XI can be used as crude products for the subsequent step, or they can be purified, for instance by chromatography, and used in purified form for the next transformation.

Scheme 7

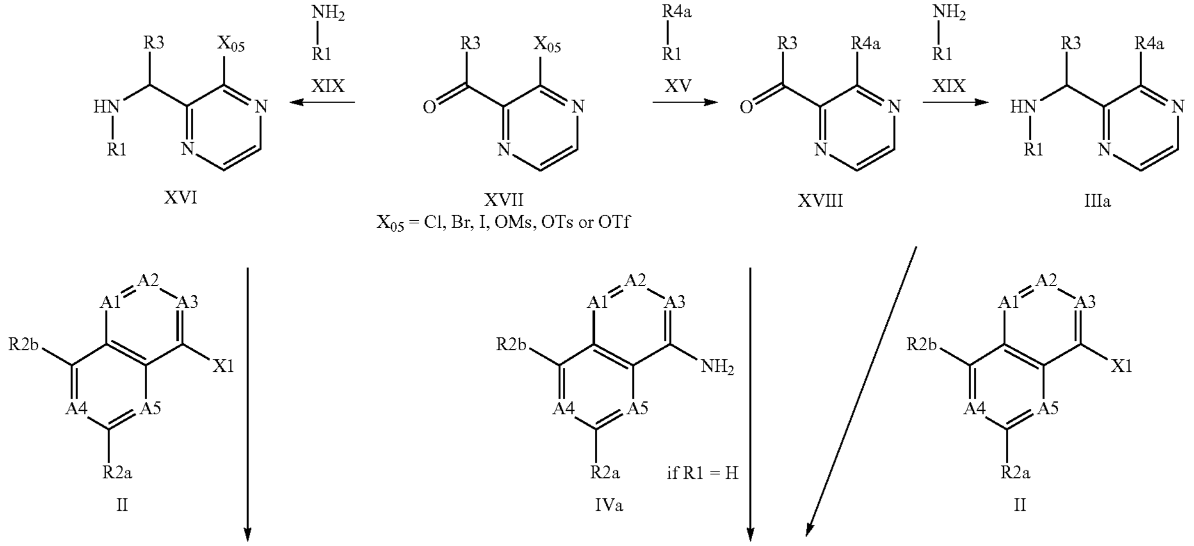

XVI XVII XVIII IIIa

II IVa II

-continued

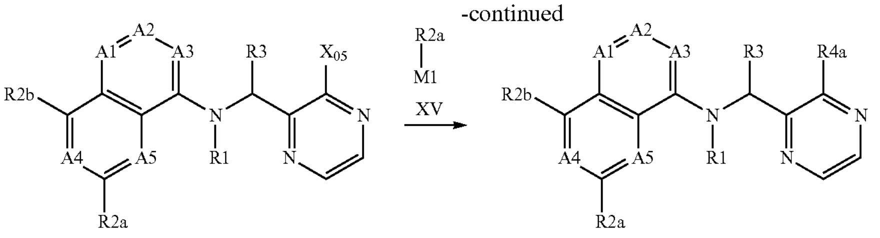

XIV Ic

Compounds of formula Ic can be made, for example, as shown in scheme 7. Reaction of a compound of the formula XVII (wherein $X_{05}$ is a leaving group such as chlorine, bromine, iodine, arysulfonate, alkylsulfonate or trifluoromethanesulfonate) with an amine of the formula XIX, or a salt thereof, gives compounds of the formula XVI. This reaction is done in the presence of a reducing agent, such as for example hydrogen, or a hydride, such as sodium borohydride, with or without a catalyst, such as a hydrogenation catalyst, for example palladium on carbon, with or without the presence of an acid, such as acetic acid, or a Lewis acid, such as zinc bromide or titanium(IV) isopropoxide, in a solvent or without a solvent, such as, for instance, methanol. The reaction can be conducted in a temperature range of −100 to +300° C., preferably between ambient temperature and 200° C. Such methods, and the range of conditions to perform them, for the reductive alkylation of amines are well known to a person skilled in the art.

Subsequent reaction of the intermediate of the formula XVI, or a salt thereof, with a compound of the formula II gives a compound of the formula XIV. This reaction can be conducted neat or in a solvent, preferably in a solvent, such as an organic solvent, for instance acetonitrile, in a temperature range of −100 to +300° C., preferably between ambient temperature and 200° C., with or without the presence of a catalyst, for instance a metal catalyst, such as a palladium complex, and with or without the addition of a base, such as an inorganic base, for instance potassium carbonate, or an organic base, such as, for example, triethylamine.

Subsequently, the intermediate of the formula XIV is reacted with a compound of the formula XV to give the compound of formula Ic, wherein A1, A2, A3, A4, A5, $R_{2a}$, $R_{2b}$, R1, R3 and R4a have the same meaning as given above for compounds of the formula I, and M1 in R4a-M1 is a metal, such as for instance lithium, or —MgCl, or —ZnBr, or —$B(OH)_2$; or R4a-M1 represents a boronate, such as a pinacol ester of a boronic acid, or a stannane such as R4a-Sn(n-Bu)$_3$. Such transformations are known to a person skilled in the art as Suzuki-, Kumada-, Negishi- or Stille-coupling reactions, respectively. Such reactions are carried out in a temperature range of −100 to +300° C., preferably between ambient temperature and 200° C., in the presence of a catalyst, such as a metal catalyst, for instance a palladium catalyst, and a ligand, such as for example a phosphine ligand, or an N-heterocyclic carbene (NHC) ligand, or a phosphite ligand. The reaction can be done in the presence or absence of an additional metal catalyst, such as, for example, a copper salt, for instance CuI. The reaction is done with or without a base, which can be an inorganic base, such as potassium carbonate, or sodium hydroxide, or cesium carbonate, or an organic base, such as an amine base, for instance triethyl amine. This reaction is done with or without a solvent, preferentially in a solvent. Where the reaction mixture is heated, the reaction can be conducted under microwave irradiation or with conventional heating, such as heating the reaction vessel in an oil bath.

By an alternative route, compound XVII can be reacted with a compound of the formula XV to give intermediate XVIII. This reaction is done essentially under in the same range of conditions as described for the transformation of intermediate XIV to the compound of formula Ic.

Subsequently, the intermediate XVIII is reacted with amine IVa to give a compound of the formula Ic, wherein R1 is hydrogen and A1, A2, A3, A4, A5, $R_{2a}$, $R_{2b}$, R3 and R4a have the same meaning as given above for compounds of the formula I. This reaction is done in the presence of a reducing agent, essentially under the same conditions as described above for the transformation of compound XVII to intermediate XVI.

By yet another alternative route, the intermediate compound of the formula XVIII can be reacted with an amine of the formula XIX, or a salt thereof, to give the intermediate of the formula IIIa, or a salt thereof. This reaction is done in the presence of a reducing agent, essentially under the same conditions as described above for the transformation of compound XVII to intermediate XVI.

Subsequently, the intermediate of the formula IIIa, or a salt thereof, is reacted with a compound of the formula II to give the compound of the formula Ic, wherein A1, A2, A3, A4, A5, $R_{2a}$, $R_{2b}$, R1, R3 and R4a have the same meaning as given above for compounds of the formula I. This reaction is done essentially under the same conditions as described above for the transformation of intermediate XVI to intermediate XIV.

Within these different multistep sequences, the intermediate compounds of formulas XIV, XVI, XVIII and IIIa can be used as crude products for the respective subsequent step, or they can be purified, for instance by chromatography, and used in purified form for the next transformation. Compounds of the formula XVII are known, or they can be prepared by methods known to a person skilled in the art.

Compounds of the Formula Id

Id

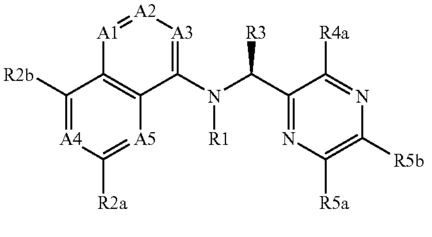

can be prepared by the reaction of an amine of the formula IIIb

IIIb

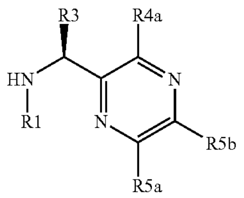

wherein R1, R3, R4a, R5a and R5b are as described in formula I with a compound of the formula II

II

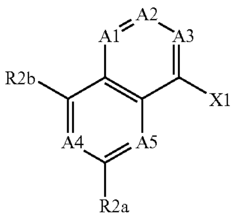

wherein A1, A2, A3, A4, A5, $R_{2a}$ and $R_{2b}$ are as described in formula I and X1 is a leaving group, such as a halogen or a sulfonate, for instance chloride.

The chemistry is described in more detail in Scheme 8.

Scheme 8

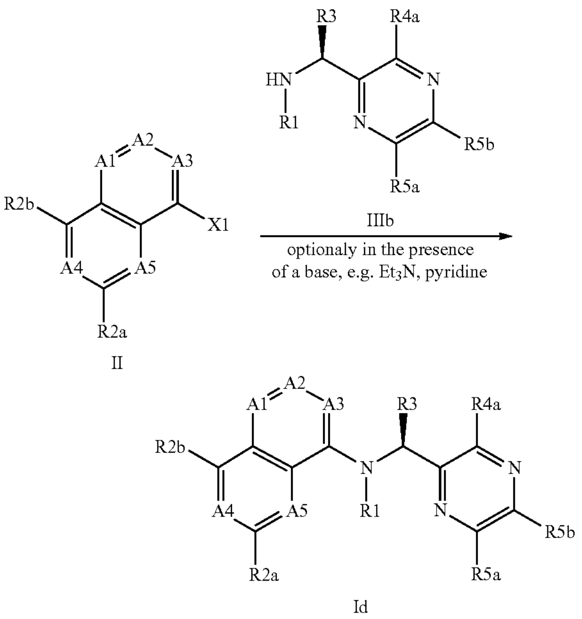

IIIb

II

Id

Reaction of a compound of the formula II, wherein X1 is a leaving group, such as a halogen or sulfonate, for instance chloride, with a compound of formula IIIb, or a salt thereof, gives a compound of the formula Id, wherein A1, A2, A3, A4, A5, R1, $R_{2a}$, $R_{2b}$, R3, R4a, R5a and R5b have the same meaning as given above for compounds of the formula I. The reaction can be conducted neat or in a solvent, preferably in a solvent, such as an organic solvent, for instance acetonitrile, in a temperature range of −100 to +300° C., preferably between ambient temperature and 200° C., with or without the presence of a catalyst, for instance a metal catalyst, such as a palladium complex, and with or without the addition of a base, such as an inorganic base, for instance sodium, potassium or cesium carbonate, or an organic base, such as, for example, triethylamine.

The formation of compounds of formula IIIb is outlined in Scheme 9.

Scheme 9

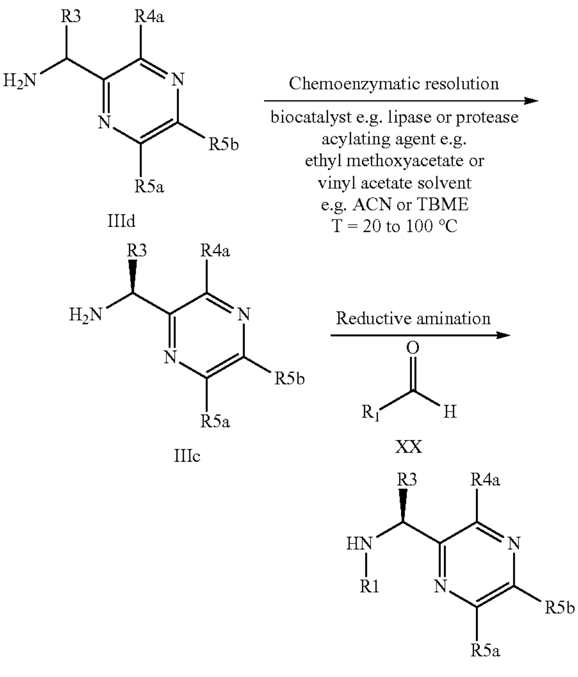

IIId

IIIc

XX

IIIb

Compounds of formula IIIb can be prepared by treatment of compounds of formula IIIc, wherein $R_3$, $R_{4a}$, $R_{5a}$, and $R_{5b}$ are as described in formula I, with compounds of formula XX wherein $R_1$ is as defined in formula I, e.g. in the presence of $NaBH(OAc)_3$ or $NaBH_3CN$, in a suitable solvent, preferably in acetic acid at room temperature analogous to WO2002/088073, page 35. Alternatively, another reagent system for the reductive amination uses a combination of $Ti(i\text{-}OiPr)_4$ and $NaBH_4$ (see Synthesis 2003 (14), 2206).

Amines of formula IIIc may be obtained by biocatalyzed deracemization of amines of formula IIId. This may be done for instance using a lipase, e.g. *Candida Antarctica* lipase B or *Pseudomonas fluorescens* lipase, eventually in immobilized form (e.g. Novozym® 435) in presence of an acyl donor, e.g. ethyl methoxyacetate or vinyl acetate, in a suitable solvent such as acetonitrile or methyl tert-butyl ether at temperatures between 20° C. to 100° C. Such processes are described for instance in *J. Org. Chem.* 2007, 72, 6918-6923 or *Adv. Synth. Catal.* 2007, 349, 1481-1488. The expected stereochemical outcome of such enzymatic deracemization are known of those skilled in the art and are documented in the literature, for instance in *J. Org. Chem.* 1991, 56, 2656-2665 or *J. Am. Chem. Soc.* 2015, 137, 3996-4009.

In an alternative process, compounds of formula IIIc, or a salt thereof (such as a hydrohalide salt, preferably a hydrochloride or a hydrobromide salt, or a trifluoroacetic acid salt, or any other equivalent salt), can be obtained from compounds of the formula XXII, wherein $R_3$, $R_{4a}$, $R_{5a}$, and $R_{5b}$ are as described in formula I, following the synthesis described in Scheme 10.

Scheme 10

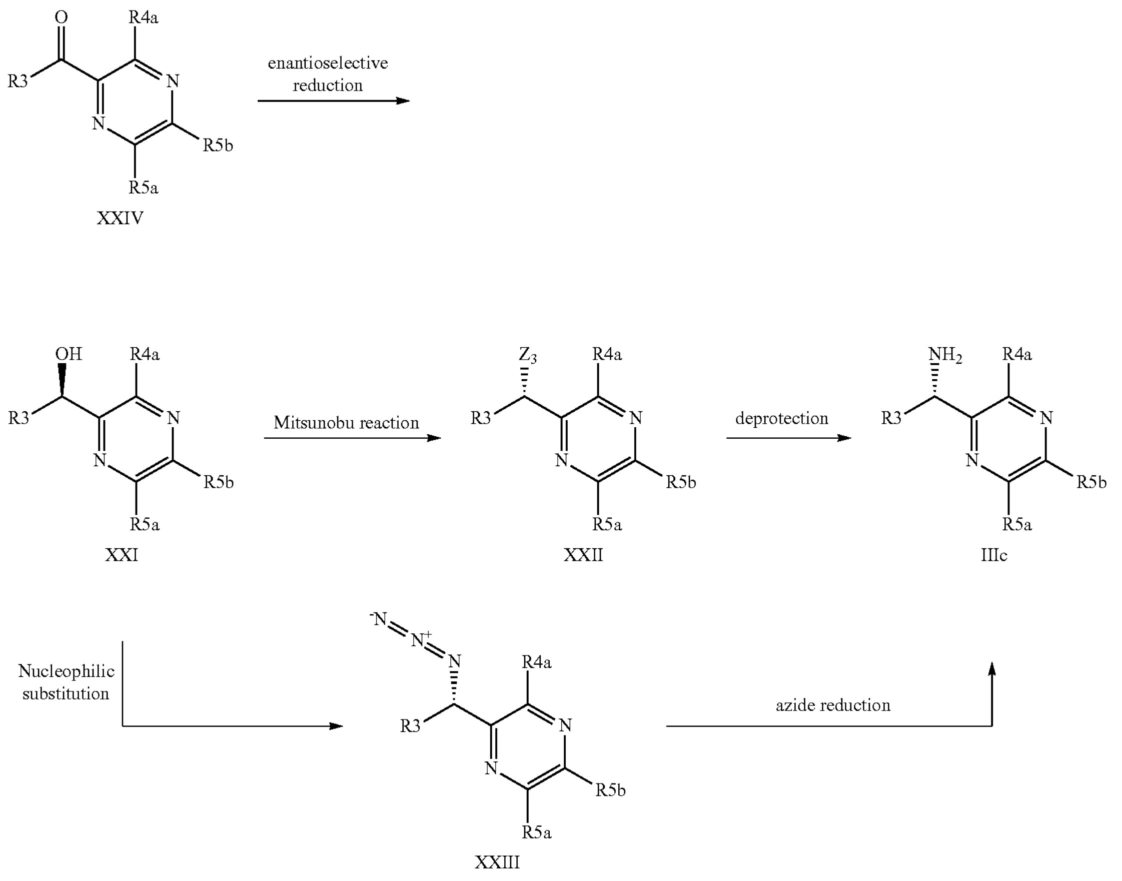

$Z_3$ = NPhth or $Boc_2N$

Amines of formula IIIc, or a salt thereof, may be obtained from intermediates of formula XXII, wherein $R_3$, $R_{4a}$, $R_{5a}$, and $R_{5b}$ are as described in formula I and $Z_3$ is —NPhth (N-phthalimide group) or —$NBoc_2$ (N-bis(tert-butyloxycarbonyl) group), typically by treatment with either hydrazine (preferably hydrazine hydrate or hydrazine monohydrate) in an alcohol solvent such as ethanol or isopropanol ($Z_3$ is —NPhth), or with an acid such as trifluoroacetic acid or hydrochloric acid in the presence of a suitable solvent such as dichloromethane, tetrahydrofuran or dioxane ($Z_3$ is —$NBoc_2$), under deprotection conditions known to a person skilled in the art, and described in the literature, such as for example in: Protective Groups in Organic Synthesis, 3rd Edition Theodora W. Green (The Rowland Institute for Science) and Peter G. M. Wuts (Pharmacia and Upjohn Company), John Wiley & Sons, Inc., New York, NY. 1999, ISBN 0-471-16019-9.

Such intermediates of formula XXII, wherein $R_3$, $R_{4a}$, $R_{5a}$, and $R_{5b}$ are as described in formula I and $Z_3$ is —NPhth (N-phthalimide group) or —$NBoc_2$ (N-bis(tert-butyloxycarbonyl) group), can be obtained from alcohols of formula XXI, wherein $R_3$, $R_{4a}$, $R_{5a}$, and $R_{5b}$ are as described in formula I, by a Mitsunobu reaction. Such a reaction involves treating alcohols of formula XXI with an azodicarboxylate, such as diethyl azodicarboxylate or diisopropyl azodicarboxylate, in the presence of a phosphine, such as triphenylphosphine or tributylphosphine, and of an amine such as phthalimide (HNPhth) or bis(tert-butoxycarbonyl)amine ($HNBoc_2$). Mitsunobu reactions are known by those skilled in the art to proceed with inversion of the stereocenter, as described for instance in *Chem. Rev.* 2009, 109, 2551-2651.

Alternatively, amines of formula IIIc may be obtained by reduction of azides of formula XXIII, wherein $R_3$, $R_{4a}$, $R_{5a}$, and $R_{5b}$ are as described in formula I, by treatment with triphenylphosphine and water (Staudinger reaction) or by hydrogenation for example using a palladium catalyst in the presence of hydrogen. Azides of formula XXIII may be obtained by treatment of alcohols of formula XXI, wherein $R_3$, $R_{4a}$, $R_{5a}$, and $R_{5b}$ are as described in formula I, with an azidation reagent such as diphenyl phosphoryl azide in a solvent such as toluene or THE in presence of a base such as DBU. Such processes are known by those skilled in the art to proceed with inversion of the stereocenter and are described in the literature for instance in *Adv. Synth. Catal.* 2018, 360, 2157-2165.

Alcohols of formula XXI may be obtained by enantioselective reduction of ketones of formula XXIV, wherein $R_3$, $R_{4a}$, $R_{5a}$, and $R_{5b}$ are as described in formula I. Such reductions can be done using a catalyst, for instance a ruthenium or a rhodium catalyst with a chiral ligand such as RuCl[(R,R)-TsDPEN](mesitylene) or $RuBF_4$[(R,R)-TsDPEN](p-cymene) in the presence of a hydrogen donor system such as for example $HCOOH/Et_3N$ or $HCO_2NH_4$. Such processes are described in the literature for instance in *J. Org. Chem.* 2017, 82, 5607.

Alternatively, compounds of formula IIIc may also be prepared as outlined in Scheme 11.

Scheme 11

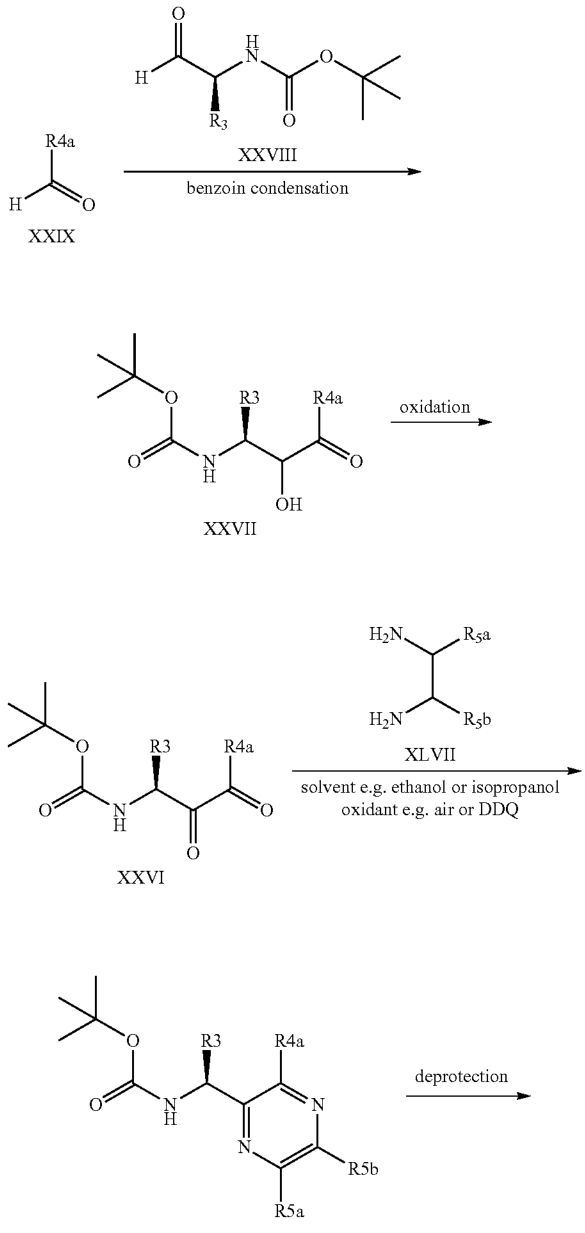

XXVIII

XXIX

XXVII

XLVII

XXVI

XXV

-continued

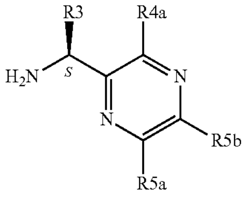

IIIc

Amines of formula IIIc, or a salt thereof (such as a hydrohalide salt, preferably a hydrochloride or a hydrobromide salt, or a trifluoroacetic acid salt, or any other equivalent salt), can be prepared by deprotection of amines of formula XXV, wherein $R_3$, $R_{4a}$, $R_{5a}$, and $R_{5b}$ are as described in formula I, for instance using an acid such as trifluoroacetic acid or hydrochloric acid, optionally in the presence of a suitable solvent such as dichloromethane, tetrahydrofuran or dioxane.

Amines of formula XXV can be obtained by condensation of diamines of formula XXVII, wherein $R_{5a}$, and $R_{5b}$ are as described in formula I, on diketones of formula XXVI, wherein $R_3$, and $R_{4a}$ are as described in formula I. This condensation can take place in the presence of a suitable solvent such as ethanol or isopropanol in presence of an oxidant such as air or DDQ.

Diketones of formula XXVI may be formed by oxidation of hydroxyketones of formula XXVII wherein $R_3$, and $R_{4a}$ are as described in formula I. This oxidation can involve for instance $SO_3$-pyridine in presence of solvents such as dichloromethane or dimethyl sulfoxide DMSO, or mixtures thereof, and a base for instance triethylamine or N,N-diisopropylethylamine, or alternatively sodium hypochlorite in presence of a catalyst such as $TEMPO/Bu_4NHSO_4$. Examples of such oxidations can be found in the literature, for instance in *Synlett,* 2014, 25, 596 or *J. Am. Chem. Soc.* 1990, 112, 5290-5313.

Hydroxyketones of formula XXVII may be synthesized by cross-benzoin condensation between aldehydes of formula XXIX, wherein $R_{4a}$ is as described in formula I, and aldehydes of formula XXVIII, wherein $R_3$ is as described in formula I.

Aldehydes of formula XXVIII are commercially available in chiral form, like for instance Boc-L-alaninal (CAS 79069-50-4) or tert-butyl N-[(1S)-1-(cyclopropylmethyl)-2-oxo-ethyl]carbamate (CAS 881902-36-9). Cross-benzoin condensations are done in the usual way by employing an organocatalyst such as a triazolium salt or a thiazolium salt in the presence of a base such as potassium tert-butoxide or N,N-diisopropylethylamine in a suitable solvent such as DCM or THE at a temperature between −20° C. and the boiling point of the solvent. Examples of catalysts for such transformations have been described in the literature for instance in *J. Am. Chem. Soc.* 2014, 136, 7539-7542 or in *Org. Lett.* 2016, 18, 4518-4521.

Scheme 12

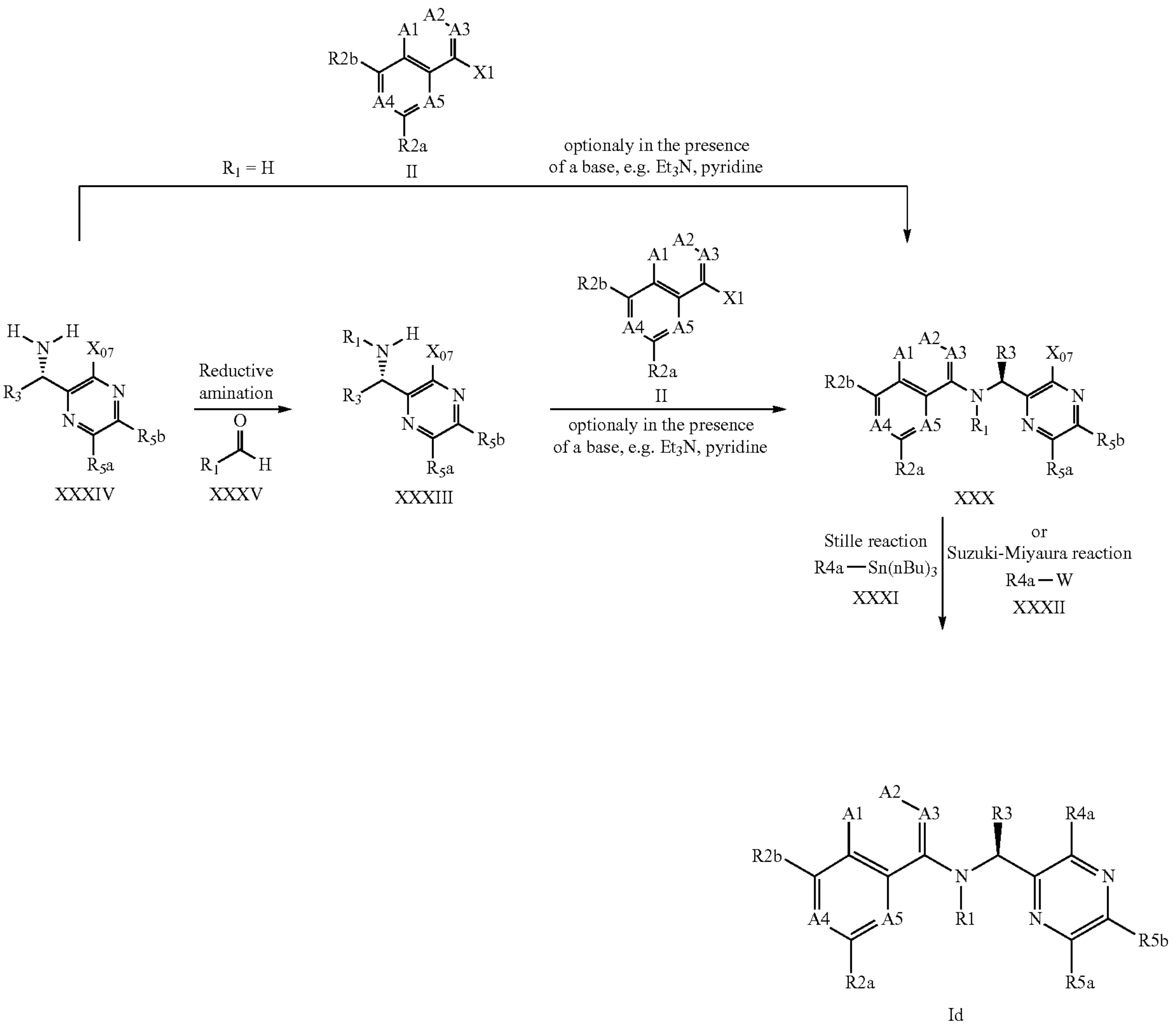

XXXIV XXXV XXXIII II XXX XXXI XXXII Id $X_{07}$ = Cl, Br, I, OMs, OTs or OTf

As shown in Scheme 12, compounds of formula Id can be alternatively prepared by reaction of compounds of formula XXX (wherein $A_1$, $A_2$, $A_3$, $A_4$, $A_5$, $R_1$, $R_{2a}$, $R_{2b}$, $R_3$, $R_{5a}$, and $R_{5b}$ are as defined in formula I and $X_{07}$ is a leaving group like, for example, chlorine, bromine, iodine) with compounds of formula XXXI (Stille reaction; $R_{4a}$ in XXXI is as defined in formula I) or compounds of formula XXXII (Suzuki-Miyaura reaction; $R_{4a}$ in XXXII is as defined in formula I and W is a boronic acid $B(OH)_2$ group, or a corresponding boronate, such as a pinacol ester of said boronic acid) in the presence of a palladium catalyst as described in detail in Scheme 7.

Compounds of formula XXX can be prepared by coupling of amines of formula XXXIII and compounds of formula II, wherein $A_1$, $A_2$, $A_3$, $A_4$, $A_5$, $R_{2a}$, $R_{2b}$ and X1 are described in Scheme 1, under the conditions described in detail in Scheme 1. Under the same conditions, if $R_1$=H, compounds of formula XXX may be obtained directly from compounds of formula XXXIV.

Compounds of formula XXXIII can be prepared by treatment of compounds of formula XXXIV, with compounds of formula XXXV (wherein $R_1$ is as defined in formula I), e.g. in the presence of $NaBH(OAc)_3$ or $NaBH_3CN$, in a suitable solvent, preferably in acetic acid at room temperature analogous to WO2002/088073, page 35.

Alternatively, another reagent system for the reductive amination uses a combination of $Ti(i\text{-}OiPr)_4$ and $NaBH_4$ (see Synthesis 2003 (14), 2206).

Amines of formula XXXIV can be prepared by deracemization procedure method, which involves for example, a selective acylation of one enantiomer. Such an example is described more in details in Scheme 13.

Scheme 13

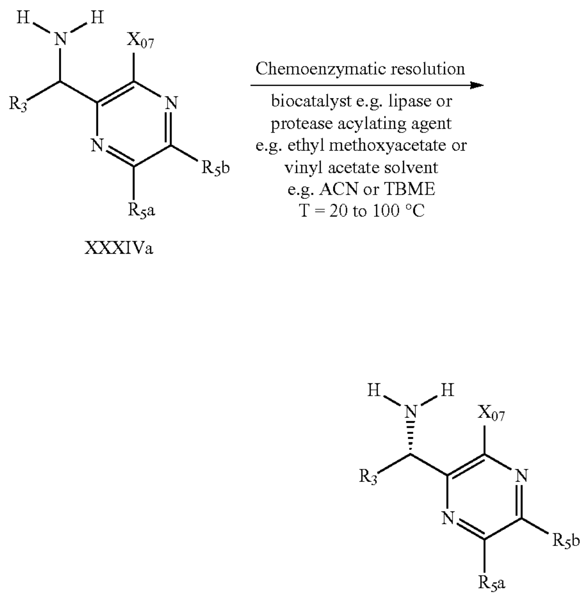

XXXIVa

XXXIV $X_{07}$ = Cl, Br, I, OMs, OTs or OTf

Amines of formula XXXIV may be obtained by biocatalyzed deracemization of amines of formula XXXIVa, wherein $R_3$, $R_{5a}$, and $R_{5b}$ are as in formula I and $X_{07}$ is a leaving group such as bromine, chlorine or iodine. This may be done for instance using a lipase, e.g. *Candida Antarctica* lipase B or *Pseudomonas fluorescens* lipase, eventually in immobilized form (e.g. Novozym® 435) in presence of an acyl donor, e.g. ethyl methoxyacetate or vinyl acetate, in a suitable solvent such as acetonitrile or methyl tert-butyl ether at temperatures between 20° C. to 100° C. Such processes are described for instance in *J. Org. Chem.* 2007, 72, 6918-6923 or *Adv. Synth. Catal.* 2007, 349, 1481-1488. The expected stereochemical outcome of such enzymatic deracemization are known of those skilled in the art and are documented in the literature, for instance in *J. Org. Chem.* 1991, 56, 2656-2665 or *J. Am. Chem. Soc.* 2015, 137, 3996-4009.

Alternatively, resolution of amines of formula XXXIVa to give amines of formula XXXIV may be achieved using a chiral auxiliary, as described in Scheme 14.

Scheme 14

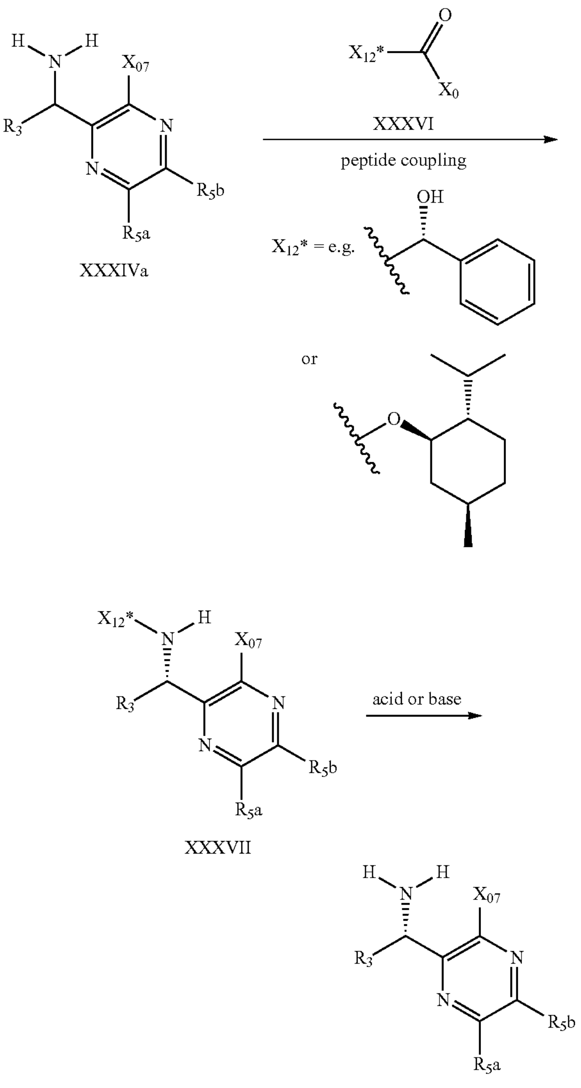

XXXIVa

XXXVI

XXXVII

XXXIV $X_{07}$ = Cl, Br, I, OMs, OTs or OTf

Amines of formula XXXIV can be prepared from intermediates of formula XXXVII, wherein $R_3$, $R_{5a}$, and $R_{5b}$ are as in compounds of the formula I, $X_{07}$ is a leaving group such as bromine, chlorine or iodine, and X12* is a chiral auxiliary, by treatment with acids such as HCl or bases such as NaOH. Chiral auxiliaries of formula XXXVI are for instance mandelic acid or (1R)-menthylchloroformate. Intermediates of formula XXXVII can be formed by coupling of a chiral auxiliary of formula XXXVI, wherein $X_0$ is a leaving group, such as chlorine, with amines of the formula XXXIVa following the conditions detailed in Scheme 1. Examples of such deracemization processes are reported in the literature, for instance in *J. Org. Chem.* 2007, 72, 485-493.

Alternatively, amines of formula XXXIV or a salt thereof (such as a hydrohalide salt, preferably a hydrochloride or a hydrobromide salt, or a trifluoroacetic acid salt, or any other equivalent salt), can be formed as described in Scheme 15.

Scheme 15

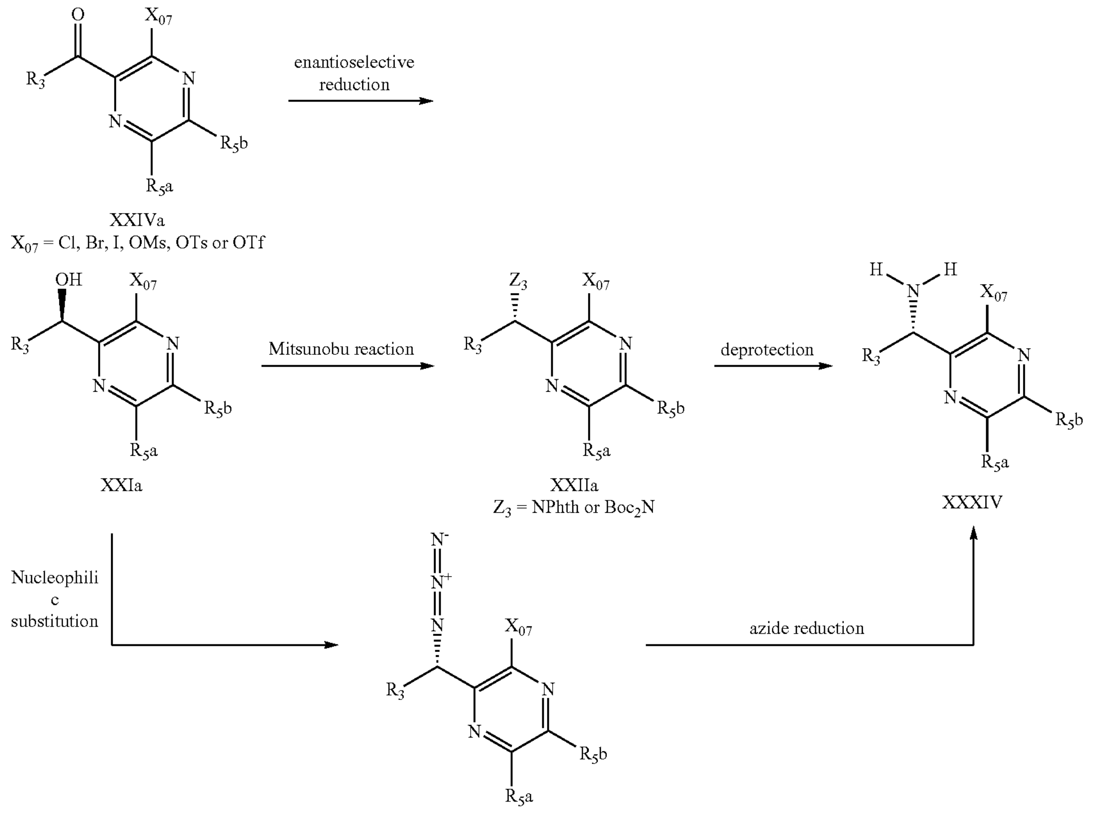

XXIVa $X_{07}$ = Cl, Br, I, OMs, OTs or OTf

XXIa

XXIIa $Z_3$ = NPhth or $Boc_2N$

XXXIV

XXIIIa

Amines of formula XXXIV, or a salt thereof, may be obtained from intermediates of formula XXIIa, wherein $R_3$, $R_{5a}$, and $R_{5b}$ are as described in formula I, X07 is a leaving group such as a halogen or sulfonate, for instance bromide, and $Z_3$ is —NPhth (N-phthalimide group) or —$NBoc_2$ (N-bis(tert-butyloxycarbonyl) group), typically by treatment with either hydrazine (preferably hydrazine hydrate or hydrazine monohydrate) in an alcohol solvent such as ethanol or isopropanol ($Z_3$ is —NPhth), or with an acid such as trifluoroacetic acid or hydrochloric acid in the presence of a suitable solvent such as dichloromethane, tetrahydrofuran or dioxane ($Z_3$ is —$NBoc_2$), under deprotection conditions known to a person skilled in the art, and described in the literature, such as for example in: Protective Groups in Organic Synthesis, 3rd Edition Theodora W. Green (The Rowland Institute for Science) and Peter G. M. Wuts (Pharmacia and Upjohn Company), John Wiley & Sons, Inc., New York, NY. 1999, ISBN 0-471-16019-9.

Such intermediates of formula XXIIa, wherein $R_3$, $R_{5a}$, and $R_{5b}$ are as described in formula I, $X_{07}$ is a leaving group such as a halogen or sulfonate, for instance bromide, and $Z_3$ is —NPhth (N-phthalimide group) or —$NBoc_2$ (N-bis(tert-butyloxycarbonyl) group), can be obtained from alcohols of formula XXIa, wherein $R_3$, $R_{5a}$, and $R_{5b}$ are as described in formula I and $X_{07}$ is a leaving group, by a Mitsunobu reaction. Such a reaction involves treating alcohols of formula XXIa with an azodicarboxylate, such as diethyl azodicarboxylate or diisopropyl azodicarboxylate, in the presence of a phosphine, such as triphenylphosphine or tributylphosphine, and of an amine such as phthalimide (HNPhth) or bis(tert-butoxycarbonyl)amine ($HNBoc_2$). Mitsunobu reactions are known by those skilled in the art to proceed with inversion of the stereocenter, as described for instance in *Chem. Rev.* 2009, 109, 2551-2651.

Alternatively, amines of formula XXXIV may be obtained by reduction of azides of formula XXIIIa, wherein $R_3$, $R_{5a}$, and $R_{5b}$ are as described in formula I and X07 is a leaving group such as a halogen or sulfonate, for instance bromide, by treatment with triphenylphosphine and water (Staudinger reaction) or by hydrogenation for example using a palladium catalyst in the presence of hydrogen. Azides of formula XXIIIa may be obtained by treatment of alcohols of formula XXIa with an azidation reagent such as diphenyl phosphoryl azide in a solvent such as toluene or THE in presence of a base such as DBU. Such processes are known by those skilled in the art to proceed with inversion of the stereocenter and are described in the literature for instance in *Adv. Synth. Catal.* 2018, 360, 2157-2165.

Alcohols of formula XXIa may be obtained by enantioselective reduction of ketones of formula XXIVa, wherein $R_3$, $R_{5a}$, and $R_{5b}$ are as described in formula I and X07 is a leaving group such as a halogen or sulfonate, for instance bromide. Such reductions can be done using catalysts, for instance a ruthenium or a rhodium catalyst with a chiral ligand such as RuCl[(R,R)-TsDPEN](mesitylene) or $RuBF_4$ [(R,R)-TsDPEN](p-cymene) in the presence of a hydrogen donor system such as for example $HCOOH/Et_3N$ or $HCO_2NH_4$. Such processes are described in the literature for instance in *J. Org. Chem.* 2017, 82, 5607.

Compounds of Formula II

II

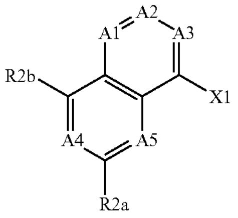

wherein X1 is a leaving group, such as a halogen or sulfonate, for instance chloride, can be made, for example, as shown in Schemes 16, 17 and 18.

Scheme 16

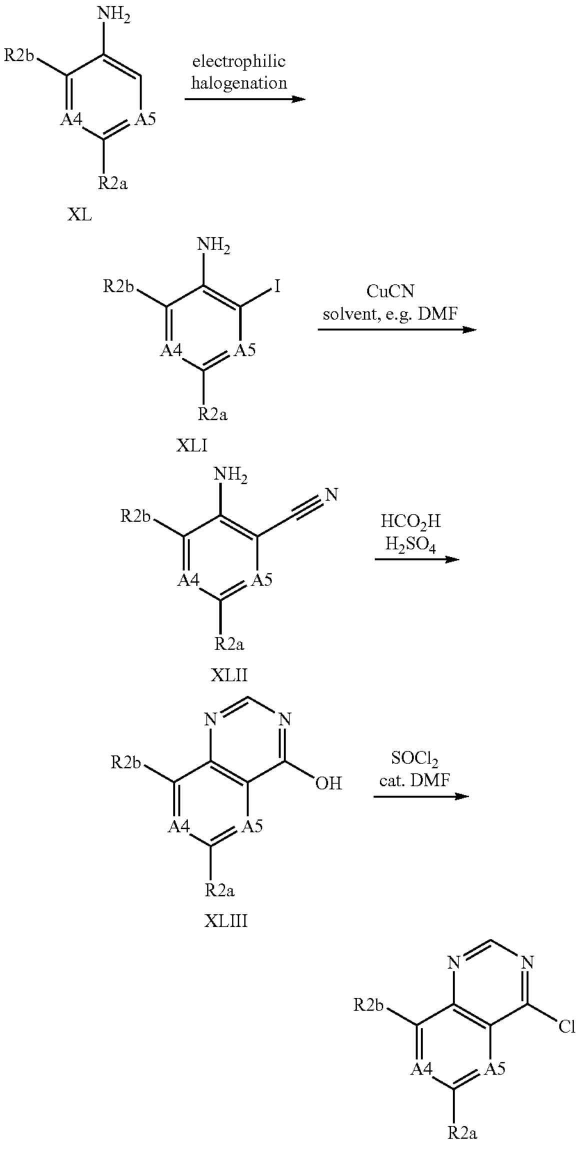

XL

XLI

XLII

XLIII

IIa

Compounds of formula IIa wherein $R_{2a}$, $R_{2b}$, A4 and A5 are as described in formula I, can be prepared according to reaction scheme 16. Compounds of formula XLII are either known, or they can be prepared by methods known to a person skilled in the art. For example, a compound of formula XL is reacted with an electrophilic iodinating reagent, such as N-iodosuccinimide, in a solvent, such as hexafluoroisopropanol, as described for example in *J. Org. Chem.* 2018, 83, 930, to obtain compounds of formula XLI. Cyanation of compounds of formula XLI with copper(I) cyanide in a solvent, such as DMF, at temperatures such as 100° C., provides compounds of formula XLII (procedure analogous to WO2005/100298, page 44). Treatment of compounds of formula XLII with formic acid and sulfuric acid at temperatures between 8° and 100° C., provides compounds of formula XLIII (procedure analogous to WO2018/206539, page 80). Subsequent conversion of compounds of formula XLIII to compounds of formula IIa is accomplished via methods known to the person skilled in the art, for example with thionyl chloride in presence of catalytic N,N-dimethylformamide at reflux, analogous to WO2015/54572, page 263.

Scheme 17

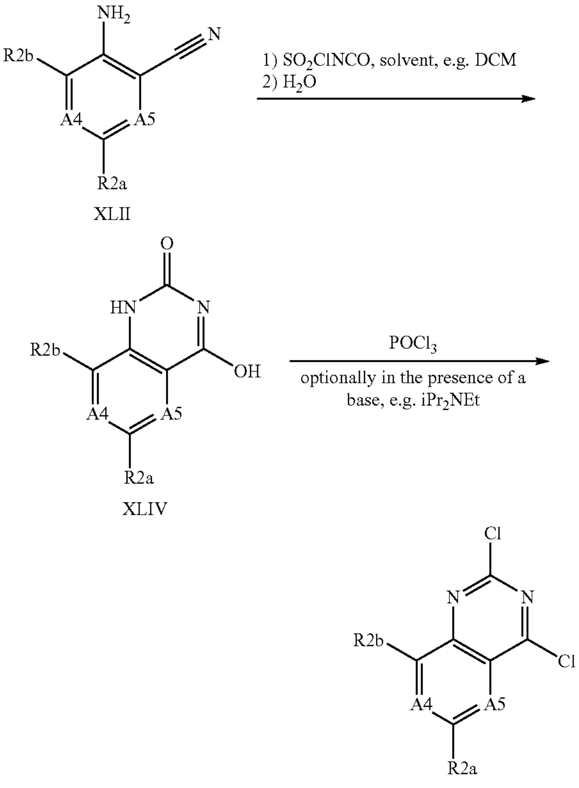

XLII

XLIV

IIb

Compounds of formula IIb wherein $R_{2a}$, $R_{2b}$, A4 and A5 are as described in formula I, can be prepared according to reaction scheme 17. A compound of formula XLII, prepared as in Scheme 16, is reacted with chlorosulfonyl isocyanate, then further reacted with water at reflux, as described for example in *Synth. Commun.* 1988, 18, 525, to provide intermediates of formula XLIV. Subsequent conversion of intermediates of formula XLIV to compounds of formula IIb is accomplished using chlorinating reagents, such as $POCl_3$, optionally in the presence of base, such as N,N-diisopropylethylamine. These chlorinating methods are well known to the person skilled in the art, and are described for example in WO2021/148639.

Scheme 18

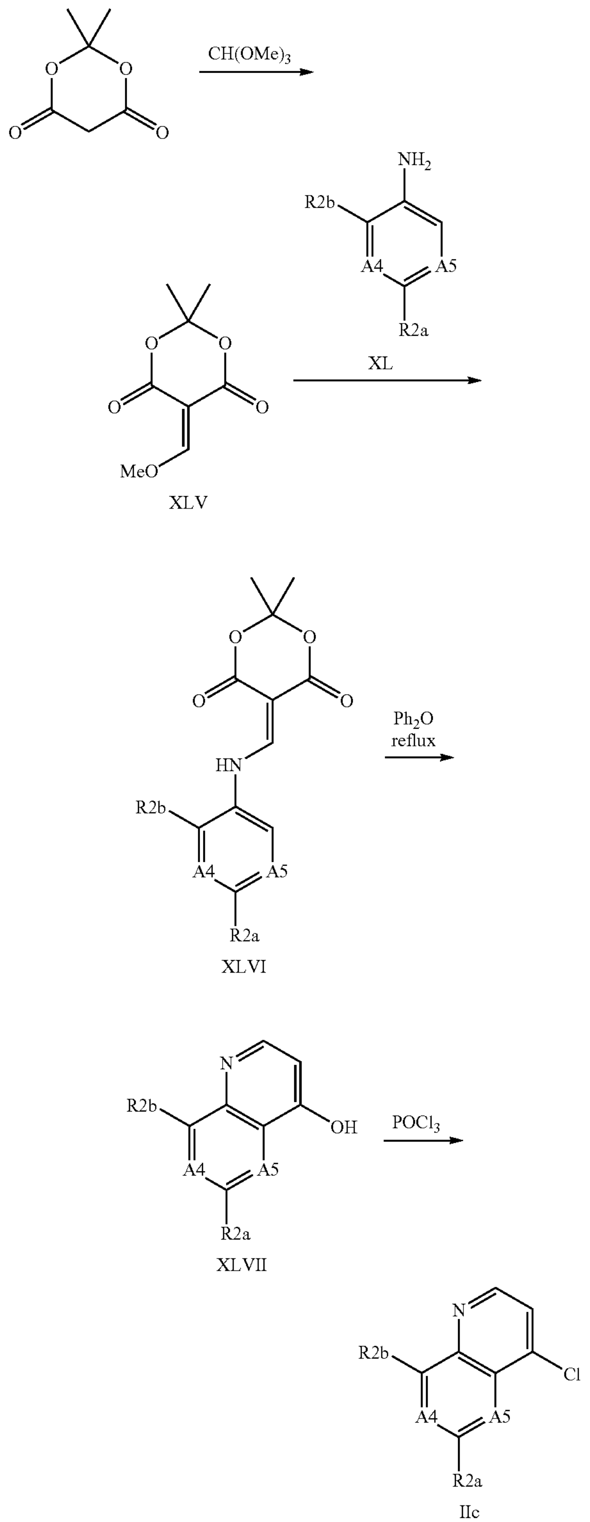

XL

XLV

XLVI

XLVII

IIc

Compounds of formula IIc wherein $R_{2a}$, $R_{2b}$, A4 and A5 are as described in formula I, can be prepared according to reaction scheme 18, analogous to procedures found in *Chem Cat Chem* 2017, 10, 965. Meldrum's acid is converted to compound XLV by refluxing in trimethyl orthoformate and further converted to compounds of formula XLVI in the same pot by addition of anilines of formula XL. Compounds of formula XLVI are refluxed in diphenyl ether to obtain 4-hydroxyquinolines of formula XLVII. Compounds of formula IIc are then obtained via chlorination of compounds of formula XLVII using chlorinating reagents, such as $POCl_3$, well known to the person skilled in the art.

Compounds of Formula IVc

IVc

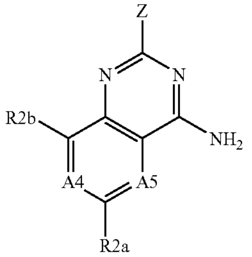

can be made, for example, as shown in Scheme 19.

Scheme 19

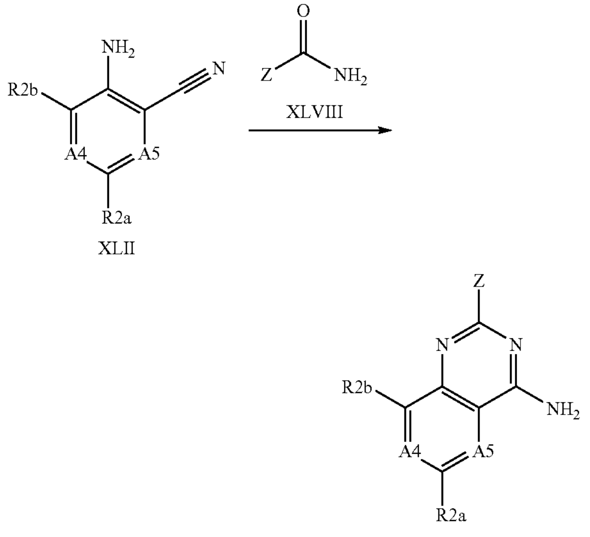

XLVIII

XLII

IVc

Compounds of formula IVc wherein Z is H, $C_1$-$C_3$ alkyl, cyclopropyl, $CF_3$, and wherein $R_{2a}$, $R_{2b}$, A4 and A5 are as described in formula I, can be prepared according to reaction scheme 19. Compounds of formula XLII, prepared as in Scheme 16, are reacted in the presence of compounds of formula XLVIII at elevated temperatures, such as 180° C., as described for example in *Eur. J. Med. Chem.* 2017, 141, 446, to provide amines of formula IVc.

Alternatively, compounds of the formula Iab can be made, for example, as shown in Scheme 20.

Scheme 20

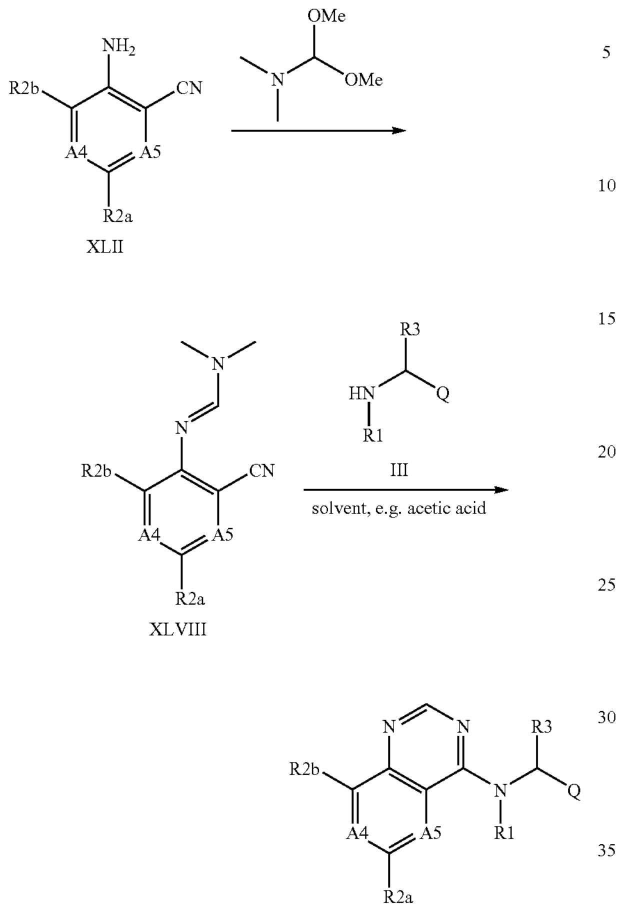

XLII

XLVIII

Iab

Compounds of formula Iab, wherein $R_1$, $R_{2a}$, $R_{2b}$, R3, A4, A5, Q is as described in formula I, can be prepared according to scheme 20, analogous to the procedures in WO2010/093419, page 225. Compounds of formula XLII, prepared as in Scheme 16, are treated with N,N-dimethylformamide dimethyl acetal at elevated temperature, preferably 90° C., to provide formamidine products of formula XLVIII. Reaction with amines of formula III at elevated temperature, preferably 120° C., in a suitable solvent, preferably acetic acid, provides compounds of formula Iab.

Compounds of the Formula if

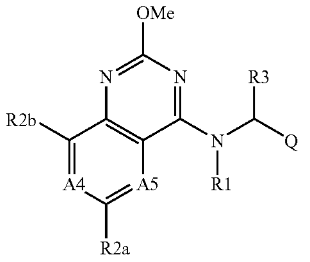

If can be made, for example, as shown in Scheme 21.

Scheme 21

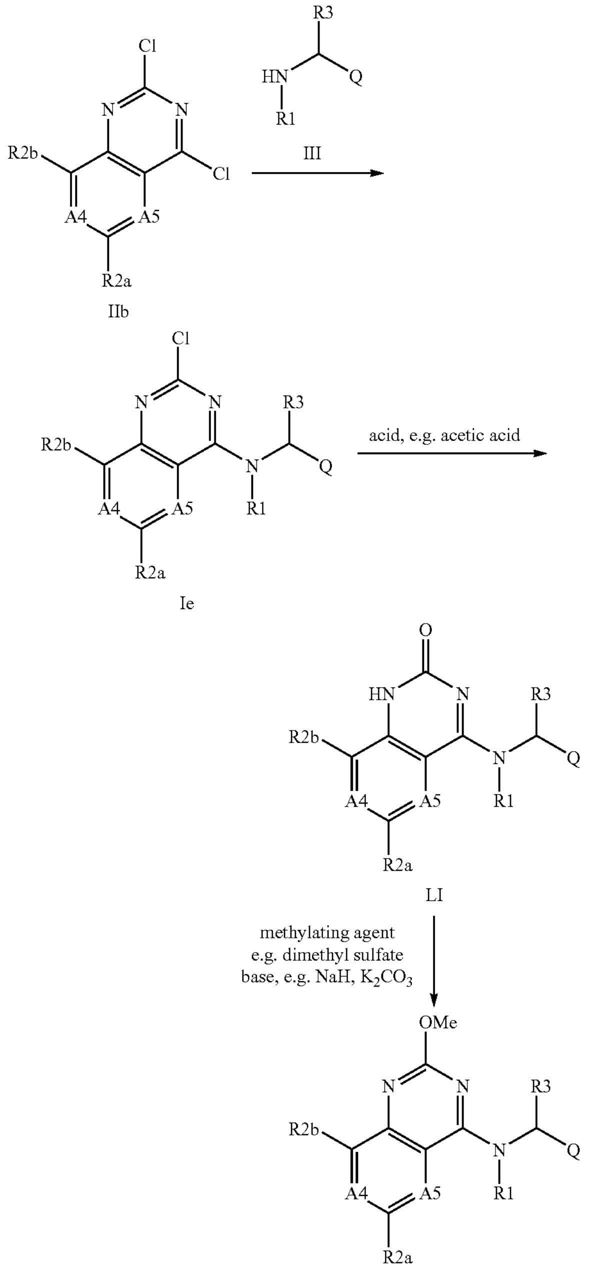

IIb

Ie

LI

If

Compounds of formula If, wherein $R_1$, $R_{2a}$, $R_{2b}$, R3, A4, A5, Q is as described in formula I, can be prepared according to Scheme 21. Reaction of compounds of formula IIb, prepared as in Scheme 17, wherein $R_{2a}$, $R_{2b}$, A4 and A5 are as described in formula I, with amines of formula III, or a salt thereof (such as a hydrohalide salt, preferably a hydrochloride or a hydrobromide salt, or a trifluoroacetic acid salt, or any other equivalent salt), wherein R1, R3 and Q are as described in formula I, using procedures presented in Scheme 1, provides compounds of formula Ie. Treatment of compounds of formula Ie under acidic conditions, preferably with acetic acid, at elevated temperatures, preferably between 7° and 80° C., as described in Heterocycles 1996, 43, 2607, provides intermediates of formula LI. Methylation of compounds of formula LI to obtain compounds of formula If can be achieved using an electrophilic methyl sources, such as dimethyl sulfate or methyl iodide, in the presence of a base, such as potassium carbonate or sodium hydride, as well known to the person skilled in the art.

Compounds of the Formula Ig

Ig

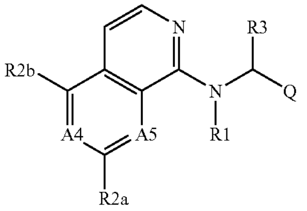

can be made, for example, as shown in Scheme 22.

Scheme 22

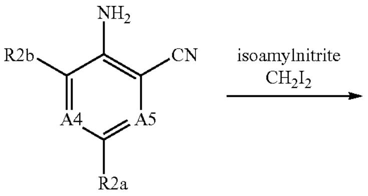

XLII

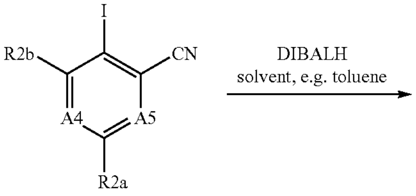

LX

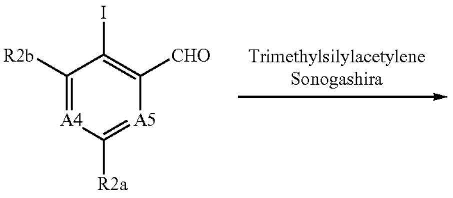

LXI

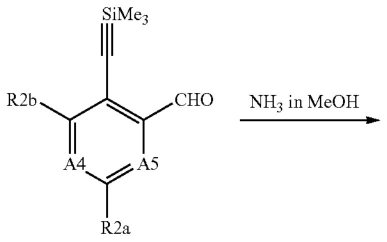

LXII

-continued

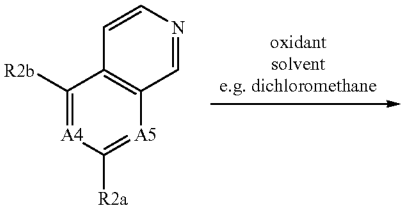

LXIII

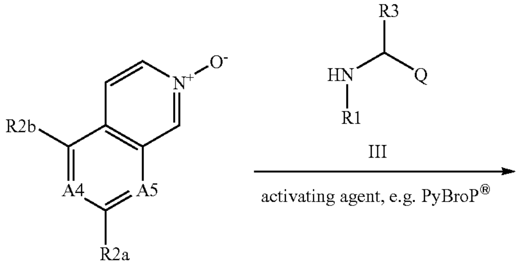

LXIV

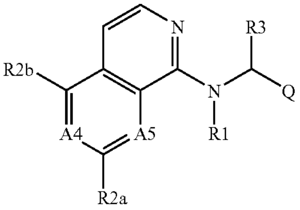

Ig

Compounds of formula Ig, wherein $R_1$, $R_{2a}$, $R_{2b}$, R3, A4, A5, Q is as described in formula I, can be prepared according to Scheme 22. A compound of formula XLII, as prepared in Scheme 16, is treated with a diazotizing reagent, preferably isoamylnitrite, in diiodomethane solvent, at elevated temperature, preferably 80° C., as described in *J. Org. Chem.* 1990, 55, 2543, to provide intermediates of formula LX. Reduction of compounds of formula LX is achieved in the presence of a selective reductant, such as diisobutylaluminum hydride (DIBALH), in a solvent, such as toluene, at low temperatures, preferably −78° C., and gives a compound of formula LXI. Subsequent Sonogashira coupling in the presence of suitable palladium and copper catalysts, preferably bis(triphenylphosphine)palladium chloride and copper (I) iodide, with trimethylsilylacetylene, in a solvent, such as triethylamine, gives compounds of formula LXII. Cyclization with ammonia in methanol gives compounds of formula LXIII. Procedures are analogous to those described for example in *Eur. J. Med. Chem.* 2016, 118, 170. Treatment of compounds of formula LXIII with an oxidant, such as 3-chloro-benzenecarboperoxoic acid or hydrogen peroxide, in a solvent, preferably dichloromethane, gives N-oxides of formula LXIV. Such oxidations are well known to the person skilled in the art. Coupling of compounds of formula LXIV with amines of formula III in the presence of a suitable activator, such as bromotripyrrolidinophosphonium hexafluorophosphate (PyBroP®), potentially in the presence of base, such as N,N-diisopropylethylamine, analogous to procedure described in WO2016/123627, page 87, gives compounds of formula Ig.

Compounds of Formula IId

IId

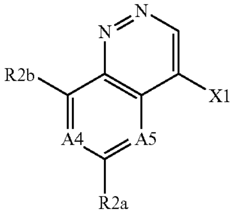

wherein X1 is a leaving group, such as a halogen or sulfonate, for instance chloride, can be made, for example, as shown in Scheme 23.

Compounds of Formula IIe

IIe

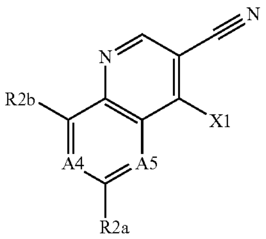

Scheme 23

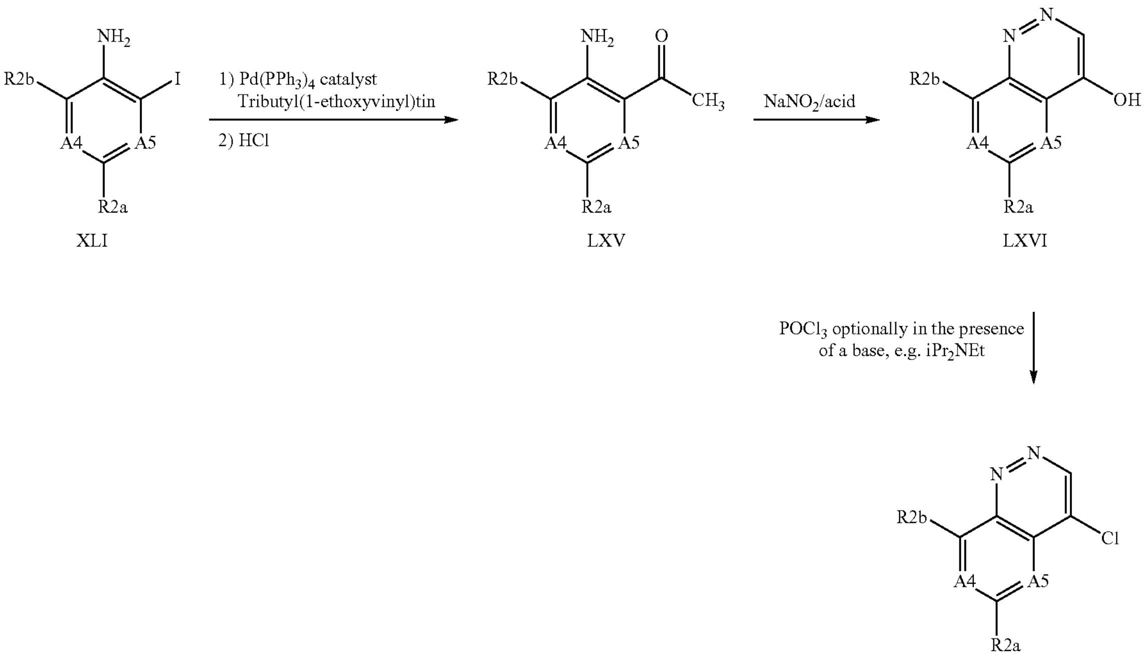

XLI LXV LXVI IId

Compounds of formula IIId, wherein $R_{2a}$, $R_{2b}$, A4, A5 are as described in formula I, can be prepared according to Scheme 23. A compound of formula XLI, as prepared in Scheme 16, is treated with a palladium catalyst, preferably $Pd(PPh_3)_4$, along with tributyl(1-ethoxyvinyl)tin, at elevated temperature, preferably 105° C., as described in EP1782811, page 57, to provide intermediates of formula LXV. Treatment of compounds of formula LXV with aqueous sodium nitrite in the presence of acids, such as hydrochloric acid or a sulfuric acid/acetic acid mixture at low temperatures, preferably between 0 and 5° C., analogous to *Bioorg. Med. Chem. Lett.*, 25, 919, gives compounds of formula LXVI. Compounds of formula IId are then obtained via chlorination of compounds of formula LXVI using chlorinating reagents, such as $POCl_3$, optionally in the presence of an amine base, such as N,N-diisopropylethylamine, well known to the person skilled in the art.

wherein X1 is a leaving group, such as a halogen or sulfonate, for instance chloride, can be made, for example, as shown in Scheme 24.

Scheme 24

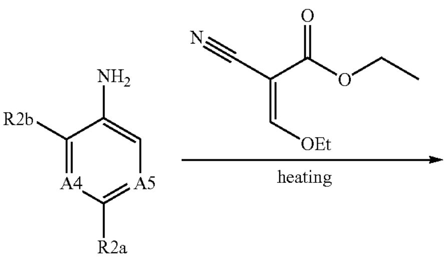

XL

-continued

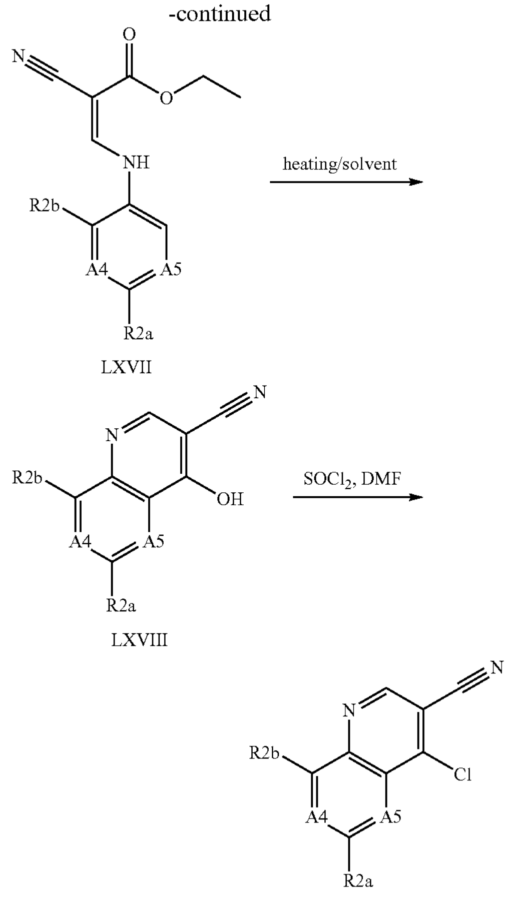

LXVII

LXVIII

IIe

Compounds of formula IIe, wherein $R_{2a}$, $R_{2b}$, A4, A5 are as described in formula I, can be prepared according to Scheme 24. A compound of formula XL is heated with ethyl 2-cyano-3-ethoxyacrylate at elevated temperature, preferably 140° C., as described in *Tetrahedron Letters,* 2015, 56, 5112, to provide intermediates of formula LXVII. Heating of compounds of formula LXVII at elevated temperatures, preferably between at 260° C., in a solvent, preferably diphenyl ether or diphenyl ether-biphenyl eutectic mixture (Dowtherm A®), gives compounds of formula LXVIII. Subsequent conversion to compounds of formula IIe is accomplished via according to methods known to the person skilled in the art, for example with thionyl chloride in presence of catalytic N,N-dimethylformamide at reflux, analogous to US2003/212276, page 15.

Compounds of the Formula Ih

Ih

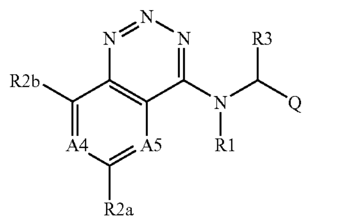

can be made, for example, as shown in Scheme 25.

Scheme 25

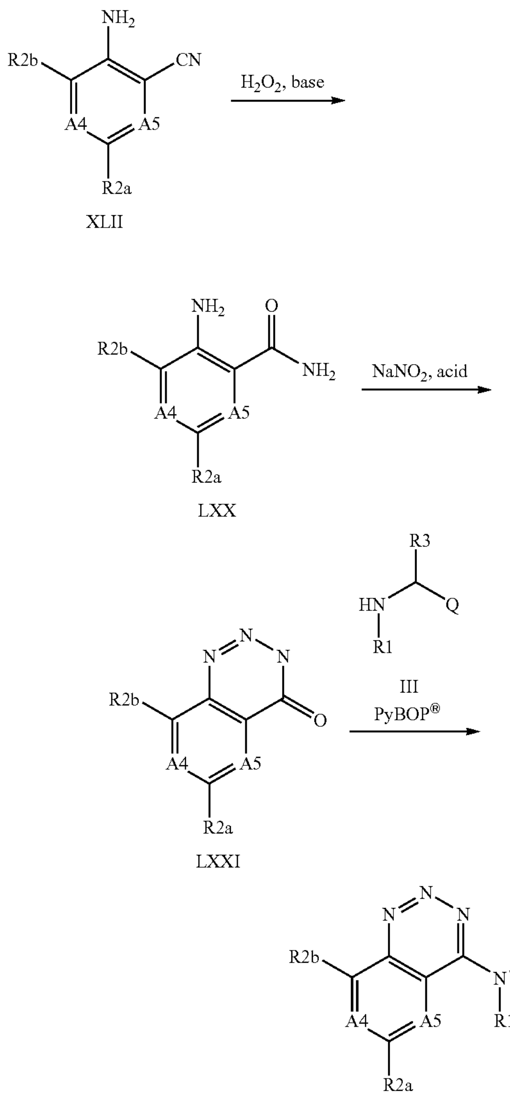

XLII

LXX

LXXI

Ih

Compounds of formula Ih, wherein R1, $R_{2a}$, $R_{2b}$, R3, A4, A5, Q is as described in formula I, can be prepared according to Scheme 25. A compound of formula XLII, as prepared in Scheme 16, is treated with hydrogen peroxide, either as an aqueous solution or as an urea adduct, in methanol-water solvent, in the presence of base, preferably potassium carbonate, analogous to WO2011/4276, page 132, to provide intermediates of formula LXX. Treatment of compounds of formula LXX with aqueous sodium nitrite in the presence of acids, such as hydrochloric acid or a sulfuric acid/acetic acid mixture at low temperatures, preferably between 0 and 5° C., analogous to US2014/0275072, paragraph 133, gives compounds of formula LXXI. Coupling of compounds of formula LXXI with amines of formula III in the presence of a suitable activator, such as (benzotriazol-1-yloxy)tripyrrolidinophosphonium hexafluorophosphate (PyBoP®), in the presence of base, such as N,N-diisopropylethylamine, analogous to procedure described in WO2014/085528, page 55, gives compounds of formula Ih.

Compounds of the Formula Ii

Ii

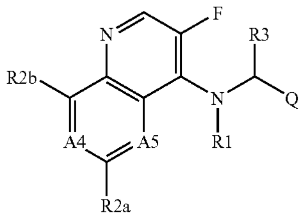

can be made, for example, as shown in Scheme 26.

Scheme 26

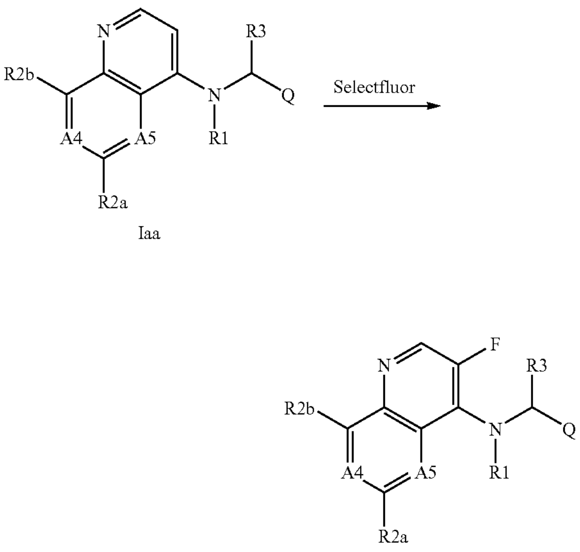

Iaa

Ii

Compounds of formula Ii, wherein $R_1$, $R_{2a}$, $R_{2b}$, $R_3$, A4, A5, Q is as described in formula I, can be prepared according to Scheme 26. A compound of formula Iaa, as prepared in Scheme 1, 5 or 6, is treated with a fluorinating reagent, preferably 1-chloromethyl-4-fluoro-1,4-diazoniabicyclo [2.2.2]octane bis(tetrafluoroborate) (Selectfluor), in a solvent, preferably acetonitrile, analogous to WO2018/34917, page 91, to provide compounds of formula Ii.

Compounds of the Formula Lj

Ij

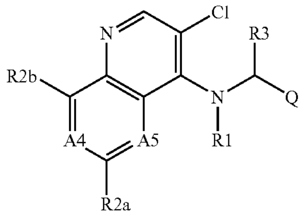

can be made, for example, as shown in Scheme 27.

Scheme 27

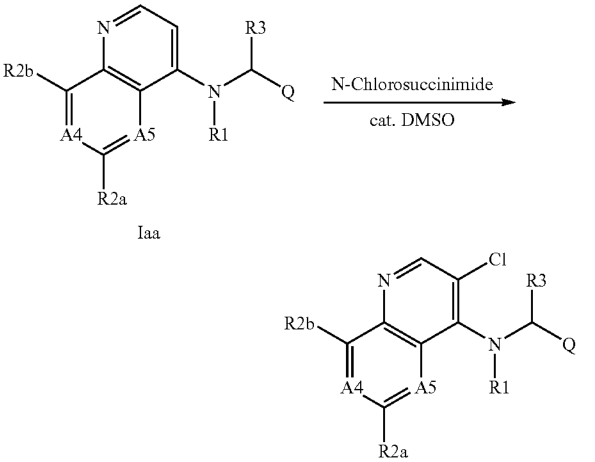

Iaa

Ij

Compounds of formula Ij, wherein $R_1$, $R_{2a}$, $R_{2b}$, $R_3$, A4, A5, Q is as described in formula I, can be prepared according to Scheme 27. A compound of formula Iaa, as prepared in Scheme 1, 5 or 6, is treated with a chlorinating reagent, preferably N-chlorosuccinimide, in the presence of catalytic dimethyl sulfoxide (DMSO), in a solvent, preferably dichloromethane, analogous to Nature Catalysis, 2020, 3, 107, to provide compounds of formula Ij.

Certain compounds of formula III, or a salt thereof (such as a hydrohalide salt, preferably a hydrochloride or a hydrobromide salt, or a trifluoroacetic acid salt, or any other equivalent salt), wherein $R_1$, $R_3$ and Q have the same meaning as given above for compounds of the formula I, can be synthesized in analogy to literature precedent.

For example, certain compounds of the formula IIIa and IIIb as defined below, or a salt thereof, wherein R1, R3, R4a, R5a and R5b are as described in formula I, can be prepared in analogy to descriptions found in WO 2021/069575, particularly those compounds of the formula IIIa and IIIb, or a salt thereof, wherein R3 and R4a are as described in formula I and in which R1, R5a and R5b are hydrogen.

IIIa

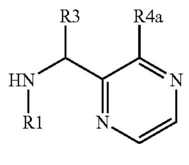

IIIb

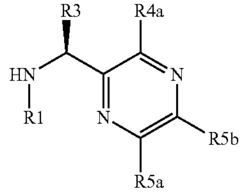

Similarly, certain compounds of the formula IIIe and IIIf as defined below, or a salt thereof, wherein R1, R3, R4 and R5 are as described in formula I, particularly those compounds of the formula IIIe and IIIf, or a salt thereof, wherein R3 and R4 are as described in formula I and in which R1 is hydrogen and R5 is hydrogen, methyl or cyclopropyl, can be prepared in analogy to descriptions found for example in WO 2021/099303, WO 2021/105091, WO 2021/165195 and WO 2021/224323.

IIIe

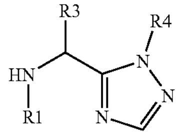

IIIf

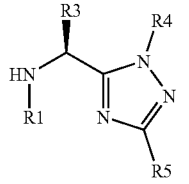

Compounds of the formula IIIa, or a salt thereof, wherein R4a is 1,2,4-thiadiazol-3-yl and R3 is methyl, defining compounds of the formula IIIa-T, or a salt thereof, wherein R1 is as defined under formula I, can be prepared as shown in Scheme 28 below, by reacting compounds of the formula IIIa-T1 with an amine of the formula XIX, or a salt thereof, wherein R1 is as defined under formula I, in the presence of a reducing agent, under conditions already detailed in schemes 2 and 7.

Compounds of the formula IIIa-T2 can be prepared by reacting compounds of the formula IIIa-T3, wherein $X_{08}$ is a halogen (or a pseudo-halogen leaving group, such as a triflate), preferably bromine or chlorine, with tributyl(1-ethoxyvinyl)tin under Stille cross-coupling conditions. Such a Stille reaction is usually carried out in the presence of a palladium catalyst, for example tetrakis(triphenylphosphine) palladium(0), or bis(triphenylphosphine) palladium(II) dichloride, in an inert solvent such as N,N-dimethylformamide, acetonitrile, toluene or dioxane, optionally in the presence of an additive, such as cesium fluoride, or lithium chloride, and optionally in the presence of a further catalyst, for example copper(I)iodide. Such Stille couplings are also well known to those skilled in the art, and have been described in for example J. Org. Chem., 2005, 70, 8601-8604, J. Org. Chem., 2009, 74, 5599-5602, and Angew. Chem. Int. Ed., 2004, 43, 1132-1136.

Alternatively, compounds of formula IIIa-T3 can be transformed directly into the compounds of formula IIIa-T1 over the two Stille reaction/hydrolysis steps without the formal isolation of the compounds of formula IIIa-T2.

Compounds of the formula IIIa-T3, wherein X08 is a halogen (or a pseudo-halogen leaving group, such as a triflate), preferably bromine or chlorine, can be prepared by saponification/decarboxylation of the compounds of the formula IIIa-T4, wherein X08 is a halogen (or a pseudo-halogen leaving group, such as a triflate), preferably bromine or chlorine, and in which Ra is $C_1$-$C_6$alkyl, under conditions known to a person skilled in the art (using for example conditions such as: aqueous sodium, potassium or Scheme 28

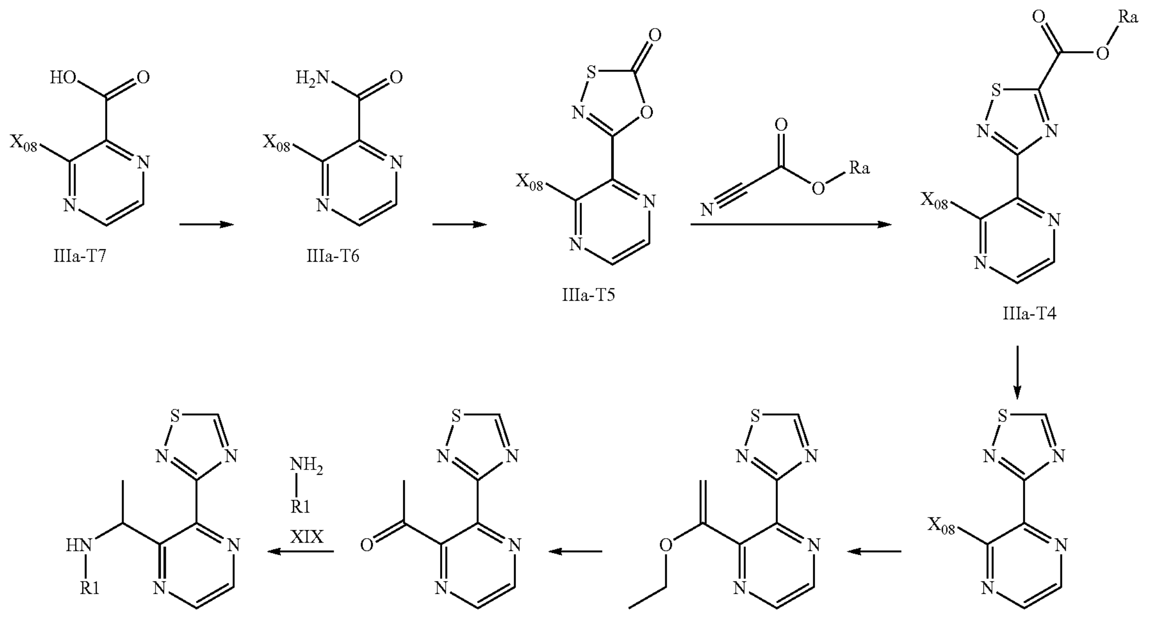

IIIa-T7 IIIa-T6 IIIa-T5 IIIa-T4

IIIa-T IIIa-T1 IIIa-T2 IIIa-T3

Compounds of the formula IIIa-T1 can be prepared by hydrolysis of enol-ether compounds of the formula IIIa-T2, typically under aqueous acidic conditions known to a person skilled in the art (e.g. HCl aq. in acetonitrile, tetrahydrofuran or dioxane), and described in, for example, J. K. Stille et al., J. Org. Chem. 55, 3114-8 (1990).

lithium hydroxide in methanol, ethanol, tetrahydrofuran or dioxane at room temperature, or up to refluxing conditions; followed by acidification of the reaction mixture under standard aqueous acid conditions or for example under acidic conditions in the presence of HCl or para-toluene sulfonic acid; see for example U.S. Pat. No. 6,444,668 B1). Alternatively, treating compounds of the formula IIIa-T4 with halide anions, preferably chloride anions, originating from, for example, lithium chloride or sodium chloride, in solvents such as N,N-dimethylformamide, N,N-dimethylacetamide, N-methyl-2-pyrrolidone or dimethylsulfoxide DMSO, optionally in presence of additional water, may also generate the compounds of compounds of the formula IIIa-T3. The reaction temperature for such a transformation (Krapcho O-dealkylation/decarboxylation) range preferentially from 20° C. to the boiling point of the reaction mixture, or the reaction may be performed under microwave irradiation. Similar chemistry has been described in, for example, Synthesis 2010, No. 19, 3332-3338.

Compounds of the formula IIIa-T4, wherein X08 is a halogen (or a pseudo-halogen leaving group, such as a triflate), preferably bromine or chlorine, and in which Ra is $C_1$-$C_6$alkyl, can be prepared by reacting compounds of the formula IIIa-T5, wherein $X_{08}$ is a halogen (or a pseudo-halogen leaving group, such as a triflate), preferably bromine or chlorine, with S-chlorochloromethanethioate, in the presence of an inert solvent, such as toluene, chlorobenzene or xylene, at temperatures ranging preferably between 80° C. up to the boiling point of the reaction mixture, alternatively under microwave irradiation. Such oxathiazolone formation have been described, for example, in Bioorg Med Chem Lett 2020, 30(16), 127286.

Compounds of the formula IIIa-T6, wherein X08 is a halogen (or a pseudo-halogen leaving group, such as a triflate), preferably bromine or chlorine, can be prepared by amidation of compounds of the formula IIIa-T7, wherein X08 is a halogen (or a pseudo-halogen leaving group, such as a triflate), preferably bromine or chlorine, under standard amide bond formation conditions known to a person skilled in the art.

Scheme 29

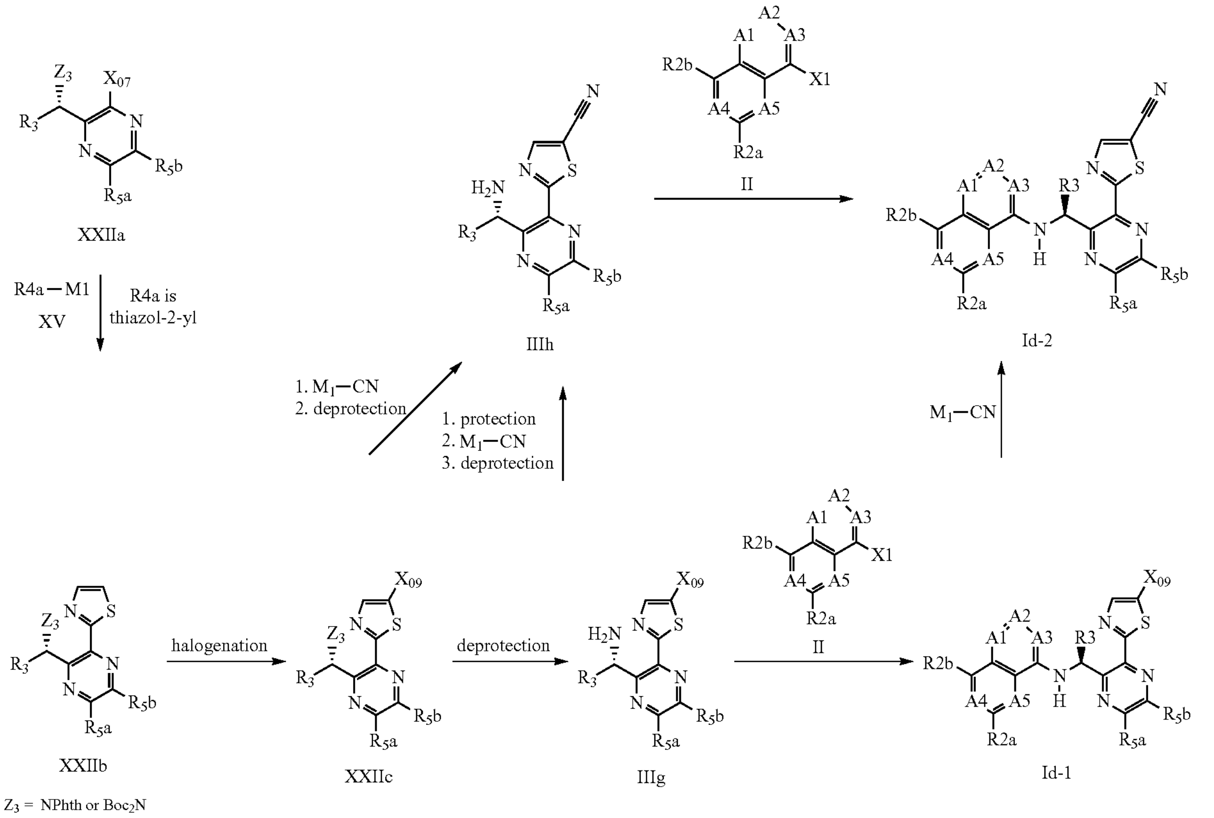

halogen leaving group, such as a triflate), preferably bromine or chlorine, with reagents of the formula NC—C(O) ORa, wherein Ra is $C_1$-$C_6$alkyl (typically ethyl cyanoformate), in the presence of an inert solvent, such as toluene, chlorobenzene or xylene, at temperatures ranging preferably between 100° C. up to the boiling point of the reaction mixture, alternatively under microwave irradiation. Such cycloaddition conditions have been described, for example, in U.S. Pat. No. 6,444,668 B1.

Compounds of the formula IIIa-T5, wherein X08 is a halogen (or a pseudo-halogen leaving group, such as a triflate), preferably bromine or chlorine, can be prepared by reacting compounds of the formula IIIa-T6, wherein X08 is Compounds of the formula Id, wherein R4a is 5-cyanothiazol-2-yl and R1 is hydrogen, defining compounds of the formula Id-2, wherein A1, A2, A3, A4, A5, R3, R2a, R2b, R5a and R5b are as described in formula I, can be prepared (scheme 29) from compounds of the formula Id-1, wherein A1, A2, A3, A4, A5, R3, R2a, R2b, R5a and R5b are as described in formula I, and in which $X_{09}$ is a halogen (or a pseudo-halogen leaving group, such as a triflate), preferably bromine or chlorine, via a cyanation reaction. Such cyanation reactions can be carried out in the presence of a metal cyanide M1-CN, such as sodium cyanide NaCN, potassium cyanide KCN, copper cyanide CuCN, zinc cyanide $Zn(CN)_2$ or potassium ferrocyanide $K_4[Fe(CN)_6]$, amongst others, optionally in the presence of a palladium catalyst and ligand, and optionally under microwave irradiation. Examples of palladium catalyst include palladium(II) acetate $Pd(OAc)_2$ or tris(dibenzylideneacetone)dipalladium(0) $Pd_2(dba)_3$, amongst others, and examples of ligands include 1,1'-bis (diphenylphosphino)ferrocene dppf, dicyclohexyl[2',4',6'-tris(propan-2-yl)[1,1'-biphenyl]-2-yl]phosphane XPhos or (9,9-dimethyl-9H-xanthene-4,5-diyl)bis(diphenylphosphane) Xantphos, amongst other phosphine based ligands. Other examples of catalyst/ligand combination include tetrakis(triphenylphosphine)palladium(0) $Pd(PPh_3)_4$, [1,1'bis (diphenylphosphino)ferrocene]dichloropalladium ($PdCl_2$ (dppf), 2nd generation XPhos precatalyst XPhos Pd G2 or 3rd generation XPhos precatalyst XPhos Pd G3, amongst others. The reaction can be carried out in the presence of solvents such as N,N-dimethylformamide DMF, dioxane, toluene, xylene, acetonitrile, cyclopentylmethylether, optionally in the presence of water, and at temperature ranging between room temperature and the boiling point of the reaction mixture.

Compounds of the formula Id-1, wherein A1, A2, A3, A4, A5, R3, R2a, R2b, R5a and R5b are as described in formula I, and in which $X_{09}$ is a halogen (or a pseudo-halogen leaving group, such as a triflate), preferably bromine or chlorine, can be prepared by reacting compounds of formula II, wherein A1, A2, A3, A4, A5, R2a and R2b are as described in formula I and X1 is a leaving group, such as a halogen or a sulfonate, for instance chloride, with compounds of formula IIIg, or a salt thereof, wherein $R_3$, $R_{5a}$ and $R_{5b}$ are as described in formula I, and in which $X_{09}$ is a halogen (or a pseudo-halogen leaving group, such as a triflate), preferably bromine or chlorine, under conditions already detailed above in scheme 8.

Compounds of formula IIIg, or a salt thereof, wherein R3, R5a and R5b are as described in formula I, and in which $X_{09}$ is a halogen (or a pseudo-halogen leaving group, such as a triflate), preferably bromine or chlorine, can be prepared by deprotection of compounds of formula XXIIc, wherein R3, R5a and R5b are as described in formula I, and in which $X_{09}$ is a halogen (or a pseudo-halogen leaving group, such as a triflate), preferably bromine or chlorine, and $Z_3$ is —NPhth (N-phthalimide group) or —$NBoc_2$ (N-bis(tert-butyloxycarbonyl) group), under conditions already detailed above in scheme 10.

Compounds of formula XXIIc, wherein R3, R5a and R5b are as described in formula I, and in which $X_{09}$ is a halogen, preferably bromine or chlorine, and $Z_3$ is —NPhth (N-phthalimide group) or —$NBoc_2$ (N-bis(tert-butyloxycarbonyl) group), can be prepared by halogenation of compounds of formula XXIIb, wherein R3, R5a and R5b are as described in formula I, and $Z_3$ is —NPhth (N-phthalimide group) or —$NBoc_2$ (N-bis(tert-butyloxycarbonyl) group), with reagents such as N-chlorosuccinimide (NCS), or N-bromosuccinimide (NBS), or alternatively chlorine or bromine, optionally in presence of a base such as sodium, potassium or cesium carbonate. Such halogenation reactions are carried out in an inert solvent, such as chloroform, carbon tetrachloride, 1,2-dichloroethane, acetic acid, ethers, N,N-dimethylformamide, acetonitrile or acetonitrile-water mixtures, at temperatures between 20-200° C., preferably room temperature to 100° C.

Compounds of formula XXIIb, wherein R3, R5a and R5b are as described in formula I, and $Z_3$ is —NPhth (N-phthalimide group) or —$NBoc_2$ (N-bis(tert-butyloxycarbonyl) group), can be prepared by reacting compounds of formula XXIIa, wherein R3, R5a and R5b are as described in formula I, $Z_3$ is —NPhth (N-phthalimide group) or —$NBoc_2$ (N-bis (tert-butyloxycarbonyl) group), and X07 is a leaving group such as a halogen or sulfonate, for instance chloride or bromide, with a reagent of the formula XV R4a-M1, wherein R4a is thiazol-2-yl and M1 is a metal as defined in scheme 7, under conditions already detailed above in scheme 7 for the transformation of compounds of formula XVII into compounds of formula XVIII. Certain compounds of formula XXIIb have been described in the literature, for example in WO 21/069575.

Alternatively, compounds of the formula Id-2 (substituents as defined above) can be prepared by reacting compounds of formula II, wherein A1, A2, A3, A4, A5, R2a and R2b are as described in formula I and X1 is a leaving group, such as a halogen or a sulfonate, for instance chloride, with compounds of formula IIIh, or a salt thereof, wherein R3, R5a and R5b are as described in formula I, under similar conditions for the transformation of II and IIIg into compounds of formula Id-1.

Compounds of formula IIIh, or a salt thereof, wherein R3, R5a and R5b are as described in formula I, can be prepared from compounds of formula IIIg, or a salt thereof, wherein R3, R5a and R5b are as described in formula I, and in which $X_{09}$ is a halogen (or a pseudo-halogen leaving group, such as a triflate), preferably bromine or chlorine, by means of a 3 steps procedure involving 1. Boc-protection of the amino group of IIIg; 2. Reaction of Boc-protected IIIg with a reagent M1-CN (M1 as defined above) under conditions described above for the transformation of Id-1 into Id-2; and 3. Boc-deprotection. The Boc-protection/deprotection steps are known to a person skilled in the art, as described for example in: Protective Groups in Organic Synthesis, 3rd Edition Theodora W. Green (The Rowland Institute for Science) and Peter G. M. Wuts (Pharmacia and Upjohn Company), John Wiley & Sons, Inc., New York, NY. 1999, ISBN 0-471-16019-9.

Alternatively, compounds of formula IIIh (substituents as defined above), or a salt thereof, may be prepared from compounds of formula XXIIc (substituents as defined above), by means of a 2 steps procedure involving 1. Reaction of XXIIc with a reagent M1-CN (M1 as defined above) under conditions described above for the transformation of Id-1 into Id-2; and 2. Deprotection under analogous conditions for the transformation of XXIIc into IIIg.

The chemistry detailed in scheme 29 remains valid when dealing with the corresponding racemic intermediates or products (as illustrated in the experimental part).

Depending on the procedure or the reaction conditions, the reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo [5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reactions are advantageously carried out in a temperature range from approximately −80° C. to approximately +140° C., preferably from approximately −30° C. to approximately +100° C., in many cases in the range between ambient temperature and approximately +80° C.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds of formula I can be prepared in a manner known perse. Thus, for example, acid addition salts of compounds of formula I are obtained by treatment with a suitable acid or a suitable ion exchanger reagent and salts with bases are obtained by treatment with a suitable base or with a suitable ion exchanger reagent.

Salts of compounds of formula I can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds of formula I can be converted in a manner known per se into other salts of compounds of formula I, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds of formula I, which have salt-forming properties can be obtained in free form or in the form of salts.

The compounds of formula I and, where appropriate, the tautomers thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds of formula I, in free form or in salt form, which can be obtained depending on which starting materials and procedures have been chosen can be separated in a known manner into the pure diastereomers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl cellulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

N-oxides can be prepared by reacting a compound of the formula I with a suitable oxidizing agent, for example the $H_2O_2$/urea adduct in the presence of an acid anhydride, e.g. trifluoroacetic anhydride. Such oxidations are known from the literature, for example from *J. Med. Chem.*, 32 (12), 2561-73, 1989 or WO 2000/15615.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds of formula I and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds of formula I according to the following Tables A-1 to A-300 and B-1 to B-108 can be prepared according to the methods described above. The examples which follow are intended to illustrate the invention and show preferred compounds of formula I, in the form of a compound of formula I-A, and in the form of a compound I-B, respectively.

I-A

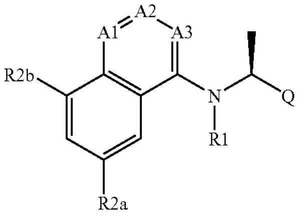

-continued

I-B

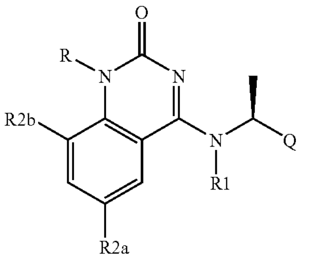

Table A-1 provides 24 compounds A-1.001 to A-1.024 of formula I-A wherein $A_1$ is N, $A_2$ is N, $A_3$ is N, $R_1$ is H, $R_{2a}$ is $CF_3$, $R_{2b}$ is $CF_3$ and Q is as defined in table Z. For example, A-1.002 is

A-1.002

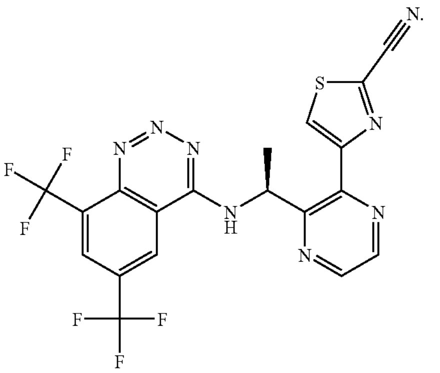

Table A-2 provides 24 compounds A-2.001 to A-2.024 of formula I-A wherein $A_1$ is N, $A_2$ is N, $A_3$ is N, $R_1$ is H, $R_{2a}$ is $CF_3$, $R_{2b}$ is Cl and Q is as defined in table Z.

Table A-3 provides 24 compounds A-3.001 to A-3.024 of formula I-A wherein $A_1$ is N, $A_2$ is N, $A_3$ is N, $R_1$ is H, $R_{2a}$ is $CF_3$, $R_{2b}$ is Br and Q is as defined in table Z.

Table A-4 provides 24 compounds A-4.001 to A-4.024 of formula I-A wherein $A_1$ is N, $A_2$ is N, $A_3$ is N, $R_1$ is H, $R_{2a}$ is Cl, $R_{2b}$ is $CF_3$ and Q is as defined in table Z.

Table A-5 provides 24 compounds A-5.001 to A-5.024 of formula I-A wherein $A_1$ is N, $A_2$ is N, $A_3$ is N, $R_1$ is H, $R_{2a}$ is Cl, $R_{2b}$ is Cl and Q is as defined in table Z.

Table A-6 provides 24 compounds A-6.001 to A-6.024 of formula I-A wherein $A_1$ is N, $A_2$ is N, $A_3$ is N, $R_1$ is H, $R_{2a}$ is Cl, $R_{2b}$ is Br and Q is as defined in table Z.

Table A-7 provides 24 compounds A-7.001 to A-7.024 of formula I-A wherein $A_1$ is N, $A_2$ is N, $A_3$ is N, $R_1$ is H, $R_{2a}$ is Br, $R_{2b}$ is $CF_3$ and Q is as defined in table Z.

Table A-8 provides 24 compounds A-8.001 to A-8.024 of formula I-A wherein $A_1$ is N, $A_2$ is N, $A_3$ is N, $R_1$ is H, $R_{2a}$ is Br, $R_{2b}$ is Cl and Q is as defined in table Z.

Table A-9 provides 24 compounds A-9.001 to A-9.024 of formula I-A wherein $A_1$ is N, $A_2$ is N, $A_3$ is N, $R_1$ is H, $R_{2a}$ is Br, $R_{2b}$ is Br and Q is as defined in table Z.

Table A-10 provides 24 compounds A-10.001 to A-10.024 of formula I-A wherein $A_1$ is N, $A_2$ is N, $A_3$ is N, $R_1$ is H, $R_{2a}$ is $SO_2$—$CF_3$, $R_{2b}$ is $CF_3$ and Q is as defined in table Z.

Table A-11 provides 24 compounds A-11.001 to A-11.024 of formula I-A wherein $A_1$ is N, $A_2$ is N, $A_3$ is N, $R_1$ is H, $R_{2a}$ is $SO_2$—$CF_3$, $R_{2b}$ is Cl and Q is as defined in table Z.

Table A-12 provides 24 compounds A-12.001 to A-12.024 of formula I-A wherein $A_1$ is N, $A_2$ is N, $A_3$ is N, $R_1$ is H, $R_{2a}$ is $SO_2$—$CF_3$, $R_{2b}$ is Br and Q is as defined in table Z.

Table A-13 provides 24 compounds A-13.001 to A-13.024 of formula I-A wherein $A_1$ is N, $A_2$ is N, $A_3$ is N, $R_1$ is $CH_3$, $R_{2a}$ is $CF_3$, $R_{2b}$ is $CF_3$ and Q is as defined in table Z.

Table A-14 provides 24 compounds A-14.001 to A-14.024 of formula I-A wherein $A_1$ is N, $A_2$ is N, $A_3$ is N, $R_1$ is $CH_3$, $R_{2a}$ is $CF_3$, $R_{2b}$ is Cl and Q is as defined in table Z.

Table A-15 provides 24 compounds A-15.001 to A-15.024 of formula I-A wherein $A_1$ is N, $A_2$ is N, $A_3$ is N, $R_1$ is $CH_3$, $R_{2a}$ is $CF_3$, $R_{2b}$ is Br and Q is as defined in table Z.

Table A-16 provides 24 compounds A-16.001 to A-16.024 of formula I-A wherein $A_1$ is N, $A_2$ is N, $A_3$ is N, $R_1$ is $CH_3$, $R_{2a}$ is Cl, $R_{2b}$ is $CF_3$ and Q is as defined in table Z.

Table A-17 provides 24 compounds A-17.001 to A-17.024 of formula I-A wherein $A_1$ is N, $A_2$ is N, $A_3$ is N, $R_1$ is $CH_3$, $R_{2a}$ is Cl, $R_{2b}$ is Cl and Q is as defined in table Z.

Table A-18 provides 24 compounds A-18.001 to A-18.024 of formula I-A wherein $A_1$ is N, $A_2$ is N, $A_3$ is N, $R_1$ is $CH_3$, $R_{2a}$ is Cl, $R_{2b}$ is Br and Q is as defined in table Z.

Table A-19 provides 24 compounds A-19.001 to A-19.024 of formula I-A wherein $A_1$ is N, $A_2$ is N, $A_3$ is N, $R_1$ is $CH_3$, $R_{2a}$ is Br, $R_{2b}$ is $CF_3$ and Q is as defined in table Z.

Table A-20 provides 24 compounds A-20.001 to A-20.024 of formula I-A wherein $A_1$ is N, $A_2$ is N, $A_3$ is N, $R_1$ is $CH_3$, $R_{2a}$ is Br, $R_{2b}$ is Cl and Q is as defined in table Z.

Table A-21 provides 24 compounds A-21.001 to A-21.024 of formula I-A wherein $A_1$ is N, $A_2$ is N, $A_3$ is N, $R_1$ is $CH_3$, $R_{2a}$ is Br, $R_{2b}$ is Br and Q is as defined in table Z.

Table A-22 provides 24 compounds A-22.001 to A-22.024 of formula I-A wherein $A_1$ is N, $A_2$ is N, $A_3$ is N, $R_1$ is $CH_3$, $R_{2a}$ is $SO_2$—$CF_3$, $R_{2b}$ is $CF_3$ and Q is as defined in table Z.

Table A-23 provides 24 compounds A-23.001 to A-23.024 of formula I-A wherein $A_1$ is N, $A_2$ is N, $A_3$ is N, $R_1$ is $CH_3$, $R_{2a}$ is $SO_2$—$CF_3$, $R_{2b}$ is Cl and Q is as defined in table Z.

Table A-24 provides 24 compounds A-24.001 to A-24.024 of formula I-A wherein $A_1$ is N, $A_2$ is N, $A_3$ is N, $R_1$ is $CH_3$, $R_{2a}$ is $SO_2$—$CF_3$, $R_{2b}$ is Br and Q is as defined in table Z.

Table A-25 provides 24 compounds A-25.001 to A-25.024 of formula I-A wherein $A_1$ is N, $A_2$ is N, $A_3$ is N, $R_1$ is $CH_2$-cyclopropyl, $R_{2a}$ is $CF_3$, $R_{2b}$ is $CF_3$ and Q is as defined in table Z.

Table A-26 provides 24 compounds A-26.001 to A-26.024 of formula I-A wherein $A_1$ is N, $A_2$ is N, $A_3$ is N, $R_1$ is $CH_2$-cyclopropyl, $R_{2a}$ is $CF_3$, $R_{2b}$ is Cl and Q is as defined in table Z.

Table A-27 provides 24 compounds A-27.001 to A-27.024 of formula I-A wherein $A_1$ is N, $A_2$ is N, $A_3$ is N, $R_1$ is $CH_2$-cyclopropyl, $R_{2a}$ is $CF_3$, $R_{2b}$ is Br and Q is as defined in table Z.

Table A-28 provides 24 compounds A-28.001 to A-28.024 of formula I-A wherein $A_1$ is N, $A_2$ is N, $A_3$ is N, $R_1$ is $CH_2$-cyclopropyl, $R_{2a}$ is Cl, $R_{2b}$ is $CF_3$ and Q is as defined in table Z.

Table A-29 provides 24 compounds A-29.001 to A-29.024 of formula I-A wherein $A_1$ is N, $A_2$ is N, $A_3$ is N, $R_1$ is $CH_2$-cyclopropyl, $R_{2a}$ is Cl, $R_{2b}$ is Cl and Q is as defined in table Z.

Table A-30 provides 24 compounds A-30.001 to A-30.024 of formula I-A wherein $A_1$ is N, $A_2$ is N, $A_3$ is N, $R_1$ is $CH_2$-cyclopropyl, $R_{2a}$ is Cl, $R_{2b}$ is Br and Q is as defined in table Z.

Table A-31 provides 24 compounds A-31.001 to A-31.024 of formula I-A wherein $A_1$ is N, $A_2$ is N, $A_3$ is N, $R_1$ is $CH_2$-cyclopropyl, $R_{2a}$ is Br, $R_{2b}$ is $CF_3$ and Q is as defined in table Z.

Table A-32 provides 24 compounds A-32.001 to A-32.024 of formula I-A wherein $A_1$ is N, $A_2$ is N, $A_3$ is N, $R_1$ is $CH_2$-cyclopropyl, $R_{2a}$ is Br, $R_{2b}$ is Cl and Q is as defined in table Z.

Table A-33 provides 24 compounds A-33.001 to A-33.024 of formula I-A wherein $A_1$ is N, $A_2$ is N, $A_3$ is N, $R_1$ is $CH_2$-cyclopropyl, $R_{2a}$ is Br, $R_{2b}$ is Br and Q is as defined in table Z.

Table A-34 provides 24 compounds A-34.001 to A-34.024 of formula I-A wherein $A_1$ is N, $A_2$ is N, $A_3$ is N, $R_1$ is $CH_2$-cyclopropyl, $R_{2a}$ is $SO_2$—$CF_3$, $R_{2b}$ is $CF_3$ and Q is as defined in table Z.

Table A-35 provides 24 compounds A-35.001 to A-35.024 of formula I-A wherein $A_1$ is N, $A_2$ is N, $A_3$ is N, $R_1$ is $CH_2$-cyclopropyl, $R_{2a}$ is $SO_2$—$CF_3$, $R_{2b}$ is Cl and Q is as defined in table Z.

Table A-36 provides 24 compounds A-36.001 to A-36.024 of formula I-A wherein $A_1$ is N, $A_2$ is N, $A_3$ is N, $R_1$ is $CH_2$-cyclopropyl, $R_{2a}$ is $SO_2$—$CF_3$, $R_{2b}$ is Br and Q is as defined in table Z.

Table A-37 provides 24 compounds A-37.001 to A-37.024 of formula I-A wherein $A_1$ is N, $A_2$ is N, $A_3$ is CH, $R_1$ is H, $R_{2a}$ is $CF_3$, $R_{2b}$ is $CF_3$ and Q is as defined in table Z.

Table A-38 provides 24 compounds A-38.001 to A-38.024 of formula I-A wherein $A_1$ is N, $A_2$ is N, $A_3$ is CH, $R_1$ is H, $R_{2a}$ is $CF_3$, $R_{2b}$ is Cl and Q is as defined in table Z.

Table A-39 provides 24 compounds A-39.001 to A-39.024 of formula I-A wherein $A_1$ is N, $A_2$ is N, $A_3$ is CH, $R_1$ is H, $R_{2a}$ is $CF_3$, $R_{2b}$ is Br and Q is as defined in table Z.

Table A-40 provides 24 compounds A-40.001 to A-40.024 of formula I-A wherein $A_1$ is N, $A_2$ is N, $A_3$ is CH, $R_1$ is H, $R_{2a}$ is Cl, $R_{2b}$ is $CF_3$ and Q is as defined in table Z.

Table A-41 provides 24 compounds A-41.001 to A-41.024 of formula I-A wherein $A_1$ is N, $A_2$ is N, $A_3$ is CH, $R_1$ is H, $R_{2a}$ is Cl, $R_{2b}$ is Cl and Q is as defined in table Z.

Table A-42 provides 24 compounds A-42.001 to A-42.024 of formula I-A wherein $A_1$ is N, $A_2$ is N, $A_3$ is CH, $R_1$ is H, $R_{2a}$ is CI, $R_{2b}$ is Br and Q is as defined in table Z.

Table A-43 provides 24 compounds A-43.001 to A-43.024 of formula I-A wherein $A_1$ is N, $A_2$ is N, $A_3$ is CH, $R_1$ is H, $R_{2a}$ is Br, $R_{2b}$ is $CF_3$ and Q is as defined in table Z.

Table A-44 provides 24 compounds A-44.001 to A-44.024 of formula I-A wherein $A_1$ is N, $A_2$ is N, $A_3$ is CH, $R_1$ is H, $R_{2a}$ is Br, $R_{2b}$ is C and Q is as defined in table Z.

Table A-45 provides 24 compounds A-45.001 to A-45.024 of formula I-A wherein $A_1$ is N, $A_2$ is N, $A_3$ is CH, $R_1$ is H, $R_{2a}$ is Br, $R_{2b}$ is Br and Q is as defined in table Z.

Table A-46 provides 24 compounds A-46.001 to A-46.024 of formula I-A wherein $A_1$ is N, $A_2$ is N, $A_3$ is CH, $R_1$ is H, $R_{2a}$ is $SO_2$—$CF_3$, $R_{2b}$ is $CF_3$ and Q is as defined in table Z.

Table A-47 provides 24 compounds A-47.001 to A-47.024 of formula I-A wherein $A_1$ is N, $A_2$ is N, $A_3$ is CH, $R_1$ is H, $R_{2a}$ is $SO_2$—$CF_3$, $R_{2b}$ is C and Q is as defined in table Z.

Table A-48 provides 24 compounds A-48.001 to A-48.024 of formula I-A wherein $A_1$ is N, $A_2$ is N, $A_3$ is CH, $R_1$ is H, $R_{2a}$ is $SO_2$—$CF_3$, $R_{2b}$ is Br and Q is as defined in table Z.

Table A-49 provides 24 compounds A-49.001 to A-49.024 of formula I-A wherein $A_1$ is N, $A_2$ is N, $A_3$ is CH, $R_1$ is $CH_3$, $R_{2a}$ is $CF_3$, $R_{2b}$ is $CF_3$ and Q is as defined in table Z.

Table A-50 provides 24 compounds A-50.001 to A-50.024 of formula I-A wherein $A_1$ is N, $A_2$ is N, $A_3$ is CH, $R_1$ is $CH_3$, $R_{2a}$ is $CF_3$, $R_{2b}$ is C and Q is as defined in table Z.

Table A-51 provides 24 compounds A-51.001 to A-51.024 of formula I-A wherein $A_1$ is N, $A_2$ is N, $A_3$ is CH, $R_1$ is $CH_3$, $R_{2a}$ is $CF_3$, $R_{2b}$ is Br and Q is as defined in table Z.

Table A-52 provides 24 compounds A-52.001 to A-52.024 of formula I-A wherein $A_1$ is N, $A_2$ is N, $A_3$ is CH, $R_1$ is $CH_3$, $R_{2a}$ is Cl, $R_{2b}$ is $CF_3$ and Q is as defined in table Z.

Table A-53 provides 24 compounds A-53.001 to A-53.024 of formula I-A wherein $A_1$ is N, $A_2$ is N, $A_3$ is CH, $R_1$ is $CH_3$, $R_{2a}$ is Cl, $R_{2b}$ is Cl and Q is as defined in table Z.

Table A-54 provides 24 compounds A-54.001 to A-54.024 of formula I-A wherein $A_1$ is N, $A_2$ is N, $A_3$ is CH, $R_1$ is $CH_3$, $R_{2a}$ is Cl, $R_{2b}$ is Br and Q is as defined in table Z.

Table A-55 provides 24 compounds A-55.001 to A-55.024 of formula I-A wherein $A_1$ is N, $A_2$ is N, $A_3$ is CH, $R_1$ is $CH_3$, $R_{2a}$ is Br, $R_{2b}$ is $CF_3$ and Q is as defined in table Z.

Table A-56 provides 24 compounds A-56.001 to A-56.024 of formula I-A wherein $A_1$ is N, $A_2$ is N, $A_3$ is CH, $R_1$ is $CH_3$, $R_{2a}$ is Br, $R_{2b}$ is Cl and Q is as defined in table Z.

Table A-57 provides 24 compounds A-57.001 to A-57.024 of formula I-A wherein $A_1$ is N, $A_2$ is N, $A_3$ is CH, $R_1$ is $CH_3$, $R_{2a}$ is Br, $R_{2b}$ is Br and Q is as defined in table Z.

Table A-58 provides 24 compounds A-58.001 to A-58.024 of formula I-A wherein $A_1$ is N, $A_2$ is N, $A_3$ is CH, $R_1$ is $CH_3$, $R_{2a}$ is $SO_2$—$CF_3$, $R_{2b}$ is $CF_3$ and Q is as defined in table Z.

Table A-59 provides 24 compounds A-59.001 to A-59.024 of formula I-A wherein $A_1$ is N, $A_2$ is N, $A_3$ is CH, $R_1$ is $CH_3$, $R_{2a}$ is $SO_2$—$CF_3$, $R_{2b}$ is C and Q is as defined in table Z.

Table A-60 provides 24 compounds A-60.001 to A-60.024 of formula I-A wherein $A_1$ is N, $A_2$ is N, $A_3$ is CH, $R_1$ is $CH_3$, $R_{2a}$ is $SO_2$—$CF_3$, $R_{2b}$ is Br and Q is as defined in table Z.

Table A-61 provides 24 compounds A-61.001 to A-61.024 of formula I-A wherein $A_1$ is N, $A_2$ is N, $A_3$ is CH, $R_1$ is $CH_2$-cyclopropyl, $R_{2a}$ is $CF_3$, $R_{2b}$ is $CF_3$ and Q is as defined in table Z.

Table A-62 provides 24 compounds A-62.001 to A-62.024 of formula I-A wherein $A_1$ is N, $A_2$ is N, $A_3$ is CH, $R_1$ is $CH_2$-cyclopropyl, $R_{2a}$ is $CF_3$, $R_{2b}$ is C and Q is as defined in table Z.

Table A-63 provides 24 compounds A-63.001 to A-63.024 of formula I-A wherein $A_1$ is N, $A_2$ is N, $A_3$ is CH, $R_1$ is $CH_2$-cyclopropyl, $R_{2a}$ is $CF_3$, $R_{2b}$ is Br and Q is as defined in table Z.

Table A-64 provides 24 compounds A-64.001 to A-64.024 of formula I-A wherein $A_1$ is N, $A_2$ is N, $A_3$ is CH, $R_1$ is $CH_2$-cyclopropyl, $R_{2a}$ is CI, $R_{2b}$ is $CF_3$ and Q is as defined in table Z.

Table A-65 provides 24 compounds A-65.001 to A-65.024 of formula I-A wherein $A_1$ is N, $A_2$ is N, $A_3$ is CH, $R_1$ is $CH_2$-cyclopropyl, $R_{2a}$ is CI, $R_{2b}$ is C and Q is as defined in table Z.

Table A-66 provides 24 compounds A-66.001 to A-66.024 of formula I-A wherein $A_1$ is N, $A_2$ is N, $A_3$ is CH, $R_1$ is $CH_2$-cyclopropyl, $R_{2a}$ is CI, $R_{2b}$ is Br and Q is as defined in table Z.

Table A-67 provides 24 compounds A-67.001 to A-67.024 of formula I-A wherein $A_1$ is N, $A_2$ is N, $A_3$ is CH, $R_1$ is $CH_2$-cyclopropyl, $R_{2a}$ is Br, $R_{2b}$ is $CF_3$ and Q is as defined in table Z.

Table A-68 provides 24 compounds A-68.001 to A-68.024 of formula I-A wherein $A_1$ is N, $A_2$ is N, $A_3$ is CH, $R_1$ is $CH_2$-cyclopropyl, $R_{2a}$ is Br, $R_{2b}$ is C and Q is as defined in table Z.

Table A-69 provides 24 compounds A-69.001 to A-69.024 of formula I-A wherein $A_1$ is N, $A_2$ is N, $A_3$ is CH, $R_1$ is $CH_2$-cyclopropyl, $R_{2a}$ is Br, $R_{2b}$ is Br and Q is as defined in table Z.

Table A-70 provides 24 compounds A-70.001 to A-70.024 of formula I-A wherein $A_1$ is N, $A_2$ is N, $A_3$ is CH, $R_1$ is $CH_2$-cyclopropyl, $R_{2a}$ is $SO_2$—$CF_3$, $R_{2b}$ is $CF_3$ and Q is as defined in table Z.

Table A-71 provides 24 compounds A-71.001 to A-71.024 of formula I-A wherein $A_1$ is N, $A_2$ is N, $A_3$ is CH, $R_1$ is $CH_2$-cyclopropyl, $R_{2a}$ is $SO_2$—$CF_3$, $R_{2b}$ is Cl and Q is as defined in table Z.

Table A-72 provides 24 compounds A-72.001 to A-72.024 of formula I-A wherein $A_1$ is N, $A_2$ is N, $A_3$ is CH, $R_1$ is $CH_2$-cyclopropyl, $R_{2a}$ is $SO_2$—$CF_3$, $R_{2b}$ is Br and Q is as defined in table Z.

Table A-73 provides 24 compounds A-73.001 to A-73.024 of formula I-A wherein $A_1$ is N, $A_2$ is CH, $A_3$ is N, $R_1$ is H, $R_{2a}$ is $CF_3$, $R_{2b}$ is $CF_3$ and Q is as defined in table Z.

Table A-74 provides 24 compounds A-74.001 to A-74.024 of formula I-A wherein $A_1$ is N, $A_2$ is CH, $A_3$ is N, $R_1$ is H, $R_{2a}$ is $CF_3$, $R_{2b}$ is Cl and Q is as defined in table Z.

Table A-75 provides 24 compounds A-75.001 to A-75.024 of formula I-A wherein $A_1$ is N, $A_2$ is CH, $A_3$ is N, $R_1$ is H, $R_{2a}$ is $CF_3$, $R_{2b}$ is Br and Q is as defined in table Z.

Table A-76 provides 24 compounds A-76.001 to A-76.024 of formula I-A wherein $A_1$ is N, $A_2$ is CH, $A_3$ is N, $R_1$ is H, $R_{2a}$ is CI, $R_{2b}$ is $CF_3$ and Q is as defined in table Z.

Table A-77 provides 24 compounds A-77.001 to A-77.024 of formula I-A wherein $A_1$ is N, $A_2$ is CH, $A_3$ is N, $R_1$ is H, $R_{2a}$ is CI, $R_{2b}$ is C and Q is as defined in table Z.

Table A-78 provides 24 compounds A-78.001 to A-78.024 of formula I-A wherein $A_1$ is N, $A_2$ is CH, $A_3$ is N, $R_1$ is H, $R_{2a}$ is CI, $R_{2b}$ is Br and Q is as defined in table Z.

Table A-79 provides 24 compounds A-79.001 to A-79.024 of formula I-A wherein $A_1$ is N, $A_2$ is CH, $A_3$ is N, $R_1$ is H, $R_{2a}$ is Br, $R_{2b}$ is $CF_3$ and Q is as defined in table Z.

Table A-80 provides 24 compounds A-80.001 to A-80.024 of formula I-A wherein $A_1$ is N, $A_2$ is CH, $A_3$ is N, $R_1$ is H, $R_{2a}$ is Br, $R_{2b}$ is C and Q is as defined in table Z.

Table A-81 provides 24 compounds A-81.001 to A-81.024 of formula I-A wherein $A_1$ is N, $A_2$ is CH, $A_3$ is N, $R_1$ is H, $R_{2a}$ is Br, $R_{2b}$ is Br and Q is as defined in table Z.

Table A-82 provides 24 compounds A-82.001 to A-82.024 of formula I-A wherein $A_1$ is N, $A_2$ is CH, $A_3$ is N, $R_1$ is H, $R_{2a}$ is $SO_2$—$CF_3$, $R_{2b}$ is $CF_3$ and Q is as defined in table Z.

Table A-83 provides 24 compounds A-83.001 to A-83.024 of formula I-A wherein $A_1$ is N, $A_2$ is CH, $A_3$ is N, $R_1$ is H, $R_{2a}$ is $SO_2$—$CF_3$, $R_{2b}$ is C and Q is as defined in table Z.

Table A-84 provides 24 compounds A-84.001 to A-84.024 of formula I-A wherein $A_1$ is N, $A_2$ is CH, $A_3$ is N, $R_1$ is H, $R_{2a}$ is $SO_2$—$CF_3$, $R_{2b}$ is Br and Q is as defined in table Z.

Table A-85 provides 24 compounds A-85.001 to A-85.024 of formula I-A wherein $A_1$ is N, $A_2$ is CH, $A_3$ is N, $R_1$ is $CH_3$, $R_{2a}$ is $CF_3$, $R_{2b}$ is $CF_3$ and Q is as defined in table Z.

Table A-86 provides 24 compounds A-86.001 to A-86.024 of formula I-A wherein $A_1$ is N, $A_2$ is CH, $A_3$ is N, $R_1$ is $CH_3$, $R_{2a}$ is $CF_3$, $R_{2b}$ is Cl and Q is as defined in table Z.

Table A-87 provides 24 compounds A-87.001 to A-87.024 of formula I-A wherein $A_1$ is N, $A_2$ is CH, $A_3$ is N, $R_1$ is $CH_3$, $R_{2a}$ is $CF_3$, $R_{2b}$ is Br and Q is as defined in table Z.

Table A-88 provides 24 compounds A-88.001 to A-88.024 of formula I-A wherein $A_1$ is N, $A_2$ is CH, $A_3$ is N, $R_1$ is $CH_3$, $R_{2a}$ is Cl, $R_{2b}$ is $CF_3$ and Q is as defined in table Z.

Table A-89 provides 24 compounds A-89.001 to A-89.024 of formula I-A wherein $A_1$ is N, $A_2$ is CH, $A_3$ is N, $R_1$ is $CH_3$, $R_{2a}$ is Cl, $R_{2b}$ is Cl and Q is as defined in table Z.

Table A-90 provides 24 compounds A-90.001 to A-90.024 of formula I-A wherein $A_1$ is N, $A_2$ is CH, $A_3$ is N, $R_1$ is $CH_3$, $R_{2a}$ is Cl, $R_{2b}$ is Br and Q is as defined in table Z.

Table A-91 provides 24 compounds A-91.001 to A-91.024 of formula I-A wherein $A_1$ is N, $A_2$ is CH, $A_3$ is N, $R_1$ is $CH_3$, $R_{2a}$ is Br, $R_{2b}$ is $CF_3$ and Q is as defined in table Z.

Table A-92 provides 24 compounds A-92.001 to A-92.024 of formula I-A wherein $A_1$ is N, $A_2$ is CH, $A_3$ is N, $R_1$ is $CH_3$, $R_{2a}$ is Br, $R_{2b}$ is Cl and Q is as defined in table Z.

Table A-93 provides 24 compounds A-93.001 to A-93.024 of formula I-A wherein $A_1$ is N, $A_2$ is CH, $A_3$ is N, $R_1$ is $CH_3$, $R_{2a}$ is Br, $R_{2b}$ is Br and Q is as defined in table Z.

Table A-94 provides 24 compounds A-94.001 to A-94.024 of formula I-A wherein $A_1$ is N, $A_2$ is CH, $A_3$ is N, $R_1$ is $CH_3$, $R_{2a}$ is $SO_2$—$CF_3$, $R_{2b}$ is $CF_3$ and Q is as defined in table Z.

Table A-95 provides 24 compounds A-95.001 to A-95.024 of formula I-A wherein $A_1$ is N, $A_2$ is CH, $A_3$ is N, $R_1$ is $CH_3$, $R_{2a}$ is $SO_2$—$CF_3$, $R_{2b}$ is C and Q is as defined in table Z.

Table A-96 provides 24 compounds A-96.001 to A-96.024 of formula I-A wherein $A_1$ is N, $A_2$ is CH, $A_3$ is N, $R_1$ is $CH_3$, $R_{2a}$ is $SO_2$—$CF_3$, $R_{2b}$ is Br and Q is as defined in table Z.

Table A-97 provides 24 compounds A-97.001 to A-97.024 of formula I-A wherein $A_1$ is N, $A_2$ is CH, $A_3$ is N, $R_1$ is $CH_2$-cyclopropyl, $R_{2a}$ is $CF_3$, $R_{2b}$ is $CF_3$ and Q is as defined in table Z.

Table A-98 provides 24 compounds A-98.001 to A-98.024 of formula I-A wherein $A_1$ is N, $A_2$ is CH, $A_3$ is N, $R_1$ is $CH_2$-cyclopropyl, $R_{2a}$ is $CF_3$, $R_{2b}$ is C and Q is as defined in table Z.

Table A-99 provides 24 compounds A-99.001 to A-99.024 of formula I-A wherein $A_1$ is N, $A_2$ is CH, $A_3$ is N, $R_1$ is $CH_2$-cyclopropyl, $R_{2a}$ is $CF_3$, $R_{2b}$ is Br and Q is as defined in table Z.

Table A-100 provides 24 compounds A-100.001 to A-100.024 of formula I-A wherein $A_1$ is N, $A_2$ is CH, $A_3$ is N, $R_1$ is $CH_2$-cyclopropyl, $R_{2a}$ is CI, $R_{2b}$ is $CF_3$ and Q is as defined in table Z.

Table A-101 provides 24 compounds A-101.001 to A-101.024 of formula I-A wherein $A_1$ is N, $A_2$ is CH, $A_3$ is N, $R_1$ is $CH_2$-cyclopropyl, $R_{2a}$ is CI, $R_{2b}$ is C and Q is as defined in table Z.

Table A-102 provides 24 compounds A-102.001 to A-102.024 of formula I-A wherein $A_1$ is N, $A_2$ is CH, $A_3$ is N, $R_1$ is $CH_2$-cyclopropyl, $R_{2a}$ is CI, $R_{2b}$ is Br and Q is as defined in table Z.

Table A-103 provides 24 compounds A-103.001 to A-103.024 of formula I-A wherein $A_1$ is N, $A_2$ is CH, $A_3$ is N, $R_1$ is $CH_2$-cyclopropyl, $R_{2a}$ is Br, $R_{2b}$ is $CF_3$ and Q is as defined in table Z.

Table A-104 provides 24 compounds A-104.001 to A-104.024 of formula I-A wherein $A_1$ is N, $A_2$ is CH, $A_3$ is N, $R_1$ is $CH_2$-cyclopropyl, $R_{2a}$ is Br, $R_{2b}$ is Cl and Q is as defined in table Z.

Table A-105 provides 24 compounds A-105.001 to A-105.024 of formula I-A wherein $A_1$ is N, $A_2$ is CH, $A_3$ is N, $R_1$ is $CH_2$-cyclopropyl, $R_{2a}$ is Br, $R_{2b}$ is Br and Q is as defined in table Z.

Table A-106 provides 24 compounds A-106.001 to A-106.024 of formula I-A wherein $A_1$ is N, $A_2$ is CH, $A_3$ is N, $R_1$ is $CH_2$-cyclopropyl, $R_{2a}$ is $SO_2$—$CF_3$, $R_{2b}$ is $CF_3$ and Q is as defined in table Z.

Table A-107 provides 24 compounds A-107.001 to A-107.024 of formula I-A wherein $A_1$ is N, $A_2$ is CH, $A_3$ is N, $R_1$ is $CH_2$-cyclopropyl, $R_{2a}$ is $SO_2$—$CF_3$, $R_{2b}$ is Cl and Q is as defined in table Z.

Table A-108 provides 24 compounds A-108.001 to A-108.024 of formula I-A wherein $A_1$ is N, $A_2$ is CH, $A_3$ is N, $R_1$ is $CH_2$-cyclopropyl, $R_{2a}$ is $SO_2$—$CF_3$, $R_{2b}$ is Br and Q is as defined in table Z.

Table A-109 provides 24 compounds A-109.001 to A-109.024 of formula I-A wherein $A_1$ is N, $A_2$ is CH, $A_3$ is CH, $R_1$ is H, $R_{2a}$ is $CF_3$, $R_{2b}$ is $CF_3$ and Q is as defined in table Z.

Table A-110 provides 24 compounds A-110.001 to A-110.024 of formula I-A wherein $A_1$ is N, $A_2$ is CH, $A_3$ is CH, $R_1$ is H, $R_{2a}$ is $CF_3$, $R_{2b}$ is C and Q is as defined in table Z.

Table A-111 provides 24 compounds A-111.001 to A-111.024 of formula I-A wherein $A_1$ is N, $A_2$ is CH, $A_3$ is CH, $R_1$ is H, $R_{2a}$ is $CF_3$, $R_{2b}$ is Br and Q is as defined in table Z.

Table A-112 provides 24 compounds A-112.001 to A-112.024 of formula I-A wherein $A_1$ is N, $A_2$ is CH, $A_3$ is CH, $R_1$ is H, $R_{2a}$ is CI, $R_{2b}$ is $CF_3$ and Q is as defined in table Z.

Table A-113 provides 24 compounds A-113.001 to A-113.024 of formula I-A wherein $A_1$ is N, $A_2$ is CH, $A_3$ is CH, $R_1$ is H, $R_{2a}$ is CI, $R_{2b}$ is C and Q is as defined in table Z.

Table A-114 provides 24 compounds A-114.001 to A-114.024 of formula I-A wherein $A_1$ is N, $A_2$ is CH, $A_3$ is CH, $R_1$ is H, $R_{2a}$ is CI, $R_{2b}$ is Br and Q is as defined in table Z.

Table A-115 provides 24 compounds A-115.001 to A-115.024 of formula I-A wherein $A_1$ is N, $A_2$ is CH, $A_3$ is CH, $R_1$ is H, $R_{2a}$ is Br, $R_{2b}$ is $CF_3$ and Q is as defined in table Z.

Table A-116 provides 24 compounds A-116.001 to A-116.024 of formula I-A wherein $A_1$ is N, $A_2$ is CH, $A_3$ is CH, $R_1$ is H, $R_{2a}$ is Br, $R_{2b}$ is C and Q is as defined in table Z.

Table A-117 provides 24 compounds A-117.001 to A-117.024 of formula I-A wherein $A_1$ is N, $A_2$ is CH, $A_3$ is CH, $R_1$ is H, $R_{2a}$ is Br, $R_{2b}$ is Br and Q is as defined in table Z.

Table A-118 provides 24 compounds A-118.001 to A-118.024 of formula I-A wherein $A_1$ is N, $A_2$ is CH, $A_3$ is CH, $R_1$ is H, $R_{2a}$ is $SO_2$—$CF_3$, $R_{2b}$ is $CF_3$ and Q is as defined in table Z.

Table A-119 provides 24 compounds A-119.001 to A-119.024 of formula I-A wherein $A_1$ is N, $A_2$ is CH, $A_3$ is CH, $R_1$ is H, $R_{2a}$ is $SO_2$—$CF_3$, $R_{2b}$ is C and Q is as defined in table Z.

Table A-120 provides 24 compounds A-120.001 to A-120.024 of formula I-A wherein $A_1$ is N, $A_2$ is CH, $A_3$ is CH, $R_1$ is H, $R_{2a}$ is $SO_2$—$CF_3$, $R_{2b}$ is Br and Q is as defined in table Z.

Table A-121 provides 24 compounds A-121.001 to A-121.024 of formula I-A wherein $A_1$ is N, $A_2$ is CH, $A_3$ is CH, $R_1$ is $CH_3$, $R_{2a}$ is $CF_3$, $R_{2b}$ is $CF_3$ and Q is as defined in table Z.

Table A-122 provides 24 compounds A-122.001 to A-122.024 of formula I-A wherein $A_1$ is N, $A_2$ is CH, $A_3$ is CH, $R_1$ is $CH_3$, $R_{2a}$ is $CF_3$, $R_{2b}$ is Cl and Q is as defined in table Z.

Table A-123 provides 24 compounds A-123.001 to A-123.024 of formula I-A wherein $A_1$ is N, $A_2$ is CH, $A_3$ is CH, $R_1$ is $CH_3$, $R_{2a}$ is $CF_3$, $R_{2b}$ is Br and Q is as defined in table Z.

Table A-124 provides 24 compounds A-124.001 to A-124.024 of formula I-A wherein $A_1$ is N, $A_2$ is CH, $A_3$ is CH, $R_1$ is $CH_3$, $R_{2a}$ is CI, $R_{2b}$ is $CF_3$ and Q is as defined in table Z.

Table A-125 provides 24 compounds A-125.001 to A-125.024 of formula I-A wherein $A_1$ is N, $A_2$ is CH, $A_3$ is CH, $R_1$ is $CH_3$, $R_{2a}$ is CI, $R_{2b}$ is C and Q is as defined in table Z.

Table A-126 provides 24 compounds A-126.001 to A-126.024 of formula I-A wherein $A_1$ is N, $A_2$ is CH, $A_3$ is CH, $R_1$ is $CH_3$, $R_{2a}$ is CI, $R_{2b}$ is Br and Q is as defined in table Z.

Table A-127 provides 24 compounds A-127.001 to A-127.024 of formula I-A wherein $A_1$ is N, $A_2$ is CH, $A_3$ is CH, $R_1$ is $CH_3$, $R_{2a}$ is Br, $R_{2b}$ is $CF_3$ and Q is as defined in table Z.

Table A-128 provides 24 compounds A-128.001 to A-128.024 of formula I-A wherein $A_1$ is N, $A_2$ is CH, $A_3$ is CH, $R_1$ is $CH_3$, $R_{2a}$ is Br, $R_{2b}$ is C and Q is as defined in table Z.

Table A-129 provides 24 compounds A-129.001 to A-129.024 of formula I-A wherein $A_1$ is N, $A_2$ is CH, $A_3$ is CH, $R_1$ is $CH_3$, $R_{2a}$ is Br, $R_{2b}$ is Br and Q is as defined in table Z.

Table A-130 provides 24 compounds A-130.001 to A-130.024 of formula I-A wherein $A_1$ is N, $A_2$ is CH, $A_3$ is CH, $R_1$ is $CH_3$, $R_{2a}$ is $SO_2$—$CF_3$, $R_{2b}$ is $CF_3$ and Q is as defined in table Z.

Table A-131 provides 24 compounds A-131.001 to A-131.024 of formula I-A wherein $A_1$ is N, $A_2$ is CH, $A_3$ is CH, $R_1$ is $CH_3$, $R_{2a}$ is $SO_2$—$CF_3$, $R_{2b}$ is C and Q is as defined in table Z.

Table A-132 provides 24 compounds A-132.001 to A-132.024 of formula I-A wherein $A_1$ is N, $A_2$ is CH, $A_3$ is CH, $R_1$ is $CH_3$, $R_{2a}$ is $SO_2$—$CF_3$, $R_{2b}$ is Br and Q is as defined in table Z.

Table A-133 provides 24 compounds A-133.001 to A-133.024 of formula I-A wherein $A_1$ is N, $A_2$ is CH, $A_3$ is CH, $R_1$ is $CH_2$-cyclopropyl, $R_{2a}$ is $CF_3$, $R_{2b}$ is $CF_3$ and Q is as defined in table Z.

Table A-134 provides 24 compounds A-134.001 to A-134.024 of formula I-A wherein $A_1$ is N, $A_2$ is CH, $A_3$ is CH, $R_1$ is $CH_2$-cyclopropyl, $R_{2a}$ is $CF_3$, $R_{2b}$ is C and Q is as defined in table Z.

Table A-135 provides 24 compounds A-135.001 to A-135.024 of formula I-A wherein $A_1$ is N, $A_2$ is CH, $A_3$ is CH, $R_1$ is $CH_2$-cyclopropyl, $R_{2a}$ is $CF_3$, $R_{2b}$ is Br and Q is as defined in table Z.

Table A-136 provides 24 compounds A-136.001 to A-136.024 of formula I-A wherein $A_1$ is N, $A_2$ is CH, $A_3$ is CH, $R_1$ is $CH_2$-cyclopropyl, $R_{2a}$ is CI, $R_{2b}$ is $CF_3$ and Q is as defined in table Z.

Table A-137 provides 24 compounds A-137.001 to A-137.024 of formula I-A wherein $A_1$ is N, $A_2$ is CH, $A_3$ is CH, $R_1$ is $CH_2$-cyclopropyl, $R_{2a}$ is Cl, $R_{2b}$ is Cl and Q is as defined in table Z.

Table A-138 provides 24 compounds A-138.001 to A-138.024 of formula I-A wherein $A_1$ is N, $A_2$ is CH, $A_3$ is CH, $R_1$ is $CH_2$-cyclopropyl, $R_{2a}$ is Cl, $R_{2b}$ is Br and Q is as defined in table Z.

Table A-139 provides 24 compounds A-139.001 to A-139.024 of formula I-A wherein $A_1$ is N, $A_2$ is CH, $A_3$ is CH, $R_1$ is $CH_2$-cyclopropyl, $R_{2a}$ is Br, $R_{2b}$ is $CF_3$ and Q is as defined in table Z.

Table A-140 provides 24 compounds A-140.001 to A-140.024 of formula I-A wherein $A_1$ is N, $A_2$ is CH, $A_3$ is CH, $R_1$ is $CH_2$-cyclopropyl, $R_{2a}$ is Br, $R_{2b}$ is Cl and Q is as defined in table Z.

Table A-141 provides 24 compounds A-141.001 to A-141.024 of formula I-A wherein $A_1$ is N, $A_2$ is CH, $A_3$ is CH, $R_1$ is $CH_2$-cyclopropyl, $R_{2a}$ is Br, $R_{2b}$ is Br and Q is as defined in table Z.

Table A-142 provides 24 compounds A-142.001 to A-142.024 of formula I-A wherein $A_1$ is N, $A_2$ is CH, $A_3$ is CH, $R_1$ is $CH_2$-cyclopropyl, $R_{2a}$ is $SO_2$—$CF_3$, $R_{2b}$ is $CF_3$ and Q is as defined in table Z.

Table A-143 provides 24 compounds A-143.001 to A-143.024 of formula I-A wherein $A_1$ is N, $A_2$ is CH, $A_3$ is CH, $R_1$ is $CH_2$-cyclopropyl, $R_{2a}$ is $SO_2$—$CF_3$, $R_{2b}$ is C and Q is as defined in table Z.

Table A-144 provides 24 compounds A-144.001 to A-144.024 of formula I-A wherein $A_1$ is N, $A_2$ is CH, $A_3$ is CH, $R_1$ is $CH_2$-cyclopropyl, $R_{2a}$ is $SO_2$—$CF_3$, $R_{2b}$ is Br and Q is as defined in table Z.

Table A-145 provides 24 compounds A-145.001 to A-145.024 of formula I-A wherein $A_1$ is CH, $A_2$ is N, $A_3$ is N, $R_1$ is H, $R_{2a}$ is $CF_3$, $R_{2b}$ is $CF_3$ and Q is as defined in table Z.

Table A-146 provides 24 compounds A-146.001 to A-146.024 of formula I-A wherein $A_1$ is CH, $A_2$ is N, $A_3$ is N, $R_1$ is H, $R_{2a}$ is $CF_3$, $R_{2b}$ is C and Q is as defined in table Z.

Table A-147 provides 24 compounds A-147.001 to A-147.024 of formula I-A wherein $A_1$ is CH, $A_2$ is N, $A_3$ is N, $R_1$ is H, $R_{2a}$ is $CF_3$, $R_{2b}$ is Br and Q is as defined in table Z.

Table A-148 provides 24 compounds A-148.001 to A-148.024 of formula I-A wherein $A_1$ is CH, $A_2$ is N, $A_3$ is N, $R_1$ is H, $R_{2a}$ is CI, $R_{2b}$ is $CF_3$ and Q is as defined in table Z.

Table A-149 provides 24 compounds A-149.001 to A-149.024 of formula I-A wherein $A_1$ is CH, $A_2$ is N, $A_3$ is N, $R_1$ is H, $R_{2a}$ is CI, $R_{2b}$ is C and Q is as defined in table Z.

Table A-150 provides 24 compounds A-150.001 to A-150.024 of formula I-A wherein $A_1$ is CH, $A_2$ is N, $A_3$ is N, $R_1$ is H, $R_{2a}$ is CI, $R_{2b}$ is Br and Q is as defined in table Z.

Table A-151 provides 24 compounds A-151.001 to A-151.024 of formula I-A wherein $A_1$ is CH, $A_2$ is N, $A_3$ is N, $R_1$ is H, $R_{2a}$ is Br, $R_{2b}$ is $CF_3$ and Q is as defined in table Z.

Table A-152 provides 24 compounds A-152.001 to A-152.024 of formula I-A wherein $A_1$ is CH, $A_2$ is N, $A_3$ is N, $R_1$ is H, $R_{2a}$ is Br, $R_{2b}$ is C and Q is as defined in table Z.

Table A-153 provides 24 compounds A-153.001 to A-153.024 of formula I-A wherein $A_1$ is CH, $A_2$ is N, $A_3$ is N, $R_1$ is H, $R_{2a}$ is Br, $R_{2b}$ is Br and Q is as defined in table Z.

Table A-154 provides 24 compounds A-154.001 to A-154.024 of formula I-A wherein $A_1$ is CH, $A_2$ is N, $A_3$ is N, $R_1$ is H, $R_{2a}$ is $SO_2$—$CF_3$, $R_{2b}$ is $CF_3$ and Q is as defined in table Z.

Table A-155 provides 24 compounds A-155.001 to A-155.024 of formula I-A wherein $A_1$ is CH, $A_2$ is N, $A_3$ is N, $R_1$ is H, $R_{2a}$ is $SO_2$—$CF_3$, $R_{2b}$ is Cl and Q is as defined in table Z.

Table A-156 provides 24 compounds A-156.001 to A-156.024 of formula I-A wherein $A_1$ is CH, $A_2$ is N, $A_3$ is N, $R_1$ is H, $R_{2a}$ is $SO_2$—$CF_3$, $R_{2b}$ is Br and Q is as defined in table Z.

Table A-157 provides 24 compounds A-157.001 to A-157.024 of formula I-A wherein $A_1$ is CH, $A_2$ is N, $A_3$ is N, $R_1$ is $CH_3$, $R_{2a}$ is $CF_3$, $R_{2b}$ is $CF_3$ and Q is as defined in table Z.

Table A-158 provides 24 compounds A-158.001 to A-158.024 of formula I-A wherein $A_1$ is CH, $A_2$ is N, $A_3$ is N, $R_1$ is $CH_3$, $R_{2a}$ is $CF_3$, $R_{2b}$ is Cl and Q is as defined in table Z.

Table A-159 provides 24 compounds A-159.001 to A-159.024 of formula I-A wherein $A_1$ is CH, $A_2$ is N, $A_3$ is N, $R_1$ is $CH_3$, $R_{2a}$ is $CF_3$, $R_{2b}$ is Br and Q is as defined in table Z.

Table A-160 provides 24 compounds A-160.001 to A-160.024 of formula I-A wherein $A_1$ is CH, $A_2$ is N, $A_3$ is N, $R_1$ is $CH_3$, $R_{2a}$ is Cl, $R_{2b}$ is $CF_3$ and Q is as defined in table Z.

Table A-161 provides 24 compounds A-161.001 to A-161.024 of formula I-A wherein $A_1$ is CH, $A_2$ is N, $A_3$ is N, $R_1$ is $CH_3$, $R_{2a}$ is CI, $R_{2b}$ is C and Q is as defined in table Z.

Table A-162 provides 24 compounds A-162.001 to A-162.024 of formula I-A wherein $A_1$ is CH, $A_2$ is N, $A_3$ is N, $R_1$ is $CH_3$, $R_{2a}$ is CI, $R_{2b}$ is Br and Q is as defined in table Z.

Table A-163 provides 24 compounds A-163.001 to A-163.024 of formula I-A wherein $A_1$ is CH, $A_2$ is N, $A_3$ is N, $R_1$ is $CH_3$, $R_{2a}$ is Br, $R_{2b}$ is $CF_3$ and Q is as defined in table Z.

Table A-164 provides 24 compounds A-164.001 to A-164.024 of formula I-A wherein $A_1$ is CH, $A_2$ is N, $A_3$ is N, $R_1$ is $CH_3$, $R_{2a}$ is Br, $R_{2b}$ is C and Q is as defined in table Z.

Table A-165 provides 24 compounds A-165.001 to A-165.024 of formula I-A wherein $A_1$ is CH, $A_2$ is N, $A_3$ is N, $R_1$ is $CH_3$, $R_{2a}$ is Br, $R_{2b}$ is Br and Q is as defined in table Z.

Table A-166 provides 24 compounds A-166.001 to A-166.024 of formula I-A wherein $A_1$ is CH, $A_2$ is N, $A_3$ is N, $R_1$ is $CH_3$, $R_{2a}$ is $SO_2$—$CF_3$, $R_{2b}$ is $CF_3$ and Q is as defined in table Z.

Table A-167 provides 24 compounds A-167.001 to A-167.024 of formula I-A wherein $A_1$ is CH, $A_2$ is N, $A_3$ is N, $R_1$ is $CH_3$, $R_{2a}$ is $SO_2$—$CF_3$, $R_{2b}$ is C and Q is as defined in table Z.

Table A-168 provides 24 compounds A-168.001 to A-168.024 of formula I-A wherein $A_1$ is CH, $A_2$ is N, $A_3$ is N, $R_1$ is $CH_3$, $R_{2a}$ is $SO_2$—$CF_3$, $R_{2b}$ is Br and Q is as defined in table Z.

Table A-169 provides 24 compounds A-169.001 to A-169.024 of formula I-A wherein $A_1$ is CH, $A_2$ is N, $A_3$ is N, $R_1$ is $CH_2$-cyclopropyl, $R_{2a}$ is $CF_3$, $R_{2b}$ is $CF_3$ and Q is as defined in table Z.

Table A-170 provides 24 compounds A-170.001 to A-170.024 of formula I-A wherein $A_1$ is CH, $A_2$ is N, $A_3$ is N, $R_1$ is $CH_2$-cyclopropyl, $R_{2a}$ is $CF_3$, $R_{2b}$ is C and Q is as defined in table Z.

Table A-171 provides 24 compounds A-171.001 to A-171.024 of formula I-A wherein $A_1$ is CH, $A_2$ is N, $A_3$ is N, $R_1$ is $CH_2$-cyclopropyl, $R_{2a}$ is $CF_3$, $R_{2b}$ is Br and Q is as defined in table Z.

Table A-172 provides 24 compounds A-172.001 to A-172.024 of formula I-A wherein $A_1$ is CH, $A_2$ is N, $A_3$ is N, $R_1$ is $CH_2$-cyclopropyl, $R_{2a}$ is Cl, $R_{2b}$ is $CF_3$ and Q is as defined in table Z.

Table A-173 provides 24 compounds A-173.001 to A-173.024 of formula I-A wherein $A_1$ is CH, $A_2$ is N, $A_3$ is N, $R_1$ is $CH_2$-cyclopropyl, $R_{2a}$ is Cl, $R_{2b}$ is Cl and Q is as defined in table Z.

Table A-174 provides 24 compounds A-174.001 to A-174.024 of formula I-A wherein $A_1$ is CH, $A_2$ is N, $A_3$ is N, $R_1$ is $CH_2$-cyclopropyl, $R_{2a}$ is Cl, $R_{2b}$ is Br and Q is as defined in table Z.

Table A-175 provides 24 compounds A-175.001 to A-175.024 of formula I-A wherein $A_1$ is CH, $A_2$ is N, $A_3$ is N, $R_1$ is $CH_2$-cyclopropyl, $R_{2a}$ is Br, $R_{2b}$ is $CF_3$ and Q is as defined in table Z.

Table A-176 provides 24 compounds A-176.001 to A-176.024 of formula I-A wherein $A_1$ is CH, $A_2$ is N, $A_3$ is N, $R_1$ is $CH_2$-cyclopropyl, $R_{2a}$ is Br, $R_{2b}$ is Cl and Q is as defined in table Z.

Table A-177 provides 24 compounds A-177.001 to A-177.024 of formula I-A wherein $A_1$ is CH, $A_2$ is N, $A_3$ is N, $R_1$ is $CH_2$-cyclopropyl, $R_{2a}$ is Br, $R_{2b}$ is Br and Q is as defined in table Z.

Table A-178 provides 24 compounds A-178.001 to A-178.024 of formula I-A wherein $A_1$ is CH, $A_2$ is N, $A_3$ is N, $R_1$ is $CH_2$-cyclopropyl, $R_{2a}$ is $SO_2$—$CF_3$, $R_{2b}$ is $CF_3$ and Q is as defined in table Z.

Table A-179 provides 24 compounds A-179.001 to A-179.024 of formula I-A wherein $A_1$ is CH, $A_2$ is N, $A_3$ is N, $R_1$ is $CH_2$-cyclopropyl, $R_{2a}$ is $SO_2$—$CF_3$, $R_{2b}$ is C and Q is as defined in table Z.

Table A-180 provides 24 compounds A-180.001 to A-180.024 of formula I-A wherein $A_1$ is CH, $A_2$ is N, $A_3$ is N, $R_1$ is $CH_2$-cyclopropyl, $R_{2a}$ is $SO_2$—$CF_3$, $R_{2b}$ is Br and Q is as defined in table Z.

Table A-181 provides 24 compounds A-181.001 to A-181.024 of formula I-A wherein $A_1$ is CH, $A_2$ is N, $A_3$ is CH, $R_1$ is H, $R_{2a}$ is $CF_3$, $R_{2b}$ is $CF_3$ and Q is as defined in table Z.

Table A-182 provides 24 compounds A-182.001 to A-182.024 of formula I-A wherein $A_1$ is CH, $A_2$ is N, $A_3$ is CH, $R_1$ is H, $R_{2a}$ is $CF_3$, $R_{2b}$ is C and Q is as defined in table Z.

Table A-183 provides 24 compounds A-183.001 to A-183.024 of formula I-A wherein $A_1$ is CH, $A_2$ is N, $A_3$ is CH, $R_1$ is H, $R_{2a}$ is $CF_3$, $R_{2b}$ is Br and Q is as defined in table Z.

Table A-184 provides 24 compounds A-184.001 to A-184.024 of formula I-A wherein $A_1$ is CH, $A_2$ is N, $A_3$ is CH, $R_1$ is H, $R_{2a}$ is CI, $R_{2b}$ is $CF_3$ and Q is as defined in table Z.

Table A-185 provides 24 compounds A-185.001 to A-185.024 of formula I-A wherein $A_1$ is CH, $A_2$ is N, $A_3$ is CH, $R_1$ is H, $R_{2a}$ is CI, $R_{2b}$ is C and Q is as defined in table Z.

Table A-186 provides 24 compounds A-186.001 to A-186.024 of formula I-A wherein $A_1$ is CH, $A_2$ is N, $A_3$ is CH, $R_1$ is H, $R_{2a}$ is CI, $R_{2b}$ is Br and Q is as defined in table Z.

Table A-187 provides 24 compounds A-187.001 to A-187.024 of formula I-A wherein $A_1$ is CH, $A_2$ is N, $A_3$ is CH, $R_1$ is H, $R_{2a}$ is Br, $R_{2b}$ is $CF_3$ and Q is as defined in table Z.

Table A-188 provides 24 compounds A-188.001 to A-188.024 of formula I-A wherein $A_1$ is CH, $A_2$ is N, $A_3$ is CH, $R_1$ is H, $R_{2a}$ is Br, $R_{2b}$ is Cl and Q is as defined in table Z.

Table A-189 provides 24 compounds A-189.001 to A-189.024 of formula I-A wherein $A_1$ is CH, $A_2$ is N, $A_3$ is CH, $R_1$ is H, $R_{2a}$ is Br, $R_{2b}$ is Br and Q is as defined in table Z.

Table A-190 provides 24 compounds A-190.001 to A-190.024 of formula I-A wherein $A_1$ is CH, $A_2$ is N, $A_3$ is CH, $R_1$ is H, $R_{2a}$ is $SO_2$—$CF_3$, $R_{2b}$ is $CF_3$ and Q is as defined in table Z.

Table A-191 provides 24 compounds A-191.001 to A-191.024 of formula I-A wherein $A_1$ is CH, $A_2$ is N, $A_3$ is CH, $R_1$ is H, $R_{2a}$ is $SO_2$—$CF_3$, $R_{2b}$ is Cl and Q is as defined in table Z.

Table A-192 provides 24 compounds A-192.001 to A-192.024 of formula I-A wherein $A_1$ is CH, $A_2$ is N, $A_3$ is CH, $R_1$ is H, $R_{2a}$ is $SO_2$—$CF_3$, $R_{2b}$ is Br and Q is as defined in table Z.

Table A-193 provides 24 compounds A-193.001 to A-193.024 of formula I-A wherein $A_1$ is CH, $A_2$ is N, $A_3$ is CH, $R_1$ is $CH_3$, $R_{2a}$ is $CF_3$, $R_{2b}$ is $CF_3$ and Q is as defined in table Z.

Table A-194 provides 24 compounds A-194.001 to A-194.024 of formula I-A wherein $A_1$ is CH, $A_2$ is N, $A_3$ is CH, $R_1$ is $CH_3$, $R_{2a}$ is $CF_3$, $R_{2b}$ is C and Q is as defined in table Z.

Table A-195 provides 24 compounds A-195.001 to A-195.024 of formula I-A wherein $A_1$ is CH, $A_2$ is N, $A_3$ is CH, $R_1$ is $CH_3$, $R_{2a}$ is $CF_3$, $R_{2b}$ is Br and Q is as defined in table Z.

Table A-196 provides 24 compounds A-196.001 to A-196.024 of formula I-A wherein $A_1$ is CH, $A_2$ is N, $A_3$ is CH, $R_1$ is $CH_3$, $R_{2a}$ is CI, $R_{2b}$ is $CF_3$ and Q is as defined in table Z.

Table A-197 provides 24 compounds A-197.001 to A-197.024 of formula I-A wherein $A_1$ is CH, $A_2$ is N, $A_3$ is CH, $R_1$ is $CH_3$, $R_{2a}$ is CI, $R_{2b}$ is C and Q is as defined in table Z.

Table A-198 provides 24 compounds A-198.001 to A-198.024 of formula I-A wherein $A_1$ is CH, $A_2$ is N, $A_3$ is CH, $R_1$ is $CH_3$, $R_{2a}$ is CI, $R_{2b}$ is Br and Q is as defined in table Z.

Table A-199 provides 24 compounds A-199.001 to A-199.024 of formula I-A wherein $A_1$ is CH, $A_2$ is N, $A_3$ is CH, $R_1$ is $CH_3$, $R_{2a}$ is Br, $R_{2b}$ is $CF_3$ and Q is as defined in table Z.

Table A-200 provides 24 compounds A-200.001 to A-200.024 of formula I-A wherein $A_1$ is CH, $A_2$ is N, $A_3$ is CH, $R_1$ is $CH_3$, $R_{2a}$ is Br, $R_{2b}$ is C and Q is as defined in table Z.

Table A-201 provides 24 compounds A-201.001 to A-201.024 of formula I-A wherein $A_1$ is CH, $A_2$ is N, $A_3$ is CH, $R_1$ is $CH_3$, $R_{2a}$ is Br, $R_{2b}$ is Br and Q is as defined in table Z.

Table A-202 provides 24 compounds A-202.001 to A-202.024 of formula I-A wherein $A_1$ is CH, $A_2$ is N, $A_3$ is CH, $R_1$ is $CH_3$, $R_{2a}$ is $SO_2$—$CF_3$, $R_{2b}$ is $CF_3$ and Q is as defined in table Z.

Table A-203 provides 24 compounds A-203.001 to A-203.024 of formula I-A wherein $A_1$ is CH, $A_2$ is N, $A_3$ is CH, $R_1$ is $CH_3$, $R_{2a}$ is $SO_2$—$CF_3$, $R_{2b}$ is C and Q is as defined in table Z.

Table A-204 provides 24 compounds A-204.001 to A-204.024 of formula I-A wherein $A_1$ is CH, $A_2$ is N, $A_3$ is CH, $R_1$ is $CH_3$, $R_{2a}$ is $SO_2$—$CF_3$, $R_{2b}$ is Br and Q is as defined in table Z.

Table A-205 provides 24 compounds A-205.001 to A-205.024 of formula I-A wherein $A_1$ is CH, $A_2$ is N, $A_3$ is CH, $R_1$ is $CH_2$-cyclopropyl, $R_{2a}$ is $CF_3$, $R_{2b}$ is $CF_3$ and Q is as defined in table Z.

Table A-206 provides 24 compounds A-206.001 to A-206.024 of formula I-A wherein $A_1$ is CH, $A_2$ is N, $A_3$ is CH, $R_1$ is $CH_2$-cyclopropyl, $R_{2a}$ is $CF_3$, $R_{2b}$ is Cl and Q is as defined in table Z.

Table A-207 provides 24 compounds A-207.001 to A-207.024 of formula I-A wherein $A_1$ is CH, $A_2$ is N, $A_3$ is CH, $R_1$ is $CH_2$-cyclopropyl, $R_{2a}$ is $CF_3$, $R_{2b}$ is Br and Q is as defined in table Z.

Table A-208 provides 24 compounds A-208.001 to A-208.024 of formula I-A wherein $A_1$ is CH, $A_2$ is N, $A_3$ is CH, $R_1$ is $CH_2$-cyclopropyl, $R_{2a}$ is Cl, $R_{2b}$ is $CF_3$ and Q is as defined in table Z.

Table A-209 provides 24 compounds A-209.001 to A-209.024 of formula I-A wherein $A_1$ is CH, $A_2$ is N, $A_3$ is CH, $R_1$ is $CH_2$-cyclopropyl, $R_{2a}$ is CI, $R_{2b}$ is C and Q is as defined in table Z.

Table A-210 provides 24 compounds A-210.001 to A-210.024 of formula I-A wherein $A_1$ is CH, $A_2$ is N, $A_3$ is CH, $R_1$ is $CH_2$-cyclopropyl, $R_{2a}$ is CI, $R_{2b}$ is Br and Q is as defined in table Z.

Table A-211 provides 24 compounds A-211.001 to A-211.024 of formula I-A wherein $A_1$ is CH, $A_2$ is N, $A_3$ is CH, $R_1$ is $CH_2$-cyclopropyl, $R_{2a}$ is Br, $R_{2b}$ is $CF_3$ and Q is as defined in table Z.

Table A-212 provides 24 compounds A-212.001 to A-212.024 of formula I-A wherein $A_1$ is CH, $A_2$ is N, $A_3$ is CH, $R_1$ is $CH_2$-cyclopropyl, $R_{2a}$ is Br, $R_{2b}$ is C and Q is as defined in table Z.

Table A-213 provides 24 compounds A-213.001 to A-213.024 of formula I-A wherein $A_1$ is CH, $A_2$ is N, $A_3$ is CH, $R_1$ is $CH_2$-cyclopropyl, $R_{2a}$ is Br, $R_{2b}$ is Br and Q is as defined in table Z.

Table A-214 provides 24 compounds A-214.001 to A-214.024 of formula I-A wherein $A_1$ is CH, $A_2$ is N, $A_3$ is CH, $R_1$ is $CH_2$-cyclopropyl, $R_{2a}$ is $SO_2$—$CF_3$, $R_{2b}$ is $CF_3$ and Q is as defined in table Z.

Table A-215 provides 24 compounds A-215.001 to A-215.024 of formula I-A wherein $A_1$ is CH, $A_2$ is N, $A_3$ is CH, $R_1$ is $CH_2$-cyclopropyl, $R_{2a}$ is $SO_2$—$CF_3$, $R_{2b}$ is C and Q is as defined in table Z.

Table A-216 provides 24 compounds A-216.001 to A-216.024 of formula I-A wherein $A_1$ is CH, $A_2$ is N, $A_3$ is CH, $R_1$ is $CH_2$-cyclopropyl, $R_{2a}$ is $SO_2$—$CF_3$, $R_{2b}$ is Br and Q is as defined in table Z.

Table A-217 provides 24 compounds A-217.001 to A-217.024 of formula I-A wherein $A_1$ is CH, $A_2$ is CH, $A_3$ is N, $R_1$ is H, $R_{2a}$ is $CF_3$, $R_{2b}$ is $CF_3$ and Q is as defined in table Z.

Table A-218 provides 24 compounds A-218.001 to A-218.024 of formula I-A wherein $A_1$ is CH, $A_2$ is CH, $A_3$ is N, $R_1$ is H, $R_{2a}$ is $CF_3$, $R_{2b}$ is C and Q is as defined in table Z.

Table A-219 provides 24 compounds A-219.001 to A-219.024 of formula I-A wherein $A_1$ is CH, $A_2$ is CH, $A_3$ is N, $R_1$ is H, $R_{2a}$ is $CF_3$, $R_{2b}$ is Br and Q is as defined in table Z.

Table A-220 provides 24 compounds A-220.001 to A-220.024 of formula I-A wherein $A_1$ is CH, $A_2$ is CH, $A_3$ is N, $R_1$ is H, $R_{2a}$ is CI, $R_{2b}$ is $CF_3$ and Q is as defined in table Z.

Table A-221 provides 24 compounds A-221.001 to A-221.024 of formula I-A wherein $A_1$ is CH, $A_2$ is CH, $A_3$ is N, $R_1$ is H, $R_{2a}$ is CI, $R_{2b}$ is C and Q is as defined in table Z.

Table A-222 provides 24 compounds A-222.001 to A-222.024 of formula I-A wherein $A_1$ is CH, $A_2$ is CH, $A_3$ is N, $R_1$ is H, $R_{2a}$ is Cl, $R_{2b}$ is Br and Q is as defined in table Z.

Table A-223 provides 24 compounds A-223.001 to A-223.024 of formula I-A wherein $A_1$ is CH, $A_2$ is CH, $A_3$ is N, $R_1$ is H, $R_{2a}$ is Br, $R_{2b}$ is $CF_3$ and Q is as defined in table Z.

Table A-224 provides 24 compounds A-224.001 to A-224.024 of formula I-A wherein $A_1$ is CH, $A_2$ is CH, $A_3$ is N, $R_1$ is H, $R_{2a}$ is Br, $R_{2b}$ is Cl and Q is as defined in table Z.

Table A-225 provides 24 compounds A-225.001 to A-225.024 of formula I-A wherein $A_1$ is CH, $A_2$ is CH, $A_3$ is N, $R_1$ is H, $R_{2a}$ is Br, $R_{2b}$ is Br and Q is as defined in table Z.

Table A-226 provides 24 compounds A-226.001 to A-226.024 of formula I-A wherein $A_1$ is CH, $A_2$ is CH, $A_3$ is N, $R_1$ is H, $R_{2a}$ is $SO_2$—$CF_3$, $R_{2b}$ is $CF_3$ and Q is as defined in table Z.

Table A-227 provides 24 compounds A-227.001 to A-227.024 of formula I-A wherein $A_1$ is CH, $A_2$ is CH, $A_3$ is N, $R_1$ is H, $R_{2a}$ is $SO_2$—$CF_3$, $R_{2b}$ is C and Q is as defined in table Z.

Table A-228 provides 24 compounds A-228.001 to A-228.024 of formula I-A wherein $A_1$ is CH, $A_2$ is CH, $A_3$ is N, $R_1$ is H, $R_{2a}$ is $SO_2$—$CF_3$, $R_{2b}$ is Br and Q is as defined in table Z.

Table A-229 provides 24 compounds A-229.001 to A-229.024 of formula I-A wherein $A_1$ is CH, $A_2$ is CH, $A_3$ is N, $R_1$ is $CH_3$, $R_{2a}$ is $CF_3$, $R_{2b}$ is $CF_3$ and Q is as defined in table Z.

Table A-230 provides 24 compounds A-230.001 to A-230.024 of formula I-A wherein $A_1$ is CH, $A_2$ is CH, $A_3$ is N, $R_1$ is $CH_3$, $R_{2a}$ is $CF_3$, $R_{2b}$ is C and Q is as defined in table Z.

Table A-231 provides 24 compounds A-231.001 to A-231.024 of formula I-A wherein $A_1$ is CH, $A_2$ is CH, $A_3$ is N, $R_1$ is $CH_3$, $R_{2a}$ is $CF_3$, $R_{2b}$ is Br and Q is as defined in table Z.

Table A-232 provides 24 compounds A-232.001 to A-232.024 of formula I-A wherein $A_1$ is CH, $A_2$ is CH, $A_3$ is N, $R_1$ is $CH_3$, $R_{2a}$ is CI, $R_{2b}$ is $CF_3$ and Q is as defined in table Z.

Table A-233 provides 24 compounds A-233.001 to A-233.024 of formula I-A wherein $A_1$ is CH, $A_2$ is CH, $A_3$ is N, $R_1$ is $CH_3$, $R_{2a}$ is CI, $R_{2b}$ is C and Q is as defined in table Z.

Table A-234 provides 24 compounds A-234.001 to A-234.024 of formula I-A wherein $A_1$ is CH, $A_2$ is CH, $A_3$ is N, $R_1$ is $CH_3$, $R_{2a}$ is CI, $R_{2b}$ is Br and Q is as defined in table Z.

Table A-235 provides 24 compounds A-235.001 to A-235.024 of formula I-A wherein $A_1$ is CH, $A_2$ is CH, $A_3$ is N, $R_1$ is $CH_3$, $R_{2a}$ is Br, $R_{2b}$ is $CF_3$ and Q is as defined in table Z.

Table A-236 provides 24 compounds A-236.001 to A-236.024 of formula I-A wherein $A_1$ is CH, $A_2$ is CH, $A_3$ is N, $R_1$ is $CH_3$, $R_{2a}$ is Br, $R_{2b}$ is C and Q is as defined in table Z.

Table A-237 provides 24 compounds A-237.001 to A-237.024 of formula I-A wherein $A_1$ is CH, $A_2$ is CH, $A_3$ is N, $R_1$ is $CH_3$, $R_{2a}$ is Br, $R_{2b}$ is Br and Q is as defined in table Z.

Table A-238 provides 24 compounds A-238.001 to A-238.024 of formula I-A wherein $A_1$ is CH, $A_2$ is CH, $A_3$ is N, $R_1$ is $CH_3$, $R_{2a}$ is $SO_2$—$CF_3$, $R_{2b}$ is $CF_3$ and Q is as defined in table Z.

Table A-239 provides 24 compounds A-239.001 to A-239.024 of formula I-A wherein $A_1$ is CH, $A_2$ is CH, $A_3$ is N, $R_1$ is $CH_3$, $R_{2a}$ is $SO_2$—$CF_3$, $R_{2b}$ is CI and Q is as defined in table Z.

Table A-240 provides 24 compounds A-240.001 to A-240.024 of formula I-A wherein $A_1$ is CH, $A_2$ is CH, $A_3$ is N, $R_1$ is $CH_3$, $R_{2a}$ is $SO_2$—$CF_3$, $R_{2b}$ is Br and Q is as defined in table Z.

Table A-241 provides 24 compounds A-241.001 to A-241.024 of formula I-A wherein $A_1$ is CH, $A_2$ is CH, $A_3$ is N, $R_1$ is $CH_2$-cyclopropyl, $R_{2a}$ is $CF_3$, $R_{2b}$ is $CF_3$ and Q is as defined in table Z.

Table A-242 provides 24 compounds A-242.001 to A-242.024 of formula I-A wherein $A_1$ is CH, $A_2$ is CH, $A_3$ is N, $R_1$ is $CH_2$-cyclopropyl, $R_{2a}$ is $CF_3$, $R_{2b}$ is Cl and Q is as defined in table Z.

Table A-243 provides 24 compounds A-243.001 to A-243.024 of formula I-A wherein $A_1$ is CH, $A_2$ is CH, $A_3$ is N, $R_1$ is $CH_2$-cyclopropyl, $R_{2a}$ is $CF_3$, $R_{2b}$ is Br and Q is as defined in table Z.

Table A-244 provides 24 compounds A-244.001 to A-244.024 of formula I-A wherein $A_1$ is CH, $A_2$ is CH, $A_3$ is N, $R_1$ is $CH_2$-cyclopropyl, $R_{2a}$ is CI, $R_{2b}$ is $CF_3$ and Q is as defined in table Z.

Table A-245 provides 24 compounds A-245.001 to A-245.024 of formula I-A wherein $A_1$ is CH, $A_2$ is CH, $A_3$ is N, $R_1$ is $CH_2$-cyclopropyl, $R_{2a}$ is CI, $R_{2b}$ is C and Q is as defined in table Z.

Table A-246 provides 24 compounds A-246.001 to A-246.024 of formula I-A wherein $A_1$ is CH, $A_2$ is CH, $A_3$ is N, $R_1$ is $CH_2$-cyclopropyl, $R_{2a}$ is CI, $R_{2b}$ is Br and Q is as defined in table Z.

Table A-247 provides 24 compounds A-247.001 to A-247.024 of formula I-A wherein $A_1$ is CH, $A_2$ is CH, $A_3$ is N, $R_1$ is $CH_2$-cyclopropyl, $R_{2a}$ is Br, $R_{2b}$ is $CF_3$ and Q is as defined in table Z.

Table A-248 provides 24 compounds A-248.001 to A-248.024 of formula I-A wherein $A_1$ is CH, $A_2$ is CH, $A_3$ is N, $R_1$ is $CH_2$-cyclopropyl, $R_{2a}$ is Br, $R_{2b}$ is C and Q is as defined in table Z.

Table A-249 provides 24 compounds A-249.001 to A-249.024 of formula I-A wherein $A_1$ is CH, $A_2$ is CH, $A_3$ is N, $R_1$ is $CH_2$-cyclopropyl, $R_{2a}$ is Br, $R_{2b}$ is Br and Q is as defined in table Z.

Table A-250 provides 24 compounds A-250.001 to A-250.024 of formula I-A wherein $A_1$ is CH, $A_2$ is CH, $A_3$ is N, $R_1$ is $CH_2$-cyclopropyl, $R_{2a}$ is $SO_2$—$CF_3$, $R_{2b}$ is $CF_3$ and Q is as defined in table Z.

Table A-251 provides 24 compounds A-251.001 to A-251.024 of formula I-A wherein $A_1$ is CH, $A_2$ is CH, $A_3$ is N, $R_1$ is $CH_2$-cyclopropyl, $R_{2a}$ is $SO_2$—$CF_3$, $R_{2b}$ is C and Q is as defined in table Z.

Table A-252 provides 24 compounds A-252.001 to A-252.024 of formula I-A wherein $A_1$ is CH, $A_2$ is CH, $A_3$ is N, $R_1$ is $CH_2$-cyclopropyl, $R_{2a}$ is $SO_2$—$CF_3$, $R_{2b}$ is Br and Q is as defined in table Z.

Table A-253 provides 24 compounds A-253.001 to A-253.024 of formula I-A wherein $A_1$ is CH, $A_2$ is CH, $A_3$ is CH, $R_1$ is H, $R_{2a}$ is $CF_3$, $R_{2b}$ is $CF_3$ and Q is as defined in table Z.

Table A-254 provides 24 compounds A-254.001 to A-254.024 of formula I-A wherein $A_1$ is CH, $A_2$ is CH, $A_3$ is CH, $R_1$ is H, $R_{2a}$ is $CF_3$, $R_{2b}$ is C and Q is as defined in table Z.

Table A-255 provides 24 compounds A-255.001 to A-255.024 of formula I-A wherein $A_1$ is CH, $A_2$ is CH, $A_3$ is CH, $R_1$ is H, $R_{2a}$ is $CF_3$, $R_{2b}$ is Br and Q is as defined in table Z.

Table A-256 provides 24 compounds A-256.001 to A-256.024 of formula I-A wherein $A_1$ is CH, $A_2$ is CH, $A_3$ is CH, $R_1$ is H, $R_{2a}$ is Cl, $R_{2b}$ is $CF_3$ and Q is as defined in table Z.

Table A-257 provides 24 compounds A-257.001 to A-257.024 of formula I-A wherein $A_1$ is CH, $A_2$ is CH, $A_3$ is CH, $R_1$ is H, $R_{2a}$ is Cl, $R_{2b}$ is Cl and Q is as defined in table Z.

Table A-258 provides 24 compounds A-258.001 to A-258.024 of formula I-A wherein $A_1$ is CH, $A_2$ is CH, $A_3$ is CH, $R_1$ is H, $R_{2a}$ is Cl, $R_{2b}$ is Br and Q is as defined in table Z.

Table A-259 provides 24 compounds A-259.001 to A-259.024 of formula I-A wherein $A_1$ is CH, $A_2$ is CH, $A_3$ is CH, $R_1$ is H, $R_{2a}$ is Br, $R_{2b}$ is $CF_3$ and Q is as defined in table Z.

Table A-260 provides 24 compounds A-260.001 to A-260.024 of formula I-A wherein $A_1$ is CH, $A_2$ is CH, $A_3$ is CH, $R_1$ is H, $R_{2a}$ is Br, $R_{2b}$ is C and Q is as defined in table Z.

Table A-261 provides 24 compounds A-261.001 to A-261.024 of formula I-A wherein $A_1$ is CH, $A_2$ is CH, $A_3$ is CH, $R_1$ is H, $R_{2a}$ is Br, $R_{2b}$ is Br and Q is as defined in table Z.

Table A-262 provides 24 compounds A-262.001 to A-262.024 of formula I-A wherein $A_1$ is CH, $A_2$ is CH, $A_3$ is CH, $R_1$ is H, $R_{2a}$ is $SO_2$—$CF_3$, $R_{2b}$ is $CF_3$ and Q is as defined in table Z.

Table A-263 provides 24 compounds A-263.001 to A-263.024 of formula I-A wherein $A_1$ is CH, $A_2$ is CH, $A_3$ is CH, $R_1$ is H, $R_{2a}$ is $SO_2$—$CF_3$, $R_{2b}$ is C and Q is as defined in table Z.

Table A-264 provides 24 compounds A-264.001 to A-264.024 of formula I-A wherein $A_1$ is CH, $A_2$ is CH, $A_3$ is CH, $R_1$ is H, $R_{2a}$ is $SO_2$—$CF_3$, $R_{2b}$ is Br and Q is as defined in table Z.

Table A-265 provides 24 compounds A-265.001 to A-265.024 of formula I-A wherein $A_1$ is CH, $A_2$ is CH, $A_3$ is CH, $R_1$ is $CH_3$, $R_{2a}$ is $CF_3$, $R_{2b}$ is $CF_3$ and Q is as defined in table Z.

Table A-266 provides 24 compounds A-266.001 to A-266.024 of formula I-A wherein $A_1$ is CH, $A_2$ is CH, $A_3$ is CH, $R_1$ is $CH_3$, $R_{2a}$ is $CF_3$, $R_{2b}$ is C and Q is as defined in table Z.

Table A-267 provides 24 compounds A-267.001 to A-267.024 of formula I-A wherein $A_1$ is CH, $A_2$ is CH, $A_3$ is CH, $R_1$ is $CH_3$, $R_{2a}$ is $CF_3$, $R_{2b}$ is Br and Q is as defined in table Z.

Table A-268 provides 24 compounds A-268.001 to A-268.024 of formula I-A wherein $A_1$ is CH, $A_2$ is CH, $A_3$ is CH, $R_1$ is $CH_3$, $R_{2a}$ is CI, $R_{2b}$ is $CF_3$ and Q is as defined in table Z.

Table A-269 provides 24 compounds A-269.001 to A-269.024 of formula I-A wherein $A_1$ is CH, $A_2$ is CH, $A_3$ is CH, $R_1$ is $CH_3$, $R_{2a}$ is CI, $R_{2b}$ is C and Q is as defined in table Z.

Table A-270 provides 24 compounds A-270.001 to A-270.024 of formula I-A wherein $A_1$ is CH, $A_2$ is CH, $A_3$ is CH, $R_1$ is $CH_3$, $R_{2a}$ is CI, $R_{2b}$ is Br and Q is as defined in table Z.

Table A-271 provides 24 compounds A-271.001 to A-271.024 of formula I-A wherein $A_1$ is CH, $A_2$ is CH, $A_3$ is CH, $R_1$ is $CH_3$, $R_{2a}$ is Br, $R_{2b}$ is $CF_3$ and Q is as defined in table Z.

Table A-272 provides 24 compounds A-272.001 to A-272.024 of formula I-A wherein $A_1$ is CH, $A_2$ is CH, $A_3$ is CH, $R_1$ is $CH_3$, $R_{2a}$ is Br, $R_{2b}$ is C and Q is as defined in table Z.

Table A-273 provides 24 compounds A-273.001 to A-273.024 of formula I-A wherein $A_1$ is CH, $A_2$ is CH, $A_3$ is CH, $R_1$ is $CH_3$, $R_{2a}$ is Br, $R_{2b}$ is Br and Q is as defined in table Z.

Table A-274 provides 24 compounds A-274.001 to A-274.024 of formula I-A wherein $A_1$ is CH, $A_2$ is CH, $A_3$ is CH, $R_1$ is $CH_3$, $R_{2a}$ is $SO_2$—$CF_3$, $R_{2b}$ is $CF_3$ and Q is as defined in table Z.

Table A-275 provides 24 compounds A-275.001 to A-275.024 of formula I-A wherein $A_1$ is CH, $A_2$ is CH, $A_3$ is CH, $R_1$ is $CH_3$, $R_{2a}$ is $SO_2$—$CF_3$, $R_{2b}$ is CI and Q is as defined in table Z.

Table A-276 provides 24 compounds A-276.001 to A-276.024 of formula I-A wherein $A_1$ is CH, $A_2$ is CH, $A_3$ is CH, $R_1$ is $CH_3$, $R_{2a}$ is $SO_2$—$CF_3$, $R_{2b}$ is Br and Q is as defined in table Z.

Table A-277 provides 24 compounds A-277.001 to A-277.024 of formula I-A wherein $A_1$ is CH, $A_2$ is CH, $A_3$ is CH, $R_1$ is $CH_2$-cyclopropyl, $R_{2a}$ is $CF_3$, $R_{2b}$ is $CF_3$ and Q is as defined in table Z.

Table A-278 provides 24 compounds A-278.001 to A-278.024 of formula I-A wherein $A_1$ is CH, $A_2$ is CH, $A_3$ is CH, $R_1$ is $CH_2$-cyclopropyl, $R_{2a}$ is $CF_3$, $R_{2b}$ is C and Q is as defined in table Z.

Table A-279 provides 24 compounds A-279.001 to A-279.024 of formula I-A wherein $A_1$ is CH, $A_2$ is CH, $A_3$ is CH, $R_1$ is $CH_2$-cyclopropyl, $R_{2a}$ is $CF_3$, $R_{2b}$ is Br and Q is as defined in table Z.

Table A-280 provides 24 compounds A-280.001 to A-280.024 of formula I-A wherein $A_1$ is CH, $A_2$ is CH, $A_3$ is CH, $R_1$ is $CH_2$-cyclopropyl, $R_{2a}$ is CI, $R_{2b}$ is $CF_3$ and Q is as defined in table Z.

Table A-281 provides 24 compounds A-281.001 to A-281.024 of formula I-A wherein $A_1$ is CH, $A_2$ is CH, $A_3$ is CH, $R_1$ is $CH_2$-cyclopropyl, $R_{2a}$ is CI, $R_{2b}$ is C and Q is as defined in table Z.

Table A-282 provides 24 compounds A-282.001 to A-282.024 of formula I-A wherein $A_1$ is CH, $A_2$ is CH, $A_3$ is CH, $R_1$ is $CH_2$-cyclopropyl, $R_{2a}$ is CI, $R_{2b}$ is Br and Q is as defined in table Z.

Table A-283 provides 24 compounds A-283.001 to A-283.024 of formula I-A wherein $A_1$ is CH, $A_2$ is CH, $A_3$ is CH, $R_1$ is $CH_2$-cyclopropyl, $R_{2a}$ is Br, $R_{2b}$ is $CF_3$ and Q is as defined in table Z.

Table A-284 provides 24 compounds A-284.001 to A-284.024 of formula I-A wherein $A_1$ is CH, $A_2$ is CH, $A_3$ is CH, $R_1$ is $CH_2$-cyclopropyl, $R_{2a}$ is Br, $R_{2b}$ is C and Q is as defined in table Z.

Table A-285 provides 24 compounds A-285.001 to A-285.024 of formula I-A wherein $A_1$ is CH, $A_2$ is CH, $A_3$ is CH, $R_1$ is $CH_2$-cyclopropyl, $R_{2a}$ is Br, $R_{2b}$ is Br and Q is as defined in table Z.

Table A-286 provides 24 compounds A-286.001 to A-286.024 of formula I-A wherein $A_1$ is CH, $A_2$ is CH, $A_3$ is CH, $R_1$ is $CH_2$-cyclopropyl, $R_{2a}$ is $SO_2$—$CF_3$, $R_{2b}$ is $CF_3$ and Q is as defined in table Z.

Table A-287 provides 24 compounds A-287.001 to A-287.024 of formula I-A wherein $A_1$ is CH, $A_2$ is CH, $A_3$ is CH, $R_1$ is $CH_2$-cyclopropyl, $R_{2a}$ is $SO_2$—$CF_3$, $R_{2b}$ is C and Q is as defined in table Z.

Table A-288 provides 24 compounds A-288.001 to A-288.024 of formula I-A wherein $A_1$ is CH, $A_2$ is CH, $A_3$ is CH, $R_1$ is $CH_2$-cyclopropyl, $R_{2a}$ is $SO_2$—$CF_3$, $R_{2b}$ is Br and Q is as defined in table Z.

Table A-289 provides 24 compounds A-289.001 to A-289.024 of formula I-A wherein $A_1$ is N, $A_2$ is CH, $A_3$ is N, $R_1$ is H, $R_{2a}$ is I, $R_{2b}$ is C and Q is as defined in table Z.

Table A-290 provides 24 compounds A-290.001 to A-290.024 of formula I-A wherein $A_1$ is N, $A_2$ is CH, $A_3$ is N, $R_1$ is $CH_3$, $R_{2a}$ is I, $R_{2b}$ is CI and Q is as defined in table Z.

Table A-291 provides 24 compounds A-291.001 to A-291.024 of formula I-A wherein $A_1$ is N, $A_2$ is CH, $A_3$ is N, $R_1$ is $CH_2$-cyclopropyl, $R_{2a}$ is I, $R_{2b}$ is CI and Q is as defined in table Z.

Table A-292 provides 24 compounds A-292.001 to A-292.024 of formula I-A wherein $A_1$ is N, $A_2$ is CH, $A_3$ is N, $R_1$ is H, $R_{2a}$ is $CF_3$, $R_{2b}$ is $SO_2$—$CF_3$ and Q is as defined in table Z.

Table A-293 provides 24 compounds A-293.001 to A-293.024 of formula I-A wherein $A_1$ is N, $A_2$ is CH, $A_3$ is N, $R_1$ is $CH_3$, $R_{2a}$ is $CF_3$, $R_{2b}$ is $SO_2$—$CF_3$ and Q is as defined in table Z.

Table A-294 provides 24 compounds A-294.001 to A-294.024 of formula I-A wherein $A_1$ is N, $A_2$ is CH, $A_3$ is N, $R_1$ is $CH_2$-cyclopropyl, $R_{2a}$ is $CF_3$, $R_{2b}$ is $SO_2$—$CF_3$ and Q is as defined in table Z.

Table A-295 provides 24 compounds A-295.001 to A-295.024 of formula I-A wherein $A_1$ is N, $A_2$ is CH, $A_3$ is N, $R_1$ is H, $R_{2a}$ is Cl, $R_{2b}$ is $SO_2$—$CF_3$ and Q is as defined in table Z.

Table A-296 provides 24 compounds A-296.001 to A-296.024 of formula I-A wherein $A_1$ is N, $A_2$ is CH, $A_3$ is N, $R_1$ is $CH_3$, $R_{2a}$ is Cl, $R_{2b}$ is $SO_2$—$CF_3$ and Q is as defined in table Z.

Table A-297 provides 24 compounds A-297.001 to A-297.024 of formula I-A wherein $A_1$ is N, $A_2$ is CH, $A_3$ is N, $R_1$ is $CH_2$-cyclopropyl, $R_{2a}$ is CI, $R_{2b}$ is $SO_2$—$CF_3$ and Q is as defined in table Z.

Table A-298 provides 24 compounds A-298.001 to A-298.024 of formula I-A wherein $A_1$ is N, $A_2$ is CH, $A_3$ is N, $R_1$ is H, $R_{2a}$ is Br, $R_{2b}$ is $SO_2$—$CF_3$ and Q is as defined in table Z.

Table A-299 provides 24 compounds A-299.001 to A-299.024 of formula I-A wherein $A_1$ is N, $A_2$ is CH, $A_3$ is N, $R_1$ is $CH_3$, $R_{2a}$ is Br, $R_{2b}$ is $SO_2$—$CF_3$ and Q is as defined in table Z.

Table A-300 provides 24 compounds A-300.001 to A-300.024 of formula I-A wherein $A_1$ is N, $A_2$ is CH, $A_3$ is N, $R_1$ is $CH_2$-cyclopropyl, $R_{2a}$ is Br, $R_{2b}$ is $SO_2$—$CF_3$ and Q is as defined in table Z.

Table B-1 provides 24 compounds B-1.001 to B-1.024 of formula I-B wherein R is H, $R_1$ is H, $R_{2a}$ is $CF_3$, $R_{2b}$ is $CF_3$ and Q is as defined in table Z.

Table B-2 provides 24 compounds B-2.001 to B-2.024 of formula I-B wherein R is H, $R_1$ is H, $R_{2a}$ is $CF_3$, $R_{2b}$ is C and Q is as defined in table Z.

Table B-3 provides 24 compounds B-3.001 to B-3.024 of formula I-B wherein R is H, $R_1$ is H, $R_{2a}$ is $CF_3$, $R_{2b}$ is Br and Q is as defined in table Z.

Table B-4 provides 24 compounds B-4.001 to B-4.024 of formula I-B wherein R is H, $R_1$ is H, $R_{2a}$ is CI, $R_{2b}$ is $CF_3$ and Q is as defined in table Z.

Table B-5 provides 24 compounds B-5.001 to B-5.024 of formula I-B wherein R is H, $R_1$ is H, $R_{2a}$ is CI, $R_{2b}$ is C and Q is as defined in table Z.

Table B-6 provides 24 compounds B-6.001 to B-6.024 of formula I-B wherein R is H, $R_1$ is H, $R_{2a}$ is CI, $R_{2b}$ is Br and Q is as defined in table Z.

Table B-7 provides 24 compounds B-7.001 to B-7.024 of formula I-B wherein R is H, $R_1$ is H, $R_{2a}$ is Br, $R_{2b}$ is $CF_3$ and Q is as defined in table Z.

Table B-8 provides 24 compounds B-8.001 to B-8.024 of formula I-B wherein R is H, $R_1$ is H, $R_{2a}$ is Br, $R_{2b}$ is Cl and Q is as defined in table Z.

Table B-9 provides 24 compounds B-9.001 to B-9.024 of formula I-B wherein R is H, $R_1$ is H, $R_{2a}$ is Br, $R_{2b}$ is Br and Q is as defined in table Z.

Table B-10 provides 24 compounds B-10.001 to B-10.024 of formula I-B wherein R is H, $R_1$ is H, $R_{2a}$ is $SO_2$—$CF_3$, $R_{2b}$ is $CF_3$ and Q is as defined in table Z.

Table B-11 provides 24 compounds B-11.001 to B-11.024 of formula I-B wherein R is H, $R_1$ is H, $R_{2a}$ is $SO_2$—$CF_3$, $R_{2b}$ is Cl and Q is as defined in table Z.

Table B-12 provides 24 compounds B-12.001 to B-12.024 of formula I-B wherein R is H, $R_1$ is H, $R_{2a}$ is $SO_2$—$CF_3$, $R_{2b}$ is Br and Q is as defined in table Z.

Table B-13 provides 24 compounds B-13.001 to B-13.024 of formula I-B wherein R is H, $R_1$ is $CH_3$, $R_{2a}$ is $CF_3$, $R_{2b}$ is $CF_3$ and Q is as defined in table Z.

Table B-14 provides 24 compounds B-14.001 to B-14.024 of formula I-B wherein R is H, $R_1$ is $CH_3$, $R_{2a}$ is $CF_3$, $R_{2b}$ is Cl and Q is as defined in table Z.

Table B-15 provides 24 compounds B-15.001 to B-15.024 of formula I-B wherein R is H, $R_1$ is $CH_3$, $R_{2a}$ is $CF_3$, $R_{2b}$ is Br and Q is as defined in table Z.

Table B-16 provides 24 compounds B-16.001 to B-16.024 of formula I-B wherein R is H, $R_1$ is $CH_3$, $R_{2a}$ is Cl, $R_{2b}$ is $CF_3$ and Q is as defined in table Z.

Table B-17 provides 24 compounds B-17.001 to B-17.024 of formula I-B wherein R is H, $R_1$ is $CH_3$, $R_{2a}$ is Cl, $R_{2b}$ is Cl and Q is as defined in table Z.

Table B-18 provides 24 compounds B-18.001 to B-18.024 of formula I-B wherein R is H, $R_1$ is $CH_3$, $R_{2a}$ is Cl, $R_{2b}$ is Br and Q is as defined in table Z.

Table B-19 provides 24 compounds B-19.001 to B-19.024 of formula I-B wherein R is H, $R_1$ is $CH_3$, $R_{2a}$ is Br, $R_{2b}$ is $CF_3$ and Q is as defined in table Z.

Table B-20 provides 24 compounds B-20.001 to B-20.024 of formula I-B wherein R is H, $R_1$ is $CH_3$, $R_{2a}$ is Br, $R_{2b}$ is Cl and Q is as defined in table Z.

Table B-21 provides 24 compounds B-21.001 to B-21.024 of formula I-B wherein R is H, $R_1$ is $CH_3$, $R_{2a}$ is Br, $R_{2b}$ is Br and Q is as defined in table Z.

Table B-22 provides 24 compounds B-22.001 to B-22.024 of formula I-B wherein R is H, $R_1$ is $CH_3$, $R_{2a}$ is $SO_2$—$CF_3$, $R_{2b}$ is $CF_3$ and Q is as defined in table Z.

Table B-23 provides 24 compounds B-23.001 to B-23.024 of formula I-B wherein R is H, $R_1$ is $CH_3$, $R_{2a}$ is $SO_2$—$CF_3$, $R_{2b}$ is Cl and Q is as defined in table Z.

Table B-24 provides 24 compounds B-24.001 to B-24.024 of formula I-B wherein R is H, $R_1$ is $CH_3$, $R_{2a}$ is $SO_2$—$CF_3$, $R_{2b}$ is Br and Q is as defined in table Z.

Table B-25 provides 24 compounds B-25.001 to B-25.024 of formula I-B wherein R is H, $R_1$ is $CH_2$-cyclopropyl, $R_{2a}$ is $CF_3$, $R_{2b}$ is $CF_3$ and Q is as defined in table Z.

Table B-26 provides 24 compounds B-26.001 to B-26.024 of formula I-B wherein R is H, $R_1$ is $CH_2$-cyclopropyl, $R_{2a}$ is $CF_3$, $R_{2b}$ is Cl and Q is as defined in table Z.

Table B-27 provides 24 compounds B-27.001 to B-27.024 of formula I-B wherein R is H, $R_1$ is $CH_2$-cyclopropyl, $R_{2a}$ is $CF_3$, $R_{2b}$ is Br and Q is as defined in table Z.

Table B-28 provides 24 compounds B-28.001 to B-28.024 of formula I-B wherein R is H, $R_1$ is $CH_2$-cyclopropyl, $R_{2a}$ is Cl, $R_{2b}$ is $CF_3$ and Q is as defined in table Z.

Table B-29 provides 24 compounds B-29.001 to B-29.024 of formula I-B wherein R is H, $R_1$ is $CH_2$-cyclopropyl, $R_{2a}$ is Cl, $R_{2b}$ is Cl and Q is as defined in table Z.

Table B-30 provides 24 compounds B-30.001 to B-30.024 of formula I-B wherein R is H, $R_1$ is $CH_2$-cyclopropyl, $R_{2a}$ is Cl, $R_{2b}$ is Br and Q is as defined in table Z.

Table B-31 provides 24 compounds B-31.001 to B-31.024 of formula I-B wherein R is H, $R_1$ is $CH_2$-cyclopropyl, $R_{2a}$ is Br, $R_{2b}$ is $CF_3$ and Q is as defined in table Z.

Table B-32 provides 24 compounds B-32.001 to B-32.024 of formula I-B wherein R is H, $R_1$ is $CH_2$-cyclopropyl, $R_{2a}$ is Br, $R_{2b}$ is Cl and Q is as defined in table Z.

Table B-33 provides 24 compounds B-33.001 to B-33.024 of formula I-B wherein R is H, $R_1$ is $CH_2$-cyclopropyl, $R_{2a}$ is Br, $R_{2b}$ is Br and Q is as defined in table Z.

Table B-34 provides 24 compounds B-34.001 to B-34.024 of formula I-B wherein R is H, $R_1$ is $CH_2$-cyclopropyl, $R_{2a}$ is $SO_2$—$CF_3$, $R_{2b}$ is $CF_3$ and Q is as defined in table Z.

Table B-35 provides 24 compounds B-35.001 to B-35.024 of formula I-B wherein R is H, $R_1$ is $CH_2$-cyclopropyl, $R_{2a}$ is $SO_2$—$CF_3$, $R_{2b}$ is Cl and Q is as defined in table Z.

Table B-36 provides 24 compounds B-36.001 to B-36.024 of formula I-B wherein R is H, $R_1$ is $CH_2$-cyclopropyl, $R_{2a}$ is $SO_2$—$CF_3$, $R_{2b}$ is Br and Q is as defined in table Z.

Table B-37 provides 24 compounds B-37.001 to B-37.024 of formula I-B wherein R is $CH_3$, $R_1$ is H, $R_{2a}$ is $CF_3$, $R_{2b}$ is $CF_3$ and Q is as defined in table Z.

Table B-38 provides 24 compounds B-38.001 to B-38.024 of formula I-B wherein R is $CH_3$, $R_1$ is H, $R_{2a}$ is $CF_3$, $R_{2b}$ is Cl and Q is as defined in table Z.

Table B-39 provides 24 compounds B-39.001 to B-39.024 of formula I-B wherein R is $CH_3$, $R_1$ is H, $R_{2a}$ is $CF_3$, $R_{2b}$ is Br and Q is as defined in table Z.

Table B-40 provides 24 compounds B-40.001 to B-40.024 of formula I-B wherein R is $CH_3$, $R_1$ is H, $R_{2a}$ is Cl, $R_{2b}$ is $CF_3$ and Q is as defined in table Z.

Table B-41 provides 24 compounds B-41.001 to B-41.024 of formula I-B wherein R is $CH_3$, $R_1$ is H, $R_{2a}$ is Cl, $R_{2b}$ is Cl and Q is as defined in table Z.

Table B-42 provides 24 compounds B-42.001 to B-42.024 of formula I-B wherein R is $CH_3$, $R_1$ is H, $R_{2a}$ is Cl, $R_{2b}$ is Br and Q is as defined in table Z.

Table B-43 provides 24 compounds B-43.001 to B-43.024 of formula I-B wherein R is $CH_3$, $R_1$ is H, $R_{2a}$ is Br, $R_{2b}$ is $CF_3$ and Q is as defined in table Z.

Table B-44 provides 24 compounds B-44.001 to B-44.024 of formula I-B wherein R is $CH_3$, $R_1$ is H, $R_{2a}$ is Br, $R_{2b}$ is Cl and Q is as defined in table Z.

Table B-45 provides 24 compounds B-45.001 to B-45.024 of formula I-B wherein R is $CH_3$, $R_1$ is H, $R_{2a}$ is Br, $R_{2b}$ is Br and Q is as defined in table Z.

Table B-46 provides 24 compounds B-46.001 to B-46.024 of formula I-B wherein R is $CH_3$, $R_1$ is H, $R_{2a}$ is $SO_2$—$CF_3$, $R_{2b}$ is $CF_3$ and Q is as defined in table Z.

Table B-47 provides 24 compounds B-47.001 to B-47.024 of formula I-B wherein R is $CH_3$, $R_1$ is H, $R_{2a}$ is $SO_2$—$CF_3$, $R_{2b}$ is Cl and Q is as defined in table Z.

Table B-48 provides 24 compounds B-48.001 to B-48.024 of formula I-B wherein R is $CH_3$, $R_1$ is H, $R_{2a}$ is $SO_2$—$CF_3$, $R_{2b}$ is Br and Q is as defined in table Z.

Table B-49 provides 24 compounds B-49.001 to B-49.024 of formula I-B wherein R is $CH_3$, $R_1$ is $CH_3$, $R_{2a}$ is $CF_3$, $R_{2b}$ is $CF_3$ and Q is as defined in table Z.

Table B-50 provides 24 compounds B-50.001 to B-50.024 of formula I-B wherein R is $CH_3$, $R_1$ is $CH_3$, $R_{2a}$ is $CF_3$, $R_{2b}$ is Cl and Q is as defined in table Z.

Table B-51 provides 24 compounds B-51.001 to B-51.024 of formula I-B wherein R is $CH_3$, $R_1$ is $CH_3$, $R_{2a}$ is $CF_3$, $R_{2b}$ is Br and Q is as defined in table Z.

Table B-52 provides 24 compounds B-52.001 to B-52.024 of formula I-B wherein R is $CH_3$, $R_1$ is $CH_3$, $R_{2a}$ is Cl, $R_{2b}$ is $CF_3$ and Q is as defined in table Z.

Table B-53 provides 24 compounds B-53.001 to B-53.024 of formula I-B wherein R is $CH_3$, $R_1$ is $CH_3$, $R_{2a}$ is Cl, $R_{2b}$ is Cl and Q is as defined in table Z.

Table B-54 provides 24 compounds B-54.001 to B-54.024 of formula I-B wherein R is $CH_3$, $R_1$ is $CH_3$, $R_{2a}$ is Cl, $R_{2b}$ is Br and Q is as defined in table Z.

Table B-55 provides 24 compounds B-55.001 to B-55.024 of formula I-B wherein R is $CH_3$, $R_1$ is $CH_3$, $R_{2a}$ is Br, $R_{2b}$ is $CF_3$ and Q is as defined in table Z.

Table B-56 provides 24 compounds B-56.001 to B-56.024 of formula I-B wherein R is $CH_3$, $R_1$ is $CH_3$, $R_{2a}$ is Br, $R_{2b}$ is Cl and Q is as defined in table Z.

Table B-57 provides 24 compounds B-57.001 to B-57.024 of formula I-B wherein R is $CH_3$, $R_1$ is $CH_3$, $R_{2a}$ is Br, $R_{2b}$ is Br and Q is as defined in table Z.

Table B-58 provides 24 compounds B-58.001 to B-58.024 of formula I-B wherein R is $CH_3$, $R_1$ is $CH_3$, $R_{2a}$ is $SO_2$—$CF_3$, $R_{2b}$ is $CF_3$ and Q is as defined in table Z.

Table B-59 provides 24 compounds B-59.001 to B-59.024 of formula I-B wherein R is $CH_3$, $R_1$ is $CH_3$, $R_{2a}$ is $SO_2$—$CF_3$, $R_{2b}$ is Cl and Q is as defined in table Z.

Table B-60 provides 24 compounds B-60.001 to B-60.024 of formula I-B wherein R is $CH_3$, $R_1$ is $CH_3$, $R_{2a}$ is $SO_2$—$CF_3$, $R_{2b}$ is Br and Q is as defined in table Z.

Table B-61 provides 24 compounds B-61.001 to B-61.024 of formula I-B wherein R is $CH_3$, $R_1$ is $CH_2$-cyclopropyl, $R_{2a}$ is $CF_3$, $R_{2b}$ is $CF_3$ and Q is as defined in table Z.

Table B-62 provides 24 compounds B-62.001 to B-62.024 of formula I-B wherein R is $CH_3$, $R_1$ is $CH_2$-cyclopropyl, $R_{2a}$ is $CF_3$, $R_{2b}$ is Cl and Q is as defined in table Z.

Table B-63 provides 24 compounds B-63.001 to B-63.024 of formula I-B wherein R is $CH_3$, $R_1$ is $CH_2$-cyclopropyl, $R_{2a}$ is $CF_3$, $R_{2b}$ is Br and Q is as defined in table Z.

Table B-64 provides 24 compounds B-64.001 to B-64.024 of formula I-B wherein R is $CH_3$, $R_1$ is $CH_2$-cyclopropyl, $R_{2a}$ is Cl, $R_{2b}$ is $CF_3$ and Q is as defined in table Z.

Table B-65 provides 24 compounds B-65.001 to B-65.024 of formula I-B wherein R is $CH_3$, $R_1$ is $CH_2$-cyclopropyl, $R_{2a}$ is Cl, $R_{2b}$ is Cl and Q is as defined in table Z.

Table B-66 provides 24 compounds B-66.001 to B-66.024 of formula I-B wherein R is $CH_3$, $R_1$ is $CH_2$-cyclopropyl, $R_{2a}$ is Cl, $R_{2b}$ is Br and Q is as defined in table Z.

Table B-67 provides 24 compounds B-67.001 to B-67.024 of formula I-B wherein R is $CH_3$, $R_1$ is $CH_2$-cyclopropyl, $R_{2a}$ is Br, $R_{2b}$ is $CF_3$ and Q is as defined in table Z.

Table B-68 provides 24 compounds B-68.001 to B-68.024 of formula I-B wherein R is $CH_3$, $R_1$ is $CH_2$-cyclopropyl, $R_{2a}$ is Br, $R_{2b}$ is Cl and Q is as defined in table Z.

Table B-69 provides 24 compounds B-69.001 to B-69.024 of formula I-B wherein R is $CH_3$, $R_1$ is $CH_2$-cyclopropyl, $R_{2a}$ is Br, $R_{2b}$ is Br and Q is as defined in table Z.

Table B-70 provides 24 compounds B-70.001 to B-70.024 of formula I-B wherein R is $CH_3$, $R_1$ is $CH_2$-cyclopropyl, $R_{2a}$ is $SO_2$—$CF_3$, $R_{2b}$ is $CF_3$ and Q is as defined in table Z.

Table B-71 provides 24 compounds B-71.001 to B-71.024 of formula I-B wherein R is $CH_3$, $R_1$ is $CH_2$-cyclopropyl, $R_{2a}$ is $SO_2$—$CF_3$, $R_{2b}$ is Cl and Q is as defined in table Z.

Table B-72 provides 24 compounds B-72.001 to B-72.024 of formula I-B wherein R is $CH_3$, $R_1$ is $CH_2$-cyclopropyl, $R_{2a}$ is $SO_2$—$CF_3$, $R_{2b}$ is Br and Q is as defined in table Z.

Table B-73 provides 24 compounds B-73.001 to B-73.024 of formula I-B wherein R is $CH_2$—$CF_3$, $R_1$ is H, $R_{2a}$ is $CF_3$, $R_{2b}$ is $CF_3$ and Q is as defined in table Z.

Table B-74 provides 24 compounds B-74.001 to B-74.024 of formula I-B wherein R is $CH_2$—$CF_3$, $R_1$ is H, $R_{2a}$ is $CF_3$, $R_{2b}$ is Cl and Q is as defined in table Z.

Table B-75 provides 24 compounds B-75.001 to B-75.024 of formula I-B wherein R is $CH_2$—$CF_3$, $R_1$ is H, $R_{2a}$ is $CF_3$, $R_{2b}$ is Br and Q is as defined in table Z.

Table B-76 provides 24 compounds B-76.001 to B-76.024 of formula I-B wherein R is $CH_2$—$CF_3$, $R_1$ is H, $R_{2a}$ is Cl, $R_{2b}$ is $CF_3$ and Q is as defined in table Z.

Table B-77 provides 24 compounds B-77.001 to B-77.024 of formula I-B wherein R is $CH_2$—$CF_3$, $R_1$ is H, $R_{2a}$ is Cl, $R_{2b}$ is Cl and Q is as defined in table Z.

Table B-78 provides 24 compounds B-78.001 to B-78.024 of formula I-B wherein R is $CH_2$—$CF_3$, $R_1$ is H, $R_{2a}$ is Cl, $R_{2b}$ is Br and Q is as defined in table Z.

Table B-79 provides 24 compounds B-79.001 to B-79.024 of formula I-B wherein R is $CH_2$—$CF_3$, $R_1$ is H, $R_{2a}$ is Br, $R_{2b}$ is $CF_3$ and Q is as defined in table Z.

Table B-80 provides 24 compounds B-80.001 to B-80.024 of formula I-B wherein R is $CH_2$—$CF_3$, $R_1$ is H, $R_{2a}$ is Br, $R_{2b}$ is Cl and Q is as defined in table Z.

Table B-81 provides 24 compounds B-81.001 to B-81.024 of formula I-B wherein R is $CH_2$—$CF_3$, $R_1$ is H, $R_{2a}$ is Br, $R_{2b}$ is Br and Q is as defined in table Z.

Table B-82 provides 24 compounds B-82.001 to B-82.024 of formula I-B wherein R is $CH_2$—$CF_3$, $R_1$ is H, $R_{2a}$ is $SO_2$—$CF_3$, $R_{2b}$ is $CF_3$ and Q is as defined in table Z.

Table B-83 provides 24 compounds B-83.001 to B-83.024 of formula I-B wherein R is $CH_2$—$CF_3$, $R_1$ is H, $R_{2a}$ is $SO_2$—$CF_3$, $R_{2b}$ is Cl and Q is as defined in table Z.

Table B-84 provides 24 compounds B-84.001 to B-84.024 of formula I-B wherein R is $CH_2$—$CF_3$, $R_1$ is H, $R_{2a}$ is $SO_2$—$CF_3$, $R_{2b}$ is Br and Q is as defined in table Z.

Table B-85 provides 24 compounds B-85.001 to B-85.024 of formula I-B wherein R is $CH_2$—$CF_3$, $R_1$ is $CH_3$, $R_{2a}$ is $CF_3$, $R_{2b}$ is $CF_3$ and Q is as defined in table Z.

Table B-86 provides 24 compounds B-86.001 to B-86.024 of formula I-B wherein R is $CH_2$—$CF_3$, $R_1$ is $CH_3$, $R_{2a}$ is $CF_3$, $R_{2b}$ is Cl and Q is as defined in table Z.

Table B-87 provides 24 compounds B-87.001 to B-87.024 of formula I-B wherein R is $CH_2$—$CF_3$, $R_1$ is $CH_3$, $R_{2a}$ is $CF_3$, $R_{2b}$ is Br and Q is as defined in table Z.

Table B-88 provides 24 compounds B-88.001 to B-88.024 of formula I-B wherein R is $CH_2$—$CF_3$, $R_1$ is $CH_3$, $R_{2a}$ is Cl, $R_{2b}$ is $CF_3$ and Q is as defined in table Z.

Table B-89 provides 24 compounds B-89.001 to B-89.024 of formula I-B wherein R is $CH_2$—$CF_3$, $R_1$ is $CH_3$, $R_{2a}$ is Cl, $R_{2b}$ is Cl and Q is as defined in table Z.

Table B-90 provides 24 compounds B-90.001 to B-90.024 of formula I-B wherein R is $CH_2$—$CF_3$, $R_1$ is $CH_3$, $R_{2a}$ is Cl, $R_{2b}$ is Br and Q is as defined in table Z.

Table B-91 provides 24 compounds B-91.001 to B-91.024 of formula I-B wherein R is $CH_2$—$CF_3$, $R_1$ is $CH_3$, $R_{2a}$ is Br, $R_{2b}$ is $CF_3$ and Q is as defined in table Z.

Table B-92 provides 24 compounds B-92.001 to B-92.024 of formula I-B wherein R is $CH_2$—$CF_3$, $R_1$ is $CH_3$, $R_{2a}$ is Br, $R_{2b}$ is Cl and Q is as defined in table Z.

Table B-93 provides 24 compounds B-93.001 to B-93.024 of formula I-B wherein R is $CH_2$—$CF_3$, $R_1$ is $CH_3$, $R_{2a}$ is Br, $R_{2b}$ is Br and Q is as defined in table Z.

Table B-94 provides 24 compounds B-94.001 to B-94.024 of formula I-B wherein R is $CH_2$—$CF_3$, $R_1$ is $CH_3$, $R_{2a}$ is $SO_2$—$CF_3$, $R_{2b}$ is $CF_3$ and Q is as defined in table Z.

Table B-95 provides 24 compounds B-95.001 to B-95.024 of formula I-B wherein R is $CH_2$—$CF_3$, $R_1$ is $CH_3$, $R_{2a}$ is $SO_2$—$CF_3$, $R_{2b}$ is Cl and Q is as defined in table Z.

Table B-96 provides 24 compounds B-96.001 to B-96.024 of formula I-B wherein R is $CH_2$—$CF_3$, $R_1$ is $CH_3$, $R_{2a}$ is $SO_2$—$CF_3$, $R_{2b}$ is Br and Q is as defined in table Z.

Table B-97 provides 24 compounds B-97.001 to B-97.024 of formula I-B wherein R is $CH_2$—$CF_3$, $R_1$ is $CH_2$-cyclopropyl, $R_{2a}$ is $CF_3$, $R_{2b}$ is $CF_3$ and Q is as defined in table Z.

Table B-98 provides 24 compounds B-98.001 to B-98.024 of formula I-B wherein R is $CH_2$—$CF_3$, $R_1$ is $CH_2$-cyclopropyl, $R_{2a}$ is $CF_3$, $R_{2b}$ is Cl and Q is as defined in table Z.

Table B-99 provides 24 compounds B-99.001 to B-99.024 of formula I-B wherein R is $CH_2$—$CF_3$, $R_1$ is $CH_2$-cyclopropyl, $R_{2a}$ is $CF_3$, $R_{2b}$ is Br and Q is as defined in table Z.

Table B-100 provides 24 compounds B-100.001 to B-100.024 of formula I-B wherein R is $CH_2$—$CF_3$, $R_1$ is $CH_2$-cyclopropyl, $R_{2a}$ is Cl, $R_{2b}$ is $CF_3$ and Q is as defined in table Z.

Table B-101 provides 24 compounds B-101.001 to B-101.024 of formula I-B wherein R is $CH_2$—$CF_3$, $R_1$ is $CH_2$-cyclopropyl, $R_{2a}$ is Cl, $R_{2b}$ is Cl and Q is as defined in table Z.

Table B-102 provides 24 compounds B-102.001 to B-102.024 of formula I-B wherein R is $CH_2$—$CF_3$, $R_1$ is $CH_2$-cyclopropyl, $R_{2a}$ is Cl, $R_{2b}$ is Br and Q is as defined in table Z.

Table B-103 provides 24 compounds B-103.001 to B-103.024 of formula I-B wherein R is $CH_2$—$CF_3$, $R_1$ is $CH_2$-cyclopropyl, $R_{2a}$ is Br, $R_{2b}$ is $CF_3$ and Q is as defined in table Z.

Table B-104 provides 24 compounds B-104.001 to B-104.024 of formula I-B wherein R is $CH_2$—$CF_3$, $R_1$ is $CH_2$-cyclopropyl, $R_{2a}$ is Br, $R_{2b}$ is Cl and Q is as defined in table Z.

Table B-105 provides 24 compounds B-105.001 to B-105.024 of formula I-B wherein R is $CH_2$—$CF_3$, $R_1$ is $CH_2$-cyclopropyl, $R_{2a}$ is Br, $R_{2b}$ is Br and Q is as defined in table Z.

Table B-106 provides 24 compounds B-106.001 to B-106.024 of formula I-B wherein R is $CH_2$—$CF_3$, $R_1$ is $CH_2$-cyclopropyl, $R_{2a}$ is $SO_2$—$CF_3$, $R_{2b}$ is $CF_3$ and Q is as defined in table Z.

Table B-107 provides 24 compounds B-107.001 to B-107.024 of formula I-B wherein R is $CH_2$—$CF_3$, $R_1$ is $CH_2$-cyclopropyl, $R_{2a}$ is $SO_2$—$CF_3$, $R_{2b}$ is Cl and Q is as defined in table Z.

Table B-108 provides 24 compounds B-108.001 to B-108.024 of formula I-B wherein R is $CH_2$—$CF_3$, $R_1$ is $CH_2$-cyclopropyl, $R_{2a}$ is $SO_2$—$CF_3$, $R_{2b}$ is Br and Q is as defined in table Z.

TABLE Z

| Substituent definitions of Q: | |
|---|---|
| Index | Q |
| 1 | 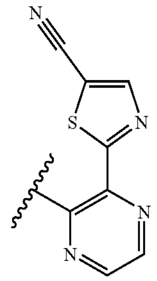 [SMILES: *c1nccnc1-c1ncc(C#N)s1] |
| 2 | 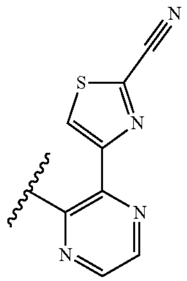 [SMILES: *c1nccnc1-c1csc(C#N)n1] |
| 3 | 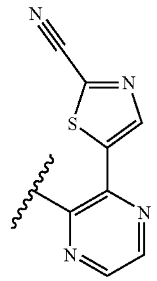 [SMILES: *c1nccnc1-c1cnc(C#N)s1] |
| 4 | 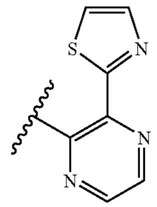 [SMILES: *c1nccnc1-c1nccs1] |
| 5 | 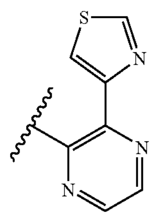 [SMILES: *c1nccnc1-c1cscn1] |
| 6 | 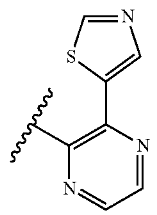 [SMILES: *c1nccnc1-c1cncs1] |

TABLE Z-continued
Substituent definitions of Q:
| Index | Q |
|---|---|
| 7 | 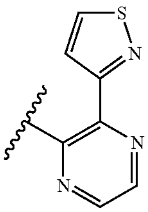 [SMILES: *c1nccnc1-c1ccsn1] |
| 8 | 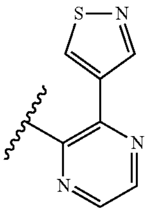 [SMILES: *c1nccnc1-c1cnsc1] |
| 9 | 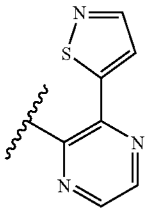 [SMILES: *c1nccnc1-c1ccns1] |
| 10 | 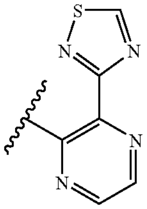 [SMILES: *c1nccnc1-c1ncsn1] |
| 11 | 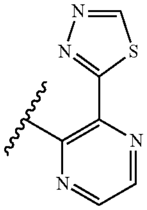 [SMILES: *c1nccnc1-c1nncs1] |
| 12 | 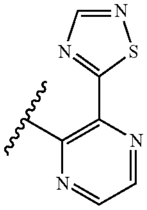 [SMILES: *c1nccnc1-c1ncns1] |
| 13 | 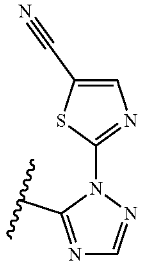 [SMILES: *c1ncnn1-c1ncc(C#N)s1] |
| 14 | 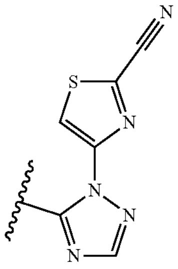 [SMILES: *c1ncnn1-c1csc(C#N)n1] |
| 15 | 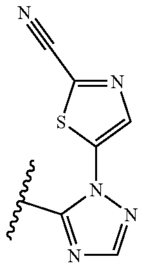 [SMILES: *c1ncnn1-c1cnc(C#N)s1] |
| 16 | 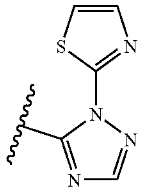 [SMILES: *c1ncnn1-c1nccs1] |
| 17 | 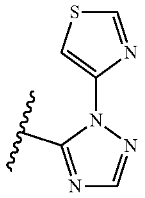 [SMILES: *c1ncnn1-c1cscn1] |
| 18 | 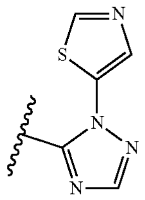 [SMILES: *c1ncnn1-c1cncs1] |

TABLE Z-continued

| Substituent definitions of Q: | |
|---|---|
| Index | Q |
| 19 | 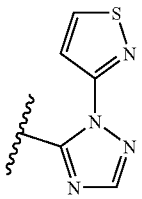 [SMILES: *c1ncnn1-c1ccsn1] |
| 20 | 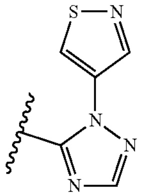 [SMILES: *c1ncnn1-c1cnsc1] |
| 21 | 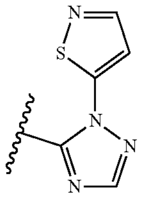 [SMILES: *c1ncnn1-c1ccns1] |
| 22 | 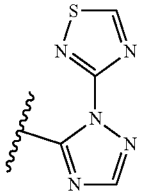 [SMILES: *c1ncnn1-c1ncsn1] |
| 23 | 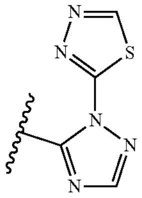 [SMILES: *c1ncnn1-c1nncs1] |
| 24 | 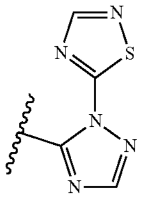 [SMILES: *c1ncnn1-c1ncns1] |

Also made available are certain intermediate compounds of formulae II(i), III(i), IV(i), V(i), VII(i), XI(i), and XIV(i), some of which are novel. For example, A compound of formula II(i), wherein (i) X1 is Cl and $A_1$, $A_2$, $A_3$, $A_4$, $A_5$, $R_{2a}$ and $R_{2b}$ are as defined in any one of Tables A-1 to A-300; or wherein (ii) X1 is Br and $A_1$, $A_2$, $A_3$, $A_4$, $A_5$, $R_{2a}$ and $R_{2b}$ are as defined in any one of Tables A-1 to A-300.

II(i)

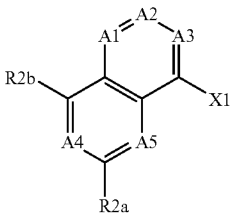

A compound of formula III(i), as a free base or salt thereof, wherein (i) $R_1$ is H and Q is as defined in table Z; or wherein (ii) $R_1$ is $CH_3$ and Q is as defined in table Z; or wherein (iii) $R_1$ is $CH_2$-cyclopropyl and Q is as defined in table Z.

III(i)

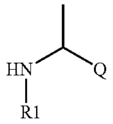

For instance, a compound of formula IIIh(i) or of formula IIIa-T(i), as a free base or salt thereof, wherein $R_1$, $R_3$, $R_{5a}$ and $R_{5b}$ are as defined for compound of formula I, preferably wherein $R_1$ is H, $CH_3$ or cyclopropylmethyl; $R_3$ is methyl; and $R_{5a}$ and $R_{5b}$ are hydrogen IIIh(i)

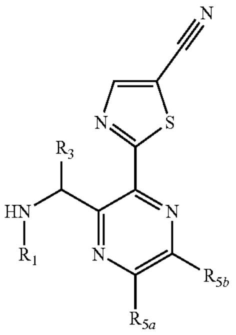

IIIa-T(i)

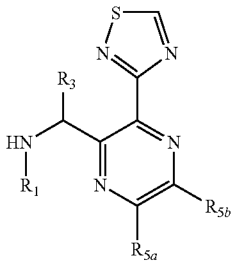

A compound of formula IV(i), wherein $A_1$, $A_2$, $A_3$, $A_4$, $A_5$, $R_{2a}$ and $R_{2b}$ are as defined in any one of Tables A-1 to A-300.

IV(i)

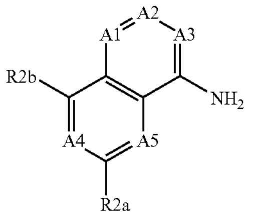

A compound of formula V(i), wherein (i) X2 is Cl and Q is as defined in table Z; or wherein (ii) X2 is Br and Q is as defined in table Z; or wherein (iii) X2 is I and Q is as defined in table Z.

V(i)

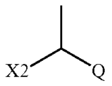

A compound of formula VII(i), wherein Q is as defined in table Z.

VII(i)

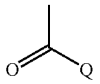

A compound of formula XI(i), wherein $A_1$, $A_2$, $A_3$, $A_4$, $A_5$, $R_1$, $R_{2a}$ and $R_{2b}$ are as defined in any one of Tables A-1 to A-300.

XI(i)

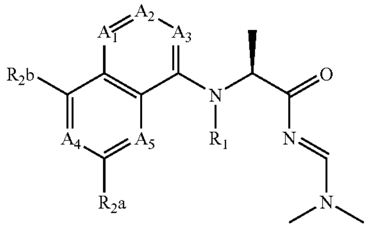

A compound of formula XIV(i), wherein $A_1$, $A_2$, $A_3$, $A_4$, $A_5$, $R_1$, $R_{2a}$ and $R_{2b}$ are as defined in any one of Tables A-1 to A-300.

XIV(i)

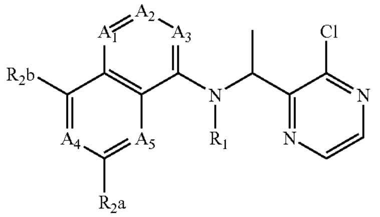

In further aspect, the present invention accordingly makes available compounds of formulae II(i), III(i), IV(i), V(i), VII(i), XI(i), and XIV(i), wherein in each case, as applicable, $A_1$, $A_2$, $A_3$, $A_4$, $A_5$, $R_1$, $R_{2a}$ and $R_{2b}$ and Q is as defined for formula I in the first aspect; and in respect of formula II(i), X1 is a halogen, preferably chloro or bromo. Furthermore, the corresponding embodiments illustrated for formula I also apply to the compounds of formulae II(i), III(i), IV(i), V(i), VII(i), XI(i), and XIV(i), The compounds of formula I according to the invention are preventively and/or curatively valuable active ingredients in the field of pest control, even at low rates of application, which have a very favorable biocidal spectrum and are well tolerated by warm-blooded species, fish and plants. The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i.e. in destruction of the pests, which takes place either immediately or only after some time has elapsed, for example during ecdysis, or indirectly, for example in a reduced oviposition and/or hatching rate.

Examples of the above mentioned animal pests are:

from the order Acarina, for example,

*Acalitus* spp, *Aculus* spp, *Acaricalus* spp, *Aceria* spp, *Acarus siro, Amblyomma* spp., *Argas* spp., *Boophilus* spp., *Brevipalpus* spp., *Bryobia* spp, *Calipitrimerus* spp., *Chorioptes* spp., *Dermanyssus gallinae, Dermatophagoides* spp, *Eotetranychus* spp, *Eriophyes* spp., *Hemitarsonemus* spp, *Hyalomma* spp., *Ixodes* spp., *Olygonychus* spp, *Ornithodoros* spp., *Polyphagotarsone latus, Panonychus* spp., *Phyllocoptruta oleivora, Phytonemus* spp, *Polyphagotarsonemus* spp, *Psoroptes* spp., *Rhipicephalus* spp., *Rhizoglyphus* spp., *Sarcoptes* spp., *Steneotarsonemus* spp, *Tarsonemus* spp. and *Tetranychus* spp.;

from the order Anoplura, for example, *Haematopinus* spp., *Linognathus* spp., *Pediculus* spp., *Pemphigus* spp. and *Phylloxera* spp.;

from the order Coleoptera, for example, *Agriotes* spp., *Amphimallon majale, Anomala orientalis, Anthonomus* spp., *Aphodius* spp, *Astylus atromaculatus, Ataenius* spp, *Atomaria linearis, Chaetocnema tibialis, Cerotoma* spp, *Conoderus* spp, *Cosmopolites* spp., *Cotinis nitida, Curculio* spp., *Cyclocephala* spp, *Dermestes* spp., *Diabrotica* spp., *Diloboderus abderus, Epilachna* spp., *Eremnus* spp., *Heteronychus arator, Hypothenemus hampei, Lagria vilosa, Leptinotarsa decemlineata, Lissorhoptrus* spp., *Liogenys* spp, *Maecolaspis* spp, *Maladera castanea, Megascelis* spp, *Melighetes aeneus, Melolontha* spp., *Myochrous armatus, Orycaephilus* spp., *Otiorhynchus* spp., *Phyllophaga* spp, *Phlyctinus* spp., *Popillia* spp., *Psylliodes* spp., *Rhyssomatus aubtilis, Rhizopertha* spp., *Scarabeidae, Sitophilus* spp., *Sitotroga* spp., *Somaticus* spp, *Sphenophorus* spp, *Sternechus subsignatus, Tenebrio* spp., *Tribolium* spp. and *Trogoderma* spp.;

from the order Diptera, for example,

*Aedes* spp., *Anopheles* spp, *Antherigona soccata, Bactrocea oleae, Bibio hortulanus, Bradysia* spp, *Calliphora erythrocephala, Ceratitis* spp., *Chrysomyia* spp., *Culex* spp., *Cuterebra* spp., *Dacus* spp., *Delia* spp, *Drosophila melanogaster, Fannia* spp., *Gastrophilus* spp., *Geomyza tripunctata, Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit, Pegomyia hyoscyami, Phorbia* spp., *Rhagoletis* spp, *Rivelia quadrifasciata, Scatella* spp, *Sciara* spp., *Stomoxys* spp., *Tabanus* spp., *Tannia* spp. and *Tipula* spp.;

from the order Hemiptera, for example,

*Acanthocoris scabrator, Acrosternum* spp, *Adelphocoris lineolatus, Aleurodes* spp., *Amblypelta nitida, Bathycoelia thalassina, Blissus* spp, *Cimex* spp., *Clavigralla tomentosicollis, Creontiades* spp, *Distantiella theobroma, Dichelops furcatus, Dysdercus* spp., *Edessa* spp, *Euchistus* spp., *Eurydema pulchrum, Eurygaster* spp., *Halyomorpha halys, Horcias nobilellus, Leptocorisa* spp., *Lygus* spp, *Margarodes* spp, *Murgantia histrionic, Neomegalotomus* spp, *Nesidiocoris tenuis, Nezara* spp., *Nysius simulans, Oebalus insularis, Piesma* spp., *Piezodorus* spp, *Rhodnius* spp., *Sahlbergella singularis, Scaptocoris castanea, Scotinophara* spp., *Thyanta* spp, *Triatoma* spp., *Vatiga illudens; Acyrthosium pisum, Adalges* spp, *Agalliana ensigera, Agonoscena targionii, Aleurodicus* spp, *Aleurocanthus* spp, *Aleurolobus barodensis, Aleurothrixus floccosus, Aleyrodes brassicae, Amarasca biguttula, Amritodus atkinsoni, Aonidiella* spp., *Aphididae, Aphis* spp., *Aspidiotus* spp., *Aulacorthum solani, Bactericera cockerelli, Bemisia* spp, *Brachycaudus* spp, *Brevicoryne brassicae, Cacopsylla* spp, *Cavariella aegopodii Scop., Ceroplaster* spp., *Chrysomphalus aonidium, Chrysomphalus dictyospermi, Cicadella* spp, *Cofana spectra, Cryptomyzus* spp, *Cicadulina* spp, *Coccus hesperidum, Dalbulus maidis, Dialeurodes* spp, *Diaphorina citri, Diuraphis noxia, Dysaphis* spp, *Empoasca* spp., *Eriosoma larigerum, Erythroneura* spp., *Gascardia* spp., *Glycaspis brimblecombei, Hyadaphis pseudobrassicae, Hyalopterus* spp, *Hyperomyzus pallidus, Idioscopus clypealis, Jacobiasca lybica, Laodelphax* spp., *Lecanium corni, Lepidosaphes* spp., *Lopaphis erysimi, Lyogenys maidis, Macrosiphum* spp., *Mahanarva* spp, *Metcalfa pruinosa, Metopolophium dirhodum, Myndus crudus, Myzus* spp., *Neotoxoptera* sp, *Nephotettix* spp., *Nilaparvata* spp., *Nippolachnus piri Mats, Odonaspis ruthae, Oregma lanigera Zehnter, Parabemisia myricae, Paratrioza cockerelli, Parlatoria* spp., *Pemphigus* spp., *Peregrinus maidis, Perkinsiella* spp, *Phorodon humuli, Phylloxera* spp, *Planococcus* spp., *Pseudaulacaspis* spp., *Pseudococcus* spp., *Pseudatomoscelis seriatus, Psylla* spp., *Pulvinaria aethiopica, Quadraspidiotus* spp., *Quesada gigas, Recilia dorsalis, Rhopalosiphum* spp., *Saissetia* spp., *Scaphoideus* spp., *Schizaphis* spp., *Sitobion* spp., *Sogatella furcifera, Spissistilus festinus, Tarophagus Proserpina, Toxoptera* spp, *Trialeurodes* spp, *Tridiscus sporoboli, Trionymus* spp, *Trioza erytreae, Unaspis citri, Zygina flammigera, Zyginidia scutellaris;* from the order Hymenoptera, for example,

*Acromyrmex, Arge* spp, *Atta* spp., *Cephus* spp., *Diprion* spp., *Diprionidae, Gilpinia polytoma, Hoplocampa* spp., *Lasius* spp., *Monomorium pharaonis, Neodiprion* spp., *Pogonomyrmex* spp, *Slenopsis invicta, Solenopsis* spp. and *Vespa* spp.;

from the order Isoptera, for example,

*Coptotermes* spp, *Corniternes cumulans, Incisitermes* spp, *Macrotermes* spp, *Mastotermes* spp, *Microtermes* spp, *Reticulitermes* spp.; *Solenopsis geminate* from the order Lepidoptera, for example,

*Acleris* spp., *Adoxophyes* spp., *Aegeria* spp., *Agrotis* spp., *Alabama argillaceae, Amylois* spp., *Anticarsia gemmatalis, Archips* spp., *Argyresthia* spp, *Argyrotaenia* spp., *Autographa* spp., *Bucculatrix thurberiella, Busseola fusca, Cadra cautella, Carposina nipponensis, Chilo* spp., *Choristoneura* spp., *Chrysoteuchia topiaria, Clysia ambiguella, Cnaphalocrocis* spp., *Cnephasia* spp., *Cochylis* spp., *Coleophora* spp., *Colias lesbia, Cosmophila flava, Crambus* spp, *Crocidolomia binotalis, Cryptophlebia leucotreta, Cydalima perspectalis, Cydia* spp., *Diaphania perspectalis, Diatraea* spp., *Diparopsis castanea, Earias* spp., *Elasmopalpus lignosellus, Eldana saccharina, Ephestia* spp., *Epinotia* spp, *Estigmene acrea, Etiella zinckinella, Eucosma* spp., *Eupoecilia ambiguella, Euproctis* spp., *Euxoa* spp., *Feltia jaculiferia, Grapholita* spp., *Hedya nubiferana, Heliothis* spp., *Hellula undalis, Herpetogramma* spp, *Hyphantria cunea, Keiferia lycopersicella, Lasmopalpus lignosellus, Leucoptera scitella, Lithocollethis* spp., *Lobesia botrana, Loxostege bifidalis, Lymantria* spp., *Lyonetia* spp., *Malacosoma* spp., *Mamestra brassicae, Manduca sexta, Mythimna* spp, *Noctua* spp, *Operophtera* spp., *Orniodes indica, Ostrinia nubilalis, Pammene* spp., *Pandemis* spp., *Panolis flammea, Papaipema nebris, Pectinophora gossypiela, Perileucoptera coffeella, Pseudaletia unipuncta, Phthorimaea operculella, Pieris rapae, Pieris* spp., *Plutella xylostella, Prays* spp., *Pseudoplusia* spp, *Rachiplusia nu, Richia albicosta, Scirpophaga* spp., *Sesamia* spp., *Sparganothis* spp., *Spodoptera* spp., *Sylepta derogate, Synanthedon* spp., *Thaumetopoea* spp., *Tortrixspp., Trichoplusia ni, Tuta absoluta*, and *Yponomeuta* spp.;

from the order Mallophaga, for example,

*Damalinea* spp. and *Trichodectes* spp.;

from the order Orthoptera, for example,

*Blatta* spp., *Blattella* spp., *Gryllotalpa* spp., *Leucophaea maderae, Locusta* spp., *Neocurtilla hexadactyla, Periplaneta* spp., *Scapteriscus* spp, and *Schistocerca* spp.;

from the order Psocoptera, for example,

*Liposcelis* spp.;

from the order Siphonaptera, for example,

*Ceratophyllus* spp., *Ctenocephalides* spp. and *Xenopsylla cheopis;* from the order Thysanoptera, for example,

*Calliothrips phaseoli, Frankliniella* spp., *Heliothrips* spp, *Hercinothrips* spp., *Parthenothrips* spp, *Scirtothrips aurantii, Sericothrips variabilis, Taeniothrips* spp., *Thrips* spp;

from the order Thysanura, for example, *Lepisma saccharina.*

In a further aspect, the invention may also relate to a method of controlling damage to plant and parts thereof by plant parasitic nematodes (Endoparasitic-, Semiendoparasitic- and Ectoparasitic nematodes), especially plant parasitic nematodes such as root knot nematodes, *Meloidogyne hapla, Meloidogyne incognita, Meloidogyne javanica, Meloidogyne arenaria* and other *Meloidogyne* species; cyst-forming nematodes, *Globodera rostochiensis* and other *Globodera* species; *Heterodera avenae, Heterodera glycines, Heterodera schachtii, Heterodera trifolii*, and other *Heterodera* species; Seed gall nematodes, *Anguina* species; Stem and foliar nematodes, *Aphelenchoides* species; *Sting nematodes, Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes,

*Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Pratylenchus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus, Rotylenchus reniformis* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species, such as *Subanguina* spp., *Hypsoperine* spp., *Macroposthonia* spp., *Melinius* spp., *Punctodera* spp., and *Quinisulcius* spp.

The compounds of the invention may also have activity against the molluscs. Examples of which include, for example, Ampullariidae; *Arion* (*A. ater, A. circumscriptus, A. hortensis, A. rufus*); Bradybaenidae (*Bradybaena fruticum*); Cepaea (*C. hortensis, C. Nemoralis*); *Ochlodina; Deroceras* (*D. agrestis, D. empiricorum, D. laeve, D. reticulatum*); *Discus* (*D. rotundatus*); *Euomphalia; Galba* (*G. trunculata*); *Helicelia* (*H. itala, H. obvia*); Helicidae *Helicigona arbustorum*); *Helicodiscus; Helix* (*H. aperta*); *Limax* (*L. cinereoniger, L. flavus, L. marginatus, L. maximus, L. tenellus*); Lymnaea; *Milax* (*M. gagates, M. marginatus, M. sowerbyi*); *Opeas; Pomacea* (*P. canaticulata*); *Vallonia* and *Zanitoides.*

The active ingredients according to the invention can be used for controlling, i.e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family and latex plants.

The compositions and/or methods of the present invention may be also used on any ornamental and/or vegetable crops, including flowers, shrubs, broad-leaved trees and evergreens.

For example the invention may be used on any of the following ornamental species: *Ageratum* spp., *Alonsoa* spp., *Anemone* spp., *Anisodontea capsenisis, Anthemis* spp., *Antirrhinum* spp., *Aster* spp., *Begonia* spp. (*e.g. B. elatior, B. semperflorens, B. tubereux*), *Bougainvillea* spp., *Brachycome* spp., *Brassica* spp. (*ornamental*), *Calceolaria* spp., *Capsicum annuum, Catharanthus roseus, Canna* spp., *Centaurea* spp., *Chrysanthemum* spp., *Cineraria* spp. (*C. maritime*), *Coreopsis* spp., *Crassula coccinea, Cuphea ignea, Dahlia* spp., *Delphinium* spp., *Dicentra spectabilis, Dorotheantus* spp., *Eustoma grandiflorum, Forsythia* spp., *Fuchsia* spp., *Geranium gnaphalium, Gerbera* spp., *Gomphrena globosa, Heliotropium* spp., *Helianthus* spp., *Hibiscus* spp., *Hortensia* spp., *Hydrangea* spp., *Hypoestes phyllostachya, Impatiens* spp. (*I. walleriana*), *Iresines* spp., *Kalanchoe* spp., *Lantana camara, Lavatera trimestris, Leonotis leonurus, Lilium* spp., *Mesembryanthemum* spp., *Mimulus* spp., *Monarda* spp., *Nemesia* spp., *Tagetes* spp., *Dianthus* spp. (*carnation*), *Canna* spp., *Oxalis* spp., *Bellis* spp., *Pelargonium* spp. (*P. peltatum, P. Zonale*), *Viola* spp. (*pansy*), *Petunia* spp., *Phlox* spp., *Plecthranthus* spp., *Poinsettia* spp., *Parthenocissus* spp. (*P. quinquefolia, P. tricuspidata*), *Primula* spp., *Ranunculus* spp., *Rhododendron* spp., *Rosa* spp. (*rose*), *Rudbeckia* spp., *Saintpaulia* spp., *Salvia* spp., *Scaevola aemola, Schizanthus wisetonensis, Sedum* spp., *Solanum* spp., *Surfinia* spp., *Tagetes* spp., *Nicotinia* spp., *Verbena* spp., *Zinnia* spp. and other bedding plants.

For example the invention may be used on any of the following vegetable species: *Allium* spp. (*A. sativum, A. cepa, A. oschaninii, A. Porrum, A. ascalonicum, A. fistulosum*), *Anthriscus cerefolium, Apium graveolus, Asparagus officinalis, Beta vulgarus, Brassica* spp. (*B. Oleracea, B. Pekinensis, B. rapa*), *Capsicum annuum, Cicer arietinum, Cichorium endivia, Cichorum* spp. (*C. intybus, C. endivia*), *Citrillus lanatus, Cucumis* spp. (*C. sativus, C. melo*), *Cucurbita* spp. (*C. pepo, C. maxima*), *Cyanara* spp. (*C. scolymus, C. cardunculus*), *Daucus carota, Foeniculum vulgare, Hypericum* spp., *Lactuca sativa, Lycopersicon* spp. (*L. esculentum, L. lycopersicum*), *Mentha* spp., *Ocimum basilicum, Petroselinum crispum, Phaseolus* spp. (*P. vulgaris, P. coccineus*), *Pisum sativum, Raphanus sativus, Rheum rhaponticum, Rosemarinus* spp., *Salvia* spp., *Scorzonera hispanica, Solanum melongena, Spinacea oleracea, Valerianella* spp. (*V. locusta, V. eriocarpa*) and *Vicia faba.*

Preferred ornamental species include African violet, *Begonia, Dahlia, Gerbera, Hydrangea, Verbena, Rosa, Kalanchoe, Poinsettia, Aster, Centaurea, Coreopsis, Delphinium, Monarda, Phlox, Rudbeckia, Sedum, Petunia, Viola, Impatiens, Geranium, Chrysanthemum, Ranunculus, Fuchsia, Salvia, Hortensia*, rosemary, sage, St. Johnswort, mint, sweet pepper, tomato and cucumber.

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatoes) and *Chilo supressalis* (preferably in rice).

The compounds of formula I are particularly suitable for control of

- a pest of the order Hemiptera, for example, one or more of the species *Bemisia tabaci, Aphis craccivora, Myzus persicae, Rhopalosiphum padi, Nilaparvata lugens*, and *Euschistus heros* (preferably in vegetables, soybeans, and sugarcane);
- a pest of the order Lepidoptera, for example, one or more of the species *Spodoptera littoralis, Spodoptera frugiperda, Plutella xylostella, Cnaphalocrocis medinalis, Cydia pomonella, Chrysodeixis includes, Chilo sup-*

*pressalis, Elasmopalpus lignosellus, Pseudoplusia includens*, and *Tuta absoluta* (preferably in vegetables and corn);

a pest of the order Thysanoptera, such as the family Thripidae, for example, one or more of *Thrips tabaci* and *Frankliniella occidentalis* (preferably in vegetables); and soil pests (such as of the order Coleoptera), for example, the species *Diabrotica balteata, Agriotes* spp. and *Leptinotarsa decemlineata* (preferably in vegetables and corn).

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus.*

Toxins that can be expressed by such transgenic plants include, for example, insecticidal proteins, for example insecticidal proteins from *Bacillus cereus* or *Bacillus popilliae*; or insecticidal proteins from *Bacillus thuringiensis*, such as S-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by S-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. CryI-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and moths (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1 Fa2 toxin and the enzyme phosphinothricine N-acetyltransferase (PAT) to achieve tolerance to the herbicide glufosinate ammonium); NuCOTN 33B® (cotton variety that expresses a CryIAc toxin); Bollgard I® (cotton variety that expresses a CryIAc toxin); Bollgard II® (cotton variety that expresses a CryIAc and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage ($GA_{21}$ glyphosate-tolerant trait), Agrisure® CB Advantage (Btl 1 corn borer (CB) trait) and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.
2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.
3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.
4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.
5. IPC 531 Cotton from Monsanto Europe S.A. 270-272 Avenue de Tervuren, B-1150 Brussels, Belgium, registration number C/ES/96/02.
6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603×MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

Transgenic crops of insect-resistant plants are also described in BATS (Zentrum für Biosicherheit und Nachhaltigkeit, Zentrum BATS, Clarastrasse 13, 4058 Basel, Switzerland) Report 2003, (http://bats.ch).

The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818 and EP-A-0 353 191. The methods of producing such transgenic plants are generally known to the person skilled in the art and are described, for example, in the publications mentioned above.

Crops may also be modified for enhanced resistance to fungal (for example *Fusarium*, Anthracnose, or *Phytophthora*), bacterial (for example *Pseudomonas*) or viral (for example potato leafroll virus, tomato spotted wilt virus, cucumber mosaic virus) pathogens.

Crops also include those that have enhanced resistance to nematodes, such as the soybean cyst nematode.

Crops that are tolerance to abiotic stress include those that have enhanced tolerance to drought, high salt, high temperature, chill, frost, or light radiation, for example through expression of NF-YB or other proteins known in the art.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

Further areas of use of the compositions according to the invention are the protection of stored goods and store rooms and the protection of raw materials, such as wood, textiles, floor coverings or buildings, and also in the hygiene sector, especially the protection of humans, domestic animals and productive livestock against pests of the mentioned type.

The present invention provides a compound of the first aspect for use in therapy. The present invention provides a compound of the first aspect, for use in controlling parasites in or on an animal. The present invention further provides a compound of the first aspect, for use in controlling ectoparasites on an animal.

The present invention further provides a compound of the first aspect, for use in preventing and/or treating diseases transmitted by ectoparasites.

The present invention provides the use of a compound of the first aspect, for the manufacture of a medicament for controlling parasites in or on an animal. The present invention further provides the use of a compound of the first aspect, for the manufacture of a medicament for controlling ectoparasites on an animal. The present invention further provides the use of a compound of the first aspect, for the manufacture of a medicament for preventing and/or treating diseases transmitted by ectoparasites.

The present invention provides the use of a compound of the first aspect, in controlling parasites in or on an animal. The present invention further provides the use of a compound of the first aspect, in controlling ectoparasites on an animal.

The term "controlling" when used in context of parasites in or on an animal refers to reducing the number of pests or parasites, eliminating pests or parasites and/or preventing further pest or parasite infestation.

The term "treating" when used in context of parasites in or on an animal refers to restraining, slowing, stopping or reversing the progression or severity of an existing symptom or disease.

The term "preventing" when used in context of parasites in or on an animal refers to the avoidance of a symptom or disease developing in the animal.

The term "animal" when used in context of parasites in or on an animal may refer to a mammal and a non-mammal, such as a bird or fish. In the case of a mammal, it may be a human or non-human mammal. Non-human mammals include, but are not limited to, livestock animals and companion animals. Livestock animals include, but are not limited to, cattle, camelids, pigs, sheep, goats and horses. Companion animals include, but are not limited to, dogs, cats and rabbits.

A "parasite" is a pest which lives in or on the host animal and benefits by deriving nutrients at the host animal's expense. An "endoparasite" is a parasite which lives in the host animal. An "ectoparasite" is a parasite which lives on the host animal. Ectoparasites include, but are not limited to, acari, insects and crustaceans (e.g. sea lice). The Acari (or Acarina) sub-class comprises ticks and mites. Ticks include, but are not limited to, members of the following genera: *Rhipicaphalus*, for example, *Rhipicaphalus* (*Boophilus*) *microplus* and *Rhipicephalus sanguineus; Amblyomrna; Dermacentor; Haemaphysalis; Hyalomma; Ixodes; Rhipicentor; Margaropus; Argas; Otobius*; and *Ornithodoros*. Mites include, but are not limited to, members of the following genera: *Chorioptes*, for example *Chorioptes bovis; Psoroptes*, for example *Psoroptes ovis; Cheyletiella; Dermanyssus*; for example *Dermanyssus gallinae; Ortnithonyssus; Demodex*, for example *Demodex canis; Sarcoptes*, for example *Sarcoptes scabiei*; and *Psorergates*. Insects include, but are not limited to, members of the orders: Siphonaptera, Diptera, Phthiraptera, Lepidoptera, Coleoptera and Homoptera. Members of the Siphonaptera order include, but are not limited to, *Ctenocephalides felis* and *Ctenocephalides canis*. Members of the Diptera order include, but are not limited to, *Musca* spp.; bot fly, for example *Gasterophilus intestinalis* and *Oestrus ovis*; biting flies; horse flies, for example *Haematopota* spp. and Tabunus spp.; *haematobia*, for example *haematobia irritans; Stomoxys; Lucilia*; midges; and mosquitoes. Members of the Phthiraptera class include, but are not limited to, blood sucking lice and chewing lice, for example *Bovicola Ovis* and *Bovicola Bovis.*

The term "effective amount" when used in context of parasites in or on an animal refers to the amount or dose of the compound of the invention, or a salt thereof, which, upon single or multiple dose administration to the animal, provides the desired effect in or on the animal. The effective amount can be readily determined by the attending diagnostician, as one skilled in the art, by the use of known techniques and by observing results obtained under analogous circumstances. In determining the effective amount a number of factors are considered by the attending diagnostician, including, but not limited to: the species of mammal; its size, age, and general health; the parasite to be controlled and the degree of infestation; the specific disease or disorder involved; the degree of involvement or the severity of the disease or disorder; the response of the individual; the particular compound administered; the mode of administration; the bioavailability characteristics of the preparation administered; the dose regimen selected; the use of concomitant medication; and other relevant circumstances.

The compounds of the invention may be administered to the animal by any route which has the desired effect including, but not limited to topically, orally, parenterally and subcutaneously. Topical administration is preferred. Formulations suitable for topical administration include, for example, solutions, emulsions and suspensions and may take the form of a pour-on, spot-on, spray-on, spray race or dip. In the alternative, the compounds of the invention may be administered by means of an ear tag or collar.

Salt forms of the compounds of the invention include both pharmaceutically acceptable salts and veterinary acceptable salts, which can be different to agrochemically acceptable salts. Pharmaceutically and veterinary acceptable salts and common methodology for preparing them are well known in the art. See, for example, Gould, P. L., "Salt selection for basic drugs", International Journal of Pharmaceutics, 33: 201-217 (1986); Bastin, R. J., et al. "Salt Selection and Optimization Procedures for Pharmaceutical New Chemical Entities", Organic Process Research and Development, 4: 427-435 (2000); and Berge, S. M., et al., "Pharmaceutical Salts", Journal of Pharmaceutical Sciences, 66: 1-19, (1977). One skilled in the art of synthesis will appreciate that the compounds of the invention are readily converted to and may be isolated as a salt, such as a hydrochloride salt, using techniques and conditions well known to one of ordinary skill in the art. In addition, one skilled in the art of synthesis will appreciate that the compounds of the invention are readily converted to and may be isolated as the corresponding free base from the corresponding salt.

The present invention also provides a method for controlling pests (such as mosquitoes and other disease vectors; see also http://www.who.int/malaria/vector_control/irs/en/). In one embodiment, the method for controlling pests comprises applying the compositions of the invention to the target pests, to their locus or to a surface or substrate by brushing, rolling, spraying, spreading or dipping. By way of example, an IRS (indoor residual spraying) application of a surface such as a wall, ceiling or floor surface is contemplated by the method of the invention. In another embodiment, it is contemplated to apply such compositions to a substrate such as non-woven or a fabric material in the form of (or which can be used in the manufacture of) netting, clothing, bedding, curtains and tents.

In one embodiment, the method for controlling such pests comprises applying a pesticidally effective amount of the compositions of the invention to the target pests, to their locus, or to a surface or substrate so as to provide effective residual pesticidal activity on the surface or substrate. Such application may be made by brushing, rolling, spraying, spreading or dipping the pesticidal composition of the invention. By way of example, an IRS application of a surface such as a wall, ceiling or floor surface is contemplated by the method of the invention so as to provide effective residual pesticidal activity on the surface. In another embodiment, it is contemplated to apply such compositions for residual control of pests on a substrate such as a fabric material in the form of (or which can be used in the manufacture of) netting, clothing, bedding, curtains and tents.

Substrates including non-woven, fabrics or netting to be treated may be made of natural fibres such as cotton, raffia, jute, flax, sisal, hessian, or wool, or synthetic fibres such as polyamide, polyester, polypropylene, polyacrylonitrile or the like. The polyesters are particularly suitable. The methods of textile treatment are known, e.g. WO 2008/151984, WO 2003/034823, U.S. Pat. No. 5,631,072, WO 2005/64072, WO2006/128870, EP 1724392, WO 2005113886 or WO 2007/090739.

Further areas of use of the compositions according to the invention are the field of tree injection/trunk treatment for all ornamental trees as well all sort of fruit and nut trees.

In the field of tree injection/trunk treatment, the compounds according to the present invention are especially suitable against wood-boring insects from the order Lepidoptera as mentioned above and from the order Coleoptera, especially against woodborers listed in the following tables A and B:

TABLE A

Examples of exotic woodborers of economic importance.

| Family | Species | Host or Crop Infested |
|---|---|---|
| Buprestidae | *Agrilus planipennis* | Ash |
| Cerambycidae | *Anoplura glabripennis* | Hardwoods |
| Scolytidae | *Xylosandrus crassiusculus* | Hardwoods |
| | *X. mutilatus* | Hardwoods |
| | *Tomicus piniperda* | Conifers |

TABLE B

Examples of native woodborers of economic importance.

| Family | Species | Host or Crop Infested |
|---|---|---|
| Buprestidae | *Agrilus anxius* | Birch |
| | *Agrilus politus* | Willow, Maple |
| | *Agrilus sayi* | Bayberry, Sweetfern |
| | *Agrilus vittaticolllis* | Apple, Pear, Cranberry, Serviceberry, Hawthorn |

TABLE B-continued

Examples of native woodborers of economic importance.

| Family | Species | Host or Crop Infested |
|---|---|---|
| | *Chrysobothris femorata* | Apple, Apricot, Beech, Boxelder, Cherry, Chestnut, Currant, Elm, Hawthorn, Hackberry, Hickory, Horsechestnut, Linden, Maple, Mountain-ash, Oak, Pecan, Pear, Peach, Persimmon, Plum, Poplar, Quince, Redbud, Serviceberry, Sycamore, Walnut, Willow |
| | *Texania campestris* | Basswood, Beech, Maple, Oak, Sycamore, Willow, Yellow-poplar |
| Cerambycidae | *Goes pulverulentus* | Beech, Elm, Nuttall, Willow, Black oak, Cherrybark oak, Water oak, Sycamore |
| | *Goes tigrinus* | Oak |
| | *Neoclytus acuminatus* | Ash, Hickory, Oak, Walnut, Birch, Beech, Maple, Eastern hophornbeam, Dogwood, Persimmon, Redbud, Holly, Hackberry, Black locust, Honeylocust, Yellow-poplar, Chestnut, Osage-orange, Sassafras, Lilac, Mountain-mahogany, Pear, Cherry, Plum, Peach, Apple, Elm, Basswood, Sweetgum |
| | *Neoptychodes trilineatus* | Fig, Alder, Mulberry, Willow, Netleaf hackberry |
| | *Oberea ocellata* | Sumac, Apple, Peach, Plum, Pear, Currant, Blackberry |
| | *Oberea tripunctata* | Dogwood, Viburnum, Elm, Sourwood, Blueberry, Rhododendron, Azalea, Laurel, Poplar, Willow, Mulberry |
| | *Oncideres cingulata* | Hickory, Pecan, Persimmon, Elm, Sourwood, Basswood, Honeylocust, Dogwood, Eucalyptus, Oak, Hackberry, Maple, Fruit trees |
| | *Saperda calcarata* | Poplar |
| | *Strophiona nitens* | Chestnut, Oak, Hickory, Walnut, Beech, Maple |
| Scolytidae | *Corthylus columbianus* | Maple, Oak, Yellow-poplar, Beech, Boxelder, Sycamore, Birch, Basswood, Chestnut, Elm |
| | *Dendroctonus frontalis* | Pine |
| | *Dryocoetes betulae* | Birch, Sweetgum, Wild cherry, Beech, Pear |
| | *Monarthrum fasciatum* | Oak, Maple, Birch, Chestnut, Sweetgum, Blackgum, Poplar, Hickory, Mimosa, Apple, Peach, Pine |
| | *Phloeotribus liminaris* | Peach, Cherry, Plum, Black cherry, Elm, Mulberry, Mountain-ash |
| | *Pseudopityophthorus pruinosus* | Oak, American beech, Black cherry, Chickasaw plum, Chestnut, Maple, Hickory, Hornbeam, Hophornbeam |
| Sesiidae | *Paranthrene simulans* | Oak, American chestnut |
| | *Sannina uroceriformis* | Persimmon |
| | *Synanthedon exitiosa* | Peach, Plum, Nectarine, Cherry, Apricot, Almond, Black cherry |
| | *Synanthedon pictipes* | Peach, Plum, Cherry, Beach, Black Cherry |
| | *Synanthedon rubrofascia* | Tupelo |
| | *Synanthedon scitula* | Dogwood, Pecan, Hickory, Oak, Chestnut, Beech, Birch, Black cherry, Elm, Mountain-ash, Viburnum, Willow, Apple, Loquat, Ninebark, Bayberry |
| | *Vitacea polistiformis* | Grape |

The present invention may be also used to control any insect pests that may be present in turfgrass, including for example beetles, caterpillars, fire ants, ground pearls, millipedes, sow bugs, mites, mole crickets, scales, mealybugs, ticks, spittlebugs, southern chinch bugs and white grubs. The present invention may be used to control insect pests at various stages of their life cycle, including eggs, larvae, nymphs and adults.

In particular, the present invention may be used to control insect pests that feed on the roots of turfgrass including white grubs (such as *Cyclocephala* spp. (e.g. masked chafer, *C. lurida*), *Rhizotrogus* spp. (e.g. European chafer, *R. majalis*), *Cotinus* spp. (e.g. Green June beetle, *C. nitida*), *Popillia* spp. (e.g. Japanese beetle, *P. japonica*), *Phyllophaga* spp. (e.g. May/June beetle), *Ataenius* spp. (e.g. Black turfgrass *ataenius, A. spretulus*), *Maladera* spp. (e.g. Asiatic garden beetle, *M. castanea*) and *Tomarus* spp.), ground pearls (*Margarodes* spp.), mole crickets (tawny, southern, and short-winged; *Scapteriscus* spp., *Gryllotalpa africana*) and leatherjackets (European crane fly, *Tipula* spp.).

The present invention may also be used to control insect pests of turfgrass that are thatch dwelling, including armyworms (such as fall armyworm *Spodoptera frugiperda*, and common armyworm *Pseudaletia unipuncta*), cutworms, billbugs (*Sphenophorus* spp., such as *S. venatus verstitus* and *S. parvulus*), and sod webworms (such as *Crambus* spp. and the tropical sod webworm, *Herpetogramma phaeopteralis*).

The present invention may also be used to control insect pests of turfgrass that live above the ground and feed on the turfgrass leaves, including chinch bugs (such as southern chinch bugs, *Blissus insularis*), Bermudagrass mite (*Eriophyes cynodoniensis*), rhodesgrass mealybug (*Antonina graminis*), two-lined spittlebug (*Propsapia bicincta*), leafhoppers, cutworms (Noctuidae family), and greenbugs.

The present invention may also be used to control other pests of turfgrass such as red imported fire ants (*Solenopsis invicta*) that create ant mounds in turf.

In the hygiene sector, the compositions according to the invention are active against ectoparasites such as hard ticks, soft ticks, mange mites, harvest mites, flies (biting and licking), parasitic fly larvae, lice, hair lice, bird lice and fleas.

Examples of such parasites are:

Of the order Anoplurida: *Haematopinus* spp., *Linognathus* spp., *Pediculus* spp. and *Phtirus* spp., *Solenopotes* spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* spp.

Of the order Blattarida, for example *Blatta orientalis, Periplaneta americana, Blattelagermanica* and *Supella* spp.

Of the subclass Acaria (Acarida) and the orders Meta- and Meso-stigmata, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus, Chlorophorus pilosis, Anobium punctatum, Xestobium rufovillosum, Ptilinuspecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthesrugicollis, Xyleborus* spec., *Tryptodendron* spec., *Apate monachus, Bostrychus capucins, Heterobostrychus brunneus, Sinoxylon* spec. and *Dinoderus minutus*, and also hymenopterans such as *Sirex juvencus, Urocerus gigas, Urocerus gigas taignus* and *Urocerus augur*, and termites such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus*, and bristletails such as *Lepisma saccharina*.

The compounds of formulae I, and I'a, or salts thereof, are especially suitable for controlling one or more pests selected from the family: Noctuidae, Plutellidae, Chrysomelidae, Thripidae, Pentatomidae, Tortricidae, Delphacidae, Aphididae, Noctuidae, Crambidae, Meloidogynidae, and Heteroderidae. In a preferred embodiment of each aspect, a compound TX (where the abbreviation "TX" means "one compound selected from the compounds defined in Tables A-1 to A-300, Tables B-1 to B-108, and Table P") controls one or more of pests selected from the family: Noctuidae, Plutellidae, Chrysomelidae, Thripidae, Pentatomidae, Tortricidae, Delphacidae, Aphididae, Noctuidae, Crambidae, Meloidogynidae, and Heteroderidae.

The compounds of formulae I, and I'a, or salts thereof, are especially suitable for controlling one or more of pests selected from the genus: *Spodoptera* spp, *Plutella* spp, *Frankliniella* spp, *Thrips* spp, *Euschistus* spp, *Cydia* spp, *Nilaparvata* spp, *Myzus* spp, *Aphis* spp, *Diabrotica* spp, *Rhopalosiphum* spp, *Pseudoplusia* spp and *Chilo* spp. In a preferred embodiment of each aspect, a compound TX (where the abbreviation "TX" means "one compound selected from the compounds defined in Tables A-1 to A-300, Tables B-1 to B-108, and Table P") controls one or more of pests selected from the genus: *Spodoptera* spp, *Plutella* spp, *Frankliniella* spp, *Thrips* spp, *Euschistus* spp,

*Cydia* spp, *Nilaparvata* spp, *Myzus* spp, *Aphis* spp, *Diabrotica* spp, *Rhopalosiphum* spp, *Pseudoplusia* spp and *Chilo* spp.

The compounds of formulae I, and I'a, or salts thereof, are especially suitable for controlling one or more of *Spodoptera littoralis, Plutella xylostella, Frankliniella occidentalis, Thrips tabaci, Euschistus heros, Cydia pomonella, Nilaparvata lugens, Myzus persicae, Chrysodeixis includens, Aphis craccivora, Diabrotica balteata, Rhopalosiphum padi*, and *Chilo suppressalis.*

In a preferred embodiment of each aspect, a compound TX (where the abbreviation "TX" means "one compound selected from the compounds defined in Tables A-1 to A-300, Tables B-1 to B-108, and Table P") controls one or more of *Spodoptera littoralis, Plutella xylostella, Frankliniella occidentalis, Thrips tabaci, Euschistus heros, Cydia pomonella, Nilaparvata lugens, Myzus persicae, Chrysodeixis includens, Aphis craccivora, Diabrotica balteata, Rhopalosiphum padia*, and *Chilo Suppressalis*, such as *Spodoptera littoralis*+TX, *Plutella xylostella*+TX; *Frankliniella occidentalis*+TX, *Thrips tabaci*+TX, *Euschistus heros*+TX, *Cydia pomonella*+TX, *Nilaparvata lugens*+TX, *Myzus persicae*+TX, *Chrysodeixis includens*+TX, *Aphis craccivora*+TX, *Diabrotica balteata*+TX, *Rhopalosiphum padi*+TX, and *Chilo suppressalis*+TX.

In an embodiment, of each aspect, one compound from Tables A-1 to A-300, Tables B-1 to B-108, and Table P is suitable for controlling *Spodoptera littoralis, Plutella xylostella, Frankliniella occidentalis, Thrips tabaci, Euschistus heros, Cydia pomonella, Nilaparvata lugens, Myzus persicae, Chrysodeixis includens, Aphis craccivora, Diabrotica balteata, Rhopalosiphum* Padia, and *Chilo Suppressalis* in cotton, vegetable, maize, cereal, rice and soya crops.

In an embodiment, one compound from Tables A-1 to A-300, Tables B-1 to B-108, and Table P is suitable for controlling *Mamestra* (preferably in vegetables), *Cydia pomonella* (preferably in apples), *Empoasca* (preferably in vegetables, vineyards), *Leptinotarsa* (preferably in potatoes) and *Chilo supressalis* (preferably in rice).

Compounds according to the invention may possess any number of benefits including, inter alia, advantageous levels of biological activity for protecting plants against insects or superior properties for use as agrochemical active ingredients (for example, greater biological activity, an advantageous spectrum of activity, an increased safety profile (against non-target organisms above and below ground (such as fish, birds and bees), improved physico-chemical properties, or increased biodegradability). In particular, it has been surprisingly found that certain compounds of formula I may show an advantageous safety profile with respect to non-target arthropods, in particular pollinators such as honey bees, solitary bees, and bumble bees. Most particularly, *Apis mellifera.*

The compounds according to the invention can be used as pesticidal agents in unmodified form, but they are generally formulated into compositions in various ways using formulation adjuvants, such as carriers, solvents and surface-active substances. The formulations can be in various physical forms, e.g. in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspoemulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO and WHO Specifications for Pesticides, United Nations, First Edition, Second Revision (2010). Such formulations can either be used directly or diluted prior to use. The dilutions can be made, for example, with water, liquid fertilisers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof.

The active ingredients can also be contained in very fine microcapsules. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes can comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol, propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like.

Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances.

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in McCutcheon's Detergents and Emulsifiers Annual, MC Publishing Corp., Ridgewood New Jersey (1981).

Further adjuvants that can be used in pesticidal formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, take-up enhancers, micronutrients, plasticisers, glidants, lubricants, dispersants, thickeners, antifreezes, microbicides, and liquid and solid fertilisers.

The compositions according to the invention can include an additive comprising an oil of vegetable or animal origin, a mineral oil, alkyl esters of such oils or mixtures of such oils and oil derivatives. The amount of oil additive in the composition according to the invention is generally from 0.01 to 10%, based on the mixture to be applied. For example, the oil additive can be added to a spray tank in the desired concentration after a spray mixture has been prepared. Preferred oil additives comprise mineral oils or an oil of vegetable origin, for example rapeseed oil, olive oil or sunflower oil, emulsified vegetable oil, alkyl esters of oils of vegetable origin, for example the methyl derivatives, or an oil of animal origin, such as fish oil or beef tallow. Preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid (methyl laurate, methyl palmitate and methyl oleate, respectively). Many oil derivatives are known from the Compendium of Herbicide Adjuvants, $10^{th}$ Edition, Southern Illinois University, 2010.

The inventive compositions generally comprise from 0.1 to 99% by weight, especially from 0.1 to 95% by weight, of compounds of the present invention and from 1 to 99.9% by weight of a formulation adjuvant which preferably includes from 0 to 25% by weight of a surface-active substance. Whereas commercial products may preferably be formulated as concentrates, the end user will normally employ dilute formulations.

The rates of application vary within wide limits and depend on the nature of the soil, the method of application, the crop plant, the pest to be controlled, the prevailing climatic conditions, and other factors governed by the method of application, the time of application and the target crop. As a general guideline compounds may be applied at a rate of from 1 to 2000 l/ha, especially from 10 to 1000 l/ha.

Preferred formulations can have the following compositions (weight %):

Emulsifiable Concentrates:

- active ingredient: 1 to 95%, preferably 60 to 90%
- surface-active agent: 1 to 30%, preferably 5 to 20%
- liquid carrier: 1 to 80%, preferably 1 to 35%

Dusts:

- active ingredient: 0.1 to 10%, preferably 0.1 to 5%
- solid carrier: 99.9 to 90%, preferably 99.9 to 99%

Suspension Concentrates:

- active ingredient: 5 to 75%, preferably 10 to 50%
- water: 94 to 24%, preferably 88 to 30%
- surface-active agent: 1 to 40%, preferably 2 to 30%

Wettable Powders:

- active ingredient: 0.5 to 90%, preferably 1 to 80%
- surface-active agent: 0.5 to 20%, preferably 1 to 15%
- solid carrier: 5 to 95%, preferably 15 to 90%

Granules:

- active ingredient: 0.1 to 30%, preferably 0.1 to 15%
- solid carrier: 99.5 to 70%, preferably 97 to 85%

The following Examples further illustrate, but do not limit, the invention.

| Wettable powders | a) | b) | c) |
|---|---|---|---|
| active ingredients | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The combination is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredients | 25% | 50% | 75% |
| light mineral oil | 5% | 5% | 5% |
| highly dispersed silicic acid | 5% | 5% | — |
| Kaolin | 65% | 40% | — |
| Talcum | — | | 20% |

The combination is thoroughly mixed with the adjuvants and the mixture is thoroughly ground in a suitable mill, affording powders that can be used directly for seed treatment.

| Emulsifiable concentrate | |
|---|---|
| active ingredients | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| Active ingredients | 5% | 6% | 4% |
| Talcum | 95% | — | — |
| Kaolin | — | 94% | — |
| mineral filler | — | — | 96% |

Ready-for-use dusts are obtained y mixing the combination with the carrier and grinding the mixture in a suitable mill. Such powders can also be used for dry dressings for seed.

| Extruder granules | |
|---|---|
| Active ingredients | 15% |
| sodium lignosulfonate | 2% |
| carboxymethylcellulose | 1% |
| Kaolin | 82% |

The combination is mixed and ground with the adjuvants, and the mixture is moistened with water. The mixture is extruded and then dried in a stream of air.

| Coated granules | |
|---|---|
| Active ingredients | 8% |
| polyethylene glycol (mol. wt. 200) | 3% |
| Kaolin | 89% |

The finely ground combination is uniformly applied, in a mixer, to the kaolin moistened with polyethylene glycol. Non-dusty coated granules are obtained in this manner.

Suspension Concentrate

| | |
|---|---|
| active ingredients | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Flowable Concentrate for Seed Treatment

| | |
|---|---|
| active ingredients | 40% |
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of the combination are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent. The capsule suspension formulation contains 28% of the active ingredients. The medium capsule diameter is 8-15 microns. The resulting formulation is applied to seeds as an aqueous suspension in an apparatus suitable for that purpose.

Formulation types include an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP), a soluble granule (SG) or any technically feasible formulation in combination with agriculturally acceptable adjuvants.

The activity of the compositions according to the invention can be broadened considerably, and adapted to prevailing circumstances, by adding other insecticidally, acaricidally and/or fungicidally active ingredients.

The mixtures of the compounds of formula I with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use.

Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridylmethyleneamino derivatives, macrolides, neonicotinoids and *Bacillus thuringiensis* preparations.

The following mixtures of a compound of formula I with an active substance are preferred (the abbreviation "TX" means "one compound selected from the compounds defined in Tables A-1 to A-300, Tables B-1 to B-108, and Table P"):

an adjuvant selected from the group of substances consisting of petroleum oils (alternative name) (628)+TX;

abamectin+TX, acequinocyl+TX, acetamiprid+TX, acetoprole+TX, acrinathrin+TX, acynonapyr+TX, afidopyropen+TX, afoxolaner+TX, alanycarb+TX, allethrin+TX, alpha-cypermethrin+TX, alphamethrin+TX, amidoflumet+TX, aminocarb+TX, azocyclotin+TX, bensultap+TX, benzoximate+TX, benzpyrimoxan+TX, betacyfluthrin+TX, beta-cypermethrin+TX, bifenazate+TX, bifenthrin+TX, binapacryl+TX, bioallethrin+TX, S-bioallethrin+TX, bioresmethrin+TX, bistrifluron+TX, broflanilide+TX, brofluthrinate+TX, bromophos-ethyl+TX, buprofezine+TX, butocarboxim+TX, cadusafos+TX, carbaryl+TX, carbosulfan+TX, cartap+TX, CAS number: 1632218-00-8+TX, CAS number: 1808115-49-2+TX, CAS number: 2032403-97-5+TX, CAS number: 2044701-44-0+TX, CAS number: 2128706-05-6+TX, CAS number: 2095470-94-1+TX, CAS number: 2377084-09-6+TX, CAS number: 1445683-71-5+TX, CAS number: 2408220-94-8+TX, CAS number: 2408220-91-5+TX, CAS number: 1365070-72-9+TX, CAS number: 2171099-09-3+TX, CAS number: 2396747-83-2+TX, CAS number: 2133042-31-4+TX, CAS number: 2133042-44-9+TX, CAS number: 1445684-82-1+TX, CAS number: 1445684-82-1+TX, CAS number: 1922957-45-6+TX, CAS number: 1922957-46-7+TX, CAS number: 1922957-47-8+TX, CAS number: 1922957-48-9+TX, CAS number: 2415706-16-8+TX, CAS number: 1594624-87-9+TX, CAS number: 1594637-65-6+TX, CAS number: 1594626-19-3+TX, CAS number: 1990457-52-7+TX, CAS number: 1990457-55-0+TX, CAS number: 1990457-57-2+TX, CAS number: 1990457-77-6+TX, CAS number: 1990457-66-3+TX, CAS number: 1990457-85-6+TX, CAS number: 2220132-55-6+TX, CAS number: 1255091-74-7+TX, CAS number: RNA (*Leptinotarsa decemlineata*-specific recombinant double-stranded interfering GS2)+TX, CAS number: 2719848-60-7+TX, CAS number: 1956329-03-5+TX, chlorantraniliprole+TX, chlordane+TX, chlorfenapyr+TX, chloroprallethrin+TX, chromafenozide+TX, clenpirin+TX, cloethocarb+TX, clothianidin+TX, 2-chlorophenyl N-methylcarbamate (CPMC)+TX, cyanofenphos+TX, cyantraniliprole+TX, cyclaniliprole+TX, cyclobutrifluram+TX, cycloprothrin+TX, cycloxaprid+TX, cyenopyrafen+TX, cyetpyrafen (or etpyrafen)+TX, cyflumetofen+TX, cyfluthrin+TX, cyhalodiamide+TX, cyhalothrin+TX, cypermethrin+TX, cyphenothrin+TX, cyproflanilide+TX, cyromazine+TX, deltamethrin+TX, diafenthiuron+TX, dialifos+TX, dibrom+TX, dicloromezotiaz+TX, diflovidazine+TX, diflubenzuron+TX, dimpropyridaz+TX, dinactin+TX, dinocap+TX, dinotefuran+TX, dioxabenzofos+TX, emamectin (or emamectin benzoate)+TX, empenthrin+TX, epsilon-momfluorothrin+TX, epsilon-metofluthrin+TX, esfenvalerate+TX, ethion+TX, ethiprole+TX, etofenprox+TX, etoxazole+TX, famphur+TX, fenazaquin+TX, fenfluthrin+TX, fenmezoditiaz+TX, fenitrothion+TX, fenobucarb+TX, fenothiocarb+TX, fenoxycarb+TX, fenpropathrin+TX, fenpyroximate+TX, fensulfothion+TX, fenthion+TX, fentinacetate+TX, fenvalerate+TX, fipronil+TX, flometoquin+TX, flonicamid+TX, fluacrypyrim+TX, fluazaindolizine+TX, fluazuron+TX, flubendiamide+TX, flubenzimine+TX, fluchlordiniliprole+TX, flucitrinate+TX, flucycloxuron+TX, flucythrinate+TX, fluensulfone+TX, flufenerim+TX, flufenprox+TX, flufiprole+TX, fluhexafon+TX, flumethrin+TX, fluopyram+TX, flupentiofenox+TX, flupyradifurone+TX, flupyrimin+TX, fluralaner+TX, fluvalinate+TX, fluxametamide+TX, fosthiazate+TX, gamma-cyhalothrin+TX, guadipyr+TX, halofenozide+TX, halfenprox+TX, heptafluthrin+TX, hexythiazox+TX, hydramethylnon+TX, imicyafos+TX, imidacloprid+TX, imiprothrin+TX, indazapyroxamet+TX, indoxacarb+TX, iodomethane+TX, iprodione+TX, isocycloseram+TX, isothioate+TX, ivermectin+TX, kappa-bifenthrin+TX, kappa-tefluthrin+TX, lambda-Cyhalothrin+TX, lepimectin+TX, lotilaner+TX, lufenuron+TX, metaflumizone+TX, metaldehyde+TX, metam+TX, methomyl+TX, methoxyfenozide+TX, metofluthrin+TX, metolcarb+TX, mexacarbate+TX, milbemectin+TX, momfluorothrin+TX, niclosamide+TX, nicofluprole+TX; nitenpyram+TX, nithiazine+TX, omethoate+TX, oxamyl+TX, oxazosulfyl+TX, parathion-ethyl+TX, permethrin+TX, phenothrin+TX, phosphocarb+TX, piperonylbutoxide+TX, pirimicarb+TX, pirimiphos-ethyl+TX, pirimiphos-methyl+TX, Polyhedrosis virus+TX, prallethrin+TX, profenofos+TX, profluthrin+TX, propargite+TX, propetamphos+TX, propoxur+TX, prothiophos+TX, protrifenbute+TX, pyflubumide+TX, pymetrozine+TX, pyraclofos+TX, pyrafluprole+TX, pyridaben+TX, pyridalyl+TX, pyrifluquinazon+TX, pyrimidifen+TX, pyriminostrobin+TX, pyriprole+TX, pyriproxyfen+TX, resmethrin+TX, sarolaner+TX, selamectin+TX, silafluofen+TX, spinetoram+TX, spinosad+TX, spirobudifen+TX; spirodiclofen+TX, spiromesifen+TX, spiropidion+TX, spirotetramat+TX, spidoxamat+TX, sulfoxaflor+TX, tebufenozide+TX, tebufenpyrad+TX, tebupirimiphos+TX, tefluthrin+TX, temephos+TX, tetrachlorantraniliprole+TX, tetradiphon+TX, tetramethrin+TX, tetramethylfluthrin+TX, tetranactin+TX, tetraniliprole+TX, theta-cypermethrin+TX, thiacloprid+TX, thiamethoxam+TX, thiocyclam+TX, thiodicarb+TX, thiofanox+TX, thiometon+TX, thiosultap+TX, tigolaner+TX, tiorantraniliprole+TX; tioxazafen+TX, tolfenpyrad+TX, toxaphene+TX, tralomethrin+TX, transfluthrin+TX, triazamate+TX, triazophos+TX, trichlorfon+TX, trichloronate+TX, trichlorphon+TX, trifluenfuronate+TX, triflumezopyrim+TX, tyclopyrazoflor+TX, zeta-cypermethrin+TX, Extract of seaweed and fermentation product derived from melasse+TX, Extract of seaweed and fermentation product derived from melasse comprising urea+TX, amino acids+TX, potassium and molybdenum and EDTA-chelated manganese+TX, Extract of seaweed and fermented plant products+TX, Extract of seaweed and fermented plant products comprising phytohormones+TX, vitamins+TX, EDTA-chelated copper+TX, zinc+TX, and iron+TX, azadirachtin+TX, *Bacillus aizawai*+TX, *Bacillus chitinosporus* $AQ_{746}$ (NRRL Accession No B-21 618)+TX, *Bacillus firmus*+TX, *Bacillus kurstaki*+TX, *Bacillus mycoides* $AQ_{726}$ (NRRL Accession No. B-21664)+TX, *Bacillus pumilus* (NRRL Accession No B-30087)+TX, *Bacillus pumilus* $AQ_{717}$ (NRRL Accession No.

B-21662)+TX, *Bacillus* sp. $AQ_{178}$ (ATCC Accession No. 53522)+TX, *Bacillus* sp. $AQ_{175}$ (ATCC Accession No. 55608)+TX, *Bacillus* sp. $AQ_{177}$ (ATCC Accession No. 55609)+TX, *Bacillus subtilis* unspecified+TX, *Bacillus subtilis* $AQ_{153}$ (ATCC Accession No. 55614)+TX, *Bacillus subtilis* $AQ_{30002}$ (NRRL Accession No. B-50421)+TX, *Bacillus subtilis* $AQ_{30004}$ (NRRL Accession No. B-50455)+TX, *Bacillus subtilis* $AQ_{713}$ (NRRL Accession No. B-21661)+TX, *Bacillus subtilis* $AQ_{743}$ (NRRL Accession No. B-21665)+TX, *Bacillus thuringiensis* $AQ_{52}$ (NRRL Accession No. B-21619)+TX, *Bacillus thuringiensis* BD #32 (NRRL Accession No B-21530)+TX, *Bacillus thuringiensis* subspec. *kurstaki* BMP 123+TX, *Beauveria bassiana*+TX, D-limonene+TX, Granulovirus+TX, Harpin+TX, *Helicoverpa armigera* Nucleopolyhedrovirus+TX, *Helicoverpa zea* Nucleopolyhedrovirus+TX, *Heliothis virescens* Nucleopolyhedrovirus+TX, *Heliothis punctigera* Nucleopolyhedrovirus+TX, *Metarhizium* spp.+TX, *Muscodor albus* 620 (NRRL Accession No. 30547)+TX, *Muscodor roseus* A3-5 (NRRL Accession No. 30548)+TX, Neem tree based products+TX, *Paecilomyces fumosoroseus*+TX, *Paecilomyces lilacinus*+TX, *Pasteuria nishizawae*+TX, *Pasteuria penetrans*+TX, *Pasteuria ramosa*+TX, *Pasteuria thornei*+TX, *Pasteuria usgae*+TX, P-cymene+TX, *Plutella xylostella* Granulosis virus+TX, *Plutella xylostella* Nucleopolyhedrovirus+TX, Polyhedrosis virus+TX, *pyrethrum*+TX, QRD 420 (a terpenoid blend)+TX, QRD 452 (a terpenoid blend)+TX, QRD 460 (a terpenoid blend)+TX, *Quillaja saponaria*+TX, *Rhodococcus globerulus* $AQ_{719}$ (NRRL Accession No B-21663)+TX, *Spodoptera frugiperda* Nucleopolyhedrovirus+TX, *Streptomyces galbus* (NRRL Accession No. 30232)+TX, *Streptomyces* sp. (NRRL Accession No. B-30145)+TX, Terpenoid blend+TX, and *Verticillium* spp.+TX; an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX;

an anthelmintic selected from the group of substances consisting of abamectin (1)+TX, crufomate (1011)+TX, cyclobutrifluram+TX, doramectin (alternative name) [CCN]+TX, emamectin (291)+TX, emamectin benzoate (291)+TX, eprinomectin (alternative name) [CCN]+TX, ivermectin (alternative name) [CCN]+TX, milbemycin oxime (alternative name) [CCN]+TX, moxidectin (alternative name) [CCN]+TX, piperazine [CCN]+TX, selamectin (alternative name) [CCN]+TX, spinosad (737) and thiophanate (1435)+TX;

an avicide selected from the group of substances consisting of chloralose (127)+TX, endrin (1122)+TX, fenthion (346)+TX, pyridin-4-amine (IUPAC name) (23) and strychnine (745)+TX;

a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen (alternative name) [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal (alternative name) [CCN]+TX;

a biological agent selected from the group of substances consisting of *Adoxophyes orana* GV (alternative name) (12)+TX, *Agrobacterium radiobacter* (alternative name) (13)+TX, *Amblyseius* spp. (alternative name) (19)+TX, *Anagrapha falcifera* NPV (alternative name) (28)+TX, *Anagrus atomus* (alternative name) (29)+TX, *Aphelinus abdominalis* (alternative name) (33)+TX, *Aphidius colemani* (alternative name) (34)+TX, *Aphidoletes aphidimyza* (alternative name) (35)+TX, *Autographa californica* NPV (alternative name) (38)+TX, *Bacillus firmus* (alternative name) (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (alternative name) (53)+TX, *Beauveria brongniartii* (alternative name) (54)+TX, *Chrysoperla carnea* (alternative name) (151)+TX, *Cryptolaemus montrouzieri* (alternative name) (178)+TX, *Cydia pomonella* GV (alternative name) (191)+TX, *Dacnusa sibirica* (alternative name) (212)+TX, *Diglyphus isaea* (alternative name) (254)+TX, *Encarsia formosa* (scientific name) (293)+TX, *Eretmocerus eremicus* (alternative name) (300)+TX, *Helicoverpa zea* NPV (alternative name) (431)+TX, *Heterorhabditis bacteriophora* and *H. megidis* (alternative name) (433)+TX, *Hippodamia convergens* (alternative name) (442)+TX, *Leptomastix dactylopii* (alternative name) (488)+TX, *Macrolophus caliginosus* (alternative name) (491)+TX, *Mamestra brassicae* NPV (alternative name) (494)+TX, *Metaphycus helvolus* (alternative name) (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (alternative name) (575)+TX, *Orius* spp. (alternative name) (596)+TX, *Paecilomyces fumosoroseus* (alternative name) (613)+TX, *Phytoseiulus persimilis* (alternative name) (644)+TX, *Spodoptera exigua* multicapsid nuclear polyhedrosis virus (scientific name) (741)+TX, *Steinernema bibionis* (alternative name) (742)+TX, *Steinernema carpocapsae* (alternative name) (742)+TX, *Steinernema feltiae* (alternative name) (742)+TX, *Steinernema glaseri* (alternative name) (742)+TX, *Steinernema riobrave* (alternative name) (742)+TX, *Steinernema riobravis* (alternative name) (742)+TX, *Steinernema scapterisci* (alternative name) (742)+TX, *Steinernema* spp. (alternative name) (742)+TX, *Trichogramma* spp. (alternative name) (826)+TX, *Typhlodromus occidentalis* (alternative name) (844) and *Verticillium lecanii* (alternative name) (848)+TX;

a soil sterilant selected from the group of substances consisting of iodomethane (IUPAC name) (542) and methyl bromide (537)+TX;

a chemosterilant selected from the group of substances consisting of apholate [CCN]+TX, bisazir (alternative name) [CCN]+TX, busulfan (alternative name) [CCN]+TX, diflubenzuron (250)+TX, dimatif (alternative name) [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron (alternative name) [CCN]+TX, tepa [CCN]+TX, thiohempa (alternative name) [CCN]+TX, thiotepa (alternative name) [CCN]+TX, tretamine (alternative name) [CCN] and uredepa (alternative name) [CCN]+TX;

an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin (alternative name) [CCN]+TX, brevicomin (alternative name) [CCN]+TX, codlelure (alternative name) [CCN]+TX, codlemone (alternative name) (167)+TX, cuelure (alternative name) (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure (alternative name) [CCN]+TX, ethyl 4-methyloctanoate (IUPAC name) (317)+TX, eugenol (alternative name) [CCN]+TX, frontalin (alternative name) [CCN]+TX, Gossyplure® (alternative name; 1:1 mixture of the (Z,E) and (Z,Z) isomers of hexadeca-7,11-dien-1-yl-acetate) (420)+TX, grandlure (421)+TX, grandlure I (alternative name) (421)+TX, grandlure II (alternative name) (421)+TX, grandlure III (alternative name) (421)+TX, grandlure IV (alternative name) (421)+TX, hexalure [CCN]+TX, ipsdienol (alternative name) [CCN]+TX, ipsenol (alternative name) [CCN]+TX, japonilure (alternative name) (481)+TX, lineatin (alternative name) [CCN]+TX, litlure (alternative name) [CCN]+TX, looplure (alternative name) [CCN]+TX, medlure [CCN]+TX, megatomoic acid (alternative name) [CCN]+TX, methyl eugenol (alternative name) (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure (alternative name) [CCN]+TX, oryctalure (alternative name) (317)+TX, ostramone (alternative name) [CCN]+TX, siglure [CCN]+TX, sordidin (alternative name) (736)+TX, sulcatol (alternative name) [CCN]+TX, tetradec-11-en-1-yl acetate (IUPAC name) (785)+TX, trimedlure (839)+TX, trimedlure A (alternative name) (839)+TX, trimedlure B1 (alternative name) (839)+TX, trimedlure B2 (alternative name) (839)+TX, trimedlure C (alternative name) (839) and trunc-call (alternative name) [CCN]+TX; an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX;

a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX;

a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (alternative name) (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben (alternative name)+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cyclobutrifluram+TX, cytokinins (alternative name) (210)+TX, dazomet (216)+TX, DBCP (1045)+TX, DCIP (218)+TX, diamidafos (1044)+TX, dichlofenthion (1051)+TX, dicliphos (alternative name)+TX, dimethoate (262)+TX, doramectin (alternative name) [CCN]+TX, emamectin (291)+TX, emamectin benzoate (291)+TX, eprinomectin (alternative name) [CCN]+TX, ethoprophos (312)+TX, ethylene dibromide (316)+TX, fenamiphos (326)+TX, fenpyrad (alternative name)+TX, fensulfothion (1158)+TX, fosthiazate (408)+TX, fosthietan (1196)+TX, furfural (alternative name) [CCN]+TX, GY-81 (development code) (423)+TX, heterophos [CCN]+TX, iodomethane (IUPAC name) (542)+TX, isamidofos (1230)+TX, isazofos (1231)+TX, ivermectin (alternative name) [CCN]+TX, kinetin (alternative name) (210)+TX, mecarphon (1258)+TX, metam (519)+TX, metam-potassium (alternative name) (519)+TX, metam-sodium (519)+TX, methyl bromide (537)+TX, methyl isothiocyanate (543)+TX, milbemycin oxime (alternative name) [CCN]+TX, moxidectin (alternative name) [CCN]+TX, *Myrothecium verrucaria* composition (alternative name) (565)+TX, NC-184 (compound code)+TX, oxamyl (602)+TX, phorate (636)+TX, phosphamidon (639)+TX, phosphocarb [CCN]+TX, sebufos (alternative name)+TX, selamectin (alternative name) [CCN]+TX, spinosad (737)+TX, terbam (alternative name)+TX, terbufos (773)+TX, tetrachlorothiophene (IUPAC/Chemical Abstracts name) (1422)+TX, thiafenox (alternative name)+TX, thionazin (1434)+TX, triazophos (820)+TX, triazuron (alternative name)+TX, xylenols [CCN]+TX, YI-5302 (compound code) and zeatin (alternative name) (210)+TX, fluensulfone [318290-98-1]+TX, fluopyram+TX;

a nitrification inhibitor selected from the group of substances consisting of potassium ethylxanthate [CCN] and nitrapyrin (580)+TX;

a plant activator selected from the group of substances consisting of acibenzolar (6)+TX, acibenzolar-S-methyl (6)+TX, probenazole (658) and *Reynoutria sachalinensis* extract (alternative name) (720)+TX; a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (including alpha-bromadiolone)+TX, bromethalin (92)+TX, calcium cyanide (444)+TX, chloralose (127)+TX, chlorophacinone (140)+TX, cholecalciferol (alternative name) (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX;

a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (alternative name) (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX;

an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX;

a virucide selected from the group of substances consisting of imanin (alternative name) [CCN] and ribavirin (alternative name) [CCN]+TX;

a wound protectant selected from the group of substances consisting of mercuric oxide (512)+TX, octhilinone (590) and thiophanate-methyl (802)+TX;

a biologically active substance selected from 1,1-bis(4-chlorophenyl)-2-ethoxyethanol+TX, 2,4-dichlorophenyl benzenesulfonate+TX, 2-fluoro-N-methyl-N-1-naphthylacetamide+TX, 4-chlorophenyl phenyl sulfone+TX, acetoprole+TX, aldoxycarb+TX, amidithion+TX, amidothioate+TX, amiton+TX, amiton hydrogen oxalate+TX, amitraz+TX, aramite+TX, arsenous oxide+TX, azobenzene+TX, azothoate+TX, benomyl+TX, benoxafos+TX, benzyl benzoate+TX, bixafen+TX, brofenvalerate+TX, bromocyclen+TX, bromophos+TX, bromopropylate+TX, buprofezin+TX, butocarboxim+TX, butoxycarboxim+TX, butylpyridaben+TX, calcium polysulfide+TX, camphechlor+TX, carbanolate+TX, carbophenothion+TX, cymiazole+TX, chinomethionat+TX, chlorbenside+TX, chlordimeform+TX, chlordimeform hydrochloride+TX, chlorfenethol+TX, chlorfenson+TX, chlorfensulfide+TX, chlorobenzilate+TX, chloromebuform+TX, chloromethiuron+TX, chloropropylate+TX, chlorthiophos+TX, cinerin I+TX, cinerin II+TX, cinerins+TX, closantel+TX, coumaphos+TX, crotamiton+TX, crotoxyphos+TX, cufraneb+TX, cyanthoate+TX, DCPM+TX, DDT+TX, demephion+TX, demephion-O+TX, demephion-S+TX, demeton-methyl+TX, demeton-O+TX, demeton-O-methyl+TX, demeton-S+TX, demeton-S-methyl+TX, demeton-S-methylsulfon+TX, dichlofluanid+TX, dichlorvos+TX, dicliphos+TX, dienochlor+TX, dimefox+TX, dinex+TX, dinex-diclexine+TX, dinocap-4+TX, dinocap-6+TX, dinocton+TX, dinopenton+TX, dinosulfon+TX, dinoterbon+TX, dioxathion+TX, diphenyl sulfone+TX, disulfiram+TX, DNOC+TX, dofenapyn+TX, doramectin+TX, endothion+TX, eprinomectin+TX, ethoate-methyl+TX, etrimfos+TX, fenazaflor+TX, fenbutatin oxide+TX, fenothiocarb+TX, fenpyrad+TX, fenpyroximate+TX, fenpyrazamine+TX, fenson+TX, fentrifanil+TX, flubenzimine+TX, flucycloxuron+TX, fluenetil+TX, fluorbenside+TX, FMC 1137+TX, formetanate+TX, formetanate hydrochloride+TX, formparanate+TX, gamma-HCH+TX, glyodin+TX, halfenprox+TX, hexadecyl cyclopropanecarboxylate+TX, isocarbophos+TX, jasmolin I+TX, jasmolin II+TX, jodfenphos+TX, lindane+TX, malonoben+TX, mecarbam+TX, mephosfolan+TX, mesulfen+TX, methacrifos+TX, methyl bromide+TX, metolcarb+TX, mexacarbate+TX, milbemycin oxime+TX, mipafox+TX, monocrotophos+TX, morphothion+TX, moxidectin+TX, naled+TX, 4-chloro-2-(2-chloro-2-methylpropyl)-5-[(6-iodo-3-pyridyl)methoxy]pyridazin-3-one+TX, nifluridide+TX, nikkomycins+TX, nitrilacarb+TX, nitrilacarb 1:1 zinc chloride complex+TX, omethoate+TX, oxydeprofos+TX, oxydisulfoton+

TX, pp'-DDT+TX, parathion+TX, permethrin+TX, phenkapton+TX, phosalone+TX, phosfolan+TX, phosphamidon+TX, polychloroterpenes+TX, polynactins+TX, proclonol+TX, promacyl+TX, propoxur+TX, prothidathion+TX, prothoate+TX, pyrethrin I+TX, pyrethrin II+TX, pyrethrins+TX, pyridaphenthion+TX, pyrimitate+TX, quinalphos+TX, quintiofos+TX, R-1492+TX, phosglycin+TX, rotenone+TX, schradan+TX, sebufos+TX, selamectin+TX, sophamide+TX, SSI-121+TX, sulfiram+TX, sulfluramid+TX, sulfotep+TX, sulfur+TX, diflovidazin+TX, tau-fluvalinate+TX, TEPP+TX, terbam+TX, tetradifon+TX, tetrasul+TX, thiafenox+TX, thiocarboxime+TX, thiofanox+TX, thiometon+TX, thioquinox+TX, thuringiensin+TX, triamiphos+TX, triarathene+TX, triazophos+TX, triazuron+TX, trifenofos+TX, trinactin+TX, vamidothion+TX, vaniliprole+TX, bethoxazin+TX, copper dioctanoate+TX, copper sulfate+TX, cybutryne+TX, dichlone+TX, dichlorophen+TX, endothal+TX, fentin+TX, hydrated lime+TX, nabam+TX, quinoclamine+TX, quinonamid+TX, simazine+TX, triphenyltin acetate+TX, triphenyltin hydroxide+TX, crufomate+TX, piperazine+TX, thiophanate+TX, chloralose+TX, fenthion+TX, pyridin-4-amine+TX, strychnine+TX, 1-hydroxy-1H-pyridine-2-thione+TX, 4-(quinoxalin-2-ylamino)benzenesulfonamide+TX, 8-hydroxyquinoline sulfate+TX, bronopol+TX, copper hydroxide+TX, cresol+TX, dipyrithione+TX, dodicin+TX, fenaminosulf+TX, formaldehyde+TX, hydrargaphen+TX, kasugamycin+TX, kasugamycin hydrochloride hydrate+TX, nickel bis (dimethyldithiocarbamate)+TX, nitrapyrin+TX, octhilinone+TX, oxolinic acid+TX, oxytetracycline+TX, potassium hydroxyquinoline sulfate+TX, probenazole+TX, streptomycin+TX, streptomycin sesquisulfate+TX, tecloftalam+TX, thiomersal+TX, *Adoxophyes orana* GV+TX, *Agrobacterium radiobacter*+TX, *Amblyseius* spp.+TX, *Anagrapha falcifera* NPV+TX, *Anagrus atomus*+TX, *Aphelinus abdominalis*+TX, *Aphidius colemani*+TX, *Aphidoletes aphidimyza*+TX, *Autographa californica* NPV+TX, *Bacillus sphaericus* Neide+TX, *Beauveria brongniartii*+TX, *Chrysoperla carnea*+TX, *Cryptolaemus montrouzieri*+TX, *Cydia pomonella* GV+TX, *Dacnusa sibirica*+TX, *Diglyphus isaea*+TX, *Encarsia formosa*+TX, *Eretmocerus eremicus*+TX, *Heterorhabditis bacteriophora* and *H. megidis*+TX, *Hippodamia convergens*+TX, *Leptomastix dactylopii*+TX, *Macrolophus caliginosus*+TX, *Mamestra brassicae* NPV+TX, *Metaphycus helvolus*+TX, *Metarhizium anisopliae* var. *acridum*+TX, *Metarhizium anisopliae* var. *anisopliae*+TX, *Neodiprion sertifer* NPV and *N. lecontei* NPV+TX, *Orius* spp.+TX, *Paecilomyces fumosoroseus*+TX, *Phytoseiulus persimilis*+TX, *Steinernema bibionis*+TX, *Steinernema carpocapsae*+TX, *Steinernema feltiae*+TX, *Steinernema glaseri*+TX, *Steinernema riobrave*+TX, *Steinernema riobravis*+TX, *Steinernema scapterisci*+TX, *Steinernema* spp.+TX, *Trichogramma* spp.+TX, *Typhlodromus occidentalis*+TX, *Verticillium lecanii*+TX, apholate+TX, bisazir+TX, busulfan+TX, dimatif+TX, hemel+TX, hempa+TX, metepa+TX, methiotepa+TX, methyl apholate+TX, morzid+TX, penfluron+TX, tepa+TX, thiohempa+TX, thiotepa+TX, tretamine+TX, uredepa+TX, (E)-dec-5-en-1-yl acetate with (E)-dec-5-en-1-ol+TX, (E)-tridec-4-en-1-yl acetate+TX, (E)-6-methylhept-2-en-4-ol+TX, (E,Z)-tetradeca-4,10-dien-1-yl acetate+TX, (Z)-dodec-7-en-1-yl acetate+TX, (Z)-hexadec-11-enal+TX, (Z)-hexadec-11-en-1-yl acetate+TX, (Z)-hexadec-13-en-11-yn-1-yl acetate+TX, (Z)-icos-13-en-10-one+TX, (Z)-tetradec-7-en-1-al+TX, (Z)-tetradec-9-en-1-ol+TX, (Z)-tetradec-9-en-1-yl acetate+TX, (7E,9Z)-dodeca-7,9-dien-1-yl acetate+TX, (9Z,11E)-tetradeca-9,11-dien-1-yl acetate+TX, (9Z,12E)-tetradeca-9,12-dien-1-yl acetate+TX, 14-methyloctadec-1-ene+TX, 4-methylnonan-5-ol with 4-methylnonan-5-one+TX, alpha-multistriatin+TX, brevicomin+TX, codlelure+TX, codlemone+TX, cuelure+TX, disparlure+TX, dodec-8-en-1-yl acetate+TX, dodec-9-en-1-yl acetate+TX, dodeca-8+TX, 10-dien-1-yl acetate+TX, dominicalure+TX, ethyl 4-methyloctanoate+TX, eugenol+TX, frontalin+TX, grandlure+TX, grandlure I+TX, grandlure II+TX, grandlure III+TX, grandlure IV+TX, hexalure+TX, ipsdienol+TX, ipsenol+TX, japonilure+TX, lineatin+TX, litlure+TX, looplure+TX, medlure+TX, megatomoic acid+TX, methyl eugenol+TX, muscalure+TX, octadeca-2,13-dien-1-yl acetate+TX, octadeca-3,13-dien-1-yl acetate+TX, orfralure+TX, oryctalure+TX, ostramone+TX, siglure+TX, sordidin+TX, sulcatol+TX, tetradec-11-en-1-yl acetate+TX, trimedlure+TX, trimedlure A+TX, trimedlure B1+TX, trimedlure B2+TX, trimedlure C+TX, trunc-call+TX, 2-(octylthio)ethanol+TX, butopyronoxyl+TX, butoxy(polypropylene glycol)+TX, dibutyl adipate+TX, dibutyl phthalate+TX, dibutyl succinate+TX, diethyltoluamide+TX, dimethyl carbate+TX, dimethyl phthalate+TX, ethyl hexanediol+TX, hexamide+TX, methoquin-butyl+TX, methylneodecanamide+TX, oxamate+TX, picaridin+TX, 1-dichloro-1-nitroethane+TX, 1,1-dichloro-2,2-bis (4-ethylphenyl)ethane+TX, 1,2-dichloropropane with 1,3-dichloropropene+TX, 1-bromo-2-chloroethane+TX, 2,2,2-trichloro-1-(3,4-dichlorophenyl)ethyl acetate+TX, 2,2-dichlorovinyl 2-ethylsulfinylethyl methyl phosphate+TX, 2-(1,3-dithiolan-2-yl)phenyl dimethylcarbamate+TX, 2-(2-butoxyethoxy)ethyl thiocyanate+TX, 2-(4,5-dimethyl-1,3-dioxolan-2-yl)phenyl methylcarbamate+TX, 2-(4-chloro-3,5-xylyloxy) ethanol+TX, 2-chlorovinyl diethyl phosphate+TX, 2-imidazolidone+TX, 2-isovalerylindan-1,3-dione+TX, 2-methyl(prop-2-ynyl)aminophenyl methylcarbamate+TX, 2-thiocyanatoethyl laurate+TX, 3-bromo-1-chloroprop-1-ene+TX, 3-methyl-1-phenylpyrazol-5-yl dimethylcarbamate+TX, 4-methyl(prop-2-ynyl) amino-3,5-xylyl methylcarbamate+TX, 5,5-dimethyl-3-oxocyclohex-1-enyl dimethylcarbamate+TX, acethion+TX, acrylonitrile+TX, aldrin+TX, allosamidin+TX, allyxycarb+TX, alpha-ecdysone+TX, aluminium phosphide+TX, aminocarb+TX, anabasine+TX, athidathion+TX, azamethiphos+TX, *Bacillus thuringiensis* delta endotoxins+TX, barium hexafluorosilicate+TX, barium polysulfide+TX, barthrin+TX, Bayer 22/190+TX, Bayer 22408+TX, beta-cyfluthrin+TX, beta-cypermethrin+TX, bioethanomethrin+TX, biopermethrin+TX, bis(2-chloroethyl) ether+TX, borax+TX, bromfenvinfos+TX, bromo-DDT+TX, bufencarb+TX, butacarb+TX, butathiofos+TX, butonate+TX, calcium arsenate+TX, calcium cyanide+TX, carbon disulfide+TX, carbon tetrachloride+TX, cartap hydrochloride+TX, cevadine+TX, chlorbicyclen+TX, chlordane+TX, chlordecone+TX, chloroform+TX, chloropicrin+TX, chlorphoxim+TX, chlorprazophos+TX, cis-resmethrin+TX, cismethrin+TX, clocythrin+TX, copper acetoarsenite+TX, copper arsenate+TX, copper oleate+TX, coumithoate+TX, cryolite+TX, CS 708+TX, cyanofenphos+TX, cyanophos+TX, cyclethrin+TX, cythioate+TX, d-tetramethrin+TX, DAEP+TX, dazomet+TX, decarbofuran+TX, diamidafos+TX, dicapthon+TX, dichlofenthion+TX, dicresyl+TX, dicyclanil+TX, dieldrin+TX, diethyl 5-methylpyrazol-3-yl phosphate+TX, dilor+TX, dimefluthrin+TX, dimetan+TX, dimethrin+TX, dimethylvinphos+TX, dimetilan+TX, dinoprop+TX, dinosam+TX, dinoseb+TX, diofenolan+TX, dioxabenzofos+TX, dithicrofos+TX, DSP+TX, ecdysterone+TX, EI 1642+TX, EMPC+TX, EPBP+TX, etaphos+TX, ethiofencarb+TX, ethyl formate+TX, ethylene dibromide+TX, ethylene dichloride+TX, ethylene oxide+TX, EXD+TX, fenchlorphos+TX, fenethacarb+TX, fenitrothion+TX, fenoxacrim+TX, fenpirithrin+TX, fensulfothion+TX, fenthion-ethyl+TX, flucofuron+TX, fosmethilan+TX, fospirate+TX, fosthietan+TX, furathiocarb+TX, furethrin+TX, guazatine+TX, guazatine acetates+TX, sodium tetrathiocarbonate+TX, halfenprox+TX, HCH+TX, HEOD+TX, heptachlor+TX, heterophos+TX, HHDN+TX, hydrogen cyanide+TX, hyquincarb+TX, IPSP+TX, isazofos+TX, isobenzan+TX, isodrin+TX, isofenphos+TX, isolane+TX, isoprothiolane+TX, isoxathion+TX, juvenile hormone I+TX, juvenile hormone II+TX, juvenile hormone III+TX, kelevan+TX, kinoprene+TX, lead arsenate+TX, leptophos+TX, lirimfos+TX, lythidathion+TX, m-cumenyl methylcarbamate+TX, magnesium phosphide+TX, mazidox+TX, mecarphon+TX, menazon+TX, mercurous chloride+TX, mesulfenfos+TX, metam+TX, metam-potassium+TX, metam-sodium+TX, methanesulfonyl fluoride+TX, methocrotophos+TX, methoprene+TX, methothrin+TX, methoxychlor+TX, methyl isothiocyanate+TX, methylchloroform+TX, methylene chloride+TX, metoxadiazone+TX, mirex+TX, naftalofos+TX, naphthalene+TX, NC-170+TX, nicotine+TX, nicotine sulfate+TX, nithiazine+TX, nornicotine+TX, 0-5-dichloro-4-iodophenyl O-ethyl ethylphosphonothioate+TX, O,O-diethyl 0-4-methyl-2-oxo-2H-chromen-7-yl phosphorothioate+TX, O,O-diethyl O-6-methyl-2-propylpyrimidin-4-yl phosphorothioate+TX, O,O,O',O'-tetrapropyl dithiopyrophosphate+TX, oleic acid+TX, para-dichlorobenzene+TX, parathion-methyl+TX, pentachlorophenol+TX, pentachlorophenyl laurate+TX, PH 60-38+TX, phenkapton+TX, phosnichlor+TX, phosphine+TX, phoxim-methyl+TX, pirimetaphos+TX, polychlorodicyclopentadiene isomers+TX, potassium arsenite+TX, potassium thiocyanate+TX, precocene I+TX, precocene II+TX, precocene III+TX, primidophos+TX, profluthrin+TX, promecarb+TX, prothiofos+TX, pyrazophos+TX, pyresmethrin+TX, *quassia*+TX, quinalphos-methyl+TX, quinothion+TX, rafoxanide+TX, resmethrin+TX, rotenone+TX, kadethrin+TX, ryania+TX, ryanodine+TX, sabadilla+TX, schradan+TX, sebufos+TX, SI-0009+TX, thiapronil+TX, sodium arsenite+TX, sodium cyanide+TX, sodium fluoride+TX, sodium hexafluorosilicate+TX, sodium pentachlorophenoxide+TX, sodium selenate+TX, sodium thiocyanate+TX, sulcofuron+TX, sulcofuron-sodium+TX, sulfuryl fluoride+TX, sulprofos+TX, tar oils+TX, tazimcarb+TX, TDE+TX, tebupirimfos+TX, temephos+TX, terallethrin+TX, tetrachloroethane+TX, thicrofos+TX, thiocyclam+TX, thiocyclam hydrogen oxalate+TX, thionazin+TX, thiosultap+TX, thiosultap-sodium+TX, tralomethrin+TX, transpermethrin+TX, triazamate+TX, trichlormetaphos-3+TX, trichloronat+TX, trimethacarb+TX, tolprocarb+TX, triclopyricarb+TX, triprene+TX, veratridine+TX, veratrine+TX, XMC+TX, zetamethrin+TX, zinc phosphide+TX, zolaprofos+TX, meperfluthrin+TX, tetramethylfluthrin+TX, bis(tributyltin) oxide+TX, bromoacetamide+TX, ferric phosphate+TX, niclosamide-olamine+TX, tributyltin oxide+TX, pyrimorph+TX, trifenmorph+TX, 1,2-dibromo-3-chloropropane+TX, 1,3-dichloropropene+TX, 3,4-dichlorotetrahydrothiophene 1,1-dioxide+TX, 3-(4-chlorophenyl)-5-methylrhodanine+TX, 5-methyl-6-thioxo-1,3,5-thiadiazinan-3-ylacetic acid+TX, 6-isopentenylaminopurine+TX, anisiflupurin+TX, benclothiaz+TX, cytokinins+TX, DCIP+TX, furfural+TX, isamidofos+TX, kinetin+TX, *Myrothecium verrucaria* composition+TX, tetrachlorothiophene+TX, xylenols+TX, zeatin+TX, potassium ethylxanthate+TX, acibenzolar+TX, acibenzolar-S-methyl+TX, *Reynoutria sachalinensis* extract+TX, alpha-chlorohydrin+TX, antu+TX, barium carbonate+TX, bisthiosemi+TX, brodifacoum+TX, bromadiolone+TX, bromethalin+TX, chlorophacinone+TX, cholecalciferol+TX, coumachlor+TX, coumafuryl+TX, coumatetralyl+TX, crimidine+TX, difenacoum+TX, difethialone+TX, diphacinone+TX, ergocalciferol+TX, flocoumafen+TX, fluoroacetamide+TX, flupropadine+TX, flupropadine hydrochloride+TX, norbormide+TX, phosacetim+TX, phosphorus+TX, pindone+TX, pyrinuron+TX, scilliroside+TX, sodium fluoroacetate+TX, thallium sulfate+TX, warfarin+TX, 2-(2-butoxyethoxy)ethyl piperonylate+TX, 5-(1,3-benzodioxol-5-yl)-3-hexylcyclohex-2-enone+TX, farnesol with nerolidol+TX, verbutin+TX, MGK 264+TX, piperonyl butoxide+TX, piprotal+TX, propyl isomer+TX, S421+TX, sesamex+TX, sesasmolin+TX, sulfoxide+TX, anthraquinone+TX, copper naphthenate+TX, copper oxychloride+TX, dicyclopentadiene+TX, thiram+TX, zinc naphthenate+TX, ziram+TX, imanin+TX, ribavirin+TX, chloroinconazide+TX, mercuric oxide+TX, thiophanate-methyl+TX, azaconazole+TX, bitertanol+TX, bromuconazole+TX, cyproconazole+TX, difenoconazole+TX, diniconazole+TX, epoxiconazole+TX, fenbuconazole+TX, fluquinconazole+TX, flusilazole+TX, flutriafol+TX, furametpyr+TX, hexaconazole+TX, imazalil+TX, imibenconazole+TX, ipconazole+TX, metconazole+TX, myclobutanil+TX, paclobutrazole+TX, pefurazoate+TX, penconazole+TX, prothioconazole+TX, pyrifenox+TX, prochloraz+TX, propiconazole+TX, pyrisoxazole+TX, -simeconazole+TX, tebuconazole+TX, tetraconazole+TX, triadimefon+TX, triadimenol+TX, triflumizole+TX, triticonazole+TX, ancymidol+TX, fenarimol+TX, nuarimol+TX, bupirimate+TX, dimethirimol+TX, ethirimol+TX, dodemorph+TX, fenpropidin+TX, fenpropimorph+TX, spiroxamine+TX, tridemorph+TX, cyprodinil+TX, mepanipyrim+TX, pyrimethanil+TX, fenpiclonil+TX, fludioxonil+TX, benalaxyl+TX, furalaxyl+TX, metalaxyl-+TX, Rmetalaxyl+TX, ofurace+TX, oxadixyl+TX, carbendazim+TX, debacarb+TX, fuberidazole+TX, thiabendazole+TX, chlozolinate+TX, dichlozoline+TX, myclozoline+TX, procymidone+TX, vinclozoline+TX, boscalid+TX, carboxin+TX, fenfuram+TX, flutolanil+TX, mepronil+TX, oxycarboxin+TX, penthiopyrad+TX, thifluzamide+TX, dodine+TX, iminoctadine+TX, azoxystrobin+TX, dimoxystrobin+TX, enestroburin+TX, fenaminstrobin+TX, flufenoxystrobin+TX, fluoxastrobin+TX, kresoxim-methyl+TX, metominostrobin+TX, trifloxystrobin+TX, orysastrobin+TX, picoxystrobin+TX, pyraclostrobin+TX, pyrametostrobin+TX, pyraoxystrobin+TX, ferbam+TX, mancozeb+TX, maneb+TX, metiram+TX, propineb+TX, zineb+TX, captafol+TX, captan+TX, fluoroimide+TX, folpet+TX, tolylfluanid+TX, bordeaux mixture+TX, copper oxide+TX, mancopper+TX, oxine-copper+TX, nitrothal-isopropyl+TX, edifenphos+TX, iprobenphos+TX, phosdiphen+TX, tolclofos-methyl+TX, anilazine+TX, benthiavalicarb+TX, blasticidin-S+TX, chloroneb+TX, chlorothalonil+TX, cyflufenamid+TX, cymoxanil+TX, cyclobutrifluram+TX, diclocymet+TX, diclomezine+TX, dicloran+TX, diethofencarb+TX, dimethomorph+TX, flumorph+TX, dithianon+TX, ethaboxam+TX, etridiazole+TX, famoxadone+TX, fenamidone+TX, fenoxanil+TX, ferimzone+TX, fluazinam+TX, flumetylsulforim+TX, fluopicolide+TX, fluoxytioconazole+TX, flusulfamide+TX, fluxapyroxad+TX, fenhexamid+TX, fosetyl-aluminium+TX, hymexazol+TX, iprovalicarb+TX, cyazofamid+TX, methasulfocarb+TX, metrafenone+TX, pencycuron+TX, phthalide+TX, polyoxins+TX, propamocarb+TX, pyribencarb+TX, proquinazid+TX, pyroquilon+TX, pyriofenone+TX, quinoxyfen+TX, quintozene+TX, tiadinil+TX, triazoxide+TX, tricyclazole+TX, triforine+TX, validamycin+TX, valifenalate+TX, zoxamide+TX, mandipropamid+TX, flubeneteram+TX, isopyrazam+TX, sedaxane+TX, benzovindiflupyr+TX, pydiflumetofen+TX, 3-difluoromethyl-1-methyl-1H-pyrazole-4-carboxylic acid (3',4',5'-trifluoro-biphenyl-2-yl)-amide+TX, isoflucypram+TX, isotianil+TX, dipymetitrone+TX, 6-ethyl-5,7-dioxo-pyrrolo[4,5][1,4]dithiino[1,2-c]isothiazole-3-carbonitrile+TX, 2-(difluoromethyl)-N-[3-ethyl-1,1-dimethyl-indan-4-yl]pyridine-3-carboxamide+TX, 4-(2,6-difluorophenyl)-6-methyl-5-phenyl-pyridazine-3-carbonitrile+TX, (R)-3-(difluoromethyl)-1-methyl-N-[1,1,3-trimethylindan-4-yl]pyrazole-4-carboxamide+TX, 4-(2-bromo-4-fluoro-phenyl)-N-(2-chloro-6-fluoro-phenyl)-2,5-dimethyl-pyrazol-3-amine+TX, 4-(2-bromo-4-fluorophenyl)-N-(2-chloro-6-fluorophenyl)-1,3-dimethyl-1H-pyrazol-5-amine+TX, fluindapyr+TX, coumethoxystrobin (jiaxiangjunzhi)+TX, Ivbenmixianan+TX, dichlobentiazox+TX, mandestrobin+TX, 3-(4,4-difluoro-3,4-dihydro-3,3-dimethylisoquinolin-1-yl)quinolone+TX, 2-[2-fluoro-6-[(8-fluoro-2-methyl-3-quinolyl)oxy]phenyl]propan-2-ol+TX, oxathiapiprolin+TX, tert-butyl N-[6-[[[(1-methyltetrazol-5-yl)-phenyl-methylene]amino]oxymethyl]-2-pyridyl]carbamate+TX, pyraziflumid+TX, inpyrfluxam+TX, trolprocarb+TX, mefentrifluconazole+TX, ipfentrifluconazole+TX, 2-(difluoromethyl)-N-[(3R)-3-ethyl-1,1-dimethyl-indan-4-yl]pyridine-3-carboxamide+TX, N'-(2,5-dimethyl-4-phenoxy-phenyl)-N-ethyl-N-methyl-formamidine+TX, N'-[4-(4,5-dichlorothiazol-2-yl)oxy-2,5-dimethyl-phenyl]-N-ethyl-N-methyl-formamidine+TX, [2-[3-[2-[1-[2-[3,5-bis(difluoromethyl)pyrazol-1-yl]acetyl]-4-piperidyl]thiazol-4-yl]-4,5-dihydroisoxazol-5-yl]-3-chloro-phenyl] methanesulfonate+TX, but-3-ynyl N-[6-[[(Z)-[(1-methyltetrazol-5-yl)-phenyl-methylene]amino] oxymethyl]-2-pyridyl]carbamate+TX, methyl N-[[5-[4-(2,4-dimethylphenyl)triazol-2-yl]-2-methyl-phenyl] methyl]carbamate+TX, 3-chloro-6-methyl-5-phenyl-4-(2,4,6-trifluorophenyl)pyridazine+TX, pyridachlometyl+TX, 3-(difluoromethyl)-1-methyl-N-[1,1,3-trimethylindan-4-yl]pyrazole-4-carboxamide+TX, 1-[2-[[1-(4-chlorophenyl)pyrazol-3-yl]oxymethyl]-3-methyl-phenyl]-4-methyl-tetrazol-5-one+TX, 1-methyl-4-[3-methyl-2-[[2-methyl-4-(3,4,5-trimethylpyrazol-1-yl)phenoxy]methyl]phenyl]tetrazol-5-one+TX, aminopyrifen+TX, ametoctradin+TX, amisulbrom+TX, penflufen+TX, (Z,2E)-5-[1-(4-chlorophenyl)pyrazol-3-yl]oxy-2-methoxyimino-N,3-dimethyl-pent-3-enamide+TX, florylpicoxamid+TX, fenpicoxamid+TX, metarylpicoxamid+TX, tebufloquin+TX, ipflufenoquin+TX, quinofumelin+TX, isofetamid+TX, ethyl 1-[[4-[[2-(trifluoromethyl)-1,3-dioxolan-2-yl]methoxy]phenyl]methyl]pyrazole-3-carboxylate+TX (may be prepared from the methods described in WO 2020/056090), ethyl 1-[[4-[(Z)-2-ethoxy-3,3,3-trifluoro-prop-1-enoxy]phenyl]methyl] pyrazole-3-carboxylate+TX (may be prepared from the methods described in WO 2020/056090), methyl N-[[4-[1-(4-cyclopropyl-2,6-difluoro-phenyl)pyrazol-4-yl]-2-methyl-phenyl]methyl]carbamate+TX (may be prepared from the methods described in WO 2020/097012), methyl N-[[4-[1-(2,6-difluoro-4-isopropyl-phenyl)pyrazol-4-yl]-2-methyl-phenyl]methyl]carbamate+TX (may be prepared from the methods described in WO 2020/097012), 6-chloro-3-(3-cyclopropyl-2-fluoro-phenoxy)-N-[2-(2,4-dimethylphenyl)-2,2-difluoro-ethyl]-5-methyl-pyridazine-4-carboxamide+TX (may be prepared from the methods described in WO 2020/109391), 6-chloro-N-[2-(2-chloro-4-methyl-phenyl)-2,2-difluoro-ethyl]-3-(3-cyclopropyl-2-fluoro-phenoxy)-5-methyl-pyridazine-4-carboxamide+TX (may be prepared from the methods described in WO 2020/109391), 6-chloro-3-(3-cyclopropyl-2-fluoro-phenoxy)-N-[2-(3,4-dimethylphenyl)-2,2-difluoro-ethyl]-5-methyl-pyridazine-4-carboxamide+TX (may be prepared from the methods described in WO 2020/109391), N-[2-[2,4-dichloro-phenoxy]phenyl]-3-(difluoromethyl)-1-methyl-pyrazole-4-carboxamide+TX, N-[2-[2-chloro-4-(trifluoromethyl)phenoxy]phenyl]-3-(difluoromethyl)-1-methyl-pyrazole-4-carboxamide+TX, benzothiostrobin+TX, phenamacril+TX, 5-amino-1,3,4-thiadiazole-2-thiol zinc salt (2:1)+TX, fluopyram+TX, flufenoxadiazam+TX, flutianil+TX, fluopimomide+TX, pyrapropoyne+TX, picarbutrazox+TX, 2-(difluoromethyl)-N-(3-ethyl-1,1-dimethyl-indan-4-yl)pyridine-3-carboxamide+TX, 2-(difluoromethyl)-N-((3R)-1,1,3-trimethylindan-4-yl) pyridine-3-carboxamide+TX, 4-[[6-[2-(2,4-difluoro-phenyl)-1,1-difluoro-2-hydroxy-3-(1,2,4-triazol-1-yl) propyl]-3-pyridyl]oxy]benzonitrile+TX, metyltetraprole+TX, 2-(difluoromethyl)-N-((3R)-1,1,3-trimethylindan-4-yl) pyridine-3-carboxamide+TX, α-(1, 1-dimethylethyl)-α-[4'-(trifluoromethoxy) [1,1'-biphenyl]-4-yl]-5-pyrimidinemethanol+TX, fluoxapiprolin+TX, enoxastrobin+TX, methyl (Z)-3-methoxy-2-[2-methyl-5-[4-(trifluoromethyl)triazol-2-yl]phenoxy]prop-2-enoate+TX, methyl (Z)-3-methoxy-2-[2-methyl-5-(4-propyltriazol-2-yl) phenoxy]prop-2-enoate+TX, methyl (Z)-2-[5-(3-isopropylpyrazol-1-yl)-2-methyl-phenoxy]-3-methoxy-prop-2-enoate+TX, methyl (Z)-3-methoxy-2-[2-methyl-5-(3-propylpyrazol-1-yl)phenoxy]prop-2-enoate+TX, methyl (Z)-3-methoxy-2-[2-methyl-5-[3-(trifluoromethyl)pyrazol-1-yl]phenoxy]prop-2-enoate+TX (these compounds may be prepared from the methods described in WO2020/079111), methyl (Z)-2-(5-cyclohexyl-2-methyl-phenoxy)-3-methoxy-prop-2-enoate+TX, methyl (Z)-2-(5-cyclopentyl-2-methyl-phenoxy)-3-methoxy-prop-2-enoate+TX (these compounds may be prepared from the methods described in WO2020/193387), 4-[[6-[2-(2,4-difluoro-phenyl)-1,1-difluoro-2-hydroxy-3-(1,2,4-triazol-1-yl) propyl]-3-pyridyl]oxy]benzonitrile+TX, 4-[[6-[2-(2,4-difluorophenyl)-1,1-difluoro-2-hydroxy-3-(5-sulfanyl-1,2,4-triazol-1-yl)propyl]-3-pyridyl]oxy]benzonitrile+TX, 4-[[6-[2-(2,4-difluorophenyl)-1,1-difluoro-2-hydroxy-3-(5-thioxo-4H-1,2,4-triazol-1-yl)propyl]-3-pyridyl]oxy]benzonitrile+TX, trinexapac+TX, coumoxystrobin+TX, zhongshengmycin+TX, thiodiazole copper+TX, zinc thiazole+TX, amectotractin+TX, iprodione+TX, seboctylamine+TX; N'-[5-bromo-2-methyl-6-[(1S)-1-methyl-2-propoxy-ethoxy]-3-pyridyl]-N-ethyl-N-methyl-formamidine+TX, N'-[5-bromo-2-methyl-6-[(1R)-1-methyl-2-propoxy-ethoxy]-3-pyridyl]-N-ethyl-N-methyl-formamidine+TX, N'-[5-bromo-2-methyl-6-(1-methyl-2-propoxy-ethoxy)-3-pyridyl]-N-ethyl-N-methyl-formamidine+TX, N'-[5-chloro-2-methyl-6-(1-methyl-2-propoxy-ethoxy)-3-pyridyl]-N-ethyl-N-methyl-formamidine+TX, N'-[5-bromo-2-methyl-6-(1-methyl-2-propoxy-ethoxy)-3-pyridyl]-N-isopropyl-N-methyl-formamidine+TX (these compounds may be prepared from the methods described in WO2015/155075); N'-[5-bromo-2-methyl-6-(2-propoxypropoxy)-3-pyridyl]-N-ethyl-N-methyl-formamidine+TX (this compound may be prepared from the methods described in IPCOM000249876D); N-isopropyl-N'-[5-methoxy-2-methyl-4-(2,2,2-trifluoro-1-hydroxy-1-phenyl-ethyl) phenyl]-N-methyl-formamidine+TX, N'-[4-(1-cyclopropyl-2,2,2-trifluoro-1-hydroxy-ethyl)-5-methoxy-2-methyl-phenyl]-N-isopropyl-N-methyl-formamidine+TX (these compounds may be prepared from the methods described in WO2018/228896); N-ethyl-N'-[5-methoxy-2-methyl-4-[(2-trifluoromethyl)oxetan-2-yl]phenyl]-N-methyl-formamidine+TX, N-ethyl-N'-[5-methoxy-2-methyl-4-[(2-trifluoromethyl) tetrahydrofuran-2-yl]phenyl]-N-methyl-formamidine+TX (these compounds may be prepared from the methods described in WO2019/110427); N-[(1R)-1-benzyl-3-chloro-1-methyl-but-3-enyl]-8-fluoro-quinoline-3-carboxamide+TX, N-[(1S)-1-benzyl-3-chloro-1-methyl-but-3-enyl]-8-fluoro-quinoline-3-carboxamide+TX, N-[(1R)-1-benzyl-3,3,3-trifluoro-1-methyl-propyl]-8-fluoro-quinoline-3-carboxamide+TX, N-[(1S)-1-benzyl-3,3,3-trifluoro-1-methyl-propyl]-8-fluoro-quinoline-3-carboxamide+TX, N-[(1R)-1-benzyl-1,3-dimethyl-butyl]-7,8-difluoro-quinoline-3-carboxamide+TX, N-[(1S)-1-benzyl-1,3-dimethyl-butyl]-7,8-difluoro-quinoline-3-carboxamide+TX, 8-fluoro-N-[(1R)-1-[(3-fluorophenyl)methyl]-1,3-dimethyl-butyl]quinoline-3-carboxamide+TX, 8-fluoro-N-[(1S)-1-[(3-fluorophenyl)methyl]-1,3-dimethyl-butyl]quinoline-3-carboxamide+TX, N-[(1R)-1-benzyl-1,3-dimethyl-butyl]-8-fluoro-quinoline-3-carboxamide+TX, N-[(1S)-1-benzyl-1,3-dimethyl-butyl]-8-fluoro-quinoline-3-carboxamide+TX, N-((1R)-1-benzyl-3-chloro-1-methyl-but-3-enyl)-8-fluoro-quinoline-3-carboxamide+TX, N-((1S)-1-benzyl-3-chloro-1-methyl-but-3-enyl)-8-fluoro-quinoline-3-carboxamide+TX (these compounds may be prepared from the methods described in WO2017/153380); 1-(6,7-dimethylpyrazolo[1,5-a]pyridin-3-yl)-4,4,5-trifluoro-3,3-dimethyl-isoquinoline+TX, 1-(6,7-dimethylpyrazolo[1,5-a]pyridin-3-yl)-4,4,6-trifluoro-3,3-dimethyl-isoquinoline+TX, 4,4-difluoro-3,3-dimethyl-1-(6-methylpyrazolo[1,5-a]pyridin-3-yl)isoquinoline+TX, 4,4-difluoro-3,3-dimethyl-1-(7-methylpyrazolo[1,5-a]pyridin-3-yl)isoquinoline+TX, 1-(6-chloro-7-methyl-pyrazolo[1,5-a]pyridin-3-yl)-4,4-difluoro-3,3-dimethyl-isoquinoline+TX (these compounds may be prepared from the methods described in WO2017/025510); 1-(4,5-dimethylbenzimidazol-1-yl)-4,4,5-trifluoro-3,3-dimethyl-isoquinoline+TX, 1-(4,5-dimethylbenzimidazol-1-yl)-4,4-difluoro-3,3-dimethyl-isoquinoline+TX, 6-chloro-4,4-difluoro-3,3-dimethyl-1-(4-methylbenzimidazol-1-yl)isoquinoline+TX, 4,4-difluoro-1-(5-fluoro-4-methyl-benzimidazol-1-yl)-3,3-dimethyl-isoquinoline+TX, 3-(4,4-difluoro-3,3-dimethyl-1-isoquinolyl)-7,8-dihydro-6H-cyclopenta[e]benzimidazole+TX (these compounds may be prepared from the methods described in WO2016/156085); N-methoxy-N-[[4-[5-(trifluoromethyl)-1,2,4-oxadiazol-3-yl]phenyl]methyl]cyclopropanecarboxamide+TX, N,2-dimethoxy-N-[[4-[5-(trifluoromethyl)-1,2,4-oxadiazol-3-yl]phenyl]methyl]propanamide+TX, N-ethyl-2-methyl-N-[[4-[5-(trifluoromethyl)-1,2,4-oxadiazol-3-yl]phenyl]methyl]propanamide+TX, 1-methoxy-3-methyl-1-[[4-[5-(trifluoromethyl)-1,2,4-oxadiazol-3-yl]phenyl]methyl]urea+TX, 1,3-dimethoxy-1-[[4-[5-(trifluoromethyl)-1,2,4-oxadiazol-3-yl]phenyl]methyl]urea+TX, 3-ethyl-1-methoxy-1-[[4-[5-(trifluoromethyl)-1,2,4-oxadiazol-3-yl]phenyl]methyl]urea+TX, N-[[4-[5-(trifluoromethyl)-1,2,4-oxadiazol-3-yl]phenyl]methyl]propanamide+TX, 4,4-dimethyl-2-[[4-[5-(trifluoromethyl)-1,2,4-oxadiazol-3-yl]phenyl]methyl]isoxazolidin-3-one+TX, 5,5-dimethyl-2-[[4-[5-(trifluoromethyl)-1,2,4-oxadiazol-3-yl]phenyl]methyl]isoxazolidin-3-one+TX, ethyl 1-[[4-[5-(trifluoromethyl)-1,2,4-oxadiazol-3-yl]phenyl]methyl]pyrazole-4-carboxylate+TX, N,N-dimethyl-1-[[4-[5-(trifluoromethyl)-1,2,4-oxadiazol-3-yl]phenyl]methyl]-1,2,4-triazol-3-amine+TX. The compounds in this paragraph may be prepared from the methods described in WO 2017/055473, WO 2017/055469, WO 2017/093348 and WO 2017/118689; 2-[6-(4-chlorophenoxy)-2-(trifluoromethyl)-3-pyridyl]-1-(1,2,4-triazol-1-yl)propan-2-ol+TX (this compound may be prepared from the methods described in WO 2017/029179); 2-[6-(4-bromophenoxy)-2-(trifluoromethyl)-3-pyridyl]-1-(1,2,4-triazol-1-yl)propan-2-ol+TX (this compound may be prepared from the methods described in WO 2017/029179); 3-[2-(1-chlorocyclopropyl)-3-(2-fluorophenyl)-2-hydroxy-propyl]imidazole-4-carbonitrile+TX (this compound may be prepared from the methods described in WO 2016/156290); 3-[2-(1-chlorocyclopropyl)-3-(3-chloro-2-fluoro-phenyl)-2-hydroxy-propyl]imidazole-4-carbonitrile+TX (this compound may be prepared from the methods described in WO 2016/156290); (4-phenoxyphenyl)methyl 2-amino-6-methyl-pyridine-3-carboxylate+TX (this compound may be prepared from the methods described in WO 2014/006945); 2,6-Dimethyl-1H,5H-[1,4]dithiino[2,3-c:5,6-c']dipyrrole-1,3,5,7(2H,6H)-tetrone+TX (this compound may be prepared from the methods described in WO 2011/138281); N-methyl-4-[5-(trifluoromethyl)-1,2,4-oxadiazol-3-yl]benzenecarbothioamide+TX; N-methyl-4-[5-(trifluoromethyl)-1,2,4-oxadiazol-3-yl]benzamide+TX; (Z,2E)-5-[1-(2,4-dichlorophenyl)pyrazol-3-yl]oxy-2-methoxyimino-N,3-dimethyl-pent-3-enamide+TX (this compound may be prepared from the methods described in WO 2018/153707); N'-(2-chloro-5-methyl-4-phenoxy-phenyl)-N-ethyl-N-methyl-formamidine+TX; N'-[2-chloro-4-(2-fluoro-phenoxy)-5-methyl-phenyl]-N-ethyl-N-methyl-formamidine+TX (this compound may be prepared from the methods described in WO 2016/202742); 2-(difluoromethyl)-N-[(3S)-3-ethyl-1,1-dimethyl-indan-4-yl]pyridine-3-carboxamide+TX (this compound may be prepared from the methods described in WO 2014/095675); (5-methyl-2-pyridyl)-[4-[5-(trifluoromethyl)-1,2,4-oxadiazol-3-yl]phenyl]methanone+TX, (3-methylisoxazol-5-yl)-[4-[5-(trifluoromethyl)-1,2,4-oxadiazol-3-yl]phenyl]methanone+TX (these compounds may be prepared from the methods described in WO 2017/220485); 2-oxo-N-propyl-2-[4-[5-(trifluoromethyl)-1,2,4-oxadiazol-3-yl]phenyl]acetamide+TX (this compound may be prepared from the methods described in WO 2018/065414); ethyl 1-[[5-[5-(trifluoromethyl)-1,2,4-oxadiazol-3-yl]-2-thienyl]methyl]pyrazole-4-carboxylate+TX (this compound may be prepared from the methods described in WO 2018/158365); 2,2-difluoro-N-methyl-2-[4-[5-(trifluoromethyl)-1,2,4-oxadiazol-3-yl]phenyl]acetamide+TX, N-[(E)-methoxyiminomethyl]-4-[5-(trifluoromethyl)-1,2,4-oxadiazol-3-yl]benzamide+TX, N-[(Z)-methoxyiminomethyl]-4-[5-(trifluoromethyl)-1,2,4-oxadiazol-3-yl]benzamide+TX, N-[N-methoxy-C-methyl-carbonimidoyl]-4-[5-(trifluoromethyl)-1,2,4-oxadiazol-3-yl]benzamide+TX (these compounds may be prepared from the methods described in WO 2018/202428);

microbials including: *Acinetobacter lwoffii*+TX, *Acremonium alternatum*+TX+TX, *Acremonium cephalosporium*+TX+TX, *Acremonium diospyri*+TX, *Acremonium obclavatum*+TX, *Adoxophyes orana* granulovirus (AdoxGV) (Capex®)+TX, *Agrobacterium radiobacter* strain K84 (Galltrol-A®)+TX, *Alternaria* alternate+TX, *Alternaria cassia*+TX, *Alternaria destruens* (Smolder®)+TX, *Ampelomyces quisqualis* ($AQ_{10}$®)+TX, *Aspergillus flavus* AF36 (AF36®)+TX, *Aspergillus flavus* NRRL 21882 (Aflaguard®)+TX, *Aspergillus* spp.+TX, *Aureobasidium pullulans*+TX, Azospirillum+TX, (MicroAZ®+TX, TAZO B®)+TX, *Azotobacter*+TX, *Azotobacter chroocuccum* (Azotomeal®)+TX, *Azotobacter* cysts (Bionatural Blooming Blossoms®)+TX, *Bacillus amyloliquefaciens*+TX, *Bacillus cereus*+TX, *Bacillus chitinosporus* strain CM-1+TX, *Bacillus chitinosporus* strain $AQ_{746}$+TX, *Bacillus licheniformis* strain HB-2 (Biostart™ Rhizoboost®)+TX, *Bacillus licheniformis* strain 3086 (EcoGuard®+TX, Green Releaf®)+TX, *Bacillus circulans*+TX, *Bacillus firmus* (BioSafe®+TX, BioNem-WP®+TX, VOTiVO®)+TX, *Bacillus firmus* strain 1-1582+TX, *Bacillus macerans*+TX, *Bacillus marismortui*+TX, *Bacillus megaterium*+TX, *Bacillus mycoides* strain $AQ_{726}$+TX, *Bacillus* papillae (Milky Spore Powder®)+TX, *Bacillus pumilus* spp.+TX, *Bacillus pumilus* strain GB34 (Yield Shield®)+TX, *Bacillus pumilus* strain $AQ_{717}$+TX, *Bacillus pumilus* strain QST 2808 (Sonata®+TX, Ballad Plus®)+TX, *Bacillus* spahericus (VectoLex®)+TX, *Bacillus* spp.+TX, *Bacillus* spp. strain $AQ_{175}$+TX, *Bacillus* spp. strain $AQ_{177}$+TX, *Bacillus* spp. strain $AQ_{178}$+TX, *Bacillus subtilis* strain QST 713 (CEASE®+TX, Serenade®+TX, Rhapsody®)+TX, *Bacillus subtilis* strain QST 714 (JAZZ®)+TX, *Bacillus subtilis* strain $AQ_{153}$+TX, *Bacillus subtilis* strain $AQ_{743}$+TX, *Bacillus subtilis* strain QST3002+TX, *Bacillus subtilis* strain QST3004+TX, *Bacillus subtilis* var. *amyloliquefaciens* strain FZB24 (Taegro®+TX, Rhizopro®)+TX, *Bacillus thuringiensis* Cry 2Ae+TX, *Bacillus thuringiensis* Cry1Ab+TX, *Bacillus thuringiensis aizawai* GC 91 (Agree®)+TX, *Bacillus thuringiensis israelensis* (BMP123®+TX, Aquabac®+TX, VectoBac®)+TX, *Bacillus thuringiensis kurstaki* (Javelin®+TX, Deliver®+TX, CryMax®+TX, Bonide®+TX, Scutella WP®+TX, Turilav WP®+TX, Astuto®+TX, Dipel WP®+TX, Biobit®+TX, Foray®)+TX, *Bacillus thuringiensis kurstaki* BMP 123 (Baritone®)+TX, *Bacillus thuringiensis kurstaki* HD-1 (Bioprotec-CAF/3P®)+TX, *Bacillus thuringiensis* strain BD #32+TX, *Bacillus thuringiensis* strain $AQ_{52}$+TX, *Bacillus thuringiensis* var. *aizawai* (XenTari®+TX, DiPel®)+TX, bacteria spp. (GROWMEND®+TX, GROWSWEET®+TX, Shootup®)+TX, bacteriophage of *Clavipacter michiganensis* (AgriPhage®)+TX, Bakflor®+TX, *Beauveria bassiana* (Beaugenic®+TX, Brocaril WP®)+TX, *Beauveria bassiana* GHA (Mycotrol ES®+TX, Mycotrol O®+TX, BotaniGuard®)+TX, *Beauveria brongniartii* (Engerlingspilz®+TX, Schweizer *Beauveria*®+TX, Melocont®)+TX, *Beauveria* spp.+TX, *Botrytis* cineria+TX, *Bradyrhizobium japonicum* (TerraMax®)+TX, *Brevibacillus brevis*+TX, *Bacillus thuringiensis tenebrionis* (Novodor®)+TX, BtBooster+TX, *Burkholderia cepacia* (Deny®+TX, Intercept®+TX, Blue Circle®)+TX, *Burkholderia* gladii+TX, *Burkholderia gladioli*+TX, *Burkholderia* spp.+TX, Canadian thistle fungus (CBH Canadian Bioherbicide®)+TX, *Candida* butyri+TX, *Candida famata*+TX, *Candida* fructus+TX, *Candida glabrata*+TX, *Candida guilliermondii*+TX, *Candida* melibiosica+TX, *Candida oleophila* strain O+TX, *Candida parapsilosis*+TX, *Candida pelliculosa*+TX, *Candida pulcherrima*+TX, *Candida reukaufii*+TX, *Candida saitoana* (Bio-Coat®+TX, Biocure®)+TX, *Candida sake*+TX, *Candida* spp.+TX, *Candida* tenius+TX, Cedecea dravisae+TX, Cellulomonas flavigena+TX, *Chaetomium* cochliodes (Nova-Cide®)+TX, *Chaetomium globosum* (Nova-Cide®)+TX, *Chromobacterium subtsugae* strain $PRAA_4$-1T (Grandevo®)+TX, *Cladosporium* cladosporioides+TX, *Cladosporium oxysporum*+TX, *Cladosporium* chlorocephalum+TX, *Cladosporium* spp.+TX, *Cladosporium* tenuissimum+TX, *Clonostachys rosea* (EndoFine®)+TX, *Colletotrichum acutatum*+TX, *Coniothyrium minitans* (Cotans WG®)+TX, *Coniothyrium* spp.+TX, *Cryptococcus albidus* (YIELDPLUS®)+TX, *Cryptococcus humicola*+TX, *Cryptococcus* infirmo-miniatus+TX, *Cryptococcus laurentii*+TX, *Cryptophlebia leucotreta* granulovirus (Cryptex®)+TX, *Cupriavidus campinensis*+TX, *Cydia pomonella* granulovirus (CYD-X®)+TX, *Cydia pomonella* granulovirus (Madex®+TX, Madex Plus®+TX, Madex Max/Carpovirusine®)+TX, Cylindrobasidium laeve (Stumpout®)+TX, Cylindrocladium+TX, *Debaryomyces hansenii*+TX, *Drechslera hawaiinensis*+TX, *Enterobacter cloacae*+TX, Enterobacteriaceae+TX, *Entomophtora virulenta* (Vektor®)+TX, *Epicoccum nigrum*+TX, *Epicoccum purpurascens*+TX, *Epicoccum* spp.+TX, *Filobasidium floriforme*+TX, *Fusarium acuminatum*+TX, *Fusarium chlamydosporum*+TX, *Fusarium oxysporum* (Fusaclean®/Biofox C®)+TX, *Fusarium proliferatum*+TX, *Fusarium* spp.+TX, *Galactomyces geotrichum*+TX, *Gliocladium catenulatum* (Primastop®+TX, Prestop®)+TX, *Gliocladium roseum*+TX, *Gliocladium* spp. (SoilGard®)+TX, *Gliocladium virens* (Soilgard®)+TX, Granulovirus (Granupom®)+TX, *Halobacillus halophilus*+TX, *Halobacillus litoralis*+TX, *Halobacillus trueperi*+TX, *Halomonas* spp.+TX, *Halomonas subglaciescola*+TX, *Halovibrio variabilis*+TX, *Hanseniaspora uvarum*+TX, *Helicoverpa armigera* nucleopolyhedrovirus (Helicovex®)+TX, *Helicoverpa zea* nuclear polyhedrosis virus (Gemstar®)+TX, Isoflavone-formononetin (Myconate®)+TX, *Kloeckera apiculata*+TX, *Kloeckera* spp.+TX, *Lagenidium giganteum* (Laginex®)+TX, *Lecanicillium longisporum* (Vertiblast®)+TX, *Lecanicillium muscarium* (Vertikil®)+TX, *Lymantria dispar* nucleopolyhedrosis virus (Disparvirus®)+TX, *Marinococcus halophilus*+TX, *Meira geulakonigii*+TX, *Metarhizium anisopliae* (Met52®)+TX, *Metarhizium anisopliae* (Destruxin WP®)+TX, *Metschnikowia fruticola* (Shemer®)+TX, *Metschnikowia pulcherrima*+TX, *Microdochium dimerum* (Antibot®)+TX, *Micromonospora coerulea*+TX, *Microsphaeropsis ochracea*+TX, *Muscodor albus* 620 (Muscudor®)+TX, *Muscodor roseus* strain A3-5+TX, *Mycorrhizae* spp. (AMykor®+TX, Root Maximizer®)+TX, *Myrothecium verrucaria* strain AARC-0255 (DiTera®)+TX, BROS PLUS®+TX, *Ophiostoma piliferum* strain D97 (Sylvanex®)+TX, *Paecilomyces farinosus*+TX, *Paecilomyces fumosoroseus* (PFR-97®+TX, PreFeRal®)+TX, *Paecilomyces linacinus* (Biostat WP®)+TX, *Paecilomyces lilacinus* strain 251 (MeloCon WG®)+TX, *Paenibacillus polymyxa*+TX, *Pantoea agglomerans* (BlightBan C9-1®)+TX, *Pantoea* spp.+TX, *Pasteuria* spp. (Econem®)+TX, *Pasteuria nishizawae*+TX, *Penicillium aurantiogriseum*+TX, *Penicillium billai* (Jumpstart®+TX, TagTeam®)+TX, *Penicillium brevicompactum*+TX, *Penicillium frequentans*+TX, *Penicillium griseofulvum*+TX, *Penicillium purpurogenum*+TX, *Penicillium* spp.+TX, *Penicillium viridicatum*+TX, *Phlebiopsis gigantean* (Rotstop®)+TX, phosphate solubilizing bacteria (Phosphomeal®)+TX, *Phytophthora cryptogea*+TX, *Phytophthora palmivora* (Devine®)+TX, *Pichia anomala*+TX, *Pichia guilermondii*+TX, *Pichia membranaefaciens*+TX, *Pichia onychis*+TX, *Pichia stipites*+TX, *Pseudomonas aeruginosa*+TX, *Pseudomonas aureofasciens* (Spot-Less Biofungicide®)+TX, *Pseudomonas cepacia*+TX, *Pseudomonas chlororaphis* (AtEze®)+TX, *Pseudomonas* corrugate+TX, *Pseudomonas fluorescens* strain A506 (BlightBan A506®)+TX, *Pseudomonas putida*+TX, *Pseudomonas* reactans+TX, *Pseudomonas* spp.+TX, *Pseudomonas syringae* (Bio-Save®)+TX, *Pseudomonas viridiflava*+TX, *Pseudomons fluorescens* (Zequanox®)+TX, *Pseudozyma flocculosa* strain PF-A22 UL (Sporodex L®)+TX, *Puccinia canaliculata*+TX, *Puccinia thlaspeos* (Wood Warrior®)+TX, *Pythium paroecandrum*+TX, *Pythium oligandrum* (Polygandron®+TX, Polyversum®)+TX, *Pythium periplocum*+TX, *Rhanella aquatilis*+TX, *Rhanella* spp.+TX, *Rhizobia* (Dormal®+TX, Vault®)+TX, *Rhizoctonia*+TX, *Rhodococcus globerulus* strain $AQ_{719}$+TX, *Rhodosporidium diobovatum*+TX, *Rhodosporidium toruloides*+TX, *Rhodotorula* spp.+TX, *Rhodotorula glutinis*+TX, *Rhodotorula graminis*+TX, *Rhodotorula mucilagnosa*+TX, *Rhodotorula rubra*+TX, *Saccharomyces cerevisiae*+TX, *Salinococcus roseus*+TX, *Sclerotinia minor*+TX, *Sclerotinia minor* (SARRITOR®)+TX, *Scytalidium* spp.+TX, *Scytalidium uredinicola*+TX, *Spodoptera exigua* nuclear polyhedrosis virus (Spod-X®+TX, Spexit®)+TX, *Serratia marcescens*+TX, *Serratia plymuthica*+TX, *Serratia* spp.+TX, *Sordaria fimicola*+TX, *Spodoptera littoralis* nucleopolyhedrovirus (Littovir®)+TX, *Sporobolomyces roseus*+TX, *Stenotrophomonas maltophilia*+TX, *Streptomyces ahygroscopicus*+TX, *Streptomyces albaduncus*+TX, *Streptomyces* exfoliates+TX, *Streptomyces galbus*+TX, *Streptomyces griseoplanus*+TX, *Streptomyces griseoviridis* (Mycostop®)+TX, *Streptomyces lydicus* (Actinovate®)+TX, *Streptomyces lydicus* WYEC-108 (ActinoGrow®)+TX, *Streptomyces violaceus*+TX, *Tilletiopsis minor*+TX, *Tilletiopsis* spp.+TX, *Trichoderma asperellum* (T34 Biocontrol®)+TX, *Trichoderma gamsii* (Tenet®)+TX, *Trichoderma atroviride* (Plantmate®)+TX, *Trichoderma hamatum* TH 382+TX, *Trichoderma harzianum* rifai (Mycostar®)+TX, *Trichoderma harzianum* T-22 (Trianum-P®+TX, PlantShield HCO+TX, RootShield®+TX, Trianum-G®)+TX, *Trichoderma harzianum* T-39 (Trichodex®)+TX, *Trichoderma inhamatum*+TX, *Trichoderma koningii*+TX, *Trichoderma* spp. LC 52 (Sentinel®)+TX, *Trichoderma lignorum*+TX, *Trichoderma longibrachiatum*+TX, *Trichoderma polysporum* (Binab T®)+TX, *Trichoderma taxi*+TX, *Trichoderma virens*+TX, *Trichoderma virens* (formerly *Gliocladium virens* GL-21) (SoilGuard®)+TX, *Trichoderma viride*+TX, *Trichoderma viride* strain ICC 080 (Remedier®)+TX, *Trichosporon pullulans*+TX, *Trichosporon* spp.+TX, *Trichothecium* spp.+TX, *Trichothecium roseum*+TX, *Typhula phacorrhiza* strain 94670+TX, *Typhula phacorrhiza* strain 94671+TX, *Ulocladium atrum*+TX, *Ulocladium oudemansii* (Botry-Zen®)+TX, *Ustilago maydis*+TX, various bacteria and supplementary micronutrients (Natural II®)+TX, various fungi (Millennium Microbes®)+TX, *Verticillium chlamydosporium*+TX, *Verticillium lecanii* (Mycotal®+TX, Vertalec®)+TX, Vip3Aa20 (VIPtera®)+TX, *Virgibaclillus marismortui*+TX, *Xanthomonas campestris* pv. *Poae* (Camperico®)+TX, *Xenorhabdus bovienii*+TX, *Xenorhabdus nematophilus;*

Plant extracts including: pine oil (Retenol®)+TX, azadirachtin (Plasma Neem Oil®+TX, AzaGuard®+TX, MeemAzal®+TX, Molt-X®+TX, Botanical IGR (Neemazad®+TX, Neemix®)+TX, canola oil (Lilly Miller Vegol®)+TX, *Chenopodium ambrosioides* near *ambrosioides* (Requiem®)+TX, *Chrysanthemum* extract (Crisant®)+TX, extract of neem oil (Trilogy®)+TX, essentials oils of Labiatae (Botania®)+TX, extracts of clove rosemary peppermint and thyme oil (Garden insect Killer®)+TX, Glycinebetaine (Greenstim®)+TX, garlic+TX, lemongrass oil (GreenMatch®)+TX, neem oil+TX, *Nepeta cataria* (Catnip oil)+TX, *Nepeta catarina*+TX, nicotine+TX, oregano oil (MossBuster®)+TX, Pedaliaceae oil (Nematon®)+TX, *pyrethrum*+TX, *Quillaja saponaria* (NemaQ®)+TX, *Reynoutria sachalinensis* (Regalia®+TX, Sakalia®)+TX, rotenone (Eco Roten®)+TX, Rutaceae plant extract (Soleo®)+TX, soybean oil (Ortho Ecosense®)+TX, tea tree oil (Timorex Gold®)+TX, thymus oil+TX, AGNIQUE® MMF+TX, BugOil®+TX, mixture of rosemary sesame pepermint thyme and cinnamon extracts (EF 300®)+TX, mixture of clove rosemary and peppermint extract (EF 400®)+TX, mixture of clove pepermint garlic oil and mint (Soil Shot®)+TX, kaolin (Screen®)+TX, storage glucam of brown algae (Laminarin®);

pheromones including: blackheaded fireworm pheromone (3M Sprayable Blackheaded Fireworm Pheromone®)+TX, Codling Moth Pheromone (Paramount dispenser-(CM)/Isomate C-Plus®)+TX, Grape Berry Moth Pheromone (3M MEC-GBM Sprayable Pheromone®)+TX, Leafroller pheromone (3M MEC-LR Sprayable Pheromone®)+TX, Muscamone (Snip7 Fly Bait®+TX, Starbar Premium Fly Bait®)+TX, Oriental Fruit Moth Pheromone (3M oriental fruit moth sprayable Pheromone®)+TX, Peachtree Borer Pheromone (Isomate-P®)+TX, Tomato Pinworm Pheromone (3M Sprayable Pheromone®)+TX, Entostat powder (extract from palm tree) (Exosex CM®)+TX, (E+TX,Z+TX,Z)-3+TX, 8+TX, 11 Tetradecatrienyl acetate+TX, (Z+TX,Z+TX,E)-7+TX, 11+TX, 13-Hexadecatrienal+TX, (E+TX,Z)-7+TX, 9-Dodecadien-1-yl acetate+TX, 2-Methyl-1-butanol+TX, Calcium acetate+TX, Scenturion®+TX, Biolure®+TX, Check-Mate®+TX, Lavandulyl senecioate;

Macrobials including: *Aphelinus abdominalis*+TX, *Aphidius ervi* (*Aphelinus*-System®)+TX, *Acerophagus papaya*+TX, *Adalia bipunctata* (*Adalia*-System®)+TX, *Adalia bipunctata* (Adaline®)+TX, *Adalia bipunctata* (Aphidalia®)+TX, *Ageniaspis citricola*+TX, *Ageniaspis fuscicollis*+TX, *Amblyseius andersoni* (Anderline®+TX, Andersoni-System®)+TX, *Amblyseius californicus* (Amblyline®+TX, Spical®)+TX, *Amblyseius cucumeris* (Thripex®+TX, Bugline *Cucumeris*®)+TX, *Amblyseius fallacis* (Fallacis®)+TX, *Amblyseius swirskii* (Bugline *Swirskii*®+TX, *Swirskii*-Mite®)+TX, *Amblyseius womersleyi* (WomerMite®)+TX, *Amitus hesperidum*+TX, *Anagrus atomus*+TX, *Anagyrus fusciventris*+TX, *Anagyrus kamali*+TX, *Anagyrus loecki*+TX, *Anagyrus pseudococci* (Citripar®)+TX, *Anicetus benefices*+TX, *Anisopteromalus calandrae*+TX, *Anthocoris nemoralis* (*Anthocoris*-System®)+TX, *Aphelinus abdominalis* (Apheline®+TX, Aphiline®)+TX, *Aphelinus asychis*+TX, *Aphidius colemani* (Aphipar®)+TX, *Aphidius ervi* (Ervipar®)+TX, *Aphidius gifuensis*+TX, *Aphidius matricariae* (Aphipar-M®)+TX, *Aphidoletes aphidimyza* (Aphidend®)+TX, *Aphidoletes aphidimyza* (Aphidoline®)+TX, *Aphytis lingnanensis*+TX, *Aphytis melinus*+TX, *Aprostocetus hagenowii*+TX, *Atheta coriaria* (Staphyline®)+TX, *Bombus* spp.+TX, *Bombus terrestris* (Natupol Beehive®)+TX, *Bombus terrestris* (Beeline®+TX, Tripol®)+TX, *Cephalonomia stephanoderis*+TX, *Chilocorus nigritus*+TX, *Chrysoperla carnea* (Chrysoline®)+TX, *Chrysoperla carnea* (Chrysopa®)+TX, *Chrysoperla rufilabris*+TX, *Cirrospilus ingenuus*+TX, *Cirrospilus quadristriatus*+TX, *Citrostichus phyllocnistoides*+TX, *Closterocerus chamaeleon*+TX, *Closterocerus* spp.+TX, *Coccidoxenoides perminutus* (Planopar®)+TX, *Coccophagus cowperi*+TX, *Coccophagus lycimnia*+TX, *Cotesia flavipes*+TX, *Cotesia plutellae*+TX, *Cryptolaemus montrouzieri* (Cryptobug®+TX, Cryptoline®)+TX, *Cybocephalus nipponicus*+TX, *Dacnusa sibirica*+TX, *Dacnusa sibirica* (Minusa®)+TX, *Diglyphus isaea* (Diminex®)+TX, *Delphastus catalinae* (*Delphastus*®)+TX, *Delphastus pusillus*+TX, *Diachasmimorpha krausii*+TX, *Diachasmimorpha longicaudata*+TX, *Diaparsis jucunda*+TX, *Diaphorencyrtus aligarhensis*+TX, *Diglyphus isaea*+TX, *Diglyphus isaea* (Miglyphus®+TX, Digline®)+TX, *Dacnusa sibirica* (DacDigline®+TX, Minex®)+TX, *Diversinervus* spp.+TX, *Encarsia citrina*+TX, *Encarsia formosa* (*Encarsia* Max®+TX, Encarline®+TX, En-Strip®)+TX, *Eretmocerus eremicus* (Enermix®)+TX, *Encarsia guadeloupae*+TX, *Encarsia haitiensis*+TX, *Episyrphus balteatus* (Syrphidend®)+TX, *Eretmoceris siphonini*+TX, *Eretmocerus californicus*+TX, *Eretmocerus eremicus* (Ercal®+TX, Eretline E®)+TX, *Eretmocerus eremicus* (Bemimix®)+TX, *Eretmocerus hayati*+TX, *Eretmocerus mundus* (Bemipar®+TX, Eretline M®)+TX, *Eretmocerus siphonini*+TX, Exochomus quadripustulatus+TX, *Feltiella acarisuga* (Spidend®)+TX, *Feltiella acarisuga* (Feltiline®)+TX, *Fopius arisanus*+TX, *Fopius ceratitivorus*+TX, Formononetin (Wirless Beehome®)+TX, *Franklinothrips vespiformis* (Vespop®)+TX, *Galendromus occidentalis*+TX, *Goniozus legneri*+TX, *Habrobracon hebetor*+TX, *Harmonia axyridis* (HarmoBeetle®)+TX, *Heterorhabditis* spp. (Lawn Patrol®)+TX, *Heterorhabditis bacteriophora* (NemaShield HB®+TX, Nemaseek®+TX, Terranem-Nam®+TX, Terranem®+TX, Larvanem®+TX, B-Green®+TX, NemAttack®+TX, Nematop®)+TX, *Heterorhabditis megidis* (Nemasys H®+TX, BioNem H®+TX, Exhibitline Hm®+TX, Larvanem-M®)+TX, *Hippodamia convergens*+TX, *Hypoaspis aculeifer* (Aculeifer-System®+TX, Entomite-A®)+TX, *Hypoaspis miles* (Hypoline M®+TX, Entomite-M®)+TX, *Lbalia leucospoides*+TX, *Lecanoideus floccissimus*+TX, *Lemophagus errabundus*+TX, *Leptomastidea abnormis*+TX, *Leptomastix dactylopii* (Leptopar®)+TX, *Leptomastix epona*+TX, *Lindorus lophanthae*+TX, *Lipolexis oregmae*+TX, *Lucilia caesar* (Natufly®)+TX, *Lysiphlebus testaceipes*+TX, *Macrolophus caliginosus* (Mirical-N®+TX, Macroline C®+TX, Mirical®)+TX, *Mesoseiulus longipes*+TX, *Metaphycus flavus*+TX, *Metaphycus lounsburyi*+TX, *Micromus angulatus* (Milacewing®)+TX, *Microterys flavus*+TX, *Muscidifurax raptorellus* and *Spalangia cameroni* (Biopar®)+TX, *Neodryinus typhlocybae*+TX, *Neoseiulus californicus*+TX, *Neoseiulus cucumeris* (THRYPEX®)+TX, *Neoseiulus fallacis*+TX, *Nesideocoris tenuis* (NesidioBug®+TX, Nesibug®)+TX, *Ophyra aenescens* (Biofly®)+TX, *Orius insidiosus* (Thripor-I®+TX, Oriline I®)+TX, *Orius laevigatus* (Thripor-L®+TX, Oriline I®)+TX, *Orius majusculus* (Oriline M®)+TX, *Orius strigicollis* (Thripor-S®)+TX, *Pauesia juniperorum*+TX, *Pediobius foveolatus*+TX, *Phasmarhabditis hermaphrodita* (Nemaslug®)+TX, *Phymastichus coffea*+TX, *Phytoseiulus macropilus*+TX, *Phytoseiulus persimilis* (Spidex®+TX, Phytoline P®)+TX, *Podisus maculiventris* (*Podisus*®)+TX, *Pseudacteon curvatus*+TX, *Pseudacteon obtusus*+TX, *Pseudacteon tricuspis*+TX, *Pseudaphycus maculipennis*+TX, *Pseudleptomastix mexicana*+TX, *Psyllaephagus pilosus*+TX, *Psyttalia concolor* (complex)+TX, *Quadrastichus* spp.+TX, *Rhyzobius lophanthae*+TX, *Rodolia cardinalis*+TX, *Rumina decollate*+TX, *Semielacher petiolatus*+TX, *Sitobion avenae* (Ervibank®)+TX, *Steinernema carpocapsae* (Nematac C®+TX, Millenium®+TX, BioNem C®+TX, NemAttack®+TX, Nemastar®+TX, Capsanem®)+TX, *Steinernema feltiae* (NemaShield®+TX, Nemasys F®+TX, BioNem F®+TX, *Steinernema*-System®+TX, NemAttack®+TX, Nemaplus®+TX, Exhibitline Sf®+TX, Scia-rid®+TX, Entonem®)+TX, *Steinernema kraussei* (Nemasys L®+TX, BioNem L®+TX, Exhibitline Srb®)+TX, *Steinernema riobrave* (BioVector®+TX, BioVektor®)+TX, *Steinernema scapterisci* (Nematac S®)+TX, *Steinernema* spp.+TX, *Steinernematid* spp. (Guardian Nematodes®)+TX, *Stethorus punctillum* (*Stethorus*®)+TX, *Tamarixia radiate*+TX, *Tetrastichus setifer*+TX, *Thripobius semiluteus*+TX, *Torymus sinensis*+TX, *Trichogramma brassicae* (Tricholine B®)+TX, *Trichogramma brassicae* (Tricho-Strip®)+TX, *Trichogramma evanescens*+TX, *Trichogramma minutum*+TX, *Trichogramma ostriniae*+TX, *Trichogramma platneri*+TX, *Trichogramma pretiosum*+TX, *Xanthopimpla stemmator;* other biologicals including: abscisic acid+TX, bioSea®+TX, *Chondrostereum purpureum* (Chontrol Paste®)+TX, *Colletotrichum gloeosporioides* (Collego®)+TX, Copper Octanoate (Cueva®)+TX, Delta traps (Trapline D®)+TX, *Erwinia amylovora* (Harpin) (ProAct®+TX, Ni-HIBIT Gold CST®)+TX, fatty acids derived from a natural by-product of extra virgin olive oil (FLIPPER®)+TX, Ferri-phosphate (Ferramol®)+TX, Funnel traps (Trapline Y®)+TX, Gallex®+TX, Grower's Secret®+TX, Homo-brassonolide+TX, Iron Phosphate (Lilly Miller Worry Free Ferramol Slug & Snail Bait®)+TX, MCP hail trap (Trapline F®)+TX, *Microctonus hyperodae*+TX, *Mycoleptodiscus terrestris* (Des-X®)+TX, BioGain®+TX, Aminomite®+TX, Zenox®+TX, Pheromone trap (Thripline Ams®)+TX, potassium bicarbonate (MilStop®)+TX, potassium salts of fatty acids (Sanova®)+TX, potassium silicate solution (Sil-Matrix®)+TX, potassium iodide+potassiumthiocyanate (Enzicur®)+TX, SuffOil-X®+TX, Spider venom+TX, *Nosema locustae* (Semaspore Organic Grasshopper Control®)+TX, Sticky traps (Trapline YF®+TX, Rebell Amarillo®)+TX and Traps (Takitrapline y+B®)+TX;

(1) antibacterial agents selected from the group of:

(1.1) bacteria, examples of which are *Bacillus mojavensis* strain R3B (Accession No. NCAIM (P) B001389) (WO 2013/034938) from Certis USA LLC, a subsidiary of Mitsui & Co.+TX; *Bacillus pumilus*, in particular strain BU F-33, having NRRL Accession No. 50185 (available as part of the CARTISSA® product from BASF, EPA Reg. No. 71840-19)+TX; *Bacillus subtilis*, in particular strain QST713/$AQ_{713}$ (available as SERENADE OPTI or SERENADE ASO from Bayer CropScience LP, US, having NRRL Accession No. B21661, U.S. Pat. No. 6,060,051)+TX; *Bacillus subtilis* strain BU1814, (available as VELONDIS® PLUS, VELONDIS® FLEX and VELONDIS® EXTRA from BASF SE)+TX; *Bacillus subtilis* var. *amyloliquefaciens* strain FZB24 having Accession No. DSM 10271 (available from Novozymes as TAEGRO® or TAEGRO® ECO (EPA Registration No. 70127-5))+TX; *Bacillus subtilis* CX-9060 from Certis USA LLC, a subsidiary of Mitsui & Co.+TX; *Bacillus* sp., in particular strain D747 (available as DOUBLE NICKEL® from Kumiai Chemical Industry Co., Ltd.), having Accession No. FERM BP-8234, U.S. Pat. No. 7,094,592+TX; *Paenibacillus* sp. strain having Accession No. NRRL B-50972 or Accession No. NRRL B-67129, WO 2016/154297+TX; *Paenibacillus polymyxa*, in particular strain AC-1 (e.g. TOPSEED® from Green Biotech Company Ltd.)+TX; *Pantoea agglomerans*, in particular strain E325 (Accession No. NRRL B-21856) (available as BLOOMTIME BIOLOGICAL™ FD BIOPESTICIDE from Northwest Agri Products)+TX; *Pseudomonas* proradix (e.g. PRORADIX® from Sourcon Padena)+TX; and (1.2) fungi, examples of which are *Aureobasidium pullulans*, in particular blastospores of strain DSM14940, blastospores of strain DSM 14941 or mixtures of blastospores of strains DSM14940 and DSM14941 (e.g., BOTECTOR® and BLOSSOM PROTECT® from bio-ferm, CH)+TX; *Pseudozyma aphidis* (as disclosed in WO2011/151819 by Yissum Research Development Company of the Hebrew University of Jerusalem)+TX; *Saccharomyces cerevisiae*, in particular strains CNCM No. 1-3936, CNCM No. 1-3937, CNCM No. 1-3938 or CNCM No. 1-3939 (WO 2010/086790) from Lesaffre et Compagnie, FR;

(2) biological fungicides selected from the group of:

(2.1) bacteria, examples of which are *Agrobacterium radiobacter* strain K84 (e.g. GALLTROL-A® from AgBioChem, CA)+TX; *Agrobacterium radiobacter* strain K1026 (e.g. NOGALL™ from BASF SE)+TX; *Bacillus subtilis* var. *amyloliquefaciens* strain FZB24 having Accession No. DSM 10271 (available from Novozymes as TAEGRO® or TAEGRO® ECO (EPA Registration No. 70127-5))+TX; *Bacillus amyloliquefaciens*, in particular strain D747 (available as Double Nickel™ from Kumiai Chemical Industry Co., Ltd., having accession number FERM BP-8234, U.S. Pat. No. 7,094,592)+TX; *Bacillus amyloliquefaciens* strain F727 (also known as strain MB1110) (NRRL Accession No. B-50768, WO 2014/028521) (STARGUS® from Marrone Bio Innovations)+TX; *Bacillus amyloliquefaciens* strain FZB42, Accession No. DSM 23117 (available as RHIZOVITAL® from ABiTEP, DE)+TX; *Bacillus amyloliquefaciens* isolate B246 (e.g. AVOGREEN™ from University of Pretoria)+TX; *Bacillus licheniformis*, in particular strain SB3086, having Accession No. ATCC 55406, WO 2003/000051 (available as ECOGUARD® Biofungicide and GREEN RELEAF™ from Novozymes)+TX+TX; *Bacillus licheniformis* $FMCH_{001}$ and *Bacillus subtilis* $FMCH_{002}$ (QUARTZO® (WG) and PRESENCE® (WP) from FMC Corporation)+TX; *Bacillus methylotrophicus* strain BAC-9912 (from Chinese Academy of Sciences' Institute of Applied Ecology)+TX; *Bacillus mojavensis* strain R3B (Accession No. NCAIM (P) B001389) (WO 2013/034938) from Certis USA LLC, a subsidiary of Mitsui & Co.+TX; *Bacillus mycoides*, isolate, having Accession No. B-30890 (available as BMJ TGAI® or WG and LifeGard™ from Certis USA LLC, a subsidiary of Mitsui & Co.)+TX; *Bacillus pumilus*, in particular strain QST2808 (available as SONATA® from Bayer CropScience LP, US, having Accession No. NRRL B-30087 and described in U.S. Pat. No. 6,245,551)+TX; *Bacillus pumilus*, in particular strain GB34 (available as Yield Shield® from Bayer AG, DE)+TX; *Bacillus pumilus*, in particular strain BU F-33, having NRRL Accession No. 50185 (available as part of the CARTISSA product from BASF, EPA Reg. No. 71840-19)+TX; *Bacillus subtilis*, in particular strain QST713/$AQ_{713}$ (available as SERENADE OPTI or SERENADE ASO from Bayer CropScience LP, US, having NRRL Accession No. B21661 and described in U.S. Pat. No. 6,060,051)+TX; *Bacillus subtilis* Y1336 (available as BIOBAC® WP from Bion-Tech, Taiwan, registered as a biological fungicide in Taiwan under Registration Nos. 4764, 5454, 5096 and 5277)+TX; *Bacillus subtilis* strain MBI 600 (available as SUBTILEX from BASF SE), having Accession Number NRRL B-50595, U.S. Pat. No. 5,061,495+TX; *Bacillus subtilis* strain GB03 (available as Kodiak® from Bayer AG, DE)+TX; *Bacillus subtilis* strain BU1814, (available as VELONDIS® PLUS, VELONDIS® FLEX and VELONDIS® EXTRA from BASF SE)+TX; *Bacillus subtilis* CX-9060 from Certis USA LLC, a subsidiary of Mitsui & Co.+TX; *Bacillus subtilis* KTSB strain (FOLIACTIVE® from Donaghys)+TX; *Bacillus subtilis* IAB/BS03 (AVIV™ from STK Bio-Ag Technologies, PORTENTO® from Idai Nature)+TX; *Bacillus subtilis* strain Y1336 (available as BIOBAC® WP from Bion-Tech, Taiwan, registered as a biological fungicide in Taiwan under Registration Nos. 4764, 5454, 5096 and 5277)+TX; *Paenibacillus* epiphyticus (WO 2016/020371) from BASF SE+TX; *Paenibacillus polymyxa* ssp. *plantarum* (WO 2016/020371) from BASF SE+TX; *Paenibacillus* sp. strain having Accession No. NRRL B-50972 or Accession No. NRRL B-67129, WO 2016/154297+TX; *Pseudomonas chlororaphis* strain AFS009, having Accession No. NRRL B-50897, WO 2017/019448 (e.g., HOWLER™ and ZIO® from AgBiome Innovations, US)+TX; *Pseudomonas chlororaphis*, in particular strain $MA_{342}$ (e.g. CEDOMON®, CERALL®, and CEDRESS® by Bioagri and Koppert)+TX; *Pseudomonas fluorescens* strain A506 (e.g. BLIGHTBAN® A506 by NuFarm)+TX; *Pseudomonas* proradix (e.g. PRORADIX® from Sourcon Padena)+TX; *Streptomyces griseoviridis* strain K61 (also known as *Streptomyces galbus* strain K61) (Accession No. DSM 7206) (MYCOSTOP® from Verdera, PREFENCE® from BioWorks, cf. Crop Protection 2006, 25, 468-475)+TX; *Streptomyces lydicus* strain $WYEC_{108}$ (also known as *Streptomyces lydicus* strain WYCD108US) (ACTINO-IRON® and ACTINOVATE® from Novozymes)+TX; and (2.2) fungi, examples of which are *Ampelomyces quisqualis*, in particular strain AQ 10 (e.g. AQ 10® by IntrachemBio Italia)+TX; *Ampelomyces quisqualis* strain $AQ_{10}$, having Accession No. CNCM 1-807 (e.g., AQ 10® by IntrachemBio Italia)+TX; *Aspergillus flavus* strain NRRL 21882 (products known as AFLA-GUARD® from Syngenta/ChemChina)+TX; *Aureobasidium pullulans*, in particular blastospores of strain DSM14940+TX; *Aureobasidium pullulans*, in particular blastospores of strain DSM 14941+TX; *Aureobasidium pullulans*, in particular mixtures of blastospores of strains DSM14940 and DSM 14941 (e.g. Botector® by bio-ferm, CH)+TX; *Chaetomium cupreum* (Accession No. CABI 353812) (e.g. BIOKUPRUM™ by AgriLife)+TX; *Chaetomium globosum* (available as RIVADIOM® by Rivale)+TX; *Cladosporium cladosporioides*, strain H39, having Accession No. CBS122244, US 2010/0291039 (by Stichting Dienst Landbouwkundig Onderzoek)+TX; *Coniothyrium minitans*, in particular strain CON/M/91-8 (Accession No. DSM9660, e.g. Contans® from Bayer CropScience Biologics GmbH)+TX; *Cryptococcus flavescens*, strain 3C (NRRL Y-50378), (B2.2.99)+TX; Dactylaria *candida*+TX; Dilophosphora alopecuri (available as TWIST FUNGUS®)+TX; *Fusarium oxysporum*, strain Fo47 (available as FUSACLEAN® by Natural Plant Protection)+TX; *Gliocladium catenulatum* (Synonym: *Clonostachys rosea* f. *catenulate*) strain J1446 (e.g. Prestop® by Lallemand)+TX; *Gliocladium roseum* (also known as *Clonostachys rosea* f *rosea*), in particular strain 321U from Adjuvants Plus, strain ACM941 as disclosed in Xue (Efficacy of *Clonostachys rosea* strain ACM941 and fungicide seed treatments for controlling the root tot complex of field pea, Can Jour Plant Sci 83(3): 519-524), or strain IK726 (Jensen D F, et al. Development of a biocontrol agent for plant disease control with special emphasis on the near commercial fungal antagonist *Clonostachys rosea* strain 'IK726', Australas Plant Pathol. 2007,36: 95-101)+TX; *Lecanicillium lecanii* (formerly known as *Verticillium lecanii*) conidia of strain KV01 (e.g. Vertalec® by Koppert/Arysta)+TX; *Metschnikowia fructicola*, in particular strain NRRL Y-30752, (B2.2.3)+TX; *Microsphaeropsis ochracea*+TX; *Muscodor roseus*, in particular strain A3-5 (Accession No. NRRL 30548)+TX; *Penicillium steckii* (DSM 27859, WO 2015/067800) from BASF SE+TX; *Penicillium vermiculatum*+TX; *Phlebiopsis gigantea* strain VRA 1992 (ROTSTOP® C from Danstar Ferment)+TX; *Pichia anomala*, strain WRL-076 (NRRL Y-30842), U.S. Pat. No. 7,579,183+TX; *Pseudozyma flocculosa*, strain PF-A22 UL (available as SPORODEX® L by Plant Products Co., CA)+TX; *Saccharomyces cerevisiae*, in particular strain LASO2 (from Agro-Levures et Derives), strain LAS117 cell walls (CEREVISANE® from Lesaffre, ROMEO® from BASF SE), strains CNCM No. 1-3936, CNCM No. 1-3937, CNCM No. 1-3938, CNCM No. 1-3939 (WO 2010/086790) from Lesaffre et Compagnie, FR+TX; Simplicillium lanosoniveum+TX; *Talaromyces flavus*, strain V117b+TX; *Trichoderma asperelloides* JM41R (Accession No. NRRL B-50759) (TRICHO PLUS® from BASF SE)+TX; *Trichoderma asperellum*, in particular, strain kd (e.g. T-Gro from Andermatt Biocontrol)+TX; *Trichoderma asperellum*, in particular strain SKT-1, having Accession No. FERM P-16510 (e.g. ECO-HOPE® from Kumiai Chemical Industry), strain T34 (e.g. T34 Biocontrol by Biocontrol Technologies S.L., ES) or strain ICC 012 from Isagro+TX; *Trichoderma atroviride*, in particular strain $SC_1$ (having Accession No. CBS 122089, WO 2009/116106 and U.S. Pat. No. 8,431,120 (from Bi-PA)), strain 77B (T77 from Andermatt Biocontrol) or strain LU132 (e.g. Sentinel from Agrimm Technologies Limited)+TX; *Trichoderma atroviride*, strain CNCM 1-1237 (e.g. Esquive® WP from Agrauxine, FR)+TX; *Trichoderma atroviride*, strain no. V08/002387+TX; *Trichoderma atroviride*, strain NMI no. V08/002388+TX; *Trichoderma atroviride*, strain NMI no. V08/002389+TX; *Trichoderma atroviride*, strain NMI no. V08/002390+TX; *Trichoderma atroviride*, strain $LC_{52}$ (e.g. Tenet by Agrimm Technologies Limited)+TX; *Trichoderma atroviride*, strain ATCC 20476 (IMI 206040)+TX; *Trichoderma atroviride*, strain T11 (IM1352941/CECT20498)+TX; *Trichoderma atroviride*, strain SKT-1 (FERM P-16510), JP Patent Publication (Kokai) 11-253151 A+TX; *Trichoderma atroviride*, strain SKT-2 (FERM P-16511), JP Patent Publication (Kokai) 11-253151 A+TX; *Trichoderma atroviride*, strain SKT-3 (FERM P-17021), JP Patent Publication (Kokai) 11-253151 A+TX; *Trichoderma* fertile (e.g. product TrichoPlus from BASF)+TX; *Trichoderma gamsii* (formerly *T. viride*), strain ICCO80 (IMI CC 392151 CABI, e.g. BioDerma by AGROBIOSOL DE MEXICO, S.A. DE C.V.)+TX; *Trichoderma gamsii* (formerly *T. viride*), strain ICC 080 (IMI CC 392151 CABI) (available as BIODERMA® by AGROBIOSOL DE MEXICO, S.A. DE C.V.)+TX; *Trichoderma harmatum*+TX; *Trichoderma harmatum*, having Accession No. ATCC 28012+TX; *Trichoderma harzianum* strain T-22 (e.g. Trianum-P from Andermatt Biocontrol or Koppert) or strain Cepa SimbT5 (from Simbiose Agro)+TX; *Trichoderma harzianum*+TX; *Trichoderma harzianum* rifai T39 (e.g. Trichodex® from Makhteshim, US)+TX; *Trichoderma harzianum*, strain ITEM 908 (e.g. Trianum-P from Koppert)+TX; *Trichoderma harzianum*, strain TH35 (e.g. Root-Pro by Mycontrol)+TX; *Trichoderma harzianum*, strain DB 103 (available as T-GRO®7456 by Dagutat Biolab)+TX; *Trichoderma polysporum*, strain IMI 206039 (e.g. Binab TF WP by BINAB Bio-Innovation AB, Sweden)+TX; *Trichoderma stromaticum*, having Accession No. Ts3550 (e.g. Tricovab by CEPLAC, Brazil)+TX; *Trichoderma virens* (also known as *Gliocladium virens*), in particular strain GL-21 (e.g. SoilGard by Certis, US)+TX; *Trichoderma virens* strain G-41, formerly known as *Gliocladium virens* (Accession No. ATCC 20906) (e.g., ROOTSHIELD® PLUS WP and TURFSHIELD® PLUS WP from BioWorks, US)+TX; *Trichoderma viride*, strain TV1 (e.g. Trianum-P by Koppert)+TX; *Trichoderma viride*, in particular strain B35 (Pietr et al., 1993, Zesz. Nauk. A R w Szczecinie 161: 125-137)+TX; mixtures of *Trichoderma asperellum* strain ICC 012 (also known as *Trichoderma harzianum* I00012), having Accession No. CABI CC IMI 392716 and *Trichoderma gamsii* (formerly *T. viride*) strain ICC 080, having Accession No. IMI 392151 (e.g., BIO-TAM™ from Isagro USA, Inc. and BIO-DERMA® by Agrobiosol de Mexico, S.A. de C.V.)+TX; *Ulocladium oudemansii* strain U3, having Accession No. NM 99/06216 (e.g., BOTRY-ZEN® by Botry-Zen Ltd, New Zealand and BOTRYSTOP® from BioWorks, Inc.)+TX; *Verticillium albo-atrum* (formerly *V. dahliae*), strain WCS850 having Accession No. WCS850, deposited at the Central Bureau for Fungi Cultures (e.g., DUTCH TRIG® by Tree Care Innovations)+TX; *Verticillium chlamydosporium*+TX;

(3) biological control agents having an effect for improving plant growth and/or plant health selected from the group of:

(3.1) bacteria, examples of which are Azospirillum brasilense (e.g., VIGOR® from KALO, Inc.)+TX; Azospirillum lipoferum (e.g., VERTEX-IF™ from TerraMax, Inc.)+TX; *Azorhizobium caulinodans*, in particular strain ZB-SK-5+TX; *Azotobacter chroococcum*, in particular strain H23+TX; *Azotobacter vinelandii*, in particular strain ATCC 12837+TX; a mixture of *Azotobacter vinelandii* and *Clostridium pasteurianum* (available as INVIGORATE® from Agrinos)+TX; *Bacillus amyloliquefaciens* pm414 (LOLI-PEPTA® from Biofilm Crop Protection)+TX; *Bacillus amyloliquefaciens* SB3281 (ATCC #PTA-7542, WO 2017/205258)+TX; *Bacillus amyloliquefaciens* TJ1000 (available as QUIKROOTS® from Novozymes)+TX; *Bacillus amyloliquefaciens*, in particular strain IN937a+TX; *Bacillus amyloliquefaciens*, in particular strain FZB42 (e.g. RHIZOVITAL® from ABiTEP, DE)+TX; *Bacillus amyloliquefaciens* BS27 (Accession No. NRRL B-5015)+TX; *Bacillus cereus* family member EE128 (NRRL No. B-50917)+TX; *Bacillus cereus* family member EE349 (NRRL No. B-50928)+TX; *Bacillus cereus*, in particular strain BPO1 (ATCC 55675, e.g. MEPICHLOR® from Arysta Lifescience, US)+TX; *Bacillus firmus*, in particular strain CNMC 1-1582 (e.g. VOTIVO® from BASF SE)+TX; *Bacillus mycoides* BT155 (NRRL No. B-50921)+TX; *Bacillus mycoides* EE118 (NRRL No. B-50918)+TX; *Bacillus mycoides* EE141 (NRRL No. B-50916)+TX; *Bacillus mycoides* BT46-3 (NRRL No. B-50922)+TX; *Bacillus pumilus*, in particular strain QST2808 (having Accession No. NRRL No. B-30087)+TX; *Bacillus pumilus*, in particular strain GB34 (e.g. YIELD SHIELD® from Bayer Crop Science, DE)+TX; *Bacillus siamensis*, in particular strain KCTC 13613T+TX; *Bacillus subtilis*, in particular strain QST713/$AQ_{713}$ (having NRRL Accession No. B-21661 and described in U.S. Pat. No. 6,060,051, available as SERENADE® OPTI or SERENADE® ASO from Bayer CropScience LP, US)+TX; *Bacillus subtilis*, in particular strain $AQ_{30002}$ (having Accession Nos. NRRL B-50421 and described in U.S. patent application Ser. No. 13/330,576)+TX; *Bacillus subtilis*, in particular strain $AQ_{30004}$ (and NRRL B-50455 and described in U.S. patent application Ser. No. 13/330,576)+TX; *Bacillus subtilis* strain BU1814, (available as TEQUALIS® from BASF SE), *Bacillus subtilis* rm303 (RHIZOMAX® from Biofilm Crop Protection)+TX; *Bacillus thuringiensis* BT013A (NRRL No. B-50924) also known as *Bacillus thuringiensis* 4Q7+TX; a mixture of *Bacillus licheniformis* $FMCH_{001}$ and *Bacillus subtilis* $FMCH_{002}$ (available as QUARTZO® (WG), PRESENCE® (WP) from FMC Corporation)+TX; *Bacillus subtilis*, in particular strain MBI 600 (e.g. SUBTILEX® from BASF SE)+TX; *Bacillus tequilensis*, in particular strain NII-0943+TX; *Bradyrhizobium japonicum* (e.g. OPTIMIZE® from Novozymes)+TX; *Delftia acidovorans*, in particular strain RAY209 (e.g. BIOBOOST® from Brett Young Seeds)+TX; *Mesorhizobium cicer* (e.g., NODULATOR from BASF SE)+TX; *Lactobacillus* sp. (e.g. LACTO-PLANT® from LactoPAFI)+TX; *Rhizobium leguminosarium* biovar *viciae* (e.g., NODULATOR from BASF SE)+TX; *Pseudomonas proradix* (e.g. PRORADIX® from Sourcon Padena)+TX; *Pseudomonas aeruginosa*, in particular strain PN1+TX; *Rhizobium leguminosarum*, in particular bv. viceae strain Z25 (Accession No. CECT 4585)+TX; *Paenibacillus polymyxa*, in particular strain AC-1 (e.g. TOPSEED® from Green Biotech Company Ltd.)+TX; *Serratia marcescens*, in particular strain SRM (Accession No. MTCC 8708)+TX; *Sinorhizobium meliloti* strain NRG-185-1 (NITRAGIN® GOLD from Bayer CropScience)+TX; *Thiobacillus* sp. (e.g. CROPAID® from Cropaid Ltd UK)+TX; and (3.2) fungi, examples of which are Purpureocillium lilacinum (previously known as *Paecilomyces lilacinus*) strain 251 (AGAL 89/030550, e.g. BioAct from Bayer CropScience Biologics GmbH)+TX; *Penicillium bilaii*, strain ATCC 22348 (e.g. JumpStart® from Acceleron BioAg), *Talaromyces flavus*, strain V117b+TX; *Trichoderma atroviride* strain CNCM 1-1237 (e.g. Esquive® WP from Agrauxine, FR), *Trichoderma viride*, e.g. strain B35 (Pietr et al., 1993, Zesz. Nauk. A R w Szczecinie 161: 125-137)+TX; *Trichoderma atroviride* strain $LC_{52}$ (also known as *Trichoderma atroviride* strain LU132, e.g. Sentinel from Agrimm Technologies Limited)+TX; *Trichoderma atroviride* strain $SC_1$ described in International Application No. PCT/IT2008/000196)+TX; *Trichoderma asperellum* strain kd (e.g. T-Gro from Andermatt Biocontrol)+TX; *Trichoderma* asperellum strain Eco-T (Plant Health Products, ZA), *Trichoderma harzianum* strain T-22 (e.g. Trianum-P from Andermatt Biocontrol or Koppert)+TX; *Myrothecium verrucaria* strain AARC-0255 (e.g. DiTera™ from Valent Biosciences)+TX; *Penicillium bilaii* strain ATCC $ATCC_{20851}$+TX; *Pythium oli-*

*gandrum* strain M1 (ATCC 38472, e.g. Polyversum from Bioprepraty, CZ)+TX; *Trichoderma virens* strain GL-21 (e.g. SoilGard® from Certis, USA)+TX; *Verticillium albo-atrum* (formerly *V. dahliae*) strain WCS850 (CBS 276.92, e.g. Dutch Trig from Tree Care Innovations)+TX; *Trichoderma atroviride*, in particular strain no. V08/002387, strain no. NMI No. V08/002388, strain no. NMI No. V08/002389, strain no. NMI No. V08/002390+TX; *Trichoderma harzianum* strain ITEM 908, *Trichoderma harzianum*, strain TSTh20+TX; *Trichoderma harzianum* strain 1295-22+TX; *Pythium oligandrum* strain DV74+TX; *Rhizopogon amylopogon* (e.g. comprised in Myco-Sol from Helena Chemical Company)+TX; *Rhizopogon fulvigleba* (e.g. comprised in Myco-Sol from Helena Chemical Company)+TX; *Trichoderma virens* strain GI-3+TX;

(4) insecticidally active biological control agents selected from (4.1) bacteria, examples of which are *Agrobacterium radiobacter* strain K84 (Galltrol from AgBiochem Inc.)+TX; *Bacillus amyloliquefaciens*, in particular strain PTS-4838 (e.g. AVEO from Valent Biosciences, US)+TX; *Bacillus firmus*, in particular strain CNMC 1-1582 (e.g. VOTIVO® from BASF SE)+TX; *Bacillus mycoides*, isolate J. (e.g. BmJ from Certis USA LLC, a subsidiary of Mitsui & Co.)+TX; *Bacillus sphaericus*, in particular Serotype H5a5b strain 2362 (strain ABTS-1743) (e.g. VECTOLEX® from Valent BioSciences, US)+TX; *Bacillus thuringiensis* subsp. *aizawai*, in particular strain ABTS-1857 (SD-1372, e.g. XENTARI® from Valent BioSciences)+TX; *Bacillus thuringiensis* subsp. *aizawai*, in particular serotype H-7 (e.g. FLORBAC® WG from Valent BioSciences, US)+TX; *Bacillus thuringiensis israelensis* strain BMP 144 (e.g. AQUABAC® by Becker Microbial Products IL)+TX; *Bacillus thuringiensis* subsp. *israelensis* (serotype H-14) strain AM65-52 (Accession No. ATCC 1276) (e.g. VECTOBAC® by Valent BioSciences, US)+TX; *Bacillus thuringiensis* subsp. *aizawai* strain GC-91+TX; *Bacillus thuringiensis* var. Colmeri (e.g. TIANBAOBTC by Changzhou Jianghai Chemical Factory)+TX; *Bacillus thuringiensis* var. *japonensis* strain Buibui+TX; *Bacillus thuringiensis* subsp. *kurstaki* strain BMP 123 from Becker Microbial Products, IL+TX; *Bacillus thuringiensis* subsp. *kurstaki* strain BMP 123 by Becker Microbial Products, IL, e.g. BARITONE from Bayer CropScience+TX; *Bacillus thuringiensis* subsp. *kurstaki* strain HD-1 (e.g. DIPEL® ES from Valent BioSciences, US)+TX; *Bacillus thuringiensis* var. *kurstaki* strain EVB-113-19 (e.g., BIOPROTEC® from AEF Global)+TX; *Bacillus thuringiensis* subsp. *kurstaki* strain ABTS 351+TX; *Bacillus thuringiensis* subsp. *kurstaki* strain PB 54+TX; *Bacillus thuringiensis* subsp. *kurstaki* strain SA 11, (JAVELIN from Certis, US)+TX; *Bacillus thuringiensis* subsp. *kurstaki* strain SA 12 (THURICIDE from Certis, US)+TX; *Bacillus thuringiensis* subsp. *kurstaki* strain EG 2348 (LEPINOX from Certis, US)+TX; *Bacillus thuringiensis* subsp. *kurstaki* strain EG 7841 (CRYMAX from Certis, US)+TX; *Bacillus thuringiensis* subsp. *tenebrionis* strain NB 176 (SD-5428, e.g. NOVODOR® FC from BioFa DE)+TX; *Brevibacillus laterosporus* (LATERAL from Ecolibrium Biologicals)+TX; *Burkholderia* spp., in particular *Burkholderia* rinojensis strain A396 (also known as *Burkholderia* rinojensis strain MBI 305) (Accession No. NRRL B-50319+TX; WO 2011/106491 and WO 2013/032693+TX; e.g. MB1206 TGAI and ZELTO® from Marrone Bio Innovations)+TX; *Chromobacterium subtsugae*, in particular strain PRAA$_4$-1T (MBI-203+TX; e.g. GRANDEVO® from Marrone Bio Innovations)+TX; *Lecanicillium muscarium* Ve6 (MYCOTAL from Koppert)+TX; *Paenibacillus popilliae* (formerly *Bacillus popilliae*+TX; e.g. MILKY SPORE POWDER™ and MILKY SPORE GRANULAR™ from St. Gabriel Laboratories)+TX; *Pasteuria nishizawae* strain Pn1 (CLARIVA from Syngenta/ChemChina)+TX; *Serratia entomophila* (e.g. INVADE® by Wrightson Seeds)+TX; *Serratia marcescens*, in particular strain SRM (Accession No. MTCC 8708)+TX; *Trichoderma* asperellum (TRICHODERMAX from Novozymes)+TX; *Wolbachia pipientis* ZAP strain (e.g., ZAP MALES® from MosquitoMate)+TX; and (4.2) fungi, examples of which are *Beauveria bassiana* strain ATCC 74040 (e.g. NATURALIS® from Intrachem Bio Italia)+TX; *Beauveria bassiana* strain GHA (Accession No. ATCC$_{74250}$, e.g. BOTANIGUARD® ES and MYCONTROL-O® from Laverlam International Corporation)+TX; *Beauveria bassiana* strain ATPO2 (Accession No. DSM 24665)+TX; *Isaria fumosorosea* (previously known as *Paecilomyces fumosoroseus*) strain Apopka 97) PREFERAL from SePRO+TX; *Metarhizium anisopliae* 3213-1 (deposited under NRRL accession number 67074) (WO 2017/066094+TX; Pioneer Hi-Bred International)+TX; *Metarhizium robertsii* 15013-1 (deposited under NRRL accession number 67073)+TX; *Metarhizium robertsii* 23013-3 (deposited under NRRL accession number 67075)+TX; *Paecilomyces lilacinus* strain 251 (MELOCON from Certis, US)+TX; *Zoophtora radicans*+TX;

(5) Viruses selected from the group consisting of *Adoxophyes orana* (summer fruit *tortrix*) granulosis virus (GV)+TX; *Cydia pomonella* (codling moth) granulosis virus (GV)+TX; *Helicoverpa armigera* (cotton bollworm) nuclear polyhedrosis virus (NPV)+TX; *Spodoptera exigua* (beet armyworm) mNPV+TX; *Spodoptera frugiperda* (fall armyworm) mNPV+TX; *Spodoptera littoralis* (African cotton leafworm) NPV+TX;

(6) Bacteria and fungi which can be added as 'inoculant' to plants or plant parts or plant organs and which, by virtue of their particular properties, promote plant growth and plant health selected from *Agrobacterium* spp.+TX; *Azorhizobium caulinodans*+TX; Azospirillum spp.+TX; *Azotobacter* spp.+TX; *Bradyrhizobium* spp.+TX; *Burkholderia* spp., in particular *Burkholderia cepacia* (formerly known as *Pseudomonas cepacia*)+TX; *Gigaspora* spp., or *Gigaspora monosporum*+TX; *Glomus* spp.+TX; *Laccaria* spp.+TX; *LactoBacillus buchneri*+TX; *Paraglomus* spp.+TX; *Pisolithus tinctorus*+TX; *Pseudomonas* spp.+TX; *Rhizobium* spp., in particular *Rhizobium trifolii*+TX; *Rhizopogon* spp.+TX; *Scleroderma* spp.+TX; *Suillus* spp.+TX; *Streptomyces* spp.+TX;

(7) Plant extracts and products formed by microorganisms including proteins and secondary metabolites which can be used as biological control agents, selected from *Allium sativum* (NEMGUARD from Eco-Spray+TX; BRALIC from ADAMA)+TX; Armour-Zen+TX; *Artemisia absinthium*+TX; Azadirachtin (e.g. AZATIN XL from Certis, US)+TX; Biokeeper WP+TX; Brassicaceae extract, in particular oilseed rape powder or mustard powder+TX; *Cassia nigricans*+TX; *Celastrus*

*angulatus*+TX; *Chenopodium* anthelminticum+TX; Chitin+TX; *Dryopteris filix-mas*+TX; *Equisetum arvense*+TX; Fortune Aza+TX; Fungastop+TX; Heads Up (*Chenopodium quinoa* saponin extract)+TX; PRO-BLAD (naturally occurring Blad polypeptide from Lupin seeds), Certis EU+TX; FRACTURE (naturally occurring Blad polypeptide from Lupin seeds), FMC+TX; *Pyrethrum*/Pyrethrins+TX; *Quassia amara*+TX; *Quercus*+TX; *Quillaja* extract (QL AGRI 35 from BASF)+TX; *Reynoutria sachalinensis* extract (REGALLIA/REGALIA MAXX from Marrone Bio)+TX; "Requiem™ Insecticide"+TX; Rotenone+TX; ryania/ryanodine+TX; *Symphytum officinale*+TX; *Tanacetum vulgare*+TX; Thymol+TX; Thymol mixed with Geraniol (CEDROZ from Eden Research)+TX; Thymol mixed with Geraniol and Eugenol (MEVALONE from Eden Research)+TX; Triact 70+TX; TriCon+TX; *Tropaeulum majus*+TX; *Melaleuca alternifolia* extract (TIMOREX GOLD from STK)+TX; *Urtica dioica*+TX; Veratrin+TX; and *Viscum album*+TX; and a safener, such as benoxacor+TX, cloquintocet (including cloquintocet-mexyl)+TX, cyprosulfamide+TX, dichlormid+TX, fenchlorazole (including fenchlorazole-ethyl)+TX, fenclorim+TX, fluxofenim+TX, furilazole+TX, isoxadifen (including isoxadifen-ethyl)+TX, mefenpyr (including mefenpyr-diethyl)+TX, metcamifen+TX and oxabetrinil+TX.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright © 1995-2004]; for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used or, if neither one of those designations nor a "common name" is used, an "alternative name" is employed. "CAS Reg. No" means the Chemical Abstracts Registry Number.

The active ingredient mixture of the compounds of formula I selected from the compounds defined in the Tables A-1 to A-300, Tables B-1 to B-108, and Table P, with active ingredients described above comprises a compound selected from one compound defined in the Tables A-1 to A-300, Tables B-1 to B-108, and Table P, and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 to 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

The compounds and mixtures as described above can be used in a method for controlling pests, which comprises applying a composition comprising a compound or mixture respectively as described above to the pests or their environment, with the exception of a method for treatment of the human or animal body by surgery or therapy and diagnostic methods practised on the human or animal body.

The mixtures comprising a compound of formula I selected from the compounds defined in the Tables A-1 to A-300, Tables B-1 to B-108, and Table P, and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I and the active ingredients as described above is not essential for working the present invention.

The compositions according to the invention can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/ortackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compounds of formula I of the invention and compositions thereof are also be suitable for the protection of plant propagation material, for example seeds, such as fruit, tubers or kernels, or nursery plants, against pests of the abovementioned type. The propagation material can be treated with the compound prior to planting, for example seed can be treated prior to sowing. Alternatively, the compound can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention. Typical treatment rates would depend on the plant and pest/fungi to be controlled and are generally between 1 to 200 grams per 100 kg of seeds, preferably between 5 to 150 grams per 100 kg of seeds, such as between 10 to 100 grams per 100 kg of seeds.

The term seed embraces seeds and plant propagules of all kinds including but not limited to true seeds, seed pieces, suckers, corns, bulbs, fruit, tubers, grains, rhizomes, cuttings, cut shoots and the like and means, in a preferred embodiment, true seeds.

The present invention also comprises seeds coated or treated with or containing a compound of formula I. The term "coated or treated with and/or containing" generally signifies that the active ingredient is for the most part on the surface of the seed at the time of application, although a greater or lesser part of the ingredient may penetrate into the seed material, depending on the method of application. When the said seed product is (re)planted, it may absorb the active ingredient. In an embodiment, the present invention makes available a plant propagation material adhered thereto with a compound of formula I. Further, it is hereby made available, a composition comprising a plant propagation material treated with a compound of formula I.

Seed treatment comprises all suitable seed treatment techniques known in the art, such as seed dressing, seed coating, seed dusting, seed soaking and seed pelleting. The seed treatment application of the compound formula I can be carried out by any known methods, such as spraying or by dusting the seeds before sowing or during the sowing/planting of the seeds.

The compounds of the invention can be distinguished from other similar compounds by virtue of greater efficacy at low application rates and/or different pest control, which can be verified by the person skilled in the art using the experimental procedures, using lower concentrations if necessary, for example 10 ppm, 5 ppm, 2 ppm, 1 ppm or 0.2 ppm; or lower application rates, such as 300, 200 or 100, mg of $A_1$ per $m^2$. The greater efficacy can be observed by an increased safety profile (against non-target organisms above and below ground (such as fish, birds and bees), improved physico-chemical properties, or increased biodegradability).

In each aspect and embodiment of the invention, "consisting essentially" and inflections thereof are a preferred embodiment of "comprising" and its inflections, and "consisting of" and inflections thereof are a preferred embodiment of "consisting essentially of" and its inflections.

The disclosure in the present application makes available each and every combination of embodiments disclosed herein.

It should be noted that the disclosure herein in respect of a compound of formula I applies equally in respect of a compound of each of formulae I*, I'a, Iaa, Iab, Iac, Iad, Iae, Iaf, Iag, I'aa, I'ab, I'ac, I'ad, I'ae, I'af, I'ag, and Tables A-1 to A-300 and Tables B-1 to B-108.

PREPARATORY EXAMPLES

"Mp" means melting point in ° C. $^1$H NMR measurements were recorded on a Brucker400 MHz spectrometer, chemical shifts are given in ppm relevant to a TMS standard. Spectra measured in deuterated solvents as indicated. The following abbreviations are used: s=singlet; br s=broad singlet; d=doublet; br d=broad doublet; dd=double doublet; dt=double triplet; t=triplet, tt=triple triplet, q=quartet, quin=quintuplet, sept=septet; m=multiplet.

Either one of the LCMS methods below was used to characterize the compounds. The characteristic LCMS values obtained for each compound were the retention time ("Rt", recorded in minutes) and the measured molecular ion $(M+H)^+$ or $(M-H)^-$.

LCMS Methods:

Method 1:

Spectra were recorded on a Mass Spectrometer from Agilent Technologies (6410 Triple Quadrupole mass spectrometer) equipped with an equipped with an electrospray source (Polarity: positive or negative ions, MS2 Scan, Capillary: 7.00 kV, Fragmentor: 120 V, Desolvation Temperature: 350° C., Gas Flow: 11 L/min, Nebulizer Gas: 40 psi, Mass range: 110 to 650 Da) and a 1200 Series HPLC from Agilent: quaternary pump, heated column compartment and diode-array detector. Column: KINETEX EVO C18, 2.6 μm, 50×4.6 mm, Temp: 40° C., DAD Wavelength (nm): 254, Solvent Gradient: A=water+5% Acetonitrile+0.1% HCOOH, B=Acetonitrile+0.1% HCOOH: gradient: 0 min 10% B, 90% A; 0.9-1.8 min 100% B; 1.8-2.2 min 100-10% B; 2.2-2.5 min 10% B; Flow (mL/min) 1.8.

Method 2:

Spectra were recorded on a Mass Spectrometer from Waters (SQD, SQDII Single quadrupole mass spectrometer) equipped with an electrospray source (Polarity: positive and negative ions, Capillary: 3.00 kV, Cone range: 41 V, Extractor: 2.00 V, Source Temperature: 150° C., Desolvation Temperature: 5000° C., Cone Gas Flow: 50 l/h, Desolvation Gas Flow: 1000 l/h, Mass range: 110 to 800 Da) and an Acquity UPLC from Waters: Binary pump, heated column compartment, diode-array detector and ELSD detector. Column: Waters UPLC HSS T3 C18, 1.8 μm, 30×2.1 mm, Temp: 40° C., PDA Wavelength range (nm): 200 to 400, Solvent Gradient: A=water+5% Acetonitrile+0.1% HCOOH, B=Acetonitrile+0.05% HCOOH, gradient: 10-100% B in 1.3 min; Flow (ml/min) 0.6.

Method 3:

Spectra were recorded on a Mass Spectrometer from Waters (Acquity QDa Mass Spectrometer) equipped with an electrospray source (Polarity: Positive and Negative Polarity Switch), Capillary: 0.8 kV, Cone range: 25 V, Extractor: V (No extractor voltage for QDa detector) Source Temperature: 120° C., Desolvation Temperature: 600° C., Cone Gas Flow: 50 L/h, Desolvation Gas Flow: 1000 L/h, Mass range: 110 to 850 Da) and an Acquity UPLC from Waters: Quaternary solvent manager, heated column compartment, diode-array detector. Column: Waters UPLC HSS T3, 1.8 μm, 30×2.1 mm, Temp: 40° C., PDA Wavelength range (nm): 230 to 400, Solvent Gradient: A=Water with 0.1% formic acid:Acetonitrile: 95:5 v/v, B=Acetonitrile with 0.05% formic acid: Gradient: 0 min-1.0 min, 10% B-90% A;

1.0 min-4.50 min 10%-100% B; 4.51 min-5.30 min, 100% B, 0% A; 5.31 min-5.50 min 100%-10% B; 5.51 min-6.00 min, 10% B, 90% A; Flow (ml/min) 0.6.

Example P1: Preparation of 2-[3-[1-[[8-bromo-2-oxo-6-(trifluoromethyl)-1H-quinazolin-4-yl]amino]ethyl]pyrazin-2-yl]thiazole-5-carbonitrile (Compound P1)

(P1)

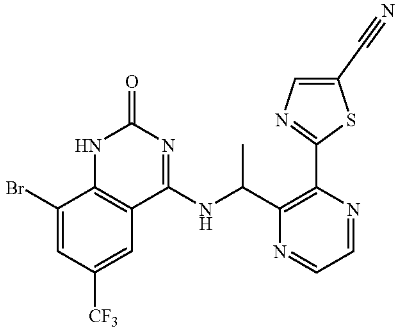

Step A: Preparation of 2-[1-(3-chloropyrazin-2-yl)ethyl]isoindoline-1,3-dione (I-1)

(I-1)

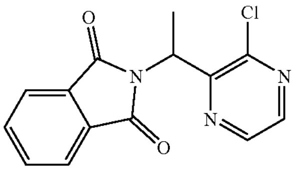

To a solution oftriphenylphosphine (12 g, 42 mmol), phthalimide (5.6 g, 36 mmol), and 1-(3-chloropyrazin-2-yl)ethanol (4.8 g, 30 mmol) in anhydrous THE (96 mL), was added diisopropyl azodicarboxylate (7.8 g, 36 mmol, 7.7 mL) slowly at 0 to 5° C. The mixture was stirred at room temperature for 12 h. The reaction mass was diluted with water and extracted with ethyl acetate. Then, the organic layer was separated, dried over sodium sulfate and concentrated to get a crude concentrate. The crude concentrate was purified by combiflash using 30% EtOAc in cyclohexane as eluent. The desired fractions were concentrated to get 2-[1-(3-chloropyrazin-2-yl)ethyl]isoindoline-1,3-dione (6.4 g, 73% yield).

$^1$H NMR (400 MHz, DMSO-d6) δ=8.71 (d, 1H), 8.49 (d, 1H), 7.86 (s, 4H), 5.71 (d, 1H), 1.79 (d, 3H).

LC-MS (method 2): retention time 1.20 min, m/z 288/290 $[M+H]^+$.

Step B: Preparation of 2-[1-(3-thiazol-2-ylpyrazin-2-yl)ethyl]isoindoline-1,3-dione (I-2)

(I-2)

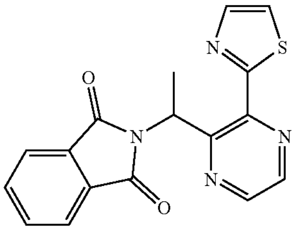

To a solution of 2-[1-(3-chloropyrazin-2-yl)ethyl]isoindoline-1,3-dione (4 g, 13.90 mmol) in toluene (60 mL), was added tributyl(thiazol-2-yl)stannane (5.203 g, 13.90 mmol). The reaction mixture was degassed with $N_2$ for 5 minutes then tetrakis(triphenylphosphine)palladium(0) (1.39 mmol) was added, and heated at 80° C. for 15 h. The reaction mass was cooled to room temperature, quenched with water and then extracted with EtOAc twice. The organic layers were combined and washed with brine, then dried over anhydrous sodium sulfate and concentrated. The crude concentrate was adsorbed on silica and purified on combiflash using 30% EtOAc in cyclohexane as eluent. The desired fractions were concentrated to get 2-[1-(3-thiazol-2-ylpyrazin-2-yl)ethyl]isoindoline-1,3-dione (3.6 g, 70 mass %, 54% yield).

$^1$H NMR (400 MHz, $CDCl_3$) δ=8.53-8.49 (m, 2H), 7.98 (d, 1H), 7.85-7.77 (m, 2H), 7.73-7.66 (m, 2H), 7.48 (d, 1H), 6.87 (q, 1H), 2.02 (d, 3H).

Step C: Preparation of 2-[1-[3-(5-bromothiazol-2-yl)pyrazin-2-yl]ethyl]isoindoline-1,3-dione (I-3)

(I-3)

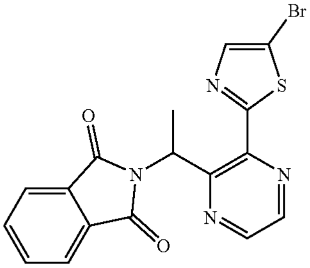

To a stirred solution of 2-[1-(3-thiazol-2-ylpyrazin-2-yl)ethyl]isoindoline-1,3-dione (1.2 g, 2.9 mmol) in acetic acid (40 mL), was added bromine (1.91 g, 11.89 mmol) dropwise at room temperature. The reaction mass was stirred at 100° C. for 4 h. The reaction was monitored by LCMS to confirm the conversion. Then, the reaction mass was diluted with water and extracted with EtOAc. The organic layer was washed with brine, dried over anhydrous sodium sulfate and concentrated. The crude concentrate was purified by combiflash using 30% EtOAc in cyclohexane as eluent. The desired fractions were dried to get 2-[1-[3-(5-bromothiazol-2-yl)pyrazin-2-yl]ethyl]isoindoline-1,3-dione (1.2 g, 49%).

$^1$H NMR (400 MHz, $CDCl_3$) δ=8.53 (d, 1H), 8.47 (d, 1H), 7.86-7.80 (m, 3H), 7.71 (dd, 2H), 6.75-6.71 (m, 1H), 2.00 (d, 3H).

LC-MS (method 2): retention time 1.24 min, m/z 415/417 $[M+H]^+$.

Step D: Preparation of 1-[3-(5-bromothiazol-2-yl) pyrazin-2-yl]ethanamine (I-4)

(I-4)

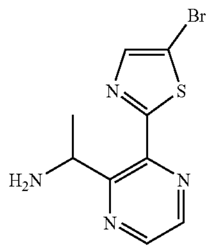

To a stirred solution of 2-[1-[3-(5-bromothiazol-2-yl) pyrazin-2-yl]ethyl]isoindoline-1,3-dione (0.98 g, 2.360 mmol) in tetrahydrofuran (10 mL/g), was added hydrazine mono hydrate (0.1808 g, 3.540 mmol). Then the reaction mass was stirred at room temperature for 4 h. The reaction was monitored by LCMS to confirm the conversion. The reaction mass was then concentrated on a rota evaporator under reduced pressure, and purified by combiflash using 90% EtOAc in cyclohexane. The desired fractions were dried to get 1-[3-(5-bromothiazol-2-yl)pyrazin-2-yl] ethanamine (0.47 g, yield 69%) as a white solid.

$^1$H NMR (400 MHz, DMSO-d6) δ=8.76 (d, 1H), 8.61 (d, 1H), 8.19 (s, 1H), 5.23 (d, 1H), 1.33 (d, 3H).

Step E: Preparation of tert-butyl N-[1-[3-(5-bromothiazol-2-yl)pyrazin-2-yl]ethyl]carbamate (I-5)

(I-5)

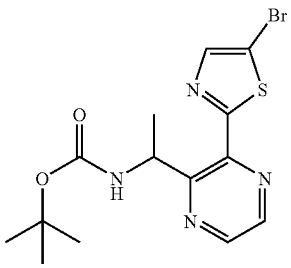

To a stirred solution of 1-[3-(5-bromothiazol-2-yl) pyrazin-2-yl]ethanamine (800 mg, 2.805 mmol) in acetonitrile (15 mL/g), was added N,N-diethylethanamine (7.013 mmol) followed by di-tert-butyl dicarbonate (1.236 g, 5.61 mmol) at room temperature. The resulting reaction mixture was stirred at room temperature for 16 h. The reaction mixture was diluted with water and extracted with ethyl acetate twice. The organic layers were then combined, washed with brine, dried over anhydrous sodium sulfate and evaporated to get a yellow solid which was washed with pentane and dried to get tert-butyl N-[1-[3-(5-bromothiazol-2-yl)pyrazin-2-yl]ethyl]carbamate (750 mg, yield 52%).

$^1$H NMR (400 MHz, $CDCl_3$) δ=8.55 (d, J=2.3 Hz, 1H), 8.47 (d, J=2.3 Hz, 1H), 7.87 (s, 1H), 6.25 (br, 1H) 5.85 (br, 1H) 1.49 (d, 2H), 1.43 (s, 9H).

LC-MS (method 2): retention time 1.19 min, m/z 285/287 $[M+H-100]^+$.

Step F: Preparation of tert-butyl N-[1-[3-(5-cyanothiazol-2-yl)pyrazin-2-yl]ethyl]carbamate (I-6)

(I-6)

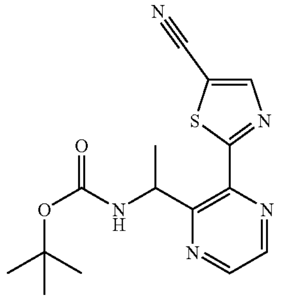

To a microwave (MW) vial were charged tert-butyl N-[1-[3-(5-bromothiazol-2-yl)pyrazin-2-yl]ethyl]carbamate (650 mg, 1.687 mmol), cyclopentylmethylether (7 mL/g) and water (7 mL/g). Then the whole was degassed with $N_2$ for 5 minutes and kept under a $N_2$ atmosphere. Then potassium acetate (2.024 mmol, 0.205 g), potassium ferrocyanide (0.6 equiv., 1.012 mmol), X-Phos (0.1 equiv., 0.1687 mmol) and (2-dicyclohexylphosphino-2',4',6'-triisopropyl-1,1'-biphenyl)[2-(2'-amino-1,1'-biphenyl)]palladium(II) methanesulfonate (0.1 equiv., 0.1687 mmol, 0.1503 g) were added in the MW vial. Then the vial was sealed and heated at 120° C. by MW for 2 h. The reaction was monitored by LCMS to confirm the conversion. Then the reaction mass was diluted with water and was extracted with EtOAc twice. The organic layers were combined and washed with brine, dried over anhydrous sodium sulfate, and concentrated to get a crude concentrate. Then the crude concentrate was purified by combiflash using 40% EtOAc in cyclohexane. The desired fractions were dried to get tert-butyl N-[1-[3-(5-cyanothiazol-2-yl)pyrazin-2-yl]ethyl]carbamate (0.21 g, yield 33.8%) as a white solid.

LC-MS (method 2): retention time 1.26 min, m/z 232 $[M+H-100]^+$.

Step G: Preparation of 1-[3-(5-cyanothiazol-2-yl) pyrazin-2-yl]ethylammonium; chloride (I-7)

(I-7)

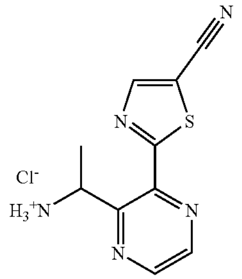

To a stirred solution of tert-butyl N-[1-[3-(5-cyanothiazol-2-yl)pyrazin-2-yl]ethyl]carbamate (0.603 mmol, 0.2 g) in 1,4-dioxane (2 mL) was added hydrochloric acid (4M in dioxane) (9.053 mmol, 0.277 mL). The reaction mixture was stirred at room temperature for 5 h. The reaction mass was concentrated. The resulting dark brown solid was washed with TBME twice and dried under vacuum to get -[3-(5-cyanothiazol-2-yl)pyrazin-2-yl]ethylammonium; chloride (0.17 g, yield 92%) as a brown solid.

Step H: Preparation of 2-[3-[1-[[8-bromo-2-chloro-6-(trifluoromethyl)quinazolin-4-yl]amino]ethyl]pyrazin-2-yl]thiazole-5-carbonitrile (Compound P23)

(P23)

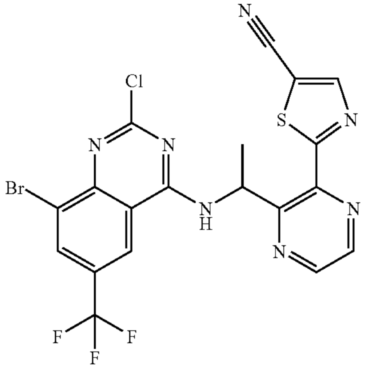

To a mixture of 1-[3-(5-cyanothiazol-2-yl)pyrazin-2-yl]ethylammonium; chloride (50 mg, 0.186 mmol), 8-bromo-2,4-dichloro-6-(trifluoromethyl)quinazoline (prepared in analogy to descriptions found in WO2021/148639) (0.204 mmol) and in acetonitrile (20 mL/g) was added cesium carbonate (0.558 mmol) at room temperature. Then the reaction mass was heated at 70° C. for 2 h. The reaction mass was cooled to room temperature, diluted with water, and extracted with ethyl acetate twice. The combined organic layers were washed with brine, dried over anhydrous sodium sulfate and concentrated under reduced pressure to get a brown gummy mass (50 mg, crude) which was purified by combiflash using EtOAc in cyclohexane (gradient). Then the desired fractions were dried to get 2-[3-[1-[[8-bromo-2-chloro-6-(trifluoromethyl)quinazolin-4-yl]amino]ethyl]pyrazin-2-yl]thiazole-5-carbonitrile (40 mg, yield 39%) as a solid.

LC-MS (method 2): retention time 1.16 min, m/z 538/540/542 [M−H]⁻.

Step I: Preparation of 2-[3-[1-[[8-bromo-2-oxo-6-(trifluoromethyl)-1H-quinazolin-4-yl]amino]ethyl]pyrazin-2-yl]thiazole-5-carbonitrile (Compound P1)

(P1)

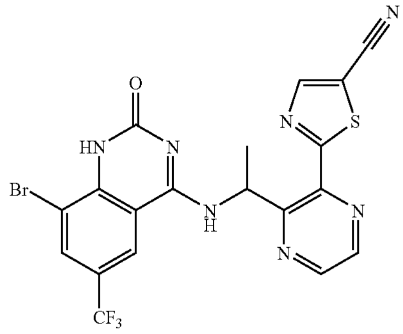

A solution of 2-[3-[1-[[8-bromo-2-chloro-6-(trifluoromethyl)quinazolin-4-yl]amino]ethyl]pyrazin-2-yl]thiazole-5-carbonitrile (0.035 g, 0.064 mmol) in acetic acid (0.35 mL, 6.047 mmol) was heated at 80° C. for 1 h. The reaction mass was cooled to room temperature. Then water was added to the reaction mass which was stirred for 5 minutes. A solid was obtained. The solid was filtered, washed with water, and dried under reduced pressure to get an off-white solid (20 mg), containing traces of acetic acid. The solid was re-dissolved in acetonitrile and water, further lyophilized to get 2-[3-[1-[[8-bromo-2-oxo-6-(trifluoromethyl)-1H-quinazolin-4-yl]amino]ethyl]pyrazin-2-yl]thiazole-5-carbonitrile (12 mg, yield 35%) as an off-white solid.

$^1$H NMR (400 MHz, DMSO-d6) δ=9.92 (s, 1H), 9.20 (br d, 1H), 8.97 (s, 1H), 8.91 (s, 1H), 8.78 (d, 1H), 8.71 (d, 1H), 8.25 (s, 1H), 6.58 (br t, 1H), 1.67 (d, 3H).

LC-MS (method 2): retention time 1.15 min, m/z 520/522 [M−H]⁻.

Example P9: Preparation of 2-[5-[(1S)-1-[[8-bromo-2-chloro-6-(trifluoromethyl)quinazolin-4-yl]amino]ethyl]-1,2,4-triazol-1-yl]thiazole-5-carbonitrile (Compound P9)

(P9)

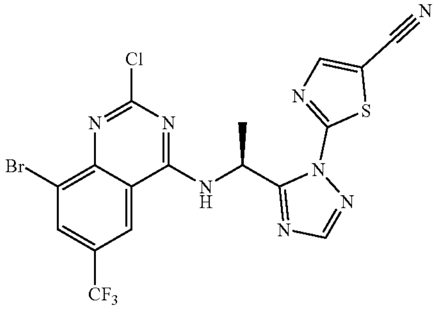

Step A: Preparation of 2-hydrazinothiazole-5-carbonitrile (I-9)

(I-9)

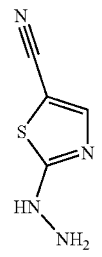

To a stirred solution of 2-bromothiazole-5-carbonitrile (3.2 g, 13.543 mmol, 80 mass %) in ethanol (32 mL) was added hydrazine monohydrate (3.389 g, 67.714 mmol). The reaction mass was heated at 80° C. for 30 minutes. Then the reaction mass was diluted with water (20 ml) and extracted with EtOAc (50 ml×2). The organic layer was washed with brine, dried over anhydrous sodium sulfate, and concentrated to get 2-hydrazinothiazole-5-carbonitrile (1.1 g, yield 58%) as a brown solid.

$^1$H NMR (400 MHz, DMSO-d6) δ: 9.79 (br s, 1H), 7.88 (s, 1H), 5.34 (s, 2H).

LC-MS (method 2): retention time 0.16 min, m/z 141.0 $[M+H]^+$.

Step B: Preparation of tert-butyl N-[(1S)-1-[2-(5-cyanothiazol-2-yl)-1,2,4-triazol-3-yl]ethyl]carbamate (I-10)

(I-10)

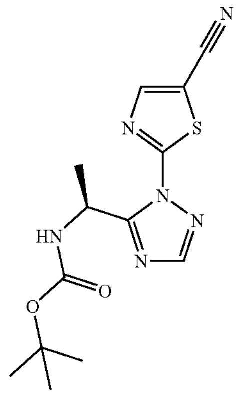

To a stirred mixture of tert-butyl N-[(1S)-2-[(E)-dimethylaminomethyleneamino]-1-methyl-2-oxo-ethyl]carbamate (0.364 g, 1.4982 mmol) and 2-hydrazinothiazole-5-carbonitrile (0.35 g, 1.498 mmol, 60 mass %) in methoxycyclopentane (3.75 mL) was added AcOH (3.75 mL). The reaction mass was heated at 90° C. for 1 h. Then the reaction mass was diluted with water and was extracted with TBME twice. The combined organic layers were washed with brine, dried over anhydrous sodium sulfate and concentrated. The crude concentrate was adsorbed on silica and purified by combiflash using a EtOAc/cyclohexane gradient system. The desired fractions were dried to get tert-butyl-N-[(1S)-1-[2-(5-cyanothiazol-2-yl)-1,2,4-triazol-3-yl]ethyl]carbamate (0.425 g, 80 mass %, 70% yield) as a pale brown solid.

$^1$H NMR (400 MHz, $CDCl_3$) δ: 8.12 (s, 1H), 7.96 (s, 1H), 7.75 (s, 1H), 5.81-5.95 (m, 1H), 5.57 (br s, 1H), 1.58 (d, 3H) 1.44 (br s, 9H).

Step C: Preparation of [(1S)-1-[2-(5-cyanothiazol-2-yl)-1,2,4-triazol-3-yl]ethyl]ammonium; chloride (I-11)

(I-11)

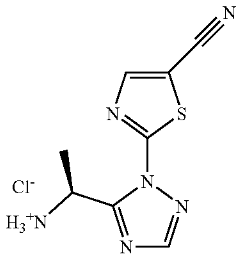

To a stirred solution of tert-butyl-N-[(1S)-1-[2-(5-cyanothiazol-2-yl)-1,2,4-triazol-3-yl]ethyl]carbamate (1 g, 3.121 mmol) in cyclopentylmethylether (10 mL) was added hydrochloric acid (4M in dioxane) (46.82 mmol). Then the reaction mass was stirred at room temperature for 20 h. The reaction mass was concentrated and a white solid was washed with TBME (3×50 ml) and then dried on rotavapor to get [(1S)-1-[2-(5-cyanothiazol-2-yl)-1,2,4-triazol-3-yl]ethyl]ammonium; chloride (0.9 g) as white solid.

$^1$H NMR (400 MHz, DMSO-d6) δ: 8.99 (br s, 3H), 8.72 (s, 1H), 8.48-8.51 (m, 1H), 5.33 (br s, 1H), 1.65 (d, 3H).

Step D: Preparation of 2-[5-[(1S)-1-[[8-bromo-2-chloro-6-(trifluoromethyl)quinazolin-4-yl]amino]ethyl]-1,2,4-triazol-1-yl]thiazole-5-carbonitrile (Compound P9)

(P9)

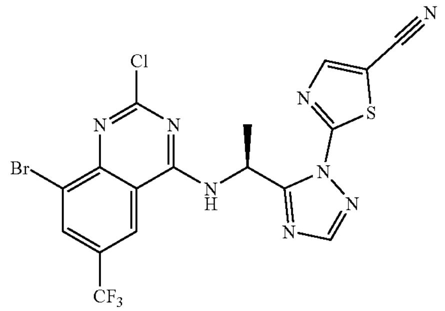

To a stirred mixture of 8-bromo-2,4-dichloro-6-(trifluoromethyl)quinazoline (prepared in analogy to descriptions found in WO2021/148639) (0.177 g, 0.514 mmol) and [(1S)-1-[2-(5-cyanothiazol-2-yl)-1,2,4-triazol-3-yl]ethyl]ammonium; chloride (0.12 g, 0.467 mmol) in acetonitrile (2.4 mL) was added cesium carbonate (0.228 g, 0.701 mmol). The reaction was heated at 80° C. for 15 minutes. The reaction mass was filtered through a celite bed. Then the celite bed was washed with EtOAc and the filtrate was concentrated to get a crude mixture. The crude mixture was adsorbed on silica and purified on a combiflash using EtOAc/cyclohexane gradient system to get 2-[5-[(1S)-1-[[8-bromo-2-chloro-6-(trifluoromethyl)quinazolin-4-yl]amino] ethyl]-1,2,4-triazol-1-yl]thiazole-5-carbonitrile (0.1 g, yield 40%) as a white solid.

$^1$H NMR (400 MHz, DMSO-d6) δ: 9.85 (d, 1H), 9.02 (s, 1H), 8.69 (s, 1H), 8.50 (d, 1H), 8.32 (s, 1H), 6.33 (quin., 1H), 1.78 (d, 3H).

LC-MS (method 2): retention time 1.23 min, m/z 529/531/533 [M+H]$^+$.

Example P2: Preparation of 2-[5-[(1S)-1-[[8-bromo-2-oxo-6-(trifluoromethyl)-1H-quinazolin-4-yl] amino]ethyl]-1,2,4-triazol-1-yl]thiazole-5-carbonitrile (Compound P2)

(P2)

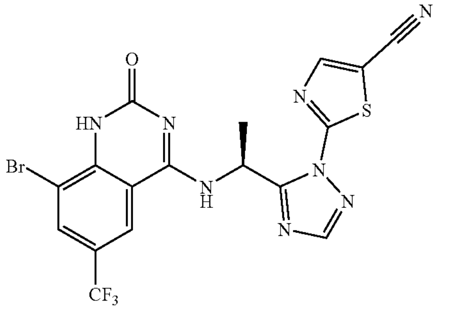

A solution of 2-[5-[(1S)-1-[[8-bromo-2-chloro-6-(trifluoromethyl)quinazolin-4-yl]amino]ethyl]-1,2,4-triazol-1-yl] thiazole-5-carbonitrile (0.09 g, 0.169 mmol) in acetic acid (0.9 mL) was heated at 80° C. for 1 h. The reaction mass was concentrated. The crude concentrate was adsorbed on celite, purified by reverse phase column chromatography on 40 g C18 (40-60 μm) and then eluted using $H_2O$:ACN (0.01% TFA). The product fractions were freeze dried to get 2-[5-[(1S)-1-[[8-bromo-2-oxo-6-(trifluoromethyl)-1H-quinazolin-4-yl]amino]ethyl]-1,2,4-triazol-1-yl]thiazole-5-carbonitrile (0.06 g, yield 69%) as a white solid.

$^1$H NMR (400 MHz, DMSO-d6) δ: 10.08 (br s, 1H), 9.25 (br d, 1H), 8.80 (s, 1H), 8.68 (s, 1H), 8.30 (s, 1H), 8.28 (s, 1H), 6.23 (quin, 1H), 1.71 (d, 3H)

LC-MS (method 2): retention time 0.90 min, m/z 511/513 [M+H]$^+$.

Example P3: Preparation of 8-bromo-N-[1-[3-(5-bromothiazol-2-yl)pyrazin-2-yl]ethyl]-2-chloro-6-(trifluoromethyl)quinazolin-4-amine (Compound P3)

(P3)

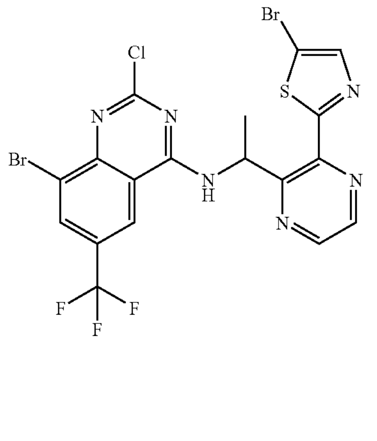

To mixture of 1-[3-(5-bromothiazol-2-yl)pyrazin-2-yl] ethanamine (100 mg, 0.350 mmol), 8-bromo-2,4-dichloro-6-(trifluoromethyl)quinazoline (prepared in analogy to descriptions found in WO2021/148639) (0.385 mmol) and in acetonitrile (20 mL/g) was added cesium carbonate (1.05 mmol) at room temperature. Then the reaction mass was heated at 70° C. for 2 h. The reaction mass was cooled to room temperature, diluted with water, and extracted with ethyl acetate twice. The combined organic layers were washed with brine, dried over anhydrous sodium sulfate and concentrated under reduced pressure to get a crude concentrate. The crude concentrate was purified by combiflash using EtOAc in cyclohexane (gradient). The desired fractions were dried to get 8-bromo-N-[1-[3-(5-bromothiazol-2-yl)pyrazin-2-yl]ethyl]-2-chloro-6-(trifluoromethyl)quinazolin-4-amine (140 mg, yield 67%) as an off-white solid.

$^1$H NMR (400 MHz, $CDCl_3$) δ=8.64 (d, 1H), 8.59 (d, 1H), 8.37-8.31 (m, 1H), 8.22 (d, 1H), 8.05 (s, 1H), 8.02 (s, 1H), 6.87-6.79 (m, 1H), 1.75-1.68 (m, 3H).

LC-MS (method 2): retention time 1.22 min, m/z 591/593/595 [M−H]$^-$.

Example P4: Preparation of 8-bromo-4-[1-[3-(5-bromothiazol-2-yl)pyrazin-2-yl]ethylamino]-6-(trifluoromethyl)-1H-quinazolin-2-one (Compound P4)

(P4)

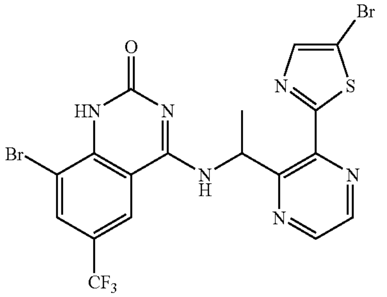

A solution of 8-bromo-N-[1-[3-(5-bromothiazol-2-yl) pyrazin-2-yl]ethyl]-2-chloro-6-(trifluoromethyl) quinazolin-4-amine (0.08 g, 0.134 mmol) in acetic acid (0.8 mL, 13.82 mmol) was heated and stirred at 80° C. for 1 h. Progress of the reaction was confirmed by LCMS. The reaction mass was cooled to room temperature, then water was added to the reaction mass which was stirred for 5 minutes. The obtained solid was filtered, then washed with water, and dried under reduced pressure to get a solid (65 mg) containing traces of acetic acid. The solid was re-dissolved in acetonitrile and water, then further lyophilized to get 8-bromo-4-[1-[3-(5-bromothiazol-2-yl)pyrazin-2-yl]ethylamino]-6-(trifluoromethyl)-1H-quinazolin-2-one (65 mg, yield 83%) as off white solid.

$^1$H NMR (400 MHz, DMSO-d6) δ=9.90 (s, 1H), 9.15 (d, 1H), 8.91 (s, 1H), 8.68 (d, 1H), 8.64 (d, 1H), 8.24 (s, 2H), 6.59-6.51 (m, 1H), 1.64 (d, 3H).

LC-MS (method 2): retention time 1.14 min, m/z 575/577/579 [M+H]$^+$.

Example P6: Preparation of N-[1-[3-(5-bromothiazol-2-yl)pyrazin-2-yl]ethyl]-6-chloro-8-(trifluoromethyl) quinazolin-4-amine (Compound P6)

(P6)

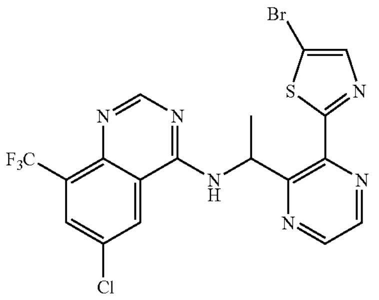

To a mixture of 1-[3-(5-bromothiazol-2-yl)pyrazin-2-yl] ethanamine (120 mg, 0.42 mmol), and 4,6-dichloro-8-(trifluoromethyl)quinazoline (prepared as described in WO2021/083936) (0.462 mmol) in acetonitrile (20 mL/g) was added cesium carbonate (1.262 mmol) at room temperature. Then the reaction mass was heated at 70° C. for 2 h. The reaction mass was cooled to room temperature, diluted with water, and extracted with ethyl acetate twice. The combined organic layers were washed with brine, dried over anhydrous sodium sulfate and concentrated under reduced pressure to get a brown gummy mass which was adsorbed on silica and purified by combiflash using EtOAc/Cyclohexane gradient system. The desired fractions were dried to get N-[1-[3-(5-bromothiazol-2-yl)pyrazin-2-yl] ethyl]-6-chloro-8-(trifluoromethyl)quinazolin-4-amine (130 mg, yield 59%) as an off-white solid.

$^1$H NMR (400 MHz, $CDCl_3$) δ=8.78 (s, 1H), 8.65 (d, J=2.4 Hz, 1H), 8.58 (d, J=2.4 Hz, 1H), 8.05-8.01 (m, 3H), 7.81 (br d, J=7.7 Hz, 1H), 6.91-6.84 (m, 1H), 1.69 (d, J=6.6 Hz, 3H)

LC-MS (method 2): retention time 1.30 min, m/z 513/515/517 $[M-H]^-$.

Example P5: Preparation of 2-[3-[1-[[6-chloro-8-(trifluoromethyl)quinazolin-4-yl]amino]ethyl] pyrazin-2-yl]thiazole-5-carbonitrile (Compound P5)

(P5)

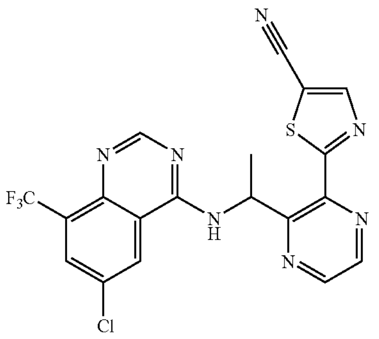

To a 10 mL microwave (MW) vial were charged N-[1-[3-(5-bromothiazol-2-yl)pyrazin-2-yl]ethyl]-6-chloro-8-(trifluoromethyl)quinazolin-4-amine (90 mg, 0.174 mmol), cyclopentylmethylether (7 mL/g) and water (7 mL/g). Then the mixture was degassed with $N_2$ for 5 minutes and kept under a $N_2$ atmosphere. Then potassium acetate (0.192 mmol, 0.0194 g), potassium ferrocyanide (0.026 mmol), X-Phos (0.0174 mmol) and (2-dicyclohexylphosphino-2',4',6'-triisopropyl-1,1'-biphenyl)[2-(2'-amino-1,1'-biphenyl)] palladium(II) methanesulfonate (0.0174 mmol, 0.015 g) were added. Then the vial was sealed and heated at 120° C. in MW for 2 h. The reaction was monitored by LCMS to confirm the conversion. The reaction mass was then diluted with water and extracted with EtOAc twice. The organic layer was washed with brine, dried over anhydrous sodium sulfate, and concentrated to get a crude concentrate. The crude concentrate was then purified by combiflash using 40% EtOAc in cyclohexane. The desired fractions were dried to get 2-[3-[1-[[6-chloro-8-(trifluoromethyl)quinazolin-4-yl]amino]ethyl]pyrazin-2-yl]thiazole-5-carbonitrile (0.015 g, yield 18%).

$^1$H NMR (400 MHz, $CDCl_3$) δ=8.77-8.73 (m, 2H), 8.64 (d, 1H), 8.55 (s, 1H), 8.05 (s, 2H), 7.52 (br d, 1H), 6.98-6.90 (m, 1H), 1.70 (d, 3H).

LC-MS (method 2): retention time: 1.18 min, m/z 462/464 $[M+H]^+$.

Example P8: Preparation of N-[1-[3-(5-bromothiazol-2-yl)pyrazin-2-yl]ethyl]-6,8-bis(trifluoromethyl)quinazolin-4-amine (Compound P8)

(P8)

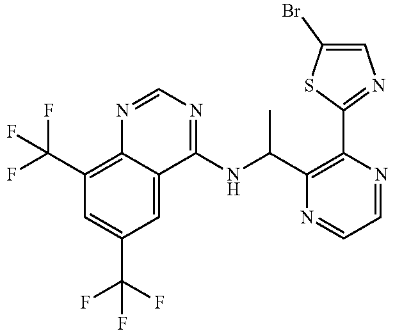

To a stirred mixture of 1-[3-(5-bromothiazol-2-yl) pyrazin-2-yl]ethanamine (100 mg, 0.35 mmol), and 4-chloro-6,8-bis(trifluoromethyl)quinazoline (prepared as described in WO2021/083936) (0.385 mmol) in acetonitrile (20 mL/g) was added cesium carbonate (1.052 mmol) at room temperature. Then reaction mass was stirred at 70° C. for 2 h. The reaction mass was cooled to room temperature, diluted with water, and extracted with ethyl acetate twice. The combined organic layers were washed with brine, dried over anhydrous sodium sulfate and concentrated under reduced pressure. The resulting brown gummy mass was adsorbed on silica and purified by combiflash using a EtOAc/cyclohexane gradient system. The desired fractions were dried to get N-[1-[3-(5-bromothiazol-2-yl)pyrazin-2-yl]ethyl]-6,8-bis(trifluoromethyl)quinazolin-4-amine (110 mg, yield 57%) as a solid.

$^1$H NMR (400 MHz, $CDCl_3$) δ=8.86 (s, 1H), 8.65 (d, 1H), 8.59 (d, 1H), 8.34 (s, 1H), 8.26 (s, 1H), 8.13 (br d, 1H), 8.02 (s, 1H), 6.92-6.85 (m, 1H), 1.71 (d, 3H).

LC-MS (method 2): retention time: 1.17 min, m/z 549/551 $[M+H]^+$.

Example P7: Preparation of 2-[3-[1-[[6,8-bis(trifluoromethyl)quinazolin-4-yl]amino]ethyl]pyrazin-2-yl]thiazole-5-carbonitrile (Compound P7)

(P7)

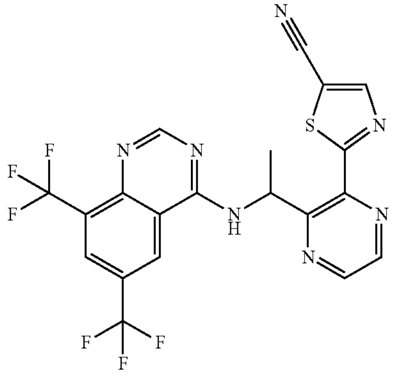

To a 10 mL microwave vial were charged N-[1-[3-(5-bromothiazol-2-yl)pyrazin-2-yl]ethyl]-6,8-bis(trifluoromethyl)quinazolin-4-amine (70 mg, 0.127 mmol) cyclopentylmethylether (7 mL/g) and water (7 mL/g). Then the mixture was degassed with $N_2$ for 5 minutes and kept under a $N_2$ atmosphere. Then potassium acetate (0.1402 mmol, 0.0142 g), potassium ferrocyanide (0.0637 mmol), X-Phos (0.0127 mmol) and (2-dicyclohexylphosphino-2',4',6'-triisopropyl-1,1'-biphenyl)[2-(2'-amino-1,1'-biphenyl)]palladium (II) methanesulfonate (0.0127 mmol, 0.011 g) were added in the vial. Then the vial was sealed and heated at 120° C. in MW for 2 h. The reaction was monitored by LCMS to confirm the conversion. The reaction mass was diluted with water and was extracted with EtOAc twice. The combined organic layers were washed with brine, dried over anhydrous sodium sulfate, and concentrated to get a crude concentrate. The crude concentrate was purified by combiflash using 40% EtOAc in cyclohexane. The desired fractions were dried to get 2-[3-[1-[[6,8-bis(trifluoromethyl)quinazolin-4-yl]amino]ethyl]pyrazin-2-yl]thiazole-5-carbonitrile (0.013 g, yield 20%) as a white solid.

$^1$H NMR (400 MHz, $CDCl_3$) δ=8.82 (s, 1H), 8.75 (d, 1H), 8.65 (d, 1H), 8.56 (s, 1H), 8.34 (s, 1H), 8.27 (s, 1H), 7.75 (br d, 1H), 7.01-6.93 (m, 1H), 1.73 (d, 3H).

LC-MS (method 2): retention time 1.12 min, m/z 496 $[M+H]^+$.

Example P10: Preparation of 2-[5-[(1S)-1-[[6-chloro-8-(trifluoromethyl)quinazolin-4-yl]amino]ethyl]-1,2,4-triazol-1-yl]thiazole-5-carbonitrile (Compound P10)

(P10)

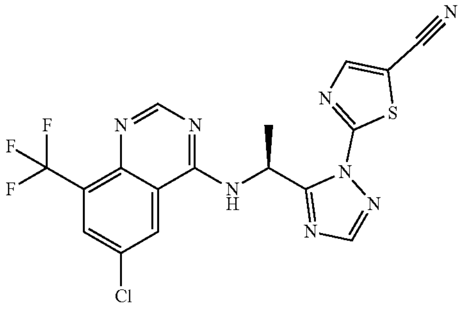

To a stirred mixture of 4,6-dichloro-8-(trifluoromethyl)quinazoline (prepared as described in WO2021/083936) (70 mg, 0.262 mmol), and [(1S)-1-[2-(5-cyanothiazol-2-yl)-1,2,4-triazol-3-yl]ethyl]ammonium; chloride (0.288 mmol) in acetonitrile (1 mL) was added potassium carbonate (0.108 g, 0.786 mmol). The reaction mass was heated at 80° C. for 45 min. Then the reaction mass was cooled to room temperature, diluted with water, and extracted with EtOAc twice. The combined organic layers were washed with brine, dried over anhydrous sodium sulfate, and concentrated. The crude concentrate was adsorbed on silica and purified on combiflash using 40% EtOAc in cyclohexane as eluent to get 2-[5-[(1S)-1-[[6-chloro-8-(trifluoromethyl)quinazolin-4-yl]amino]ethyl]-1,2,4-triazol-1-yl]thiazole-5-carbonitrile (0.05 g, yield 42%) as a pale yellow solid.

$^1$H NMR (400 MHz, DMSO-d6) δ=9.18 (d, 1H), 8.99 (d, 1H), 8.68 (s, 1H), 8.43 (s, 1H), 8.28 (s, 1H), 8.25 (d, 1H), 6.31 (t, 1H), 1.74 (d, 3H).

LC-MS (method 1): retention time 1.52 min, m/z 451/453 $[M+H]^+$.

Example P16: Preparation of 6,8-dibromo-N-[1-[3-(1,2,4-thiadiazol-3-yl)pyrazin-2-yl]ethyl]quinazolin-4-amine (Compound P16)

(P16)

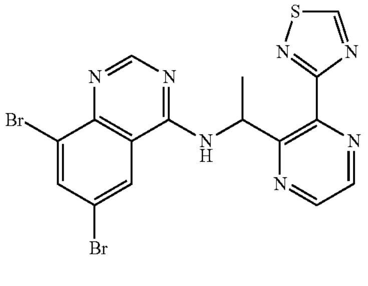

Step A: Preparation of 3-chloropyrazine-2-carboxamide (I-12)

(I-12)

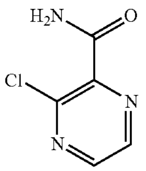

To a mixture of 3-chloropyrazine-2-carboxylic acid (10.00 g, 63.08 mmol) and ammonium chloride (33.74 g, 630.76 mmol) in acetonitrile (100 mL) was added 1-propanphosphonic acid cyclic anhydride (50 mass %) in EtOAc (80.28 g, 126.15 mmol) at room temperature and the mixture was stirred at room temperature for 5 min. The reaction mass was cooled to 0 to 5° C. and triethylamine (64.47 g, 88.8 mL, 630.76 mmol) was added dropwise at this temperature, then stirring continued at 0 to 5° C. for 30 min and at room temperature for 1 h. The reaction mixture was diluted with water (100 mL) and the product extracted with EtOAc (7x300 mL). The combined organic layers were washed with brine, dried over sodium sulfate and concentrated in vacuo. The residue was purified by combiflash using silica gel (EtOAc gradient in cyclohexane) to afford 3-chloropyrazine-2-carboxamide (8.3 g) as pale brown solid.

$^1$H NMR (DMSO-d6) δ: 8.69 (d, 1H), 8.63 (d, 1H), 8.20 (br s, 1H), 7.94 (br s, 1H).

Step B: Preparation of 5-(3-chloropyrazin-2-yl)-1,3,4-oxathiazol-2-one (I-13)

(I-13)

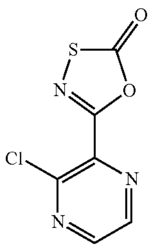

To a suspension of 3-chloropyrazine-2-carboxamide (4 g, 25.3 mmol) in toluene (60 mL) was added S-chlorochloromethanethioate (9.98 g, 6.43 mL, 76.16 mmol) at room temperature. After addition, the reaction mass was heated at 110° C. for 6 h, cooled to room temperature and poured into an aq. sat. $NaHCO_3$ solution (100 mL). After stirring at room temperature for 15 min the product was extracted with EtOAc (3x100 mL). The combined organic layers were washed with brine, dried over sodium sulfate and concentrated in vacuo. The residue was purified by combiflash using silica gel (EtOAc gradient in cyclohexane) to afford 5-(3-chloropyrazin-2-yl)-1,3,4-oxathiazol-2-one (4 g) as pale yellow solid.

$^1$H NMR ($CDCl_3$) δ: 8.69 (d, 1H), 8.59 (d, 1H).

Step C: Preparation of ethyl 3-(3-chloropyrazin-2-yl)-1,2,4-thiadiazole-5-carboxylate (I-14)

(I-14)

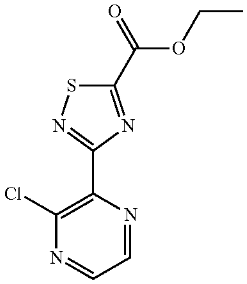

In a 20 mL microwave vial, a mixture of ethyl 5-(3-chloropyrazin-2-yl)-1,3,4-oxathiazol-2-one (0.45 g, 2.09 mmol) and ethyl cyanoformate (0.8272 g, 8.35 mmol) in p-xylene (4.5 mL) was heated in the microwave at 180° C. for 2 h. The reaction mixture was concentrated in vacuo and the residue purified by combiflash using silica gel (EtOAc gradient in cyclohexane) to afford ethyl 3-(3-chloropyrazin-2-yl)-1,2,4-thiadiazole-5-carboxylate (0.3 g) as pale brown solid.

$^1$H NMR ($CDCl_3$) δ: 8.72 (d, 1H), 8.57 (d, 1H), 4.59 (q, 2H), 1.50 (t, 3H).

LC-MS (method 3): retention time 1.05 min, m/z 271/273 $[M+H]^+$.

Step D: Preparation of 3-(3-chloropyrazin-2-yl)-1,2,4-thiadiazole (I-15)

(I-15)

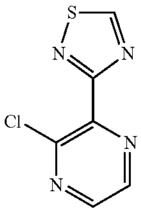

To a solution of ethyl 3-(3-chloropyrazin-2-yl)-1,2,4-thiadiazole-5-carboxylate (2.9 g, 10.71 mmol) in ethanol (43.5 mL) was added a solution of sodium hydroxide (0.47 g, 11.78 mmol) in water (29 mL) at room temperature. After addition, the reaction mass was heated at 100° C. for 1 h, cooled and concentrated in vacuo. The residue was diluted with water (290 mL), extracted with EtOAc (2x30 mL) and the aqueous layer acidified using conc. HCl (2.1426 mL, 21.426 mmol) at room temperature. The acidified aq. mixture was heated at 100° C. for 1 h, then neutralized with an aq. sat. $NaHCO_3$ solution and the product extracted with EtOAc (3x50 mL). The combined organic layers were washed with brine, dried over sodium sulfate and concentrated to afford 3-(3-chloropyrazin-2-yl)-1,2,4-thiadiazole (2 g) as brown solid.

$^1$H NMR ($CDCl_3$) δ: 10.06 (s, 1H), 8.73 (d, 1H), 8.56 (d, 1H).

LC-MS (method 3): retention time 0.67 min, m/z 199/201 $[M+H]^+$. LC-MS (method 3): retention time 1.05 min, m/z 271/273 $[M+H]^+$.

Step E: Preparation of 1-[3-(1,2,4-thiadiazol-3-yl)pyrazin-2-yl]ethanone (I-16)

(I-16)

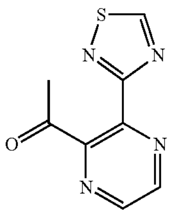

A solution of 3-(3-chloropyrazin-2-yl)-1,2,4-thiadiazole (2 g, 10.06 mmol) and tributyl(1-ethoxyvinyl) stannane (4.72 g, 13.09 mmol) in toluene (30 mL) was purged with nitrogen for 5 min. Then $Pd(PPh_3)_4$ (1.20 g, 1 mmol) was added and the reaction mass heated at 110° C. for 2 h, then at 90° C. for 20 h. The mixture was diluted with acetonitrile (20 mL), and water (20 mL) followed by conc. HCl (2 mL) were added. The reaction mixture was stirred at room temperature for 5 h, neutralized with an aq. sat. $NaHCO_3$ solution and the product extracted with EtOAc (2×50 mL). The combined organic layers were washed with brine, dried over sodium sulfate and concentrated in vacuo. The residue was purified by combiflash using silica gel (EtOAc gradient in cyclohexane) to afford 1-[3-(1,2,4-thiadiazol-3-yl)pyrazin-2-yl]ethanone (1.7 g, 80 mass %) as light yellow solid.

$^1$H NMR ($CDCl_3$) δ: 9.88 (s, 1H), 8.76 (d, 1H), 8.63 (d, 1H), 2.70 (s, 3H).

LC-MS (method 3): retention time 0.18 min, m/z 207 $[M+H]^+$.

Step F: Preparation of 1-[3-(1,2,4-thiadiazol-3-yl)pyrazin-2-yl]ethanamine (I-17)

(I-17)

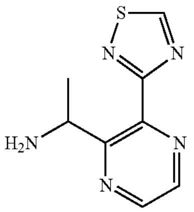

To a mixture of 1-[3-(1,2,4-thiadiazol-3-yl)pyrazin-2-yl]ethanone (1 g, 3.88 mmol, 80 mass %) and 7M ammonia in methanol (16.62 mL, 116.38 mmol) was added titanium(IV) isopropoxide (2.2 g, 2.22 mL, 7.76 mmol) at 0 to 5° C. After addition, the reaction mass was warmed to room temperature and stirred for 16 h. Then sodium borohydride (0.232 g, 5.82 mmol) was added at 0 to 5° C., the mixture warmed to room temperature and stirred for another 0.5 h. The reaction mass was diluted with water (5 mL) and concentrated. The residue was diluted with an ice cold 2N HCl solution (30 mL) and the mixture concentrated. The residue was diluted with MeOH (50 mL), solid Na2CO3 was added, the mixture stirred at room temperature for 30 min and filtered through a celite bed. The celite bed was washed with additional MeOH and the combined filtrate concentrated. The residue was purified by combiflash using silica gel (MeOH gradient in EtOAc) to afford 1-[3-(1,2,4-thiadiazol-3-yl)pyrazin-2-yl]ethanamine (0.7 g, 90 mass %) as light brown gummy mass which solidified upon standing.

$^1$H NMR (DMSO-d6) δ: 10.47 (s, 1H), 8.81 (d, 1H), 8.70 (d, 1H), 4.46 (q, 1H), 1.34 (d, 3H).

LC-MS (method 2): retention time 0.18 min, m/z 208 $[M+H]^+$.

Step G: Preparation of 6,8-dibromo-N-[1-[3-(1,2,4-thiadiazol-3-yl)pyrazin-2-yl]ethyl]quinazolin-4-amine (Compound P16)

(P16)

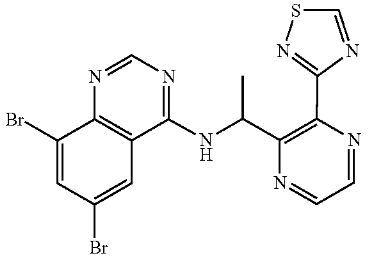

To a mixture of 6,8-dibromo-4-chloro-quinazoline (prepared as described in WO2021/083936) (0.062 g, 0.19 mmol) and 1-[3-(1,2,4-thiadiazol-3-yl)pyrazin-2-yl]ethanamine (0.04 g, 0.19 mmol) in acetonitrile (1 mL) was added potassium carbonate (0.053 g, 0.39 mmol). After addition, the reaction mass was heated at 80° C. for 20 min. The mixture was filtered through a celite bed, the celite bed washed with EtOAc and the filtrate concentrated in vacuo. The residue was purified by combiflash using silica gel (EtOAc gradient in cyclohexane) to afford 6,8-dibromo-N-[1-[3-(1,2,4-thiadiazol-3-yl)pyrazin-2-yl]ethyl]quinazolin-4-amine (0.05 g) as white solid.

$^1$H NMR (acetonitrile-d3) δ: 10.09 (s, 1H), 8.59 (d, 1H), 8.56 (d, 1H), 8.15-8.19 (m, 2H), 8.11 (d, 1H), 7.28 (br d, 1H), 6.12 (quin, 1H), 1.65 (d, 3H).

LC-MS: (method 2): retention time 1.06 min, m/z 492/494/496 $[M+H]^+$.

Example P17: Preparation of 2-[5-[(1S)-1-[[8-chloro-6-(trifluoromethyl)quinazolin-4-yl]-methyl-amino]ethyl]-1,2,4-triazol-1-yl]thiazole-5-carbonitrile (Compound P17)

(P17)

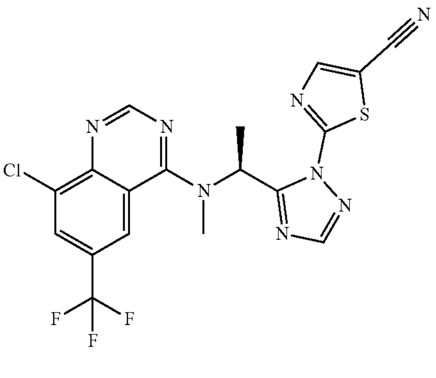

To a mixture of 2-[5-[(1S)-1-[[8-chloro-6-(trifluoromethyl)quinazolin-4-yl]amino]ethyl]-1,2,4-triazol-1-yl]thiazole-5-carbonitrile (Compound P15) (80 mg, 0.178 mmol) and cesium carbonate (173.5 mg, 0.532 mmol) in ACN (0.8 mL) was added iodomethane (127 mg, 0.0555 mL, 0.887 mmol) and the reaction mixture was stirred at room temperature for 2 h. The reaction mass was diluted with water and the product extracted with EtOAc (3×20 mL). The combined organic layers were washed with brine, dried over sodium sulfate and concentrated in vacuo. The residue was purified by silica gel column chromatography (gradient EtOAc in cyclohexane) to afford 2-[5-[(1S)-1-[[8-chloro-6-(trifluoromethyl)quinazolin-4-yl]-methyl-amino]ethyl]-1,2,4-triazol-1-yl]thiazole-5-carbonitrile (P17) as a white solid.

$^1H$ NMR (acetonitrile-d3) δ: 8.57 (s, 1H), 8.16 (d, 1H), 8.11 (d, 1H), 8.08 (s, 1H), 7.80 (s, 1H), 6.67 (q, 1H), 3.34 (s, 3H), 1.84 (d, 3H).

LC-MS (method 2): retention time 1.21 min, m/z 465/467 $[M+H]^+$.

TABLE P

Examples of compounds of formula I

| Entry | IUPAC name | STRUCTURE | RT (min) | $[M + H]^+$ (measured) | Method | MP °C |
|---|---|---|---|---|---|---|
| P1 | 2-[3-[1-[[8-bromo-2-oxo-6-(trifluoromethyl)-1H-quinazolin-4-yl]amino]ethyl]pyrazin-2-yl]thiazole-5-carbonitrile | 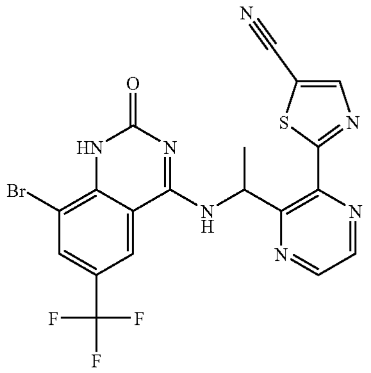 | 1.15 | 520/522 $[M - H]^-$ | 2 | 190-192 |
| P2 | 2-[5-[(1S)-1-[[8-bromo-2-oxo-6-(trifluoromethyl)-1H-quinazolin-4-yl]amino]ethyl]-1,2,4-triazol-1-yl]thiazole-5-carbonitrile | 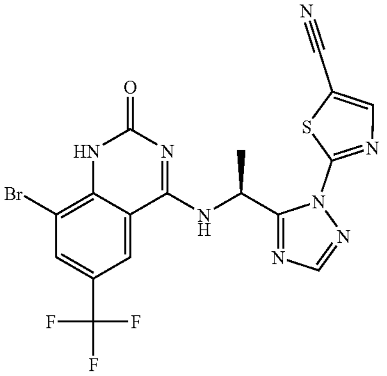 | 0.90 | 511/513 | 2 | 164-168 |
| P3 | 8-bromo-N-[1-[3-(5-bromothiazol-2-yl)pyrazin-2-yl]ethyl]-2-chloro-6-(trifluoromethyl)quinazolin-4-amine | 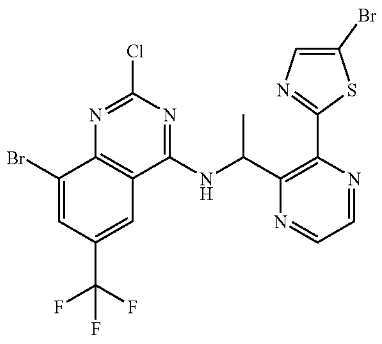 | 1.22 | 591/593/595 $[M - H]^-$ | 2 | 197-199 |

TABLE P-continued

| Entry | IUPAC name | STRUCTURE | RT (min) | [M + H]+ (measured) | Method | MP °C |
|---|---|---|---|---|---|---|
| | Examples of compounds of formula I | | | | | |
| P4 | 8-bromo-4-[1-[3-(5-bromothiazol-2-yl)pyrazin-2-yl]ethylamino]-6-(trifluoromethyl)-1H-quinazolin-2-one | 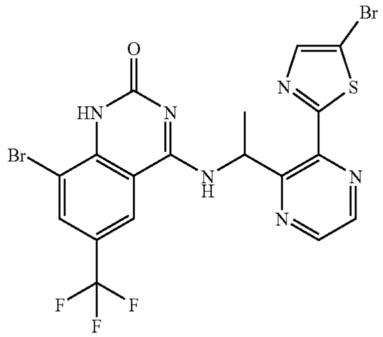 | 1.14 | 575/577/579 | 2 | 246-248 |
| P5 | 2-[3-[1-[[6-chloro-8-(trifluoromethyl)quinazolin-4-yl]amino]ethyl]pyrazin-2-yl]thiazole-5-carbonitrile | 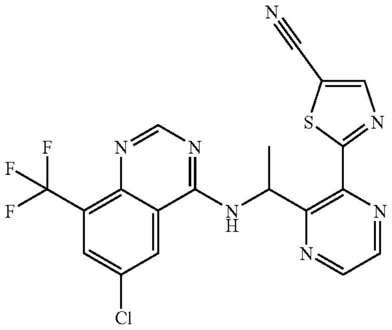 | 1.18 | 462/464 | 2 | 248-250 |
| P6 | N-[1-[3-(5-bromothiazol-2-yl)pyrazin-2-yl]ethyl]-6-chloro-8-(trifluoromethyl)quinazolin-4-amine | 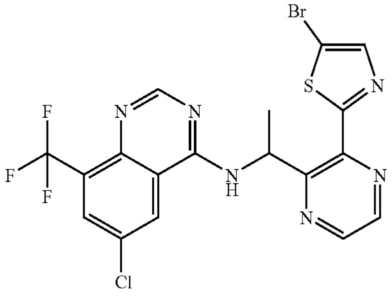 | 1.30 | 513/515/517 $[M-H]^-$ | 2 | 221-223 |
| P7 | 2-[3-[1-[6,8-bis(trifluoromethyl)quinazolin-4-yl]amino]ethyl]pyrazin-2-yl]thiazole-5-carbonitrile | 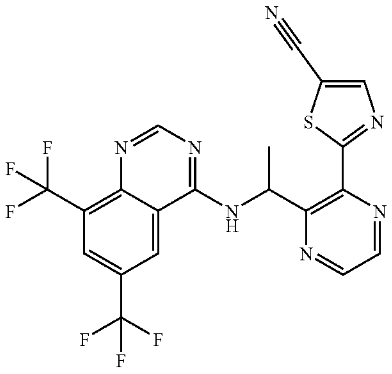 | 1.12 | 496 | 2 | 98-100 |

TABLE P-continued

Examples of compounds of formula I

| Entry | IUPAC name | STRUCTURE | RT (min) | [M + H]$^+$ (measured) | Method | MP °C |
|---|---|---|---|---|---|---|
| P8 | N-[1-[3-(5-bromothiazol-2-yl)pyrazin-2-yl]ethyl]-6,8-bis(trifluoromethyl)quinazolin-4-amine | 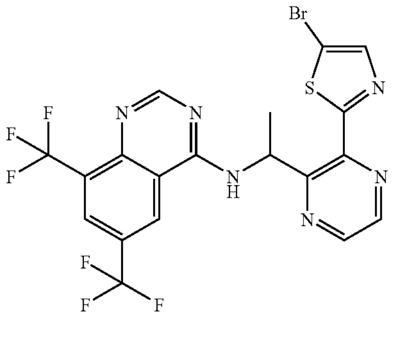 | 1.17 | 549/551 | 2 | 176-178 |
| P9 | 2-[5-[(1S)-1-[[8-bromo-2-chloro-6-(trifluoromethyl)quinazolin-4-yl]amino]ethyl]-1,2,4-triazol-1-yl]thiazole-5-carbonitrile | 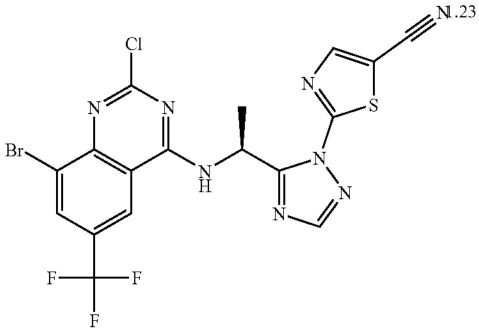 | 1.23 | 529/531/533 | 2 | |
| P10 | 2-[5-[(1S)-1-[[6-chloro-8-(trifluoromethyl)quinazolin-4-ylamino]ethyl]-1,2,4-triazol-1-yl]thiazole-5-carbonitrile | 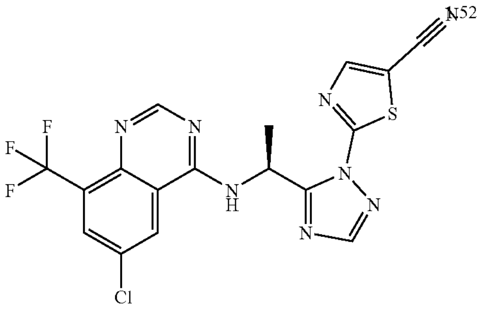 | 1.52 | 451/453 | 1 | 210-212 |
| P11 | 2-[5-[(1S)-1-[[6-chloro-8-(trifluoromethyl)quinazolin-4-yl]-methyl-amino]ethyl]-1,2,4-triazol-1-yl]thiazole-5-carbonitrile | 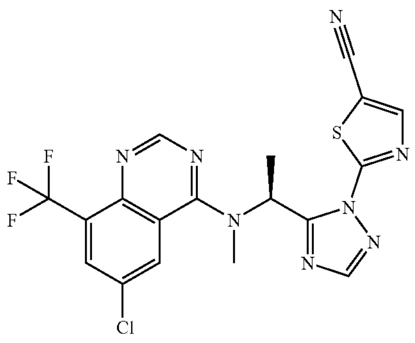 [SMILES: C[C@@H](c1ncnn1-c1ncc(C#N)s1)N(C)c1ncnc2c(C(F)(F)F)cc(Cl)cc12] | 1.14 | 465/467 | 2 | 168-171 |

TABLE P-continued

| Entry | IUPAC name | STRUCTURE | RT (min) | [M + H]+ (measured) | Method | MP °C |
|---|---|---|---|---|---|---|
| Examples of compounds of formula I | | | | | | |
| P12 | 2-[3-[1-[[8-chloro-6-(trifluoromethyl)quinazolin-4-yl]amino]ethyl]pyrazin-2-yl]thiazole-5-carbonitrile | 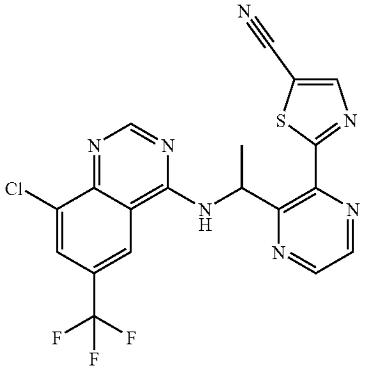 | 1.22 | 462/464 | 3 | 253-255 |
| P13 | 6-chloro-N-[1-[3-(1,2,4-thiadiazol-3-yl)pyrazin-2-yl]ethyl]-8-(trifluoromethyl)quinazolin-4-amine | 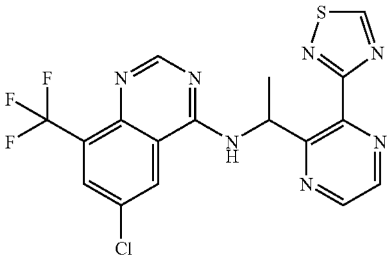 | 1.14 | 438/440 | 3 | 209-211 |
| P14 | 2-[5-[(1S)-1-[(6,8-dibromoquinazolin-4-yl)amino]ethyl]-1,2,4-triazol-1-yl]thiazole-5-carbonitrile | 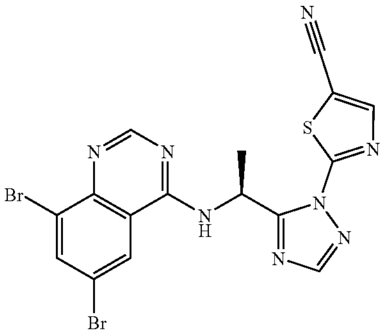 | 1.08 | 503/505/507 [M − H]− | 2 | |
| P15 | 2-[5-[(1S)-1-[[8-chloro-6-(trifluoromethyl)quinazolin-4-yl]amino]ethyl]-1,2,4-triazol-1-yl]thiazole-5-carbonitrile | 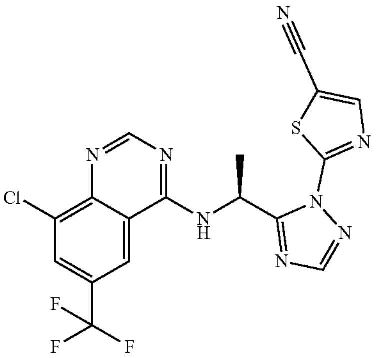 [SMILES: C[C@H](Nc1ncnc2c(Cl)cc(C(F)(F)F)cc12)c1ncnn1-c1ncc(C#N)s1] | 1.16 | 451/453 | 2 | 212-214 |

TABLE P-continued

| Examples of compounds of formula I | | | | | | |
|---|---|---|---|---|---|---|
| Entry | IUPAC name | STRUCTURE | RT (min) | [M + H]+ (measured) | Method | MP °C |
| P16 | 6,8-dibromo-N-[1-[3-(1,2,4-thiadiazol-3-yl)pyrazin-2-yl]ethyl]quinazolin-4-amine | 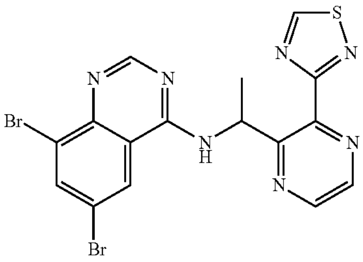 [SMILES: CC(Nc1ncnc2c(Br)cc(Br)cc12)c1nccnc1-c1ncsn1] | 1.06 | 492/494/496 | 2 | 226-229 |
| P17 | 2-[5-[(1S)-1-[[8-chloro-6-(trifluoromethyl)quinazolin-4-yl]-methyl-amino]ethyl]-1,2,4-triazol-1-yl]thiazole-5-carbonitrile | 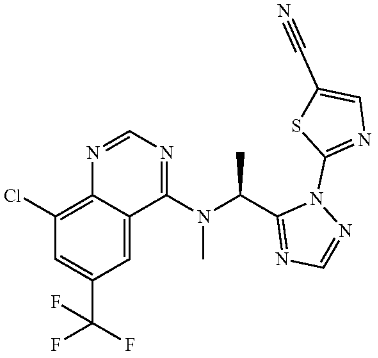 [SMILES: C[C@@H](c1ncnn1-c1ncc(C#N)s1)N(C)c1ncnc2c(Cl)cc(C(F)(F)F)cc12] | 1.21 | 465/467 | 2 | 104-107 |
| P18 | 8-chloro-N-[1-[3-(1,2,4-thiadiazol-3-yl)pyrazin-2-yl]ethyl]-6-(trifluoromethyl)quinazolin-4-amine | 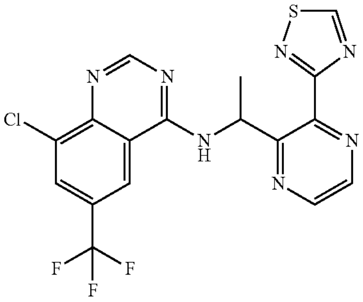 [SMILES: CC(Nc1ncnc2c(Cl)cc(C(F)(F)F)cc12)c1nccnc1-c1ncsn1] | 1.02 | 436/438 [M − H]− | 2 | 244-246 |
| P19 | 2-[3-[1-[(6,8-dibromoquinazolin-4-yl)amino]ethyl]pyrazin-2-yl]thiazole-5-carbonitrile | 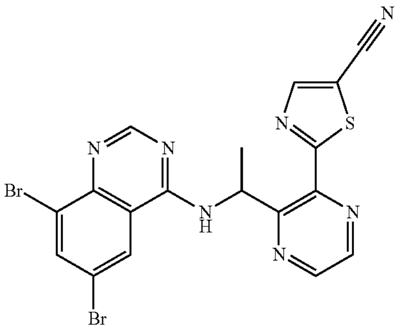 [SMILES: CC(Nc1ncnc2c(Br)cc(Br)cc12)c1nccnc1-c1ncc(C#N)s1] | 1.24 | 516/518/520 | 3 | |

TABLE P-continued

Examples of compounds of formula I

| Entry | IUPAC name | STRUCTURE | RT (min) | [M + H]$^+$ (measured) | Method | MP °C |
|---|---|---|---|---|---|---|
| P20 | 2-[5-[(1S)-1-[(8-chloro-6-iodo-quinazolin-4-yl)amino]ethyl]-1,2,4-triazol-1-yl]thiazole-5-carbonitrile | 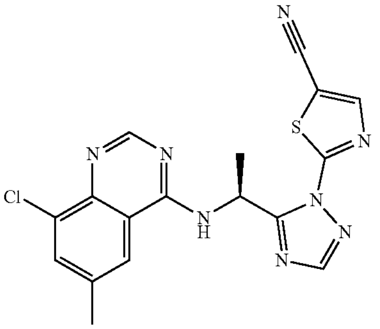 [SMILES: Cc1cc(Cl)c2ncnc(N[C@@H](C)c3ncnn3-c3ncc(C#N)s3)c2c1] | 1.17 | 509/511 | 3 | |
| P21 | 8-chloro-N-[1-[3-(1,2,4-thiadiazol-3-yl)pyrazin-2-yl]ethyl]-6-(trifluoromethylsulfonyl)quinazolin-4-amine | 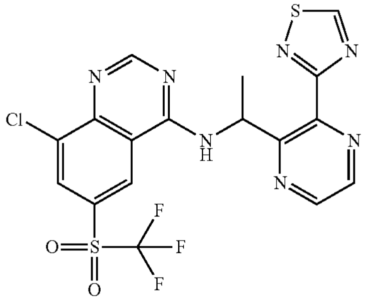 [SMILES: CC(Nc1ncnc2c(Cl)cc(S(=O)(=O)C(F)(F)F)cc12)c1nccnc1-c1ncsn1] | 1.04 | 500/502 [M − H]$^-$ | 2 | |
| P22 | 2-[5-[(1S)-1-[[8-chloro-6-(trifluoromethylsulfonyl)quinazolin-4-yl]amino]ethyl]-1,2,4-triazol-1-yl]thiazole-5-carbonitrile | 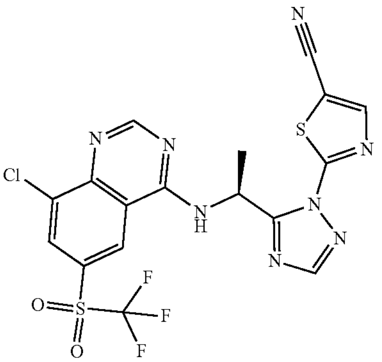 [SMILES: C[C@H](Nc1ncnc2c(Cl)cc(S(=O)(=O)C(F)(F)F)cc12)c1ncnn1-c1ncc(C#N)s1] | 1.09 | 513/515 [M − H]$^-$ | 2 | 200-202 |
| P23 | 2-[3-[1-[[8-bromo-2-chloro-6-(trifluoromethyl)quinazolin-4-yl]amino]ethyl]pyrazin-2-yl]thiazole-5-carbonitrile | 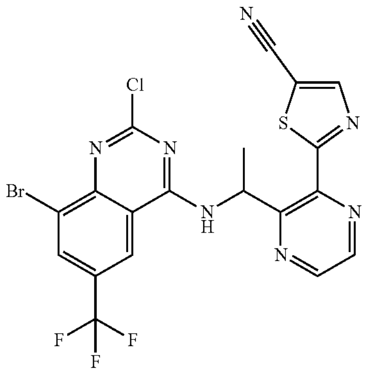 [SMILES: CC(Nc1nc(Cl)nc2c(Br)cc(C(F)(F)F)cc12)c1nccnc1-c1ncc(C#N)s1] | 1.16 | 538/540/542 [M − H]$^-$ | 2 | |

ABBREVIATIONS USED IN SYNTHESIS SCHEMES AND PREPARATORY EXAMPLES

ACN acetonitrile
AcOH acetic acid
Boc t-butoxycarbonyl
DBU 1,8-diazabicyclo[5.4.0]undec-7-ene
DCM dichloromethane
DDQ 2,3-dichloro-5,6-dicyano-1,4-benzoquinone
DMA dimethylacetamide
DMAP 4-dimethylaminopyridine
DMSO dimethyl sulfoxide DMSO-d6 deuterated dimethylsulfoxide
OPEN diphenylethylenediamine
$Et_3N$ triethylamine
EtOAc ethyl acetate
EtOH ethanol
HCl hydrochloric acid
MeCN acetonitrile
MeOH methanol
$MgSO_4$ magnesium sulfate
Ms methanesulfonyl (mesyl)
$Na_2CO_3$ sodium carbonate
$NaHCO_3$sodium hydrogencarbonate
NaOH sodium hydroxide
n-Bu n-butyl
n-BuLi n-butyl lithium
NHC N-heterocyclic carbene
$NH_4OH$ ammonium hydroxide
NPhth phthalimide-1-yl
OMs mesylate group
OTf triflate group
OTs tosylate group
$PdCl_2$dppf 1,1'-bis(diphenylphosphino)ferrocene]palladium(II) dichloride
$Pd_2(dba)_3$ Tris(dibenzylideneacetone)dipalladium(0)
T3P propanephosphonic acid anhydride
TBME tert-butyl methyl ether
TEA triethylamine
TEMPO (2,2,6,6-tetramethylpiperidin-1-yl)oxidanyl
Tf trifluoromethanesulfonyl (triflyl)
TFA trifluoroacetic acid
THE tetrahydrofuran
Ts p-toluenesulfonyl (tosyl)
X-Phos 2-dicyclohexylphosphino-2',4',6'-triisopropylbiphenyl
X-Phos Pd G2 chloro(2-dicyclohexylphosphino-2',4',6'-triisopropyl-1,1'-biphenyl)[2-(2'-amino-1,1'-biphenyl)] palladium(II)
$Zn(CN)_2$ zinc cyanide
aq. aqueous
° C. degrees Celsius
conc. concentrated
equiv. equivalent
h hour(s)
LC/MS or LC-MS liquid chromatography mass spectrometry
M molar
MHz megahertz
min minutes
mp or M.P. melting point
NMR nuclear magnetic resonance
ppm parts per million
RT room temperature
Rt retention time
RBF round-bottom flask

BIOLOGICAL EXAMPLES

The Examples which follow serve to illustrate the invention. Certain compounds of the invention can be distinguished from known compounds by virtue of greater efficacy at low application rates, which can be verified by the person skilled in the art using the experimental procedures outlined in the Examples, using lower application rates if necessary, for example 50 ppm, 24 ppm, 12.5 ppm, 6 ppm, 3 ppm, 1.5 ppm, 0.8 ppm or 0.2 ppm.

Example B1: Activity Against *Chilo suppressalis* (Striped Rice Stemborer)

24-well microtiter plates with artificial diet were treated with aqueous test solutions prepared from 10,000 ppm DMSO stock solutions by pipetting. After drying, the plates were infested with L2 larvae (6-8 per well).

The samples were assessed for mortality, anti-feeding effect, and growth inhibition in comparison to untreated samples 6 days after infestation. Control of *Chilo suppressalis* by a test sample is given when at least one of the categories mortality, anti-feedant effect, and growth inhibition is higher than the untreated sample.

The following compounds resulted in at least 80% control at an application rate of 200 ppm: P1, P2, P4, P5, P6, P7, P8, P9, P10, P11, P12, P14, P15, P17, P19, P20, P22.

Example B2: Activity Against *Diabrotica balteata* (Corn Root Worm)

Maize sprouts placed onto an agar layer in 24-well microtiter plates were treated with aqueous test solutions prepared from 10,000 ppm DMSO stock solutions by spraying. After drying, the plates were infested with L2 larvae (6 to 10 per well). The samples were assessed for mortality and growth inhibition in comparison to untreated samples 4 days after infestation.

The following compounds gave an effect of at least 80% in at least one of the two categories (mortality or growth inhibition) at an application rate of 200 ppm: P1, P4, P5, P6, P7, P8, P9, P10, P11, P12, P13, P14, P15, P16, P17, P18, P19, P20, P22.

Example B3: Activity Against *Euschistus heros* (Neotropical Brown Stink Bug)

Soybean leaves on agar in 24-well microtiter plates were sprayed with aqueous test solutions prepared from 10,000 ppm DMSO stock solutions. After drying the leaves were infested with $N_2$ nymphs. The samples were assessed for mortality and growth inhibition in comparison to untreated samples 5 days after infestation.

The following compounds gave an effect of at least 80% in at least one of the two categories (mortality or growth inhibition) at an application rate of 200 ppm: P10, P17.

Example B4: Activity Against *Plutella xylostella* (Diamond Back Moth)

24-well microtiter plates with artificial diet were treated with aqueous test solutions prepared from 10,000 ppm DMSO stock solutions by pipetting. After drying, *Plutella* eggs were pipetted through a plastic stencil onto a gel blotting paper and the plate was closed with it. The samples were assessed for mortality and growth inhibition in comparison to untreated samples 8 days after infestation.

The following compounds gave an effect of at least 80% in at least one of the two categories (mortality or growth inhibition) at an application rate of 200 ppm: P1, P2, P4, P5, P7, P8, P9, P10, P11, P12, P13, P14, P15, P16, P17, P18, P19, P20, P22.

Example B5: Activity Against *Spodoptera littoralis* (Egyptian Cotton Leaf Worm)

Cotton leaf discs were placed onto agar in 24-well microtiter plates and sprayed with aqueous test solutions prepared from 10,000 ppm DMSO stock solutions. After drying the leaf discs were infested with five L1 larvae. The samples were assessed for mortality, anti-feeding effect, and growth inhibition in comparison to untreated samples 3 days after infestation. Control of *Spodoptera littoralis* by a test sample is given when at least one of the categories mortality, anti-feedant effect, and growth inhibition is higher than the untreated sample.

The following compounds resulted in at least 80% control at an application rate of 200 ppm: P2, P5, P7, P10, P11, P12, P13, P14, P15, P16, P17, P19, P20, P22.

Example B6: Activity Against *Myzus persicae* (Green Peach Aphid) Feeding/Contact Activity Sunflower leaf discs were placed onto agar in a 24-well microtiter plate and sprayed with aqueous test solutions prepared from 10,000 ppm DMSO stock solutions. After drying, the leaf discs were infested with an aphid population of mixed ages. The samples were assessed for mortality 6 days after infestation.

The following compounds resulted in at least 80% mortality at an application rate of 200 ppm: P14.

Example B7: Activity Against *Myzus persicae* (Green Peach Aphid) Intrinsic Activity Test compounds prepared from 10,000 ppm DMSO stock solutions were applied by pipette into 24-well microtiter plates and mixed with sucrose solution. The plates were closed with a stretched Parafilm. A plastic stencil with 24 holes was placed onto the plate and infested pea seedlings were placed directly on the Parafilm. The infested plate was closed with a gel blotting paper and another plastic stencil and then turned upside down. The samples were assessed for mortality 5 days after infestation.

The following compounds resulted in at least 80% mortality at a test rate of 12 ppm: P15.

Example B8: Activity Against *Frankliniella occidentalis* (Western Flower *Thrips*)

Sunflower leaf discs were placed on agar in 24-well microtiter plates and sprayed with aqueous test solutions prepared from 10,000 DMSO stock solutions. After drying the leaf discs were infested with a *Frankliniella* population of mixed ages. The samples were assessed for mortality 7 days after infestation.

The following compounds resulted in at least 80% mortality at an application rate of 200 ppm: P20.

Example B9: Comparison of the Insecticidal Activity of Compound P5 According to the Invention with a Structurally Most Closely Comparable Compound from the State of the Art Activity of compound P5 according to the preparatory examples and of compound P.118 from WO 21/083936 against *Plutella xylostella* (Example B4) and *Diabrotica balteata* (Example B2) is summarized in Table B9.

TABLE B9

| Compound | Concentration (ppm) | Insect | Mortality (%) |
|---|---|---|---|
| Compound P5 | 12.5 | *Plutella xylostella* | 50 |
| 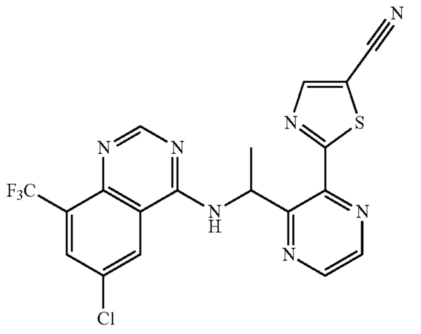 [SMILES: CC(Nc1ncnc2c(C(F)(F)F)cc(Cl)cc12)c1nccnc1-c1ncc(C#N)s1] | 3.125 | *Diabrotica balteata* | 100 |
| Present invention | | | |
| Described in WO 21/083936 as | 12.5 | *Plutella xylostella* | 0 |
| compound P.118 | 3.125 | *Diabrotica balteata* | 0 |
| 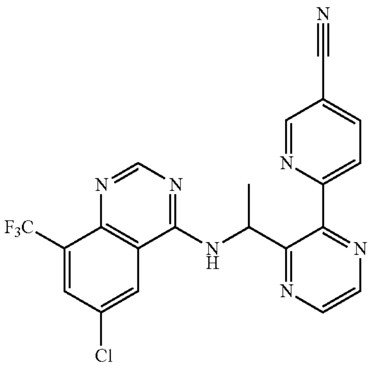 [SMILES: CC(Nc1ncnc2c(C(F)(F)F)cc(Cl)cc12)c1nccnc1-c1ccc(C#N)cn1] | | | |
| State of the art | | | |

Table B9 shows that compound P5 according to the invention exert a substantially better insecticidal action on *Plutella xylostella* and *Diabrotica balteata* than the compound from the state of the art. This enhanced effect was not to be expected on the basis of the structural similarity of these compounds.

The invention claimed is:

1. A compound of the formula I

I

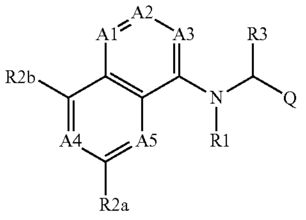

wherein:

$A_1$, $A_2$ and $A_3$ are, independently from each other, N or $CR_Y$; or $A_1$=$A_2$-$A_3$, taken together, are NR—C(=X)—N;

$A_4$ and $A_5$ are, independently from each other, N or $CR_{YY}$;

Q is $Q^a$

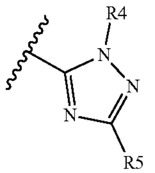

or $Q^b$

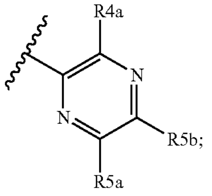

R is hydrogen, $C_1$-$C_3$alkyl, $C_1$-$C_3$haloalkyl, $C_1$-$C_3$alkoxy, or $C_1$-$C_3$haloalkoxy;

$R_1$ is hydrogen, $C_1$-$C_6$alkyl, $C_1$-$C_6$cyanoalkyl, aminocarbonyl$C_1$-$C_6$alkyl, hydroxycarbonyl$C_1$-$C_6$alkyl, $C_1$-$C_6$nitroalkyl, trimethylsilane$C_1$-$C_6$alkyl, $C_1$-$C_3$alkoxy-$C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_3$-$C_4$cycloalkyl$C_1$-$C_2$alkyl-, $C_3$-$C_4$cycloalkyl$C_1$-$C_2$alkyl- wherein the $C_3$-$C_4$cycloalkyl group is substituted with 1 or 2 halogen atoms, oxetan-3-yl-$CH_2$—, $C_1$-$C_6$alkylcarbonyl, $C_1$-$C_6$alkoxycarbonyl, phenyloxycarbonyl, benzyloxycarbonyl, benzyl, or benzyl substituted with 1 to 3 substituents independently selected from halogen, $C_1$-$C_6$alkoxy and $C_1$-$C_6$haloalkyl;

$R_{2a}$ and $R_{2b}$ are each independently selected from hydrogen, $C_1$-$C_3$alkyl, $C_1$-$C_3$haloalkyl, $C_1$-$C_3$haloalkylsulfanyl, $C_1$-$C_3$alkoxy, $C_1$-$C_3$haloalkoxy, halogen, $NO_2$, $SF_5$, CN, C(O)$NH_2$, C(O)OH, C(S)$NH_2$, $C_3$-$C_6$cycloalkyl, $C_3$-$C_6$cycloalkyl substituted with one to three substituents independently selected from $R_x$, $C_3$-$C_6$cycloalkylcarbonyl, phenyl, phenyl substituted with one to three substituents independently selected from $R_x$, heteroaryl, heteroaryl substituted with one to three substituents independently selected from $R_x$; $OR_6$, piperidin-2-one-1-yl, piperidin-2-one-1-yl substituted with one to two substituents independently selected from $R_x$, pyridin-2-one-1-yl, pyridin-2-one-1-yl substituted with one to two substituents independently selected from $R_x$, azetidin-1-yl, azetidin-1-yl substituted with one to two substituents independently selected from $R_x$, pyrrolidin-1-yl, pyrrolidin-1-yl substituted with one to two substituents independently selected from $R_x$, $C_3$-$C_6$cycloalkyl$C_1$-$C_4$alkyl, $C_3$-$C_6$cycloalkyl$C_1$-$C_4$alkyl substituted with one to two substituents independently selected from $R_z$; $C_3$-$C_6$cycloalkyl$C_1$-$C_3$alkoxy, $C_3$-$C_6$cycloalkyl$C_1$-$C_3$alkoxy substituted with one to two substituents independently selected from $R_x$, $C_1$-$C_5$cyanoalkyl, $C_1$-$C_5$cyanoalkoxy, $C_1$-$C_4$alkylsulfanyl, $C_1$-$C_4$alkylsulfanyl substituted with one to three substituents independently selected from $R_x$, $C_1$-$C_4$alkylsulfonyl, $C_1$-$C_4$alkylsulfonyl substituted with one to three substituents independently selected from $R_x$, $C_1$-$C_4$alkylsulfinyl, and $C_1$-$C_4$alkylsulfinyl substituted with one to three substituents independently selected from $R_x$;

$R_3$ is $C_1$-$C_3$alkyl or $C_1$-$C_3$haloalkyl;

$R_4$ is thiazol-2-yl, thiazol-4-yl, thiazol-5-yl, isothiazol-3-yl, isothiazol-4-yl, isothiazol-5-yl, 1,2,4-thiadiazol-3-yl, 1,3,4-thiadiazol-2-yl, or 1,2,4-thiadiazol-5-yl; or $R_4$ is thiazol-2-yl, thiazol-4-yl, thiazol-5-yl, isothiazol-3-yl, isothiazol-4-yl, isothiazol-5-yl, 1,2,4-thiadiazol-3-yl, 1,3,4-thiadiazol-2-yl, or 1,2,4-thiadiazol-5-yl, each of which, independently of each other, is substituted with one to two substituents independently selected from $C_1$-$C_3$alkyl, $C_1$-$C_3$haloalkyl, $C_1$-$C_3$alkoxy, $C_3$-$C_4$cycloalkyl, halo, hydroxyl, CN, $C_1$-$C_6$haloalkoxy, $C_2$-$C_6$haloalkenyloxy, $C_2$-$C_6$haloalkynyloxy, $C_3$-$C_4$halocycloalkoxy, $NH_2$C(O)—, $NH_2$C(S)—, (OH)N=C($NH_2$)—, and a 5-membered heteroaryl ring optionally substituted by 1 to 3 substituents independently selected from halogen, $C_1$-$C_3$alkyl, $C_1$-$C_3$haloalkyl, $C_1$-$C_3$alkoxy, and $C_1$-$C_3$haloalkoxy;

$R_{4a}$ is thiazol-2-yl, thiazol-4-yl, thiazol-5-yl, isothiazol-3-yl, isothiazol-4-yl, isothiazol-5-yl, 1,2,4-thiadiazol-3-yl, 1,3,4-thiadiazol-2-yl, or 1,2,4-thiadiazol-5-yl; or $R_{4a}$ is thiazol-2-yl, thiazol-4-yl, thiazol-5-yl, isothiazol-3-yl, isothiazol-4-yl, isothiazol-5-yl, 1,2,4-thiadiazol-3-yl, 1,3,4-thiadiazol-2-yl, or 1,2,4-thiadiazol-5-yl each of which, independently of each other, is substituted with one to two substituents independently selected from $C_1$-$C_3$alkyl, $C_1$-$C_3$haloalkyl, $C_1$-$C_3$alkoxy, $C_3$-$C_4$cycloalkyl, halogen, hydroxyl, cyano, and $C_1$-$C_3$haloalkoxy;

$R_5$ is hydrogen, $C_1$-$C_3$alkyl, $C_1$-$C_3$haloalkyl, $C_3$-$C_4$cycloalkyl, $C_1$-$C_3$alkoxy, $C_3$-$C_4$alkoxyC(O)—, ($C_1$-$C_3$alkoxy)$_2$CH—, halogen, CN, $NH_2$C(O), $NH_2$, ($C_1$-$C_3$alkyl)amino, di($C_1$-$C_3$alkyl)amino, hydroxy, $C_3$-$C_4$halocycloalkyl, $C_3$-$C_4$cyanocycloalkyl, $C_2$-$C_6$alkenyl, $C_2$-$C_6$haloalkenyl, $C_2$-$C_6$alkynyl, $C_2$-$C_6$haloalkynyl, $C_1$-$C_4$haloalkylsulfanyl, $C_1$-$C_4$haloalkylsulfinyl, $C_1$-$C_4$haloalkylsulfonyl, $C_1$-$C_4$alkylsulfanyl, $C_1$-$C_4$alkylsulfinyl, $C_1$-$C_4$alkylsulfonyl, $C_1$-$C_3$alkoxy-$C_1$-$C_3$alkyl, $C_1$-$C_3$alkoxy-$C_1$-$C_3$alkoxy-$C_1$-$C_3$alkyl, ($C_1$-$C_3$alkyl)sulfonylamino, ($C_1$-$C_3$alkyl)sulfonyl($C_1$-$C_3$alkyl)

amino, ($C_1$-$C_3$alkyl)NHC(O), ($C_1$-$C_3$alkyl)$_2$NC(O), ($C_1$-$C_3$cycloalkyl)NHC(O), ($C_1$-$C_3$cycloalkyl)($C_1$-$C_3$alkyl)NC(O), ($C_1$-$C_3$alkyl)C(O)($C_1$-$C_3$alkyl)N, ($C_1$-$C_3$alkyl)C(O)NH, ($C_1$-$C_3$alkyl)C(O), ($C_1$-$C_3$alkoxy)C(O), HC(O), diphenylmethanimine, $C_1$-$C_3$haloalkoxy, phenyl, or a 5-membered heteroaromatic ring; or $R_5$ is phenyl substituted with one to three substituents selected from $C_1$-$C_3$alkyl, $C_1$-$C_3$haloalkyl, $C_1$-$C_3$alkoxy, $C_3$-$C_4$cycloalkyl, halogen, CN and hydroxyl; or $R_5$ is a 5-membered heteroaromatic ring substituted with one to three substituents selected from $C_1$-$C_3$alkyl, $C_1$-$C_3$haloalkyl, $C_1$-$C_3$alkoxy, $C_3$-$C_4$cycloalkyl, halogen, CN and hydroxyl;

$R_{5a}$ and $R_{5b}$ are, independently of each other, selected from hydrogen, halogen, CN, $C_1$-$C_3$alkyl, $C_1$-$C_3$haloalkyl, $C_3$-$C_4$cycloalkyl, $C_1$-$C_3$alkoxy, and $C_1$-$C_3$haloalkoxy;

$R_6$ is phenyl, benzyl, heteroaryl, or $C_3$-$C_6$ cycloalkyl; or $R_6$ is phenyl, benzyl, heteroaryl, or $C_3$-$C_6$ cycloalkyl, each of which, independent of each other, is substituted with one to three substituents independently selected from $R_x$;

each $R_x$ is independently selected from halogen, $C_1$-$C_3$alkyl, $C_1$-$C_3$haloalkyl, $C_1$-$C_3$alkoxy, $C_1$-$C_3$haloalkoxy, $NO_2$, $SF_5$, CN, C(O)$NH_2$, C(S)$NH_2$, $C_1$-$C_4$haloalkylsulfanyl, $C_1$-$C_4$haloalkylsulfinyl, $C_1$-$C_4$haloalkylsulfonyl, $C_1$-$C_4$alkylsulfanyl, $C_1$-$C_4$alkylsulfinyl, and $C_1$-$C_4$alkylsulfonyl;

$R_Y$ is selected from hydrogen, $C_1$-$C_3$ alkyl, $C_1$-$C_3$ haloalkyl, hydroxy, $C_1$-$C_3$ alkoxy, $C_1$-$C_3$ haloalkoxy, halogen, CN, and cyclopropyl;

$R_{YY}$ is selected from hydrogen, $C_1$-$C_3$ alkyl, $C_1$-$C_3$ haloalkyl, hydroxy, $C_1$-$C_3$ alkoxy, $C_1$-$C_3$ haloalkoxy, halogen, CN, and cyclopropyl;

$R_Z$ is selected from oxo, halogen, $C_1$-$C_3$ alkyl, $C_1$-$C_3$haloalkyl, $C_1$-$C_3$alkoxy, $C_1$-$C_3$haloalkoxy, and CN; and X is O or S;

or an agrochemically acceptable salt, stereoisomer, enantiomer, tautomer or N-oxide of the compound of formula I.

2. The compound according to claim 1 wherein $A_1$ and, $A_3$ are N and $A_2$ is CH, and $A_4$ is $CR_{YY}$ and $A_5$ is CH.

3. The compound according to claim 1 wherein $R_1$ is hydrogen, methyl, ethyl, cyanomethyl, methoxymethyl, cyclopropyl-methyl, allyl, propargyl, benzyloxycarbonyl, or benzyl.

4. The compound according to claim 1, wherein $R_{2a}$ is halogen, $C_1$-$C_3$haloalkyl, $C_1$-$C_3$haloalkylsulfanyl, $C_1$-$C_3$haloalkoxy, $C_3$-$C_6$cycloalkyl, $C_3$-$C_6$cycloalkyl substituted with one or two substituents independently selected from $C_1$-$C_3$haloalkyl, cyano, and halogen, $C_3$-$C_6$cycloalkyl$C_1$-$C_4$alkyl, $C_3$-$C_6$cycloalkyl$C_1$-$C_4$alkyl substituted with one to three substituents independently selected from $C_1$-$C_3$haloalkyl, cyano, and halogen, $C_1$-$C_5$cyanoalkyl, $C_1$-$C_4$alkylsulfonyl, $C_1$-$C_4$haloalkylsulfonyl, $C_1$-$C_4$alkylsulfinyl, $C_1$-$C_4$haloalkylsulfinyl, $C_3$-$C_6$cycloalkylsulfanyl, $C_3$-$C_6$cycloalkylsulfinyl, or $C_3$-$C_6$cycloalkylsulfonyl.

5. The compound according to claim 1, wherein $R_{2b}$ is halogen, $C_1$-$C_3$haloalkyl, $C_1$-$C_3$haloalkylsulfanyl, $C_1$-$C_3$haloalkylsulfonyl, $C_1$-$C_3$alkoxy, $C_1$-$C_3$haloalkoxy, or CN.

6. The compound according to claim 1, wherein $R_3$ is $C_1$-$C_3$alkyl.

7. The compound according to claim 1, wherein Q is selected from $Q^a$-1 to $Q^a$-11 and $Q^a$-13 to $Q^a$-16

$Q^a$-1

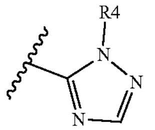

$Q^a$-2

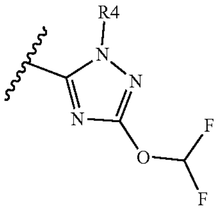

$Q^a$-3

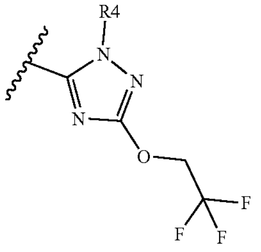

$Q^a$-4

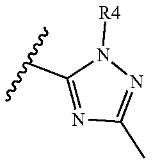

$Q^a$-5

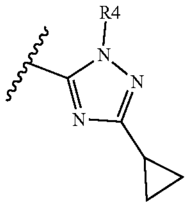

$Q^a$-6

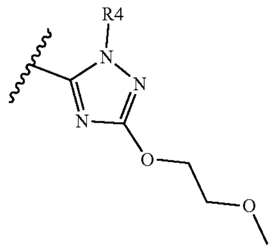

$Q^a$-7

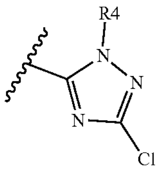

-continued

Q$^a$-8

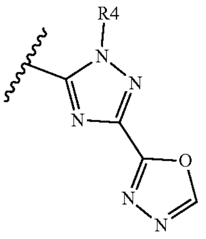

Q$^a$-9

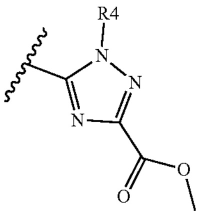

Q$^a$-10

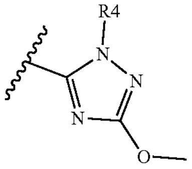

Q$^a$-11

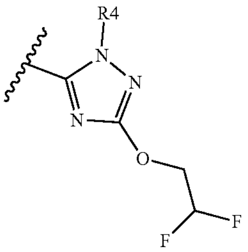

Q$^a$-13

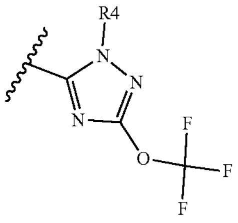

Q$^a$-14

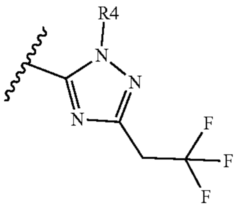

Q$^a$-15

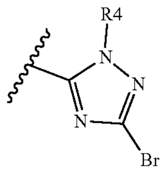

-continued

Q$^a$-16

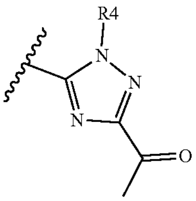

and $R_4$ is thiazol-2-yl, thiazol-4-yl, thiazol-5-yl, 1,2,4-thiadiazol-3-yl, 1,3,4-thiadiazol-2-yl, or 1,2,4-thiadiazol-5-yl, each of which, independently of each other, is unsubstituted or substituted with one to two substituents independently selected from $C_1$-$C_3$alkyl, $C_1$-$C_3$haloalkyl, $C_1$-$C_3$alkoxy, $C_3$-$C_4$cycloalkyl, halo, hydroxyl, CN, $C_1$-$C_6$haloalkoxy, $C_2$-$C_6$haloalkenyloxy, $C_2$-$C_6$haloalkynyloxy, $C_3$-$C_4$halocycloalkoxy, $NH_2C(O)$—, $NH_2C(S)$—, (OH)N═C($NH_2$)—, and a 5-membered heteroaryl ring optionally substituted by 1 to 3 substituents independently selected from halogen, $C_1$-$C_3$alkyl, $C_1$-$C_3$haloalkyl, $C_1$-$C_3$alkoxy, and $C_1$-$C_3$haloalkoxy.

8. The compound according to claim 1, wherein

Q is selected from Q$^b$-1 to Q$^b$-13

Q$^b$-1

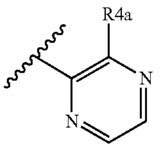

Q$^b$-2

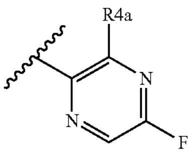

Q$^b$-3

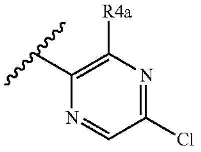

Q$^b$-4

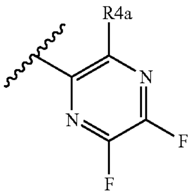

Q$^b$-5

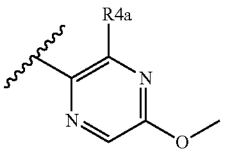

-continued $Q^b$-6

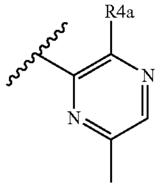

$Q^b$-7

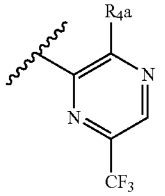

$Q^b$-8

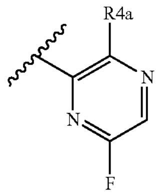

$Q^b$-9

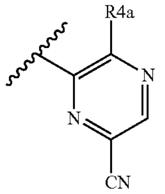

$Q^b$-10

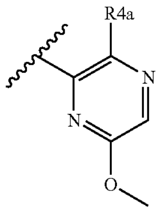

$Q^b$-11

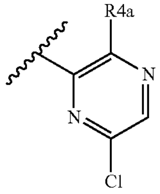

$Q^b$-12

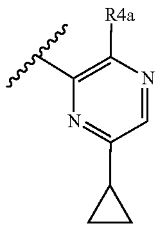

-continued $Q^b$-13

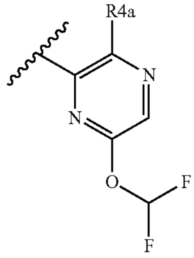

and $R_{4a}$ is thiazol-2-yl, thiazol-4-yl, thiazol-5-yl, 1,2,4-thiadiazol-3-yl, 1,3,4-thiadiazol-2-yl, or 1,2,4-thiadiazol-5-yl, each of which, independently of each other, is unsubstituted or substituted with one to two substituents independently selected from $C_1$-$C_3$alkyl, $C_1$-$C_3$haloalkyl, $C_1$-$C_3$alkoxy, $C_3$-$C_4$cycloalkyl, halogen, hydroxyl, cyano, and $C_1$-$C_3$haloalkoxy.

9. The compound according to claim 1, wherein the formula I is represented by formulae Iaa, Iab, Iac, Iae, or Iag (with asterisk indicating a stereogenic centre):

(Iaa)

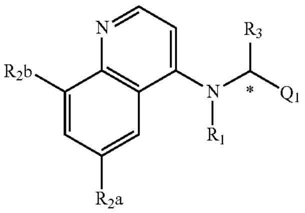

(Iab)

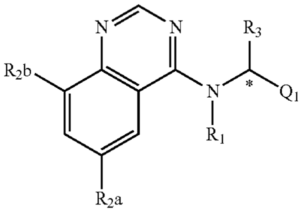

(Iac)

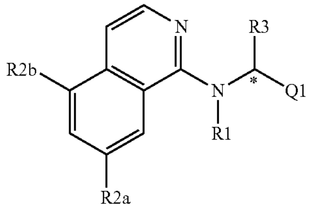

(Iae)

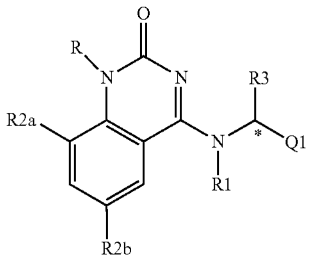

-continued
(Iag)
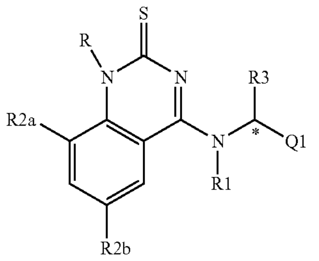
wherein R, $R_1$, $R_{2a}$, $R_{2b}$, and $R_3$, are as defined in claim 1, and $Q_1$ corresponds to Q as defined in claim 1.
10. The compound according to claim 9 wherein $Q_1$ is selected from $Q^{aa}$ to $Q^{ag}$ and $Q^{ba}$ to $Q^{bg}$
$Q^{aa}$
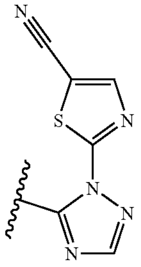
$Q^{ba}$
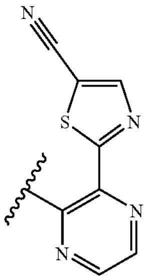
$Q^{ab}$
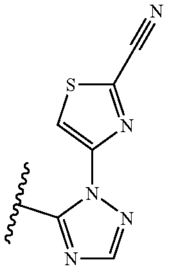
$Q^{bb}$
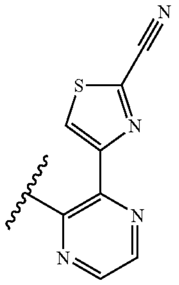
-continued
$Q^{ac}$
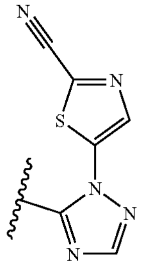
$Q^{bc}$
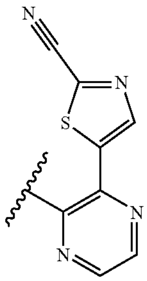
$Q^{ad}$
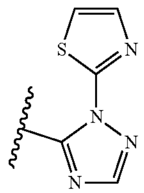
$Q^{bd}$
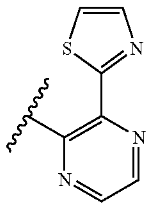
$Q^{ae}$
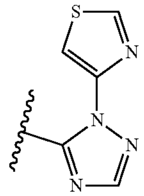
$Q^{be}$
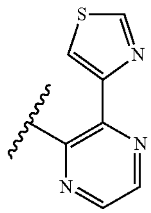
$Q^{af}$
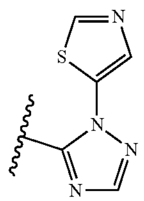

-continued $Q^{bf}$

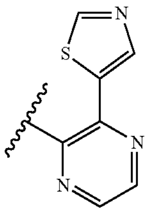

$Q^{ag}$

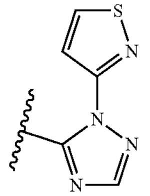

$Q^{bg}$

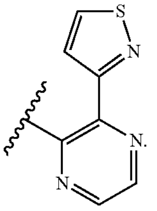

11. A composition comprising a compound as defined in claim 1, one or more auxiliaries and/or diluents, and optionally one or more other active ingredient(s).

12. A method (i) of combating and controlling insects, acarines, nematodes or molluscs which comprises applying to a pest, to a locus of a pest, or to a plant susceptible to attack by a pest an insecticidally, acaricidally, nematicidally or molluscicidally effective amount of a compound as defined in claim 1; or (ii) for the protection of plant propagation material from attack by insects, acarines, nematodes or molluscs, which comprises treating the propagation material or the site where the propagation material is planted, with an effective amount of a compound as defined in claim 1; or (iii) of controlling parasites in or on an animal in need thereof comprising administering an effective amount of a compound as defined in claim 1.

13. A plant propagation material, comprising, treated with, or adhered thereto, a compound as defined in claim 1.

14. The plant propagation material of claim 13, wherein the plant propagation material is a seed.

15. A compound selected from the group consisting of:

P1 2-[3-[1-[[8-bromo-2-oxo-6-(trifluoromethyl)-1H-quinazolin-4-yl]amino]ethyl]pyrazin-2-yl]thiazole-5-carbonitrile

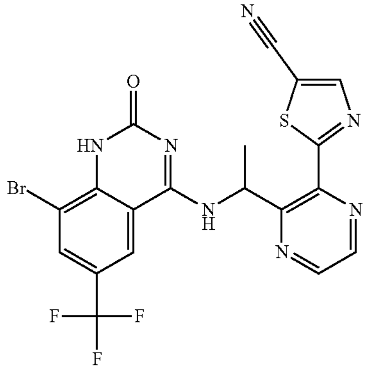 [SMILES: CC(Nc1nc(=O)[nH]c2c(Br)cc(C(F)(F)F)cc12)c1nccnc1-c1ncc(C#N)s1]

P2 2-[5-[(1S)-1-[[8-bromo-2-oxo-6-(trifluoromethyl)-1H-quinazolin-4-yl]amino]ethyl]-1,2,4-triazol-1-yl]thiazole-5-carbonitrile

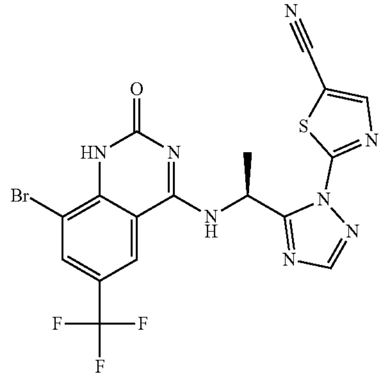 [SMILES: C[C@H](Nc1nc(=O)[nH]c2c(Br)cc(C(F)(F)F)cc12)c1ncnn1-c1ncc(C#N)s1]

-continued
P3 8-bromo-N-[1-[3-(5-bromothiazol-2-yl)pyrazin-2-yl]ethyl]-2-chloro-6-(trifluoromethyl)quinazolin-4-amine
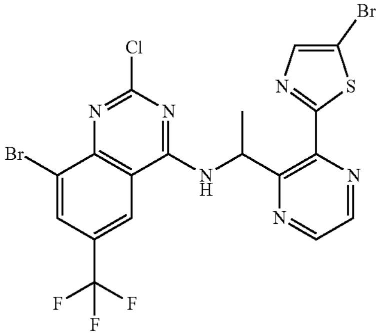 [SMILES: CC(Nc1nc(Cl)nc2c(Br)cc(C(F)(F)F)cc12)c1nccnc1-c1ncc(Br)s1]
P4 8-bromo-4-[1-[3-(5-bromothiazol-2-yl)pyrazin-2-yl]ethylamino]-6-(trifluoromethyl)-1H-quinazolin-2-one
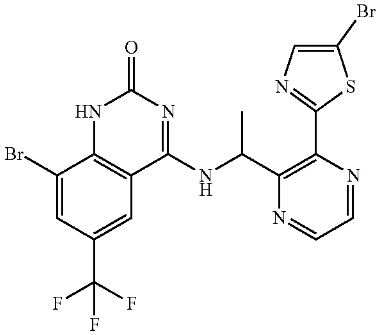 [SMILES: CC(Nc1nc(=O)[nH]c2c(Br)cc(C(F)(F)F)cc12)c1nccnc1-c1ncc(Br)s1]
P5 2-[3-[1-[6-chloro-8-(trifluoromethyl)quinazolin-4-yl]amino]ethyl]pyrazin-2-yl]thiazole-5-carbonitrile
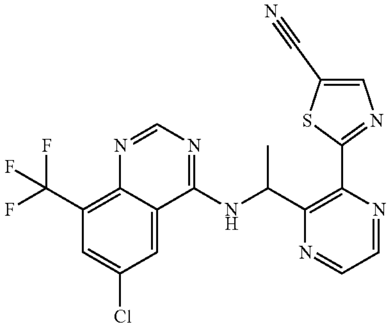 [SMILES: CC(Nc1ncnc2c(C(F)(F)F)cc(Cl)cc12)c1nccnc1-c1ncc(C#N)s1]
P6 N-[1-[3-(5-bromothiazol-2-yl)pyrazin-2-yl]ethyl]-6-chloro-8-(trifluoromethyl)quinazolin-4-amine
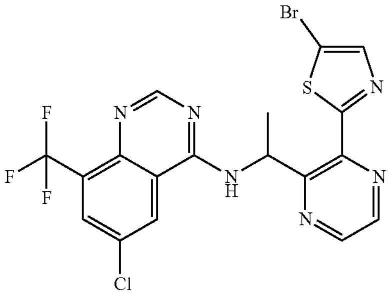 [SMILES: CC(Nc1ncnc2c(C(F)(F)F)cc(Cl)cc12)c1nccnc1-c1ncc(Br)s1]

-continued
P7 2-[3-[1-[[6,8-bis(trifluoromethyl)quinazolin-4-yl]amino]ethyl]pyrazin-2-yl]thiazole-5-carbonitrile
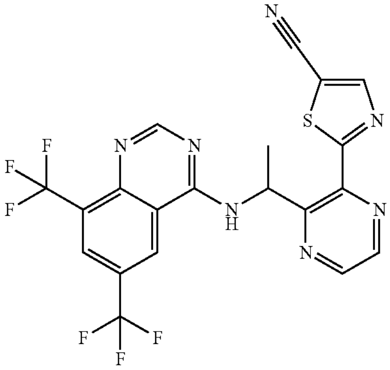 [SMILES: CC(Nc1ncnc2c(C(F)(F)F)cc(C(F)(F)F)cc12)c1nccnc1-c1ncc(C#N)s1]
P8 N-[1-[3-(5-bromothiazol-2-yl)pyrazin-2-yl]ethyl]-6,8-bis(trifluoromethyl)quinazolin-4-amine
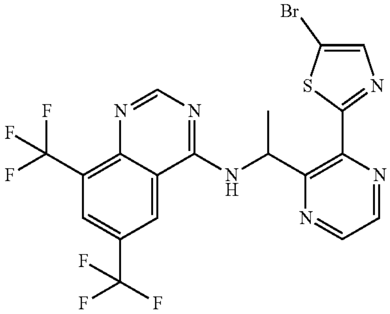 [SMILES: CC(Nc1ncnc2c(C(F)(F)F)cc(C(F)(F)F)cc12)c1nccnc1-c1ncc(Br)s1]
P9 2-[5-[(1S)-1-[[8-bromo-2-chloro-6-(trifluoromethyl)quinazolin-4-yl]amino]ethyl]-1,2,4-triazol-1-yl]thiazole-5-carbonitrile
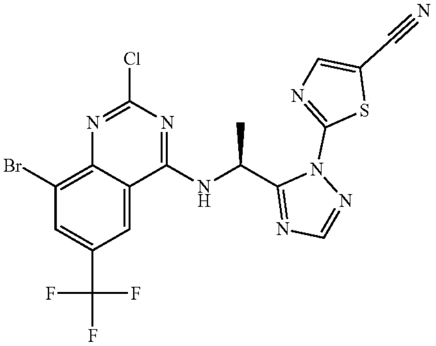 [SMILES: C[C@H](Nc1nc(Cl)nc2c(Br)cc(C(F)(F)F)cc12)c1ncnn1-c1ncc(C#N)s1]
P10 2-[5-[(1S)-1-[[6-chloro-8-(trifluoromethyl)quinazolin-4-yl]amino]ethyl]-1,2,4-triazol-1-yl]thiazole-5-carbonitrile
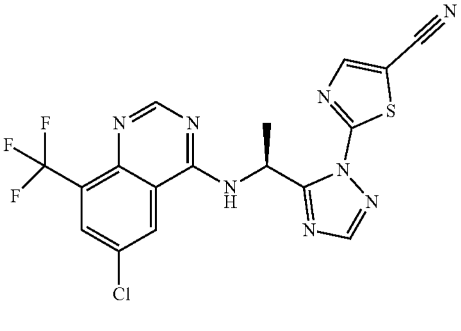 [SMILES: C[C@H](Nc1ncnc2c(C(F)(F)F)cc(Cl)cc12)c1ncnn1-c1ncc(C#N)s1]

-continued
P11 2-[5-[(1S)-1-[6-chloro-8-(trifluoromethyl)quinazolin-4-yl]-methyl-amino]ethyl]-1,2,4-triazol-1-yl]thiazole-5-carbonitrile
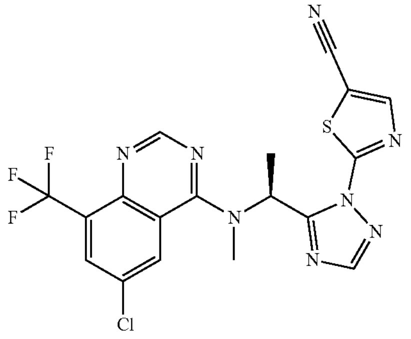 [SMILES: C[C@@H](c1ncnn1-c1ncc(C#N)s1)N(C)c1ncnc2c(C(F)(F)F)cc(Cl)cc12]
P12 2-[3-[1-[[8-chloro-6-(trifluoromethyl)quinazolin-4-yl]amino]ethyl]pyrazin-2-yl]thiazole-5-carbonitrile
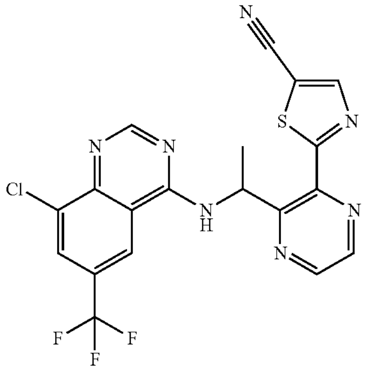 [SMILES: CC(Nc1ncnc2c(Cl)cc(C(F)(F)F)cc12)c1nccnc1-c1ncc(C#N)s1]
P13 6-chloro-N-[1-[3-(1,2,4-thiadiazol-3-yl)pyrazin-2-yl]ethyl]-8-(trifluoromethyl)quinazolin-4-amine
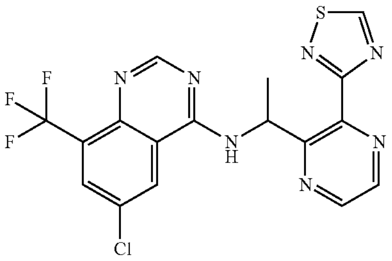 [SMILES: CC(Nc1ncnc2c(C(F)(F)F)cc(Cl)cc12)c1nccnc1-c1ncsn1]
P14 2-[5-[(1S)-1-[(6,8-dibromoquinazolin-4-yl)amino]ethyl]-1,2,4-triazol-1-yl]thiazole-5-carbonitrile
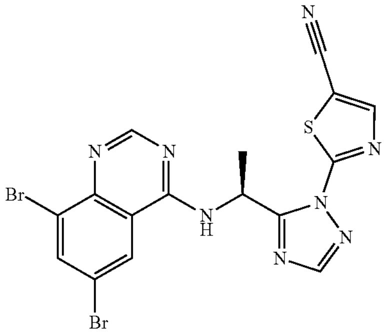 [SMILES: C[C@H](Nc1ncnc2c(Br)cc(Br)cc12)c1ncnn1-c1ncc(C#N)s1]

-continued

| | | |
|---|---|---|
| P15 | 2-[5-[(1S)-1-[[8-chloro-6-(trifluoromethyl)quinazolin-4-yl]amino]ethyl]-1,2,4-triazol-1-yl]thiazole-5-carbonitrile | 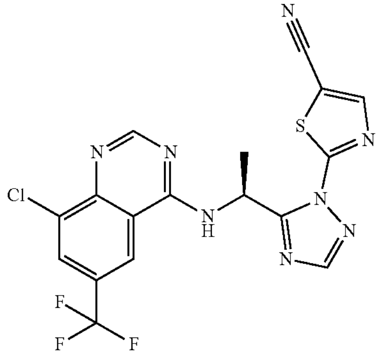 [SMILES: C[C@H](Nc1ncnc2c(Cl)cc(C(F)(F)F)cc12)c1ncnn1-c1ncc(C#N)s1] |
| P16 | 6,8-dibromo-N-[1-[3-(1,2,4-thiadiazol-3-yl)pyrazin-2-yl]ethyl]quinazolin-4-amine | 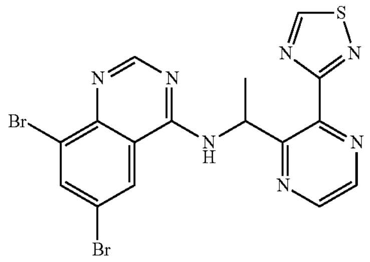 [SMILES: CC(Nc1ncnc2c(Br)cc(Br)cc12)c1nccnc1-c1ncsn1] |
| P17 | 2-[5-[(1S)-1-[[8-chloro-6-(trifluoromethyl)quinazolin-4-yl]-methyl-amino]ethyl]-1,2,4-triazol-1-yl]thiazole-5-carbonitrile | 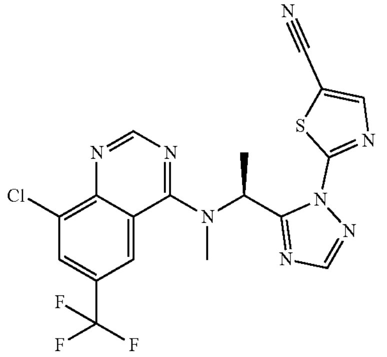 [SMILES: C[C@@H](c1ncnn1-c1ncc(C#N)s1)N(C)c1ncnc2c(Cl)cc(C(F)(F)F)cc12] |
| P18 | 8-chloro-N-[1-[3-(1,2,4-thiadiazol-3-yl)pyrazin-2-yl]ethyl]-6-(trifluoromethyl)quinazolin-4-amine | 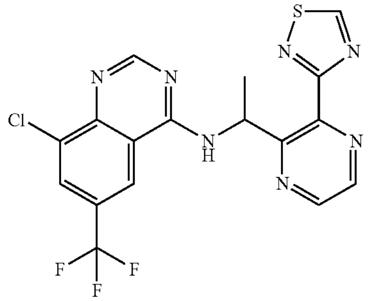 [SMILES: CC(Nc1ncnc2c(Cl)cc(C(F)(F)F)cc12)c1nccnc1-c1ncsn1] |
| P19 | 2-[3-[1-[(6,8-dibromoquinazolin-4-yl)amino]ethyl]pyrazin-2-yl]thiazole-5-carbonitrile | 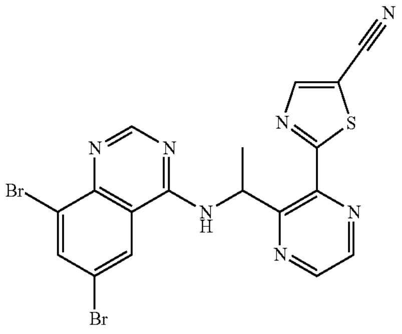 [SMILES: CC(Nc1ncnc2c(Br)cc(Br)cc12)c1nccnc1-c1ncc(C#N)s1] |

-continued

P20 2-[5-[(1S)-1-[(8-chloro-6-iodo-quinazolin-4-yl)amino]ethyl]-1,2,4-triazol-1-yl]thiazole-5-carbonitrile

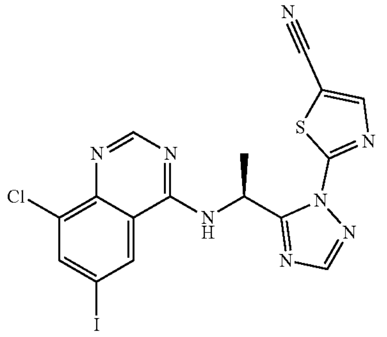 [SMILES: C[C@H](Nc1ncnc2c(Cl)cc(I)cc12)c1ncnn1-c1ncc(C#N)s1]

P21 8-chloro-N-[1-[3-(1,2,4-thiadiazol-3-yl)pyrazin-2-ylethyl]-6-(trifluoromethylsulfonyl)quinazolin-4-amine

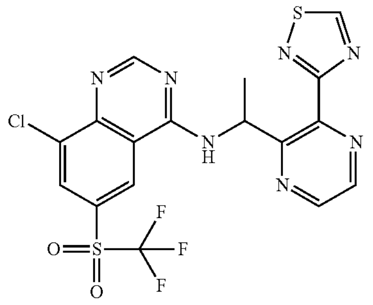 [SMILES: CC(Nc1ncnc2c(Cl)cc(S(=O)(=O)C(F)(F)F)cc12)c1nccnc1-c1ncsn1]

P22 2-[5-[(1S)-1-[8-chloro-6-(trifluoromethylsulfonyl)quinazolin-4-yl]amino]ethyl]-1,2,4-triazol-1-yl]thiazole-5-carbonitrile

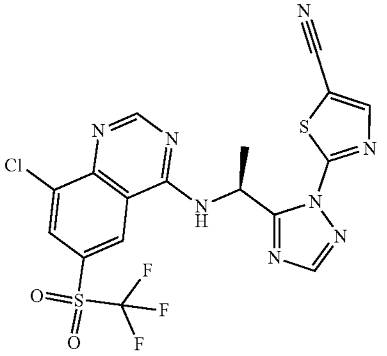 [SMILES: C[C@H](Nc1ncnc2c(Cl)cc(S(=O)(=O)C(F)(F)F)cc12)c1ncnn1-c1ncc(C#N)s1]

P23 2-[3-[1-[[8-bromo-2-chloro-6-(trifluoromethyl)quinazolin-4-yl]amino]ethyl]pyrazin-2-yl]thiazole-5-carbonitrile

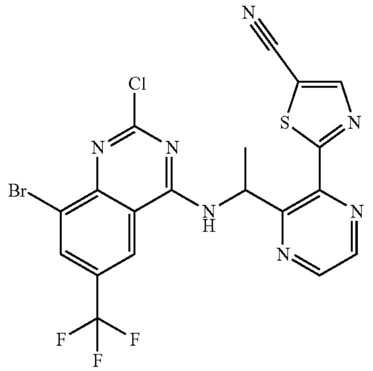 [SMILES: CC(Nc1nc(Cl)nc2c(Br)cc(C(F)(F)F)cc12)c1nccnc1-c1ncc(C#N)s1]

or an agrochemically acceptable salt, stereoisomer, enantiomer, tautomer, or N-oxide thereof.

16. A composition comprising a compound as defined in claim 15, one or more auxiliaries and/or diluents, and optionally one or more other active ingredient(s).

17. A method (i) of combating and controlling insects, acarines, nematodes or molluscs which comprises applying to a pest, to a locus of a pest, or to a plant susceptible to attack by a pest an insecticidally, acaricidally, nematicidally or molluscicidally effective amount of a compound as defined in claim 15; or (ii) for the protection of plant propagation material from attack by insects, acarines, nematodes or molluscs, which comprises treating the propagation material or the site where the propagation material is planted, with an effective amount of a compound as defined in claim 15; or (iii) of controlling parasites in or on an animal in need thereof comprising administering an effective amount of a compound as defined in claim 15.

18. A plant propagation material comprising, treated with, or adhered thereto, a compound as defined in claim 15.

19. The plant propagation material of claim 18, wherein the plant propagation material is a seed.

* * * * *